United States Patent
Atkinson et al.

(10) Patent No.: US 10,844,015 B2
(45) Date of Patent: Nov. 24, 2020

(54) PYRIDINE DICARBOXAMIDE DERIVATIVES AS BROMODOMAIN INHIBITORS

(71) Applicant: GlaxoSmithKline Intellectual Property (No. 2) Limited, Brentford, Middlesex (GB)

(72) Inventors: Stephen John Atkinson, Stevenage (GB); Emmanuel Hubert Demont, Stevenage (GB); Lee Andrew Harrison, Stevenage (GB); Etienne Levernier, Stevenage (GB); Alexander G. Preston, Stevenage (GB); Jonathan Thomas Seal, Stevenage (GB); Ian David Wall, Stevenage (GB); Robert J. Watson, Stevenage (GB); James Michael Woolven, Stevenage (GB)

(73) Assignee: GlaxoSmithKline Intellectual Property (No. 2) Limited, Middlesex (GB)

( * ) Notice: Subject to any disclaimer, the term of this patent is extended or adjusted under 35 U.S.C. 154(b) by 0 days.

(21) Appl. No.: 16/303,211

(22) PCT Filed: May 22, 2017

(86) PCT No.: PCT/EP2017/062208
§ 371 (c)(1),
(2) Date: Nov. 20, 2018

(87) PCT Pub. No.: WO2017/202742
PCT Pub. Date: Nov. 30, 2017

(65) Prior Publication Data
US 2019/0202786 A1    Jul. 4, 2019

(30) Foreign Application Priority Data

May 24, 2016 (GB) .................................. 1609096.1
Mar. 1, 2017 (GB) .................................. 1703274.9

(51) Int. Cl.
| | | |
|---|---|---|
| *C07D 213/53* | (2006.01) | |
| *C07D 487/04* | (2006.01) | |
| *C07D 213/81* | (2006.01) | |
| *C07D 401/06* | (2006.01) | |
| *C07D 213/64* | (2006.01) | |
| *C07D 401/10* | (2006.01) | |
| *C07D 401/12* | (2006.01) | |

(52) U.S. Cl.
CPC ......... *C07D 213/53* (2013.01); *C07D 213/64* (2013.01); *C07D 213/81* (2013.01); *C07D 401/06* (2013.01); *C07D 401/10* (2013.01); *C07D 401/12* (2013.01); *C07D 487/04* (2013.01)

(58) Field of Classification Search
CPC .................................................. C07D 213/53
See application file for complete search history.

(56) References Cited

U.S. PATENT DOCUMENTS

| | | |
|---|---|---|
| 2012/0208814 A1 | 8/2012 | Demont et al. |
| 2014/0179648 A1 | 6/2014 | Liu et al. |

FOREIGN PATENT DOCUMENTS

| | | |
|---|---|---|
| EP | 1 357 111 B1 | 10/2003 |
| EP | 1 433 788 A1 | 6/2004 |
| EP | 1 477 186 A1 | 11/2004 |
| WO | WO 2004/033446 A1 | 4/2004 |
| WO | WO 2014/074675 A1 | 5/2014 |
| WO | WO 2014/096965 A2 | 6/2014 |
| WO | WO 2015/015318 A2 | 2/2015 |
| WO | WO 2017/037116 A1 | 3/2017 |
| WO | WO 2017/050714 A1 | 3/2017 |
| WO | WO 2017/060180 A1 | 4/2017 |
| WO | WO 2017/174621 A1 | 10/2017 |
| WO | WO 2017/202742 A1 | 11/2017 |
| WO | WO 2018/158210 A1 | 9/2018 |

OTHER PUBLICATIONS

Dittmer et al., "Models for the Pyridine Nucleotide Coenzymes. Synthesis and Properties of Bridged Dinicotinamide Derivatives[1-3]", *J. Org. Chem.*, vol. 38, No. 16, pp. 2873-2882 (1973).
Gallenkamp et al., "Bromodomains and Their Pharmacological Inhibitors", *ChemMedChem*, vol. 9, No. 3, pp. 438-464 (2014).
Garnier et al., "BET bromodomain inhibitors: a patent review", *Expert Opinion on Therapeutic Patents*, vol. 24, No. 2, pp. 185-199 (2014).
International Search Report for International application No. PCT/EP2016/070519, ISR: dated Oct. 20, 2016, 4 pages.
International Search Report for International application No. PCT/EP2016/072216, International filing date: Sep. 20, 2016, 3 pages.
International Search Report for International application No. PCT/EP2016/073532, ISR: dated Nov. 30, 2016, 5 pages.
International Search Report for International application No. PCT/EP2017/058050, ISR: dated May 24, 2017, 5 pages.
International Search Report for International application No. PCT/EP2017/062208, ISR: dated Jul. 6, 2017, 5 pages.

(Continued)

*Primary Examiner* — Noble E Jarrell
(74) *Attorney, Agent, or Firm* — Jane F. Djung; Duke M. Fitch; Edward R. Gimmi

(57) ABSTRACT

The present invention relates to compounds of formula (I) and salts thereof, pharmaceutical compositions containing such compounds and to their use in therapy.

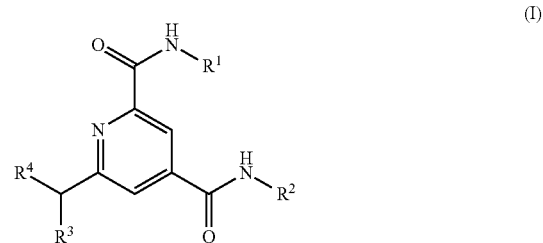

12 Claims, No Drawings

(56) References Cited

OTHER PUBLICATIONS

International Search Report for International application No. PCT/EP2018/054730, ISR: dated May 4, 2018, 5 pages.
International Search Report for International application No. PCT/EP2018/054733, ISR: dated Jun. 11, 2018, 5 pages.
Non-Final Office Action for U.S. Appl. No. 15/766,222, USPTO, notification dated Oct. 4, 2018, 9 pages.
Notice of Allowance for U.S. Appl. No. 15/762,229, USPTO, dated Dec. 11, 2018, 9 pages.
Notice of Allowance for U.S. Appl. No. 15/766,222, USPTO, dated Jan. 17, 2019, 6 pages.
Notice of Allowance for U.S. Appl. No. 15/762,229, USPTO, dated Mar. 20, 2019, 9 pages.
Restriction Requirement for U.S. Appl. No. 15/757,199, USPTO, notification dated Feb. 11, 2019, 9 pages.

PYRIDINE DICARBOXAMIDE DERIVATIVES AS BROMODOMAIN INHIBITORS

This application is a 371 of International Application No. PCT/EP2017/062208, filed May 22, 2017, which claims the priority of GB Application No. 1609096.1, filed May 24, 2016 and GB Application No. 1703274.9, filed Mar. 1, 2017, which are incorporated herein in their entireties.

FIELD OF THE INVENTION

The present invention is directed to pyridyl derivatives which are bromodomain inhibitors, processes for their preparation, pharmaceutical compositions comprising the compounds and the use of the compounds or the compositions in the treatment of various diseases or conditions, for example acute or chronic autoimmune and/or inflammatory conditions, viral infections and cancer.

BACKGROUND TO THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine residues commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem,* 2011, 54, 3827-3838).

Chan et al. report that BET bromodomain inhibition suppresses transcriptional responses to cytokine-Jak-STAT signalling in a gene-specific manner in human monocytes, which suggests that BET inhibition reduces inflammation partially through suppression of cytokine activity. (Chan et al., *Eur. J. Immunol.,* 2015, 45: 287-297).

Klein et al. report that the bromodomain protein inhibitor I-BET151 suppresses expression of inflammatory genes and matrix degrading enzymes in rheumatoid arthritis synovial fibroblasts, which suggests a therapeutic potential in the targeting of epigenetic reader proteins in rheumatoid arthritis. (Klein et al., *Ann. Rheum. Dis.,* 2014, 0:1-8).

Park-Min et al. report that I-BET151, which targets bromo and extra-terminal (BET) proteins that 'read' chromatin states by binding to acetylated histones, strongly suppresses osteoclastogenesis. (Park-Min et al. *Nature Communications,* 2014, 5, 5418).

PCT patent applications PCT/EP2016/070519, PCT/EP2016/072216 and PCT/EP2016/073532 each describe a series of pyridone derivatives as bromodomain inhibitors.

SUMMARY OF THE INVENTION

The invention is directed to compounds of formula (I)

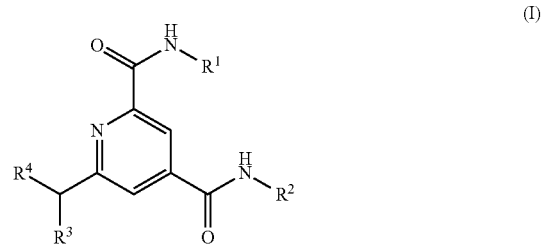

or a salt thereof
wherein:
$R^1$ is —$C_{1-3}$alkyl or cyclopropyl;
$R^2$ is —$C_{0-3}$alkyl-$C_{3-7}$cycloalkyl, wherein the $C_{3-7}$cycloalkyl group is optionally substituted with one, two or three $R^5$ groups which may be the same or different;
$R^3$ is —H, —$C_{1-4}$alkyl, cyclopropyl, fluoro, chloro, —$CH_2F$, —$C_{0-3}$alkylO$R^{10}$ or $C_{0-3}$alkylCN;
$R^4$ is phenyl or heteroaryl, wherein each is optionally substituted by one, two or three $R^6$ groups which may be the same or different;
each $R^5$ is independently selected from fluoro, —$C_{1-6}$alkyl-$R^{13}$, —$OCH_3$, —O—$C_{2-6}$alkyl-$R^{13}$, —CN, —OH, —$SO_2C_{1-3}$alkyl and —$NR^{14}R^{15}$;
each $R^6$ is independently selected from oxo, halo, —$OCF_3$, —$OCHF_2$, —$C_{1-4}$alkyl, —$C_{0-3}$alkyl-$OR^8$, —$C_{0-3}$alkyl-$NR^{14}R^{15}$, —$C_{0-3}$alkyl-$CONR^{11}R^{12}$, —$C_{0-3}$alkyl-heterocyclyl, —$C_{0-3}$alkyl-O—$C_{1-2}$alkyl-heterocyclyl, —CN and —$SO_2R^7$, wherein heterocyclyl is optionally substituted by one or two substituents independently selected from —$C_{1-3}$alkyl, —OH and fluoro;
$R^7$ is —$C_{1-3}$alkyl or —$NR^{11}R^{12}$;
$R^8$ is —H, —$C_{1-3}$alkyl, —$C_{2-3}$alkyl-$NR^{11}R^{12}$, —$C_{2-3}$alkyl-OH or —$C_{2-3}$alkyl-O—$C_{1-3}$alkyl;
$R^9$ is —H, —$C_{1-3}$alkyl, —$C_{2-3}$alkyl-$NR^{11}R^{12}$ or —$C_{2-3}$alkyl-OH;
$R^{10}$ is —H or —$C_{1-3}$alkyl;
each $R^{11}$ and each $R^{12}$ are independently selected from —H and —$C_{1-3}$alkyl; or $R^{11}$ and $R^{12}$ may join together with the nitrogen to which they are attached, to form a heterocyclyl optionally containing a further heteroatom selected from nitrogen, oxygen and sulphur and optionally substituted by one or two substituents independently selected from —$C_{1-3}$alkyl, —OH and fluoro;

$R^{13}$ is —H, —$OR^9$, —$NR^{14}R^{15}$ or —CN;

each $R^{14}$ and each $R^{15}$ are independently selected from —H, —C(O)OC(CH$_3$)$_3$, —C(O)C$_{1-3}$alkyl, —C$_{1-6}$alkyl, C$_{3-7}$cycloalkyl, heterocyclyl, —C$_{2-3}$alkyl-OH and —C$_{2-3}$alkyl-O—C$_{1-3}$alkyl, wherein —C$_{1-6}$alkyl and C$_3$-7cycloalkyl may be optionally substituted by one, two or three fluoro; or $R^{14}$ and $R^{15}$ may join together with the nitrogen to which they are attached, to form a heterocyclyl optionally containing a further heteroatom selected from nitrogen, oxygen and sulphur and optionally substituted by one or two substituents independently selected from —$C_{1-3}$alkyl, —OH and fluoro.

Compounds of the invention have been shown to be bromodomain inhibitors, in particular BD2 selective inhibitors and may be useful in the treatment of various diseases or conditions, for example acute or chronic auto-immune and/or inflammatory conditions, for example rheumatoid arthritis and cancer. Accordingly, the invention is further directed to pharmaceutical compositions comprising a compound of formula (I), or a pharmaceutically acceptable salt thereof. The invention is still further directed to methods of treatment of diseases or conditions associated with bromodomains in a subject in need thereof which comprises administering a therapeutically effective amount of a compound of formula (I) or a pharmaceutically acceptable salt thereof, or a pharmaceutical composition comprising a compound of formula (I) or a pharmaceutically acceptable salt thereof. The invention is yet further directed towards processes for the preparation of the compounds of formula (I).

DETAILED DESCRIPTION OF THE INVENTION

Compounds of formula (I) and salts thereof are referred to herein as "compounds of the invention".

"BD2" refers to Binding Domain 2 of any of the BET family of proteins BRD2, BRD3, BRD4 or BRDT.

"Alkyl" refers to a saturated hydrocarbon chain having the specified number of carbon atoms. For example, the term "$C_{1-6}$alkyl" as used herein refers to a straight or branched alkyl group having from 1 to 6 carbon atoms. For example, the term "$C_{0-3}$alkyl" refers to a straight or branched alkyl group having from 0 (i.e. a bond) to 3 carbon atoms. Representative branched alkyl groups have one, two or three branches. An alkyl group may form part of a chain, for example, —$C_{0-4}$alkyl-heterocyclyl refers to a straight or branched alkyl chain having from 0 (i.e. a bond) to 4 carbon atoms linked to a heterocyclyl. "Alkyl" includes, but is not limited to, methyl, ethyl, n-propyl, iso-propyl, n-butyl, iso-butyl, t-butyl, pentyl and hexyl.

"Cycloalkyl" refers to a saturated hydrocarbon monocylic or bicyclic ring or a saturated spiro-linked bicyclic hydrocarbon ring, having the specified number of member atoms in the ring. For example, the term "$C_{3-7}$cycloalkyl" as used herein refers to a cycloakyl group having from 3 to 7 member atoms. Examples of $C_{3-7}$cycloalkyl groups include, but are not limited to, cyclopropyl, cyclobutyl, cyclopentyl, cyclohexyl, cycloheptyl, and spiro[3.3]heptyl. A further specific example of a $C_{3-7}$cycloalkyl group is bicyclo[3.1.0]hexanyl.

"Enantiomeric excess" (ee) is the excess of one enantiomer over the other expressed as a percentage. In a racemic modification, since both enantiomers are present in equal amounts, the enantiomeric excess is zero (0% ee). However, if one enantiomer were enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess (ee) is greater than zero. For example, "enantiomerically enriched" refers to products whose enantiomeric excess is greater than 50% ee, greater than 75% ee, and greater than 90% ee.

"Enantiomerically pure" as used herein refers to products whose enantiomeric excess is 99% or greater.

"Half-life" (or "half-lives") refers to the time required for half of a quantity of a substance to be converted to another chemically distinct species in vitro or in vivo.

"Halo" refers to a halogen radical, for example, fluoro, chloro, bromo, or iodo.

"Heteroaryl" refers to a monocyclic or bicyclic group having 5, 6, 8, 9, 10 or 11 member atoms, including 1, 2 or 3 heteroatoms independently selected from nitrogen, sulphur and oxygen, wherein at least a portion of the group is aromatic. The point of attachment to the rest of the molecule may be by any suitable carbon or nitrogen atom. Examples of "heteroaryl" groups include, but are not limited to, furanyl, thienyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, triazinyl, benzofuranyl, isobenzofuryl, 2,3-dihydrobenzofuryl, 1,3-benzodioxolyl, dihydrobenzodioxinyl, benzothienyl, benzazepinyl, 2,3,4,5-tetrahydro-1H-benzo[d]azepinyl, indolizinyl, indolyl, indolinyl, isoindolyl, dihydroindolyl, benzimidazolyl, dihydrobenzimidazolyl, benzoxazolyl, dihydrobenzoxazolyl, benzthiazolyl, benzoisothiazolyl, dihydrobenzoisothiazolyl, indazolyl, imidazopyridinyl, pyrazolopyridinyl, pyrrolopyridinyl, benzotriazolyl, triazolopyridinyl, purinyl, quinolinyl, tetrahydroquinolinyl, isoquinolinyl, tetrahydroisoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl.

"Heteroatom" refers to a nitrogen, sulfur, or oxygen atom.

"Heterocyclyl" refers to a non-aromatic heterocyclic monocyclic or bicyclic ring system containing 4, 5, 6, 7, 8, 9 or 10 ring member atoms, including one heteroatom and optionally containing a further heteroatom selected from nitrogen, oxygen or sulphur. Examples of "heterocyclyl" groups include, but are not limited to, azetidinyl, oxetanyl, thietanyl, pyrrolidinyl, pyrrolinyl, pyrazolidinyl, pyrazolinyl, imidazolidinyl, imidazolinyl, oxazolinyl, thiazolinyl, tetrahydrofuranyl, dihydrofuranyl, 1,3-dioxolanyl, piperidinyl, piperazinyl, homopiperazinyl, tetrahydropyranyl, dihydropyranyl, tetrahydrothiopyranyl, 1,3-dioxanyl, 1,4-dioxanyl, 1,3-oxathiolanyl, 1,3-oxathianyl, 1,3-dithianyl, 1,4-oxathiolanyl, 1,4-oxathianyl, 1,4-dithianyl, morpholinyl, thiomorpholinyl, hexahydro-1H-1,4-diazepinyl, azabicyclo[3.2.1]octyl, azabicyclo[3.3.1]nonyl, azabicyclo[4.3.0]nonyl, oxabicyclo[2.2.1]heptyl, 1,1-dioxidotetrahydro-2H-thiopyranyl, 1,5,9-triazacyclododecyl, 3-oxabicyclo[3.1.0]hexanyl and 3-azabicyclo[3.1.0]hexanyl. "4 to 7-membered heterocyclyl" refers to a non-aromatic heterocyclic monocyclic or bicyclic ring system containing 4, 5, 6 or 7 ring member atoms, including one heteroatom and optionally containing a further heteroatom selected from nitrogen, oxygen or sulphur.

"Member atoms" refers to the atom or atoms that form a chain or ring. Where more than one member atom is present in a chain and within a ring, each member atom is covalently bound to an adjacent member atom in the chain or ring. Atoms that make up a substituent group attached to a chain or ring are not member atoms in the chain or ring.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as rearrangement, cyclisation, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problems or complications, commensurate with a reasonable benefit/risk ratio.

"Pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient are avoided.

In addition, each excipient must of course be pharmaceutically acceptable e.g. of sufficiently high purity.

"rac" refers to the racemic mixture of the compounds of formula (I). For example, "rac-(2S,3R,4R)" means a racemic mixture of the (2S,3R,4R) enantiomer and the (2R,3S,4S) enantiomer.

The compounds of the invention may exist in solid or liquid form. In the solid state, the compounds of the invention may exist in crystalline or non-crystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, iso-propyl alcohol, N,N-dimethylsulfoxide (DMSO), acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. The invention includes all such solvates.

It will be further appreciated that certain compounds of the invention that exist in crystalline form, including the various solvates thereof, may exhibit polymorphism (i.e. the capacity to occur in different crystalline structures). These different crystalline forms are typically known as "polymorphs". The invention includes such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds according to formula (I) may contain one or more asymmetric centres (also referred to as a chiral centres) and may, therefore, exist as individual enantiomers, diastereoisomers, or other stereoisomeric forms, or as mixtures thereof. Chiral centres, such as chiral carbon atoms, may also be present in a substituent such as an alkyl group. Where the stereochemistry of a chiral centre present in formula (I), or in any chemical structure illustrated herein, is not specified, the structure is intended to encompass any stereoisomer and all mixtures thereof. Thus, compounds according to formula (I) containing one or more chiral centres may be used as racemic mixtures, enantiomerically-enriched mixtures, or as enantiomerically-pure individual stereoisomers. Accordingly, the present invention encompasses all isomers of the compounds of formula (I) whether as individual isomers isolated such as to be substantially free of the other isomer (i.e. pure) or as mixtures (i.e. racemic mixtures). An individual isomer isolated such as to be substantially free of the other isomer (i.e. pure) may be isolated such that less than 10%, particularly less than about 1%, for example less than about 0.1% of the other isomer is present.

Racemic compounds with a single stereocentre are denoted with either no stereochemistry (single bond) or have the annotation (+/−) or rac. Racemic compounds with two or more stereocentres where relative stereochemistry is known are denoted cis or trans as drawn in the structure. Resolved single enantiomers with unknown absolute stereochemistry but known relative stereochemistry are referred to with (R* or S*) with the appropriate relative stereochemistry depicted.

Where diastereoisomers are represented and only the relative stereochemistry is referred to, the bold or hashed solid bond symbols (━/ⅠⅠⅠⅠⅠⅠ) are used. Where the absolute stereochemistry is known and the compound is a single enantiomer, the bold or hashed wedges symbols (▬/ⅠⅠⅠⅠⅠⅠ) are used as appropriate.

Individual stereoisomers of a compound according to formula (I) which contain one or more asymmetric centres may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesised by asymmetric synthesis using optically active reagents, substrates, catalysts or solvents, or by converting one enantiomer to the other by asymmetric transformation.

It will be appreciated that, for compounds of formula (I) tautomers may be observed. Any comment relating to the biological activity of a tautomer should be taken to include both tautomers.

It is to be understood that the references herein to compounds of formula (I) and salts thereof covers the compounds of formula (I) as free bases, or as salts thereof, for example as pharmaceutically acceptable salts thereof. Thus, in one embodiment, the invention is directed to compounds of formula (I) as the free base. In another embodiment, the invention is directed to compounds of formula (I) and salts thereof. In a further embodiment, the invention is directed to compounds of formula (I) and pharmaceutically acceptable salts thereof.

Because of their potential use in medicine, salts of the compounds of formula (I) are desirably pharmaceutically acceptable. Suitable pharmaceutically acceptable salts can include acid addition salts or base addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt.

Other non-pharmaceutically acceptable salts, e.g. formates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated from the foregoing that included within the scope of the invention are solvates, isomers and polymorphic forms of the compounds of formula (I) and salts thereof.

STATEMENT OF THE INVENTION

In a first aspect there are provided compounds of formula (I):

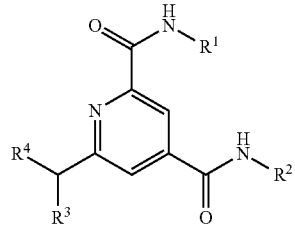

or a salt thereof
wherein:
$R^1$ is —$C_{1-3}$alkyl or cyclopropyl;
$R^2$ is —$C_{0-3}$alkyl-$C_{3-7}$cycloalkyl, wherein the $C_{3-7}$cycloalkyl group is optionally substituted with one, two or three $R^5$ groups which may be the same or different;
$R^3$ is —H, —$C_{1-4}$alkyl, cyclopropyl, fluoro, chloro, —$CH_2F$, —$C_{0-3}$alkylOR$^{10}$ or $C_{0-3}$alkylCN;
$R^4$ is phenyl or heteroaryl, wherein each is optionally substituted by one, two or three $R^6$ groups which may be the same or different;
each $R^5$ is independently selected from fluoro, —$C_{1-6}$alkyl-$R^{13}$, —$OCH_3$, —O—$C_{2-6}$alkyl-$R^{13}$, —CN, —OH, —$SO_2C_{1-3}$alkyl and —$NR^{14}R^{15}$;
each $R^6$ is independently selected from oxo, halo, —$OCF_3$, —$OCHF_2$, —$C_{1-4}$alkyl, —$C_{0-3}$alkyl-$OR^8$, —$C_{0-3}$alkyl-$NR^{14}R^{15}$, —$C_{0-3}$alkyl-$CONR^{11}R^{12}$, —$C_{0-3}$alkyl-heterocyclyl, —$C_{0-3}$alkyl-O—$C_{1-2}$alkyl-heterocyclyl, —CN and —$SO_2R^7$, wherein heterocyclyl is optionally substituted by one or two substituents independently selected from —$C_{1-3}$alkyl, —OH and fluoro;
$R^7$ is —$C_{1-3}$alkyl or —$NR^{11}R^{12}$;
$R^8$ is —H, —$C_{1-3}$alkyl, —$C_{2-3}$alkyl-$NR^{11}R^{12}$, —$C_{2-3}$alkyl-OH or —$C_{2-3}$alkyl-O—$C_{1-3}$alkyl;
$R^9$ is —H, —$C_{1-3}$alkyl, —$C_{2-3}$alkyl-$NR^{11}R^{12}$ or —$C_{2-3}$alkyl-OH;
$R^{10}$ is —H or —$C_{1-3}$alkyl;
each $R^{11}$ and each $R^{12}$ are independently selected from —H and —$C_{1-3}$alkyl; or $R^{11}$ and $R^{12}$ may join together with the nitrogen to which they are attached, to form a heterocyclyl optionally containing a further heteroatom selected from nitrogen, oxygen and sulphur and optionally substituted by one or two substituents independently selected from —$C_{1-3}$alkyl, —OH and fluoro;
$R^{13}$ is —H, —$OR^9$, —$NR^{14}R^{15}$ or —CN;
each $R^{14}$ and each $R^{15}$ are independently selected from —H, —$C(O)OC(CH_3)_3$, —$C(O)C_{1-3}$alkyl, —$C_{1-6}$alkyl, $C_{3-7}$cycloalkyl, heterocyclyl, —$C_{2-3}$alkyl-OH and —$C_{2-3}$alkyl-O—$C_{1-3}$alkyl, wherein —$C_{1-6}$alkyl and $C_3$-7cycloalkyl may be optionally substituted by one, two or three fluoro; or $R^{14}$ and $R^{15}$ may join together with the nitrogen to which they are attached, to form a heterocyclyl optionally containing a further heteroatom selected from nitrogen, oxygen and sulphur and optionally substituted by one or two substituents independently selected from —$C_{1-3}$alkyl, —OH and fluoro.

In one embodiment there is provided compounds of formula (I)
wherein:
$R^1$ is —$C_{1-3}$alkyl or cyclopropyl;
$R^2$ is —$C_{0-3}$alkyl-$C_{3-7}$cycloalkyl, wherein the $C_{3-7}$cycloalkyl group is optionally substituted with one, two or three $R^5$ groups which may be the same or different;
$R^3$ is —H, —$C_{1-4}$alkyl, fluoro or —$C_{0-3}$alkyl-$OR^{10}$;

R$^4$ is phenyl or heteroaryl, wherein each is optionally substituted by one, two or three R$^6$ groups which may be the same or different;

each R$^5$ is independently selected from fluoro, —C$_{1-6}$alkyl-R$^{13}$, —OCH$_3$, —O—C$_{2-6}$alkyl-R$^{13}$, —CN, —OH, —SO$_2$C$_{1-3}$alkyl and —NR$^{14}$R$^{15}$;

each R$^6$ is independently selected from oxo, halo, —OCF$_3$, —OCHF$_2$, —C$_{1-4}$alkyl, —C$_{0-3}$alkyl-OR$^8$, —C$_{0-3}$alkyl-NR$^{14}$R$^{15}$, —C$_{0-3}$alkyl-CONR$^{11}$R$^{12}$, —C$_{0-3}$alkyl-heterocyclyl, —C$_{0-3}$alkyl-O—C$_{1-2}$alkyl-heterocyclyl, —CN and —SO$_2$R$^7$, wherein heterocyclyl is optionally substituted by one or two substituents independently selected from —C$_{1-3}$alkyl, —OH and fluoro;

R$^7$ is —C$_{1-3}$alkyl or —NR$^{11}$R$^{12}$;

R$^8$ is —H, —C$_{1-3}$alkyl, —C$_{2-3}$alkyl-NR$^{11}$R$^{12}$, —C$_{2-3}$alkyl-OH or —C$_{2-3}$alkyl-O—C$_{1-3}$alkyl;

R$^9$ is —H, —C$_{1-3}$alkyl, —C$_{2-3}$alkyl-NR$^{11}$R$^{12}$ or —C$_{2-3}$alkyl-OH;

R$^{10}$ is —H or —C$_{1-3}$alkyl;

each R$^{11}$ and each R$^{12}$ are independently selected from —H and —C$_{1-3}$alkyl; or R$^{11}$ and R$^{12}$ may join together with the nitrogen to which they are attached, to form a heterocyclyl optionally containing a further heteroatom selected from nitrogen, oxygen and sulphur and optionally substituted by one or two substituents independently selected from —C$_{1-3}$alkyl, —OH and fluoro;

R$^{13}$ is —H, —OR$^9$, —NR$^{14}$R$^{15}$ or —CN;

each R$^{14}$ and each R$^{15}$ are independently selected from —H, —C(O)OC(CH$_3$)$_3$, —C(O)C$_{1-3}$alkyl, —C$_{1-6}$alkyl, C$_{3-7}$cycloalkyl, heterocyclyl, —C$_{2-3}$alkyl-OH and —C$_{2-3}$alkyl-O—C$_{1-3}$alkyl, wherein —C$_{1-6}$alkyl and C$_{3-7}$cycloalkyl may be optionally substituted by one, two or three fluoro; or R$^{14}$ and R$^{15}$ may join together with the nitrogen to which they are attached, to form a heterocyclyl optionally containing a further heteroatom selected from nitrogen, oxygen and sulphur and optionally substituted by one or two substituents independently selected from —C$_{1-3}$alkyl, —OH and fluoro.

In one embodiment R$^1$ is cyclopropyl. In another embodiment R$^1$ is —C$_{1-3}$alkyl. In a further embodiment R$^1$ is methyl.

In one embodiment R$^2$ is C$_{3-7}$cycloalkyl which is optionally substituted with one R$^5$ group. In another embodiment R$^2$ is unsubstituted. In another embodiment R$^2$ is substituted by one R$^5$ group.

In another embodiment R$^2$ is substituted by one R$^5$ group which is methyl. In another embodiment R$^2$ is cyclopropyl. In another embodiment R$^2$ is unsubstituted cyclopropyl. In another embodiment R$^2$ is cyclopropyl substituted by one R$^5$ group. In a further embodiment R$^2$ is cyclopropyl substituted by one R$^5$ group which is methyl.

In one embodiment R$^2$ is C$_{3-7}$cycloalkyl which is a bicyclo[3.1.0]hexanyl group optionally substituted with one or two R$^5$ groups. In one embodiment R$^2$ is C$_{3-7}$cycloalkyl which is a bicyclo[3.1.0]hexanyl group substituted with two fluoro groups. In another embodiment R$^2$ is C$_3$-7cycloalkyl which is a bicyclo[3.1.0]hexanyl group substituted with one —OH.

In one embodiment R$^3$ is —H, —C$_{1-4}$alkyl, cyclopropyl, fluoro or —C$_{0-3}$alkylOR$^{10}$. In one embodiment R$^3$ is —H, methyl, ethyl, fluoro, —OCH$_3$, —OH, —CH$_2$F, —CH$_2$OH, —CH(OH)CH$_3$, —CH$_2$OMe or —CH$_2$CN. In one embodiment R$^3$ is —H, methyl, fluoro, —OCH$_3$ or —OH. In one embodiment R$^3$ is —H, methyl or —OH.

In one embodiment R$^4$ is phenyl optionally substituted by one R$^6$ group. In another embodiment R$^4$ is unsubstituted. In another embodiment R$^4$ is substituted by one R$^6$ group. In another embodiment R$^4$ is unsubstituted phenyl. In another embodiment R$^4$ is a heteroaryl selected from the group consisting of pyridyl, pyrrolopyridinyl, indolyl, indolinyl, indazolyl and benzimidazolyl optionally substituted by one R$^6$ group. In another embodiment R$^4$ is unsubstituted pyridyl. In another embodiment R$^4$ is unsubstituted pyrrolopyridinyl. In another embodiment R$^4$ is unsubstituted indolinyl. In another embodiment R$^4$ is substituted by one R$^6$ group selected from oxo, fluoro, —OCH$_2$CH$_2$OH, —OCH$_2$CH(CH$_3$)OH, methyl, —OCH$_3$, —OH and —OCH$_2$CH$_2$-3-(4,4-difluoropiperidinyl).

In one embodiment each R$^5$ is independently selected from —C$_{1-6}$alkyl-R$^{13}$, —OH and —SO$_2$C$_{1-3}$alkyl. In another embodiment each R$^5$ is independently selected from methyl, —OH, —CH$_2$OH and —SO$_2$CH$_3$. In a further embodiment each R$^5$ is methyl.

In one embodiment each R$^6$ is independently selected from oxo, halo, —C$_{1-4}$alkyl, —C$_{0-3}$alkyl-OR$^8$ and —C$_{0-3}$alkyl-O—C$_{1-2}$alkyl-heterocyclyl. In another embodiment each R$^6$ is independently selected from oxo, fluoro, —OCH$_2$CH$_2$OH, —OCH$_2$CH(CH$_3$)OH, methyl, —OCH$_3$, —OH and —OCH$_2$CH$_2$-3-(4,4-difluoropiperidinyl). In another embodiment each R$^6$ is independently selected from oxo, fluoro, -methyl, —OCH$_3$ or —OH.

It is to be understood that the present invention covers all combinations of substituent groups described hereinabove.

Compounds of the invention include the compounds of Examples 1 to 124 and salts thereof.

Compounds of the invention include the compounds of Examples 1 to 116 and salts thereof.

Compounds of the invention include the compounds of Examples 1 to 55 and salts thereof.

In one embodiment the compound is selected from:
6-((S)-Hydroxy(phenyl)methyl)-N$^2$-methyl-N$^4$-((1S,2S)-2-methylcyclopropyl)pyridine-2,4-dicarboxamide;
6-((1H-Pyrrolo[2,3-c]pyridin-4-yl)methyl)-N$^2$-methyl-N$^4$-((1S,2S)-2-methylcyclopropyl)pyridine-2,4-dicarboxamide;
6-((S*)-1-(1H-Pyrrolo[2,3-c]pyridin-4-yl)ethyl)-N$^2$-methyl-N$^4$-((1S,2S)-2-methylcyclopropyl)pyridine-2,4-dicarboxamide; and
(R*)—N$^4$-Cyclopropyl-6-(hydroxy(phenyl)methyl)-N$^2$-methylpyridine-2,4-dicarboxamide or a salt thereof.

In one embodiment the compound is selected from:
6-((1H-Pyrrolo[2,3-b]pyridin-4-yl)methyl)-N$^2$-methyl-N$^4$-((1S,2S)-2-methylcyclopropyl)pyridine-2,4-dicarboxamide;
6-(Indolin-4-ylmethyl)-N$^2$-methyl-N$^4$-((1S,2S)-2-methylcyclopropyl)pyridine-2,4-dicarboxamide; and
6-((R*)-Methoxy(1H-pyrrolo[2,3-b]pyridin-4-yl)methyl)-N$^2$-methyl-N$^4$-((1S,2S)-2-methylcyclopropyl)pyridine-2,4-dicarboxamide or a salt thereof.

In one embodiment the compound is selected from:
6-benzyl-N$^4$-((1R,3r,5S,6r)-3-hydroxybicyclo[3.1.0]hexan-6-yl)-N$^2$-methylpyridine-2,4-dicarboxamide;
6-benzyl-N$^4$-((1R,3s,5S,6r)-3-hydroxybicyclo[3.1.0]hexan-6-yl)-N$^2$-methylpyridine-2,4-dicarboxamide;
N$^4$-((1R,3r,5S,6r)-3-hydroxybicyclo[3.1.0]hexan-6-yl)-6-(methoxy(phenyl)methyl)-N$^2$-methylpyridine-2,4-dicarboxamide;
N$^4$-((1R,3s,5S,6r)-3-hydroxybicyclo[3.1.0]hexan-6-yl)-6-(methoxy(phenyl)methyl)-N$^2$-methylpyridine-2,4-dicarboxamide;
N$^4$-((1R,3S,5S,6r)-3-hydroxybicyclo[3.1.0]hexan-6-yl)-6-((R*)-methoxy(phenyl)methyl)-N$^2$-methylpyridine-2,4-dicarboxamide;

N⁴-((1R,3S,5S,6r)-3-hydroxybicyclo[3.1.0]hexan-6-yl)-6-((S*)-methoxy(phenyl)methyl)-N²-methylpyridine-2,4-dicarboxamide;

N⁴-((1R,3R,5S,6r)-3-hydroxybicyclo[3.1.0]hexan-6-yl)-6-((R*)-methoxy(phenyl)methyl)-N²-methylpyridine-2,4-dicarboxamide; and N⁴-((1R,3S,5S,6r)-3-hydroxybicyclo[3.1.0]hexan-6-yl)-6-((S*)-methoxy(phenyl)methyl)-N²-methylpyridine-2,4-dicarboxamide or a salt thereof.

In one embodiment the compound of formula (I) is:

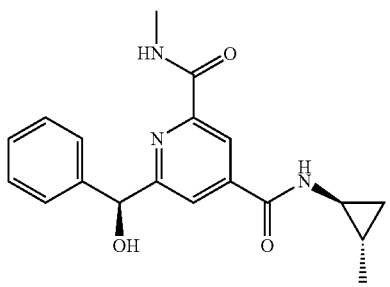 [SMILES: CNC(=O)c1cc(C(=O)N[C@H]2C[C@@H]2C)cc([C@@H](O)c2ccccc2)n1]

or a salt thereof.

In another embodiment, the compound of formula (I) is a salt of:

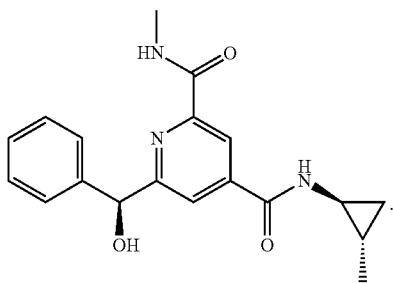 [SMILES: CNC(=O)c1cc(C(=O)N[C@H]2C[C@@H]2C)cc([C@@H](O)c2ccccc2)n1]

In a further embodiment the compound of formula (I) is

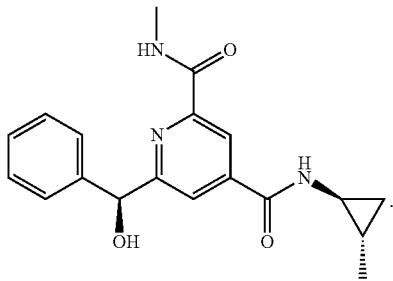 [SMILES: CNC(=O)c1cc(C(=O)N[C@H]2C[C@@H]2C)cc([C@@H](O)c2ccccc2)n1]

In one embodiment the compound of formula (I) is:

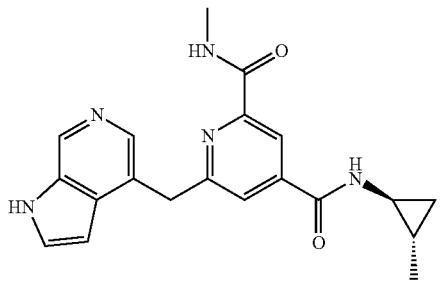 [SMILES: CNC(=O)c1cc(C(=O)N[C@H]2C[C@@H]2C)cc(Cc2cncc3[nH]ccc23)n1]

or a salt thereof.

In another embodiment, the compound of formula (I) is a salt of:

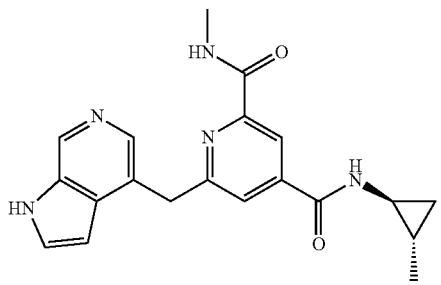

In a further embodiment the compound of formula (I) is

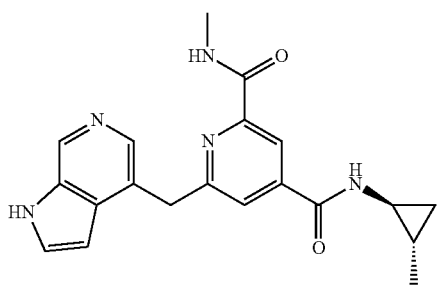

In one embodiment the compound of formula (I) is:

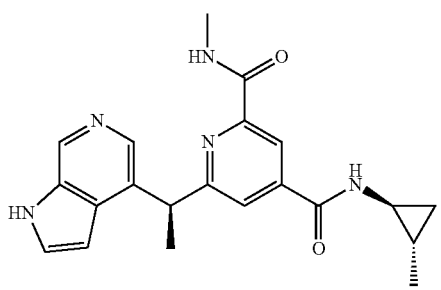 [SMILES: CNC(=O)c1cc(C(=O)N[C@H]2C[C@@H]2C)cc([C@@H](C)c2cncc3[nH]ccc23)n1]

or a salt thereof.

In another embodiment, the compound of formula (I) is a salt of:

In a further embodiment the compound of formula (I) is:

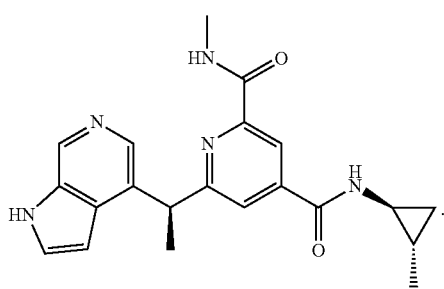 [SMILES: CNC(=O)c1cc(C(=O)N[C@H]2C[C@@H]2C)cc([C@@H](C)c2cncc3[nH]ccc23)n1]

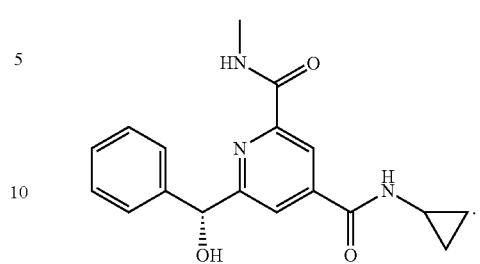

In one embodiment the compound of formula (I) is:

In a further embodiment the compound of formula (I) is:

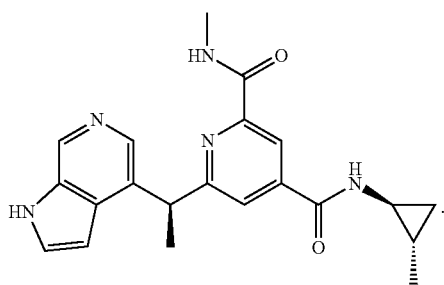 [SMILES: CNC(=O)c1cc(C(=O)N[C@H]2C[C@@H]2C)cc([C@@H](C)c2cncc3[nH]ccc23)n1]

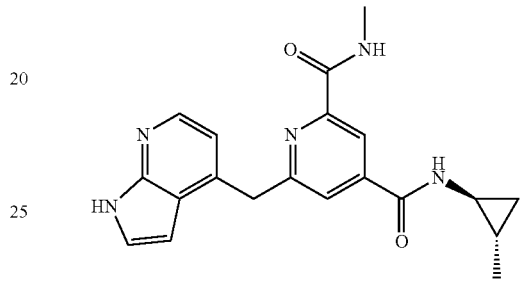

or a salt thereof.

In one embodiment the compound of formula (I) is:

In one embodiment the compound of formula (I) is:

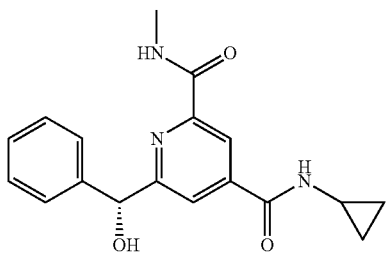 [SMILES: CNC(=O)c1cc(C(=O)NC2CC2)cc([C@H](O)c2ccccc2)n1]

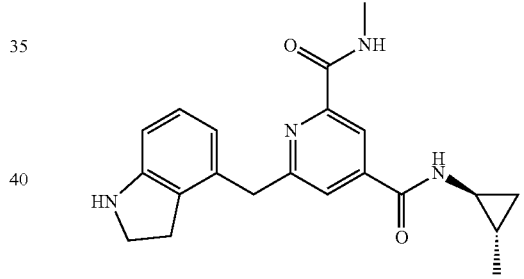

or a salt thereof.

In one embodiment the compound of formula (I) is:

or a salt thereof.

In another embodiment, the compound of formula (I) is a salt of:

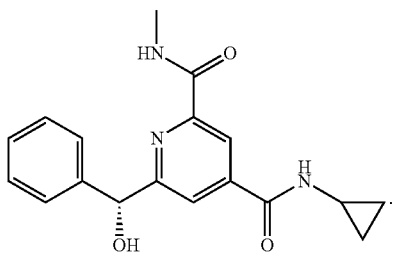 [SMILES: CNC(=O)c1cc(C(=O)NC2CC2)cc([C@H](O)c2ccccc2)n1]

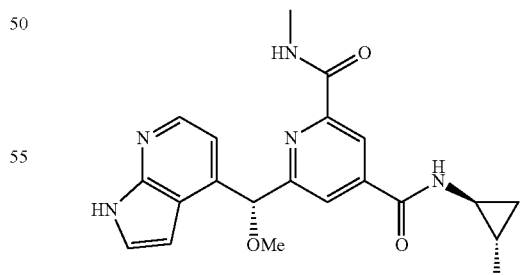

or a salt thereof.

In a second aspect of the present invention, there is provided a pharmaceutical composition comprising a compound of formula (I) or a pharmaceutically acceptable salt thereof and one or more pharmaceutically acceptable excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

Statement of Use

The compounds of formula (I) and salts thereof are bromodomain inhibitors, and thus are believed to have potential utility in the treatment of diseases or conditions for which a bromodomain inhibitor is indicated.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, psoriatic arthritis, ankylosing spondylitis, osteoarthritis, acute gout, psoriasis, systemic lupus erythematosus, multiple sclerosis, inflammatory bowel disease (Crohn's disease and ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, Type I diabetes, Type II diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement, acute rejection of transplanted organs and systemic sclerosis.

In one embodiment the acute or chronic autoimmune and/or inflammatory condition is a disorder of lipid metabolism mediated via the regulation of APO-A1 such as hypercholesterolemia, atherosclerosis or Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease or Ulcerative colitis).

In another embodiment, the acute or chronic autoimmune and/or inflammatory condition is multiple sclerosis.

In another embodiment, the acute or chronic autoimmune and/or inflammatory condition is Type I diabetes.

In another embodiment, the acute or chronic autoimmune and/or inflammatory condition is rheumatoid arthritis.

Bromodomain inhibitors may be useful in the treatment of depression.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of cardiovascular diseases such as coronary artery diseases (for example, angina or myocardial infarction), pulmonary arterial hypertension, cerebro-vascular ischaemia (stroke), hypertensive heart disease, rheumatic heart disease, cardiomyopathy, atrial fibrillation, congenital heart disease, endocarditis, aortic aneurysms or peripheral artery disease.

Bromodomain inhibitors may be useful in the treatment of fibrotic conditions such as idiopathic pulmonary fibrosis, pulmonary fibrosis, cystic fibrosis, progressive massive fibrosis, renal fibrosis, liver fibrosis, liver cirrhosis, non-alcoholic steatohepatitis (NASH), non-alcoholic fatty liver disease (NAFLD), post-operative stricture, keloid scar formation, scleroderma (including morphea and systemic sclerosis), cardiac fibrosis, atrial fibrosis, endomyocardial fibrosis, old myocardial infarction, arthrofibrosis, Dupuytren's contracture, mediastinal, myelofibrosis, Peyronie's disease, nephrogenic systemic fibrosis, retroperitoneal fibrosis and adhesive capsulitis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox or smallpox, or African swine fever virus. In one embodiment the viral infection is a HPV infection of skin or cervical epithelia. In another embodiment the viral infection is a latent HIV infection.

Bromodomain inhibitors may be useful in the treatment of a wide variety of bone disorders such as osteoporosis, osteopenia, osteoarthritis and ankylosing spondylitis.

Bromodomain inhibitors may be useful in the treatment of cancer, including hematological cancers (such as leukaemia, lymphoma and multiple myeloma), epithelial cancers (including lung, breast or colon carcinomas), midline carcinomas, or mesenchymal, hepatic, renal or neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colorectal cancer. In another embodiment the cancer is prostate cancer. In another embodiment the cancer is castration resistant prostate cancer.

Bromodomain inhibitors may be useful in the treatment of diseases associated with systemic inflammatory response syndrome, such as sepsis, burns, pancreatitis, major trauma, haemorrhage and ischaemia. In this embodiment, the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxemia. In another embodiment, the bromodomain inhibitor is indicated for the treatment of acute or chronic pancreatitis. In another embodiment the bromodomain is indicated for the treatment of burns.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of a disease or condition for which a bromodomain inhibitor is indicated. In one embodiment there is provided a compound of formula (I) or a pharmaceutically acceptable salt thereof for use in the treatment of acute or chronic auto-immune and/or inflammatory conditions. In one embodiment there is provided a compound of formula (I) or a pharmaceutically acceptable salt thereof for use in the treatment of rheumatoid arthritis. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of conditions associated with ischaemia-reperfusion injury. In another embodiment there is provided a compound of formula (I) or a pharmaceutically acceptable salt thereof for use in the treatment of cardiovascular diseases. In another embodiment there is provided a compound of formula (I) or a pharmaceutically acceptable salt thereof for use in the treatment of fibrotic conditions. In another embodiment there is provided a compound of formula (I) or a pharmaceutically acceptable salt thereof for use in the treatment of viral infections. In another embodiment there is provided a compound of formula (I) or a pharmaceutically acceptable salt thereof for use in the treatment of bone disorders.

In another embodiment there is provided a compound of formula (I) or a pharmaceutically acceptable salt thereof for use in the treatment of cancer. In a further embodiment there is provided a compound of formula (I) or a pharmaceutically acceptable salt thereof for use in the treatment of diseases associated with systemic inflammatory response syndrome.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In one embodiment there is provided the use of a compound of formula (I) or a pharmaceutically acceptable salt thereof in the manufacture of a medicament for the treatment of rheumatoid arthritis. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of conditions associated with ischaemia-reperfusion injury. In another embodiment there is provided the use of a compound of formula (I) or a pharmaceutically acceptable salt thereof in the manufacture of a medicament for the treatment of cardiovascular diseases. In another embodiment there is provided the use of a compound of formula (I) or a pharmaceutically acceptable salt thereof in the manufacture of a medicament for the treatment of fibrotic conditions. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer. In a further embodiment there is provided the use of a compound of formula (I) or a pharmaceutically acceptable salt thereof in the manufacture of a medicament for the treatment of diseases associated with systemic inflammatory response syndrome.

Also provided is a method of treating diseases or conditions for which a bromodomain inhibitor is indicated in a subject in need thereof which comprises administering a therapeutically effective amount of a compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In one embodiment there is provided a method of treating rheumatoid arthritis in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating conditions associated with ischaemia-reperfusion injury in a subject in need thereof which comprises administering a therapeutically effective amount of a compound of formula (I) or a pharmaceutically acceptable salt thereof. In another embodiment there is provided a method of treating cardiovascular diseases in a subject in need thereof which comprises administering a therapeutically effective amount of a compound of formula (I) or a pharmaceutically acceptable salt thereof. In another embodiment there is provided a method of treating fibrotic conditions in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In another embodiment there is provided a method of treating cancer in a subject in need thereof which comprises administering a therapeutically effective amount of a compound of formula (I) or a pharmaceutically acceptable salt thereof. In a further embodiment there is provided a method of treating diseases associated with systemic inflammatory response syndrome in a subject in need thereof which comprises administering a therapeutically effective amount of a compound of formula (I) or a pharmaceutically acceptable salt thereof.

Suitably the subject in need thereof is a mammal, particularly a human.

The invention further provides for a method for inhibiting a bromodomain containing protein which comprises contacting the bromodomain containing protein with a compound of formula (I) or a pharmaceutically acceptable salt thereof.

As used herein the reference to the "treatment" of a particular disease or condition includes the prevention or prophylaxis of such a disease or condition.

PHARMACEUTICAL COMPOSITIONS/ROUTES OF ADMINISTRATION/DOSAGES

Compositions

While it is possible that for use in therapy, a compound of formula (I) as well as pharmaceutically acceptable salts thereof may be administered as the raw chemical, it is common to present the active ingredient as a pharmaceutical composition. The compounds of formula (I) and pharmaceutically acceptable salts thereof will normally, but not necessarily, be formulated into pharmaceutical compositions prior to administration to a patient. Accordingly, in another aspect there is provided a pharmaceutical composition comprising a compound of formula (I), or a pharmaceutically acceptable salt thereof, and one or more pharmaceutically acceptable excipients. The compounds of formula (I) and pharmaceutically acceptable salts are as described above. The excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable excipients. A pharmaceutical composition comprising a compound of formula (I) or a pharmaceutically acceptable salt thereof may be prepared by, for example, admixture at ambient temperature and atmospheric pressure. The pharmaceutical composition can be used in the treatment of any of the conditions described herein.

In a further aspect the invention is directed to pharmaceutical compositions for the treatment of a disease or condition for which a bromodomain inhibitor is indicated comprising a compound of formula (I) or a pharmaceutically acceptable salt thereof.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.25 mg to 1 g, or from 0.5 mg to 500 mg, or from 1 mg to 100 mg, of a compound of formula (I) or a pharmaceutically acceptable salt thereof.

The compound of formula (I) or a pharmaceutically acceptable salt thereof and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the subject from one organ, or portion of the body, to another organ, or portion of the body. Certain pharmaceutically acceptable excipients may be chosen for their ability to enhance subject compliance.

Suitable pharmaceutically-acceptable excipients include the following types of excipients: carriers, diluents, fillers, binders, disintegrants, lubricants, glidants, granulating agents, coating agents, wetting agents, solvents, co-solvents, suspending agents, emulsifiers, sweetners, flavouring agents, flavour-masking agents, colouring agents, anti-caking agents, humectants, chelating agents, plasticisers, viscosity increasing agents, antioxidants, preservatives, stabilisers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of PharmaceuticalAdditives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions (which may contain anti-oxidants, buffers, bacteriostats and solutes which render the composition isotonic with the blood of the intended recipient) and aqueous and non-aqueous sterile suspensions (which may include suspending agents and thickening agents). The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents (disintegrants) and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrants include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

For compositions suitable and/or adapted for oral administration, the compound of formula (I) or a pharmaceutically acceptable salt thereof, may be in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodible polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a $D_{50}$ value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in International Patent Application Publication No. WO 2005/044354 A1.

A therapeutically effective amount of a compound of formula (I) or a pharmaceutically acceptable salt thereof, will depend upon a number of factors including, for example, the age and weight of the patient, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 mg to 3000 mg, more preferably 0.5 mg to 1000 mg, of a compound of formula (I) or a pharmaceutically acceptable salt thereof, calculated as the free base. Each dosage unit for nasal or inhaled administration preferably contains from 0.001 mg to 50 mg, more preferably 0.01 mg to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 mg to 1000 mg per day or 100 mg to 2500 mg per day, or a nasal or inhaled dose of 0.001 mg to 50 mg per day or 0.01 mg to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists, beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are described in Cancer Principles and Practice of Oncology by V. T. Devita and S. Hellman (editors), 6th edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and *vinca* alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents (such as PD-1 inhibitors, including nivolumab and pembrolizumab, and CTLA-4 inhibitors, including ipilimumab); proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

It will be clear to a person skilled in the art that, where appropriate, the other therapeutic agent(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic agent. It will be clear also that, where appropriate, the therapeutic agents may be used in optically pure form.

The combinations referred to above may conveniently be presented for use in the form of a pharmaceutical composition and thus pharmaceutical compositions comprising a combination as defined above together with a pharmaceutically acceptable excipient represent a further aspect of the invention.

General Synthetic Routes

The compounds of the invention may be made by a variety of methods. Any previously defined variable will continue to have the previously defined meaning unless otherwise indicated. Illustrative general synthetic methods are set out in the following schemes, and can be readily adapted to prepare other compounds of the invention. Specific compounds of the invention are prepared in the Examples section.

Compounds of formula (I) may be prepared as described in any of the Schemes below:

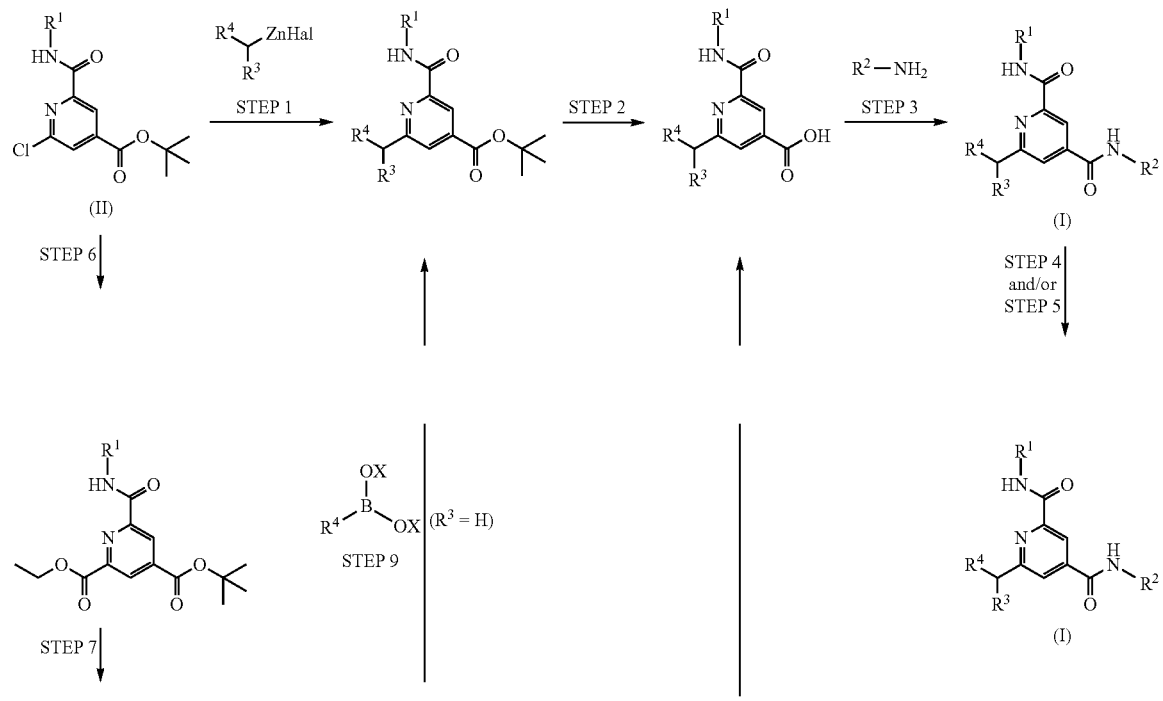

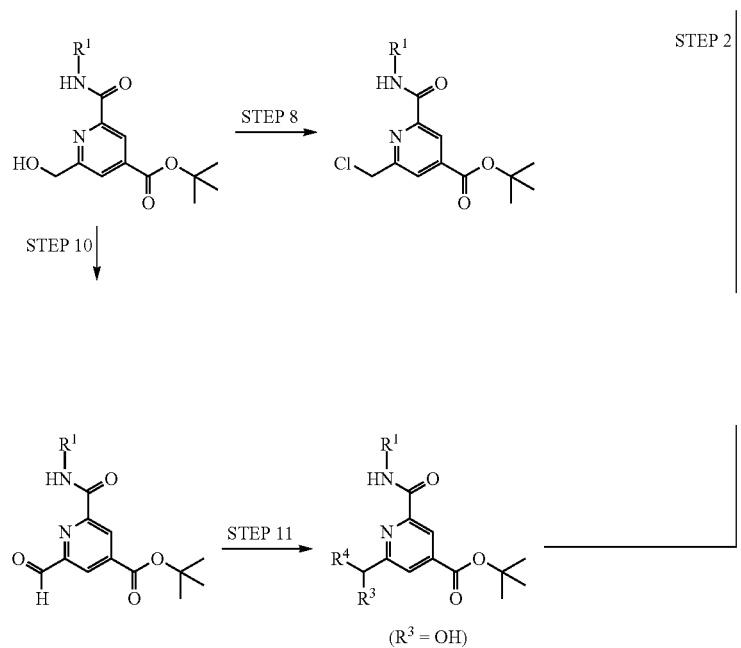

wherein $R^1$, $R^2$, $R^3$ and $R^4$ are as described above, Hal is chlorine or bromine and X is either H or joined together to form a cyclic boronate ester, such as —$C(Me)_2C(Me)_2$-. The starting pyridine compound (II), where $R^1$ is methyl, is commercially available from, for example, Anichem.

In respect of the steps shown in Scheme 1 above the following reaction conditions may be utilised:

Step 1: is a Negishi cross coupling and may be carried out using a benzylzinc halide of formula $R^4CH(R^3)ZnHal$, in the presence of a palladium catalyst, such as $PdCl_2(PPh_3)_2$, optionally in the presence of an alternative phosphine ligand, in a suitable solvent, such as THF, at a suitable temperature, such as 70° C.

Step 2: is an acid-mediated ester cleavage and may be carried out using any suitable acid, such as TFA, optionally in a suitable solvent, such as DCM, at a suitable temperature, such as rt.

Step 3: is an amide coupling reaction and may be carried out using an amine reagent, $R^2$—$NH_2$, in the presence of a suitable tertiary amine, such as triethylamine or DIPEA, in the presence of a suitable amide coupling reactant, such as HATU, in a suitable solvent, such as DCM or DMF, at a suitable temperature, such as rt.

Step 4: is an optional deprotection step to remove a protecting group, such as BOC and may be carried out using an acid such as TFA or HCl, in the presence of a suitable solvent, such as DCM or 1,4-dioxane, at a suitable temperature, such as rt.

Step 5: is an optional chiral separation, using a suitable chiral HPLC column and a suitable solvent system.

Step 6: is a carbonylation reaction and may be carried out using an alcohol reagent, such as EtOH, in the presence of a tertiary amine, such as triethylamine, in the presence of a palladium catalyst, such as [(R)-(+)-2,2'-bis(diphenylphosphino)-1,1'-binaphthyl]palladium(II) chloride, optionally in the presence of an alternative phosphine ligand, in the presence of carbon monoxide, in a suitable solvent, such as DMF, at a suitable temperature, such as 70° C.

Step 7: is a reduction and may be carried out using a reducing agent or combination of reagents, such as sodium borohydride and calcium chloride, in a suitable solvent or solvent mixture, such as ethanol and 2-MeTHF, at a suitable temperature, such as 0° C. to rt.

Step 8: is a chlorination reaction and may be carried out using a chlorinating reagent, such as thionyl chloride, in the presence of a suitable solvent, such as DCM, at a suitable temperature, such as rt.

Step 9: is a cross-coupling reaction, such as a Suzuki coupling and may be carried out using an arylmetal species, such as an arylboronic acid or arylboronate ester, $R^4$—$B(OX)_2$ in the presence of a suitable palladium catalyst, such as $PdCl_2(PPh_3)_2$, optionally in the presence of an alternative phosphine ligand, in the presence of a suitable base, such as potassium carbonate, in the presence of a suitable solvent or solvent mixture, such as 1,4-dioxane and water, at a suitable temperature, such as 120° C.

Step 10: is an oxidation and may be carried out using a suitable oxidant, such as Dess-Martin periodinane in a suitable solvent, such as DCM, at a suitable temperature, such as rt.

Step 11: is a Grignard addition to an aldehyde, using a suitable Grignard reagent, such as phenylmagnesium bromide, in a suitable solvent, such as THF, at a suitable temperature, such as 0° C.

Scheme 2:

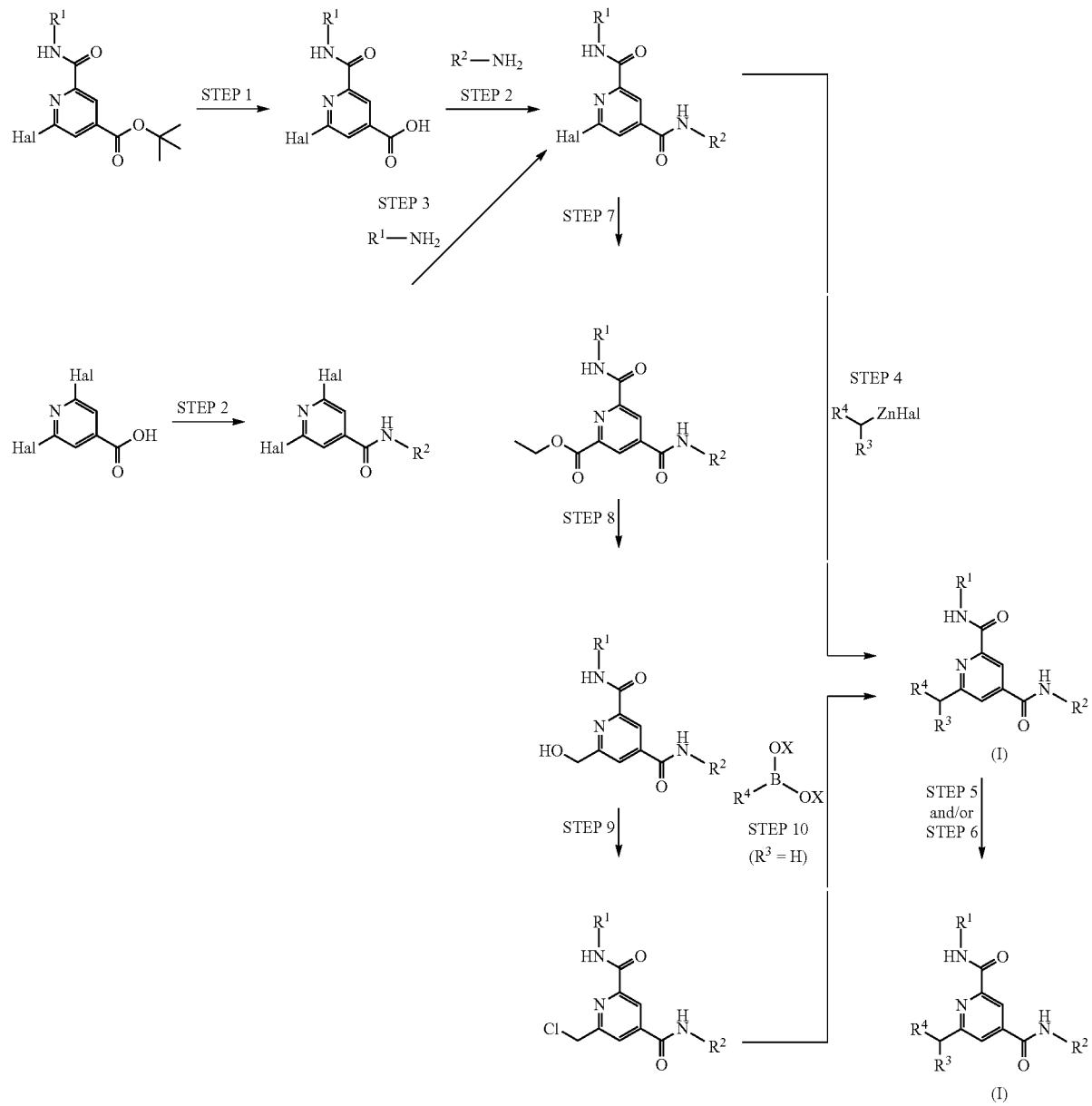

wherein $R^1$, $R^2$, $R^3$ and $R^4$ are as described above, Hal is chlorine or bromine and X is either H or joined together to form a cyclic boronate ester, such as —C(Me)$_2$C(Me)$_2$-. The starting pyridine compound (II), where $R^1$ is methyl and Hal is chlorine, is commercially available from, for example, Anichem.

In respect of the steps shown in Scheme 2 above the following reaction conditions may be utilised:

Step 1: is an acid-mediated ester cleavage and may be carried out using any suitable acid, such as TFA, optionally in a suitable solvent, such as DCM, at a suitable temperature, such as rt.

Step 2: is an amide coupling reaction and may be carried out using an amine reagent, $R^2$—NH$_2$, in the presence of a suitable tertiary amine, such as triethylamine or DIPEA, in the presence of a suitable amide coupling reactant, such as HATU, in a suitable solvent, such as DCM or DMF, at a suitable temperature, such as rt.

Step 3: is a carbonylation reaction and may be carried out using an amine reagent, $R^1$—NH$_2$, optionally in the presence of a nucleophilic catalyst, such as DMAP, in the presence of a palladium catalyst, such as palladium acetate, optionally in the presence of a phosphine ligand, such as CataCXium A, in the presence of a carbonylating reagent, such as dicobalt octacarbonyl, in a suitable solvent, such as 1,4-dioxane, at a suitable temperature, such as 80° C., optionally using microwave irradiation.

Step 4: is a Negishi cross coupling and may be carried out using a benzylzinc halide of formula $R^4$CH($R^3$)ZnHal, in the presence of a palladium catalyst, such as PdCl$_2$(PPh$_3$)$_2$, optionally in the presence of an alternative phosphine ligand, in a suitable solvent, such as THF, at a suitable temperature, such as 70° C.

Step 5: is an optional deprotection step to remove a protecting group, such as BOC and may be carried out using an acid such as TFA or HCl, in the presence of a suitable solvent, such as DCM or 1,4-dioxane, at a suitable temperature, such as rt.

Step 6: is an optional chiral separation, using a suitable chiral HPLC column and a suitable solvent system.

Step 7: is a carbonylation reaction and may be carried out using an alcohol reagent, such as EtOH, in the presence of a tertiary amine, such as triethylamine, in the presence of a palladium catalyst, such as palladium(II) acetate, optionally in the presence of a phosphine ligand, such as 1,3-bis(diphenylphosphino)propane, in the presence of carbon monoxide, in a suitable solvent, such as DMF, at a suitable temperature, such as 90° C., optionally under microwave irradiation.

Step 8: is a reduction and may be carried out using a reducing agent or combination of reagents, such as sodium borohydride and calcium chloride, in a suitable solvent or solvent mixture, such as ethanol and THF, at a suitable temperature, such as 0° C. to rt.

Step 9: is a chlorination reaction and may be carried out using a chlorinating reagent, such as thionyl chloride, in the presence of a suitable solvent, such as DCM, at a suitable temperature, such as rt.

Step 10: is a cross-coupling reaction, such as a Suzuki coupling and may be carried out using an arylmetal species, such as an arylboronic acid or arylboronate ester, $R^4$—B$(OX)_2$ in the presence of a suitable palladium catalyst, such as $PdCl_2(PPh_3)_2$, optionally in the presence of an alternative phosphine ligand, in the presence of a suitable base, such as potassium carbonate, in the presence of a suitable solvent or solvent mixture, such as 1,4-dioxane and water, at a suitable temperature, such as 120° C.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

General Methods

General Experimental Details

All temperatures referred to are in ° C.

As used herein the symbols and conventions used in these processes, schemes and examples are consistent with those used in the contemporary scientific literature, for example, the *Journal of the American Chemical Society* Unless otherwise noted, all starting materials were obtained from commercial suppliers and used without further purification. Specifically, the following abbreviations may be used in the examples and throughout the specification:

Abbreviations

ACD Advanced Chemistry Development, Inc.
AMU atomic mass unit
BOC/Boc tert-butyloxycarbonyl
cart cartridge
cat catalyst
CataCXium A di(1-adamantyl)-n-butylphosphine
CSH Water's Charged Surface Hybrid Technology
Cobalt carbonyl dicobalt octacarbonyl
CV column volume
DCM dichloromethane
DIPEA diisopropylethylamine
DMAP 4-dimethylaminopyridine
DMF dimethylformamide
DMSO dimethylsulfoxide
DMSO-$d_6$ deuterated dimethylsulfoxide
dppf 1,1'-bis(diphenylphosphino)ferrocene
dppp 1,3-bis(diphenylphosphino)propane
h hour(s)
HATU O-(7-azabenzotriazol-1-yl)-N,N,N',N'-tetramethyluronium hexafluorophosphate
IPA isopropyl alcohol
Isolera Biotage® Flash purification system
LC liquid chromatography
LCMS liquid chromatography-mass spectrometry
LiHMDS lithium hexamethyldisilazide
M molar (concentration)
MDAP mass directed autopreparative chromatography
MeI iodomethane
2-MeTHF 2-methyl tetrahydrofuran
min minute(s)
MS mass spectrometry
Ms mesylate group or methanesulfonyl group
Ms-Cl methanesulfonyl chloride
MTBE methyl tert-butyl ether
N normal (concentration)
NBS N-bromosuccinimide
NMR nuclear magnetic resonance
NUT nuclear protein in testis
obs obscured
Pd/C palladium on carbon
RBF round bottomed flask
Rt retention time
rt room temperature
sat saturated
SCX Isolute strong cation exchange sorbent SPE
sec second
$SiO_2$ silicon dioxide
SNAP Biotage® (silica) flash chromatography cartridge
SP4 Biotage® Flash purification system
SPE solid phase extraction
TFA trifluoroacetic acid
THF tetrahydrofuran
TMSCl/TMS-Cl trimethylsilyl chloride
TLC thin layer chromatography
Ts tosyl
T3P propylphosphonic anhydride
UPLC ultra performance liquid chromatography
UV ultra-violet
wt weight The names of the following compounds have been obtained using the compound naming programme "ACD Name Pro 6.02" or using the naming functionality of ChemDraw Ultra 12.0.

LCMS Methodology

Formic Method

LC Conditions

The UPLC analysis was conducted on an Acquity UPLC CSH C18 column (50 mm×2.1 mm, i.d. 1.7 µm packing diameter) at 40° C.

The solvents employed were:

A=0.1% v/v solution of formic acid in water
B=0.1% v/v solution of formic acid in acetonitrile The gradient employed was:

| Time (min) | Flow rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
High pH Method
LC Conditions The UPLC analysis was conducted on an Acquity UPLC CSH C18 column (50 mm×2.1 mm, i.d. 1.7 μm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
TFA Method
LC Conditions The UPLC analysis was conducted on an Acquity UPLC CSH C18 column (50 mm×2.1 mm, i.d. 1.7 μm packing diameter) at 40° C.

The solvents employed were:
A=0.1% v/v solution of trifluoroacetic acid in water
B=0.1% v/v solution of trifluoroacetic acid in acetonitrile
The gradient employed was:

| Time (min) | Flow rate (mL/min) | % A | % B |
|---|---|---|---|
| 0 | 1 | 95 | 5 |
| 1.5 | 1 | 5 | 95 |
| 1.9 | 1 | 5 | 95 |
| 2.0 | 1 | 95 | 5 |

The UV detection was a summed signal from wavelength of 210 nm to 350 nm.

MS Conditions
MS: Waters ZQ
Ionisation mode: Alternate-scan positive and negative electrospray
Scan range: 100 to 1000 AMU
Scan time: 0.27 sec
Inter scan delay: 0.10 sec
General MDAP Purification Methods Listed below are examples of mass-directed autopreparative chromatography (MDAP) methods that have been used or may be used in compound purification.

MDAP (High pH).

The HPLC analysis was conducted on an Xselect CSH C18 column (150 mm×30 mm i.d. 5 μm packing diameter) at ambient temperature, eluting with 10 mM ammonium bicarbonate in water adjusted to pH 10 with ammonia solution (Solvent A) and acetonitrile (Solvent B) using an elution gradient of between 0 and 100% Solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (Formic).

The HPLC analysis was conducted on an Xselect CSH C18 column (150 mm×30 mm i.d. 5 μm packing diameter) at ambient temperature, eluting with 0.1% formic acid in water (Solvent A) and 0.1% formic acid in acetonitrile (Solvent B) using an elution gradient of between 0 and 100% solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

MDAP (TFA).

The HPLC analysis was conducted on an Xselect CSH C18 column (150 mm×30 mm i.d. 5 μm packing diameter) at ambient temperature, eluting with 0.1% v/v solution of trifluoroacetic acid in water (Solvent A) and 0.1% v/v solution of trifluoroacetic acid in acetonitrile (Solvent B) using an elution gradient of between 0 and 100% solvent B over 15 or 25 min.

The UV detection was an averaged signal from wavelength of 210 nm to 350 nm. The mass spectra were recorded on a Waters ZQ Mass Spectrometer using alternate-scan positive and negative electrospray. Ionisation data was rounded to the nearest integer.

NMR

Spectra were run on either a 400 MHz or 600 MHz NMR machine at either 302 K.

Intermediates

Intermediate 1: tert-Butyl ((1S,2S)-2-methylcyclopropyl)carbamate

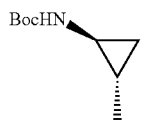

(1S,2S)-2-Methylcyclopropanecarboxylic acid (200 mg, 1.998 mmol, commercially available from, for example, Enamine) and triethylamine (0.9 mL, 6.46 mmol) were dissolved in tert-butanol (4 mL). Diphenyl phosphorylazide (0.47 mL, 2.181 mmol) was added and the reaction was heated at 90° C. The reaction was followed by TLC (eluting with 50:50 EtOAc:cyclohexane, visualising with Ninhydrin). After 2 h, TLC showed the formation of a less polar product as well as residual SM. The reaction was stirred for 3 days. The solution was partitioned between EtOAc (10 mL), and sodium bicarbonate solution (10 mL), extracted with EtOAc (2×20 mL), dried over a hydrophobic frit and concentrated to give 1.08 g of a yellow solid. This was purified by chromatography on $SiO_2$ (Biotage® SNAP 25 g cartridge, eluting with 0-50% EtOAc/cyclohexane). The appropriate fractions were concentrated to give tert-butyl ((1S,2S)-2-methylcyclopropyl)carbamate (223 mg, 1.172 mmol, 58.7% yield) as a white crystalline solid.

$^1$H NMR (400 MHz, MeOH-d) δ ppm 2.05-2.14 (m, 1H) 1.43 (br. s., 9H) 1.04 (d, J=5.9 Hz, 3H) 0.78 (m, J=8.9, 6.0, 6.0, 3.1 Hz, 1H) 0.59 (dt, J=8.9, 4.3 Hz, 1H) 0.39 (q, J=6.0 Hz, 1H). Exchangeable Proton not Observed.

Intermediate 2: (1S,2S)-2-Methylcyclopropanamine Hydrochloride

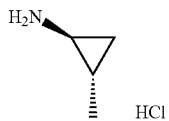

tert-Butyl ((1S,2S)-2-methylcyclopropyl)carbamate (215 mg, 1.256 mmol) was stirred in 4 M HCl in dioxane (16 mL, 64.0 mmol). The reaction was followed by TLC (50:50 EtOAc:cyclohexane, visualising with Ninhydrin). After 30 min, the solution was concentrated to give (1S,2S)-2-methylcyclopropanamine hydrochloride (151 mg, 1.123 mmol, 89% yield) as an off white solid.

$^1$H NMR (400 MHz, DMSO-$d_6$) δ ppm 8.27 (br. s., 3H) 2.25 (br. s., 1H) 1.06-1.18 (m, 1H) 0.99 (d, J=6.1 Hz, 3H) 0.85 (ddd, =7-9.4, 5.6, 3.8 Hz, 1H) 0.48 (dt, J=7.5, 5.9 Hz, 1H).

Intermediate 3: (±)-tert-Butyl 3,3-difluoro-4-(2-hydroxyethyl)piperidine-1-carboxylate

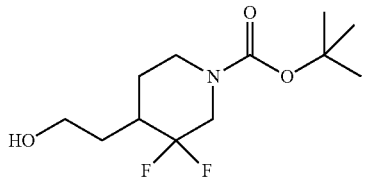 [SMILES: CC(C)(C)OC(=O)N1CCC(CCO)C(F)(F)C1]

To a stirred solution of (±)-2-(1-(tert-butoxycarbonyl)-3,3-difluoropiperidin-4-yl)acetic acid (1.99 g, 7.13 mmol, commercially available from, for example, Activate Scientific) in THF (50 mL) at rt was added portionwise (5 mL aliquots) $BH_3$.THF (1.0 M in THF, 29.0 mL, 29.0 mmol). The mixture was stirred at rt under $N_2$ for 15.5 h before MeOH (50 mL) was carefully added. After stirring for a further 20 min the mixture was evaporated in vacuo and the residue partitioned between EtOAc (50 mL) and water (50 mL). Saturated aqueous brine solution (10 mL) was added to aid phase separation and the phases were separated. The aqueous phase was extracted with further EtOAc (3×40 mL), the combined organic extracts dried by passing through a cartridge fitted with a hydrophobic frit, the solvent evaporated under a stream of $N_2$ and the residue dried in vacuo to give a pale yellow viscous oil; (±)-tert-butyl 3,3-difluoro-4-(2-hydroxyethyl)piperidine-1-carboxylate (1.942 g, 7.32 mmol, 103% yield)

$^1$H NMR (400 MHz, DMSO-$d_6$) δ ppm 4.50 (t, J=5.5 Hz, 1H) 4.06 (br s, 1H) 3.89 (br d, 1H) 3.38-3.54 (m, 2H) 3.18 (br s, 1H) 2.87 (br s, 1H) 2.02-2.19 (m, 1H) 1.79-1.87 (m, 2H) 1.40 (s, 9H) 1.19-1.34 (m, 2H).

Intermediate 4: (±)-tert-Butyl 3,3-difluoro-4-(2-((methylsulfonyl)oxy)ethyl)piperidine-1-carboxylate

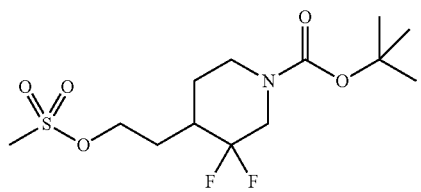 [SMILES: CC(C)(C)OC(=O)N1CCC(CCOS(C)(=O)=O)C(F)(F)C1]

(±)-tert-Butyl 3,3-difluoro-4-(2-hydroxyethyl)piperidine-1-carboxylate (1.884 g, 7.10 mmol) was dissolved in DCM (60 mL) and $Et_3N$ (1.48 mL, 10.62 mmol) and Ms-Cl (0.719 mL, 9.23 mmol) were added. The solution was stirred at rt for 2.75 h, then washed with water (100 mL) and the aqueous phase extracted with DCM (2×100 mL). The combined organic phases were dried by passing them through a cartridge fitted with a hydrophobic frit and the solvent evaporated in vacuo to give a clear oil which crystallised to give a white solid; (±)-tert-butyl 3,3-difluoro-4-(2-((methylsulfonyl)oxy)ethyl)piperidine-1-carboxylate (2.467 g, 7.18 mmol, 101% yield)

$^1$H NMR (400 MHz, DMSO-$d_6$) δ ppm 4.23-4.33 (m, 2H) 4.09 (br s, 1H) 3.91 (br d, 1H) 3.21 (br s, 1H) 3.19 (s, 3H) 2.89 (br s, 1H) 2.02-2.23 (m, 2H) 1.85 (br dt, 1H) 1.56-1.66 (m, 1H) 1.40 (s, 9H) 1.24-1.38 (m, 1H).

Intermediate 5: (±)-tert-Butyl 4-(2-azidoethyl)-3,3-difluoropiperidine-1-carboxylate

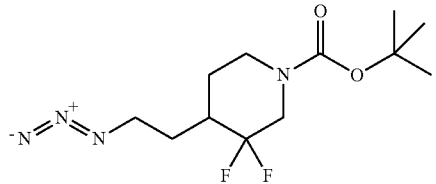

(±)-tert-Butyl 3,3-difluoro-4-(2-((methylsulfonyl)oxy)ethyl)piperidine-1-carboxylate (1.332 g, 3.88 mmol) was dissolved in DMF (10 mL) and sodium azide (301.5 mg, 4.64 mmol) was added. The mixture was stirred under $N_2$ at 80° C. for 4 h. After cooling, the mixture was diluted with 1M aqueous $Na_2CO_3$ solution (50 mL) and extracted with EtOAc (3×30 mL) [Note that 3 phases were observed in the separation, the EtOAc extracts being the least dense; on the 2nd and 3rd extractions some salting out of solid occurred in the lower phase and water (ca. ~10 mL) was added to help with this]. The combined organics were washed with water (2×40 mL) [Note that the 2nd water wash caused emulsification of the layers and saturated brine solution (ca. ~10 mL) was added to help the phases to separate], then dried and evaporated in vacuo to give a pale yellow oil; (±)-tert-butyl 4-(2-azidoethyl)-3,3-difluoropiperidine-1-carboxylate (1.23 g, 4.24 mmol, 109% yield) containing approximately 0.33 equivalents of DMF ¹H NMR (400 MHz, DMSO-d₆) δ ppm 4.08 (br s, 1H) 3.89 (br d, 1H) 3.36-3.53 (m, 2H) 3.19 (br s, 1H) 2.88 (br s, 1H) 2.01-2.17 (m, 1H) 1.79-1.94 (m, 2H) 1.42-1.51 (m, 1H) 1.40 (s, 9H) 1.22-1.33 (m, 1H).

Intermediate 6: (±)-tert-Butyl 4-(2-aminoethyl)-3,3-difluoropiperidine-1-carboxylate

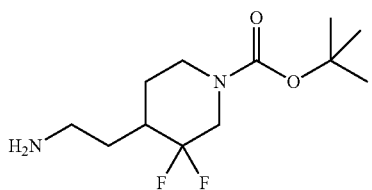 [SMILES: CC(C)(C)OC(=O)N1CCC(CCN)C(F)(F)C1]

A solution of (±)-tert-butyl 4-(2-azidoethyl)-3,3-difluoropiperidine-1-carboxylate (1.22 g, 4.20 mmol) in EtOAc (50 mL) was hydrogenated over a 10% Pd/C catalyst cartridge using a Thales 'H-Cube' flow apparatus in full hydrogen mode at 20° C. The solvent was evaporated from the collected solution in vacuo to give a colourless oil which by NMR analysis was determined to be a 6:5 mixture of starting azide to product amine. The residue was re-dissolved in EtOH (50 mL) and was again hydrogenated over a 10% Pd/C catalyst cartridge using a Thales 'H-Cube' flow apparatus in full hydrogen mode but this time at 40° C. The solvent was evaporated from the collected solution in vacuo to give a colourless oil (982.1 mg).

¹H NMR (400 MHz, DMSO-d₆) δ ppm 4.06 (br s, 1H) 3.88 (br d, 1H) 3.16 (br s, 1H) 2.86 (br s, 1H) 2.50-2.68 (m, 2H) 2.00-2.14 (m, 1H) 1.66-1.82 (m, 2H) 1.40 (s, 9H) 1.17-1.29 (m, 2H). Exchangeables not observed.

Intermediate 7: 2-((1S,2S)-2-(Hydroxymethyl)cyclopropyl)isoindoline-1,3-dione

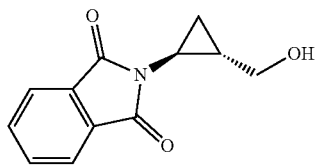 [SMILES: O=C1c2ccccc2C(=O)N1[C@H]1C[C@@H]1CO]

(+/−)-((trans)-2-Aminocyclopropyl)methanol (10 g, 115 mmol, commercially available from, for example, Enamine) was dissolved in toluene (156 mL), phthalic anhydride (22 g, 149 mmol) was added and the reaction heated at 110° C. under N₂. The reaction was stirred for 5 h. The solution was then partitioned between EtOAc (50 mL) and water (50 mL), extracted with EtOAc (2×50 mL), washed with brine (60 mL), dried over a hydrophobic frit and concentrated to give 34.0 g as a black oil. This was purified by chromatography on SiO₂ (Biotage® SNAP 750 g, eluting with 0-100% ethyl acetate/cyclohexane). The desired fractions were concentrated to give 26 g of a colourless oil. This was further purified by chromatography on SiO₂ (Biotage® SNAP 750 g, eluting with 10-60% DCM/diethyl ether). The desired fractions were concentrated to give 19.5 g as a colourless oil. This was suspended in diethyl ether (600 mL) and filtered under vacuum. The filtrate was concentrated to give (+/−)-2-((trans)-2-(hydroxymethyl)cyclopropyl)isoindoline-1,3-dione (16.4 g, 48.5 mmol, 42.3% yield) as a colourless oil.

LCMS (2 min formic); Rt=0.64 min, m/z=218.2 for [MH]⁺

(+/−)-2-((trans)-2-(hydroxymethyl)cyclopropyl)isoindoline-1,3-dione (16.4 g) was purified by chiral HPLC. The racemate was dissolved in EtOH (100 mL). Injection: 2.5 mL of the solution was injected onto the column (50% EtOH/heptane, flow rate=30 mL/min, detection wavelength=215 nm, Column 30 mm×25 cm Chiralpak AD-H (5 μm)). Total number of injections=40. Fractions from 12-14.5 min were bulked and labelled peak 1. Fractions from 19.5-26 min were bulked and labelled peak 2. The bulked fractions were concentrated in vacuo and then transferred to weighed flasks. The final compounds were recovered from DCM and heptane in order to obtain a solid The fractions corresponding to peak 1 were collected to afford 2-((1S,2S)-2-(Hydroxymethyl)cyclopropyl)isoindoline-1,3-dione, intermediate 7 (5.74 g)

The fractions corresponding to peak 2 were collected to afford the enantiomeric product (7.24 g)

Intermediate 8: ((1S,2S)-2-Aminocyclopropyl)methanol, Hydrochloride

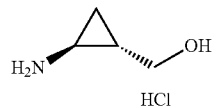

Hydrazine hydrate (0.466 mL, 9.65 mmol, 65% wt.) was added slowly to a suspension of 2-((1S,2S)-2-(hydroxymethyl)cyclopropyl)isoindoline-1,3-dione (2000 mg, 9.21 mmol) in ethanol (46 mL). The reaction mixture was heated to 50° C. under N₂ overnight. The resulting white precipitate was filtered under vacuum. The filtrate was acidified with HCl (4M in dioxane, 57.5 mL, 230 mmol) and evaporated in vacuo to give the crude product. The residue was suspended in methanol and purified by SPE on sulphonic acid (SCX) 20 g using sequential solvents: methanol followed by 2M ammonia/methanol. The appropriate fractions were combined and acidified with HCl (4M in dioxane, 6 mL, 24.00 mmol), before evaporating in vacuo to yield a white slurry. Concerned that salt formation had not completed successfully, the residue was taken up in ethanol (30 mL) and treated with aqueous 2M HCl (10 mL) and evaporated in vacuo once more to yield a white slurry (1540 mg).

The sample was dried in vacuo over 3 days to yield a white paste ((1S,2S)-2-aminocyclopropyl)methanol, hydrochloride (1035 mg, 6.70 mmol, 72.8% yield).

¹H NMR (400 MHz, DMSO-d₆) δ ppm 8.40 (br. s., 3H) 4.07-6.59 (obs., 1H) 3.36 (dd, J=11.2, 5.9 Hz, 1H) 3.27 (dd, J=10.8, 5.9 Hz, 1H) 2.37 (dsxt, J=7.9, 4.2, 4.2, 4.2, 4.2, 4.2 Hz, 1H) 1.34-1.46 (m, 1H) 0.88 (ddd, J=9.7, 5.6, 4.0 Hz, 1H) 0.65 (dt, J=7.6, 6.0 Hz, 1H)

Intermediate 9: Benzyl 4-bromoindoline-1-carboxylate

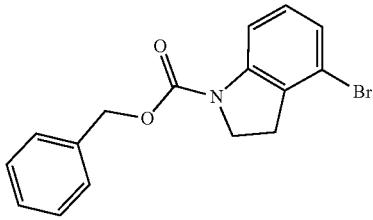 [SMILES: O=C(OCc1ccccc1)N1CCc2c(Br)cccc21]

To a solution of 4-bromoindoline (300 mg, 1.515 mmol, commercially available from, for example, Fluorochem) in DCM (10 mL) was added pyridine (0.245 mL, 3.03 mmol). The reaction mixture was stirred for 10 min, then benzyl carbonochloridate (0.281 mL, 1.969 mmol) was added. The resulting reaction mixture was stirred at rt overnight. Further benzyl carbonochloridate (0.281 mL, 1.969 mmol) and pyridine (0.245 mL, 3.03 mmol) were added to the solution and the resultant mixture was stirred for 4 h. 2M HCl was added to the solution then the organic layers were dried and concentrated. The crude product was purified by chromatography on $SiO_2$ (Biotage® SNAP 10 g, eluting with 0-30% ethyl acetate/cyclohexane). The desired fractions were concentrated to give benzyl 4-bromoindoline-1-carboxylate (456 mg, 1.235 mmol, 82% yield) as a white/brown solid.

LCMS (2 min Formic): Rt=1.45 min, [MH]+ 332.1.

Intermediate 10: Benzyl 4-(4,4,5,5-tetramethyl-1,3,2-dioxaborolan-2-yl)indoline-1-carboxylate

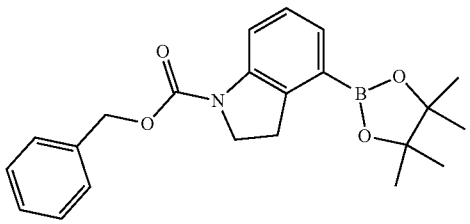 [SMILES: CC1(C)OB(c2cccc3c2CCN3C(=O)OCc2ccccc2)OC1(C)C]

To a stirred solution of benzyl 4-bromoindoline-1-carboxylate (442 mg, 1.331 mmol), bis(pinacolato)diboron (405 mg, 1.597 mmol) and potassium acetate (392 mg, 3.99 mmol) in dioxane was added $PdCl_2(dppf)$-$CH_2Cl_2$ adduct (109 mg, 0.133 mmol). The reaction mixture was purged with $N_2$ and stirred at 100° C. for 2 h. The solvent was removed, then the obtained residue was diluted with 10 mL of EtOAc. The resultant mixture was filtered through Celite® (eluent EtOAc), then 10 mL of water were added to the liquid and the organics extracted with ethyl acetate (2×35 mL). The combined organic layer was dried and then concentrated to give benzyl 4-(4,4,5,5-tetramethyl-1,3,2-dioxaborolan-2-yl)indoline-1-carboxylate (592.7 mg, 1.250 mmol, 94% yield, ~80% purity) as a black solid which was used without further purification.

LCMS (2 min Formic): Rt=1.56 min, [MH]+ 380.3.

Intermediate 11: 4-(4,4,5,5-Tetramethyl-1,3,2-dioxaborolan-2-yl)indolin-2-one

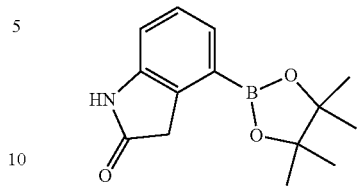

To a stirred solution of 4-bromoindolin-2-one (100 mg, 0.472 mmol, commercially available from, for example, Fluorochem), bis(pinacolato)diboron (144 mg, 0.566 mmol) and potassium acetate (139 mg, 1.415 mmol) in dioxane was added $PdCl_2(dppf)$-$CH_2Cl_2$ adduct (38.5 mg, 0.047 mmol). The reaction mixture was purged with $N_2$ and stirred at 100° C. for 2 h. The reaction mixture was filtered through Celite® (eluent EtOAc). The solvent was removed and the obtained residue was then extracted with ethyl acetate (2×35 mL). The combined organic layer was dried and concentrated to give 4-(4,4,5,5-tetramethyl-1,3,2-dioxaborolan-2-yl)indolin-2-one (554 mg, 0.428 mmol, 91% yield, ~23% purity) as a brown solid. This was used crude in the next reaction.

LCMS (2 min Formic): Rt=1.02 min, [MH]+ 260.2.

Intermediate 12: 2,6-Dibromo-N-cyclobutylisonicotinamide

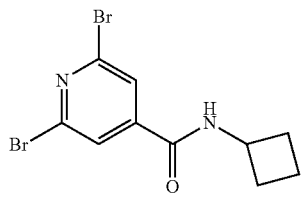 [SMILES: O=C(NC1CCC1)c1cc(Br)nc(Br)c1]

HATU (3.25 g, 8.54 mmol), cyclobutanamine (0.506 g, 7.12 mmol) and $Et_3N$ (1.191 mL, 8.54 mmol) were added to a solution of 2,6-dibromoisonicotinic acid (2 g, 7.12 mmol, commercially available from, for example, Fluorochem) in DCM (20 mL) at rt. The mixture was stirred overnight, then washed with water (2×20 mL), dried and evaporated in vacuo to give a brown solid. The product was dissolved in DCM (10 mL) and loaded onto a 50 g silica column, then eluted with 0-50% EtOAc/cyclohexane and the product-containing fractions were evaporated in vacuo to give 2,6-dibromo-N-cyclobutylisonicotinamide (2.10 g, 6.29 mmol, 88% yield) as a colourless solid.

LCMS (2 min High pH): Rt=1.10 min, [MH]$^+$=335.1.

Intermediate 13: 6-Bromo-$N^4$-cyclobutyl-$N^2$-methylpyridine-2,4-dicarboxamide

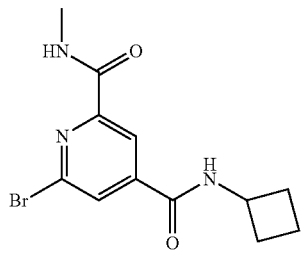 [SMILES: CNC(=O)c1cc(C(=O)NC2CCC2)cc(Br)n1]

2,6-Dibromo-N-cyclobutylisonicotinamide (0.11 g, 0.329 mmol), cobalt carbonyl (0.028 g, 0.082 mmol), methanamine (2M in THF, 0.329 ml, 0.659 mmol), DMAP (0.080 g, 0.659 mmol), palladium acetate (3.70 mg, 0.016 mmol) and CataCXium A (5.90 mg, 0.016 mmol) were combined in a microwave vial and this was sealed and purged with nitrogen, then 1,4-dioxane (3 mL) was added and the mixture was heated at 80° C. for 20 min. The mixture was heated for a further 30 min at 80° C. The reaction mixture was diluted with water (30 mL) and extracted with EtOAc (2×30 mL). The organic layer was dried and evaporated in vacuo to give a pale yellow gum. This was dissolved in DCM (3 mL) and loaded onto a 25 g silica column, then eluted with 0-100% EtOAc/cyclohexane and the product-containing fractions evaporated in vacuo to give 6-bromo-$N^4$-cyclobutyl-$N^2$-methylpyridine-2,4-dicarboxamide (138 mg, 0.442 mmol, 36.0% yield) as a pale yellow gum.

LCMS (2 min High pH): Rt=0.87 min, $[MH]^+$=312.1, 314.2.

Intermediate 14: tert-Butyl 2-bromo-6-(methylcarbamoyl)isonicotinate

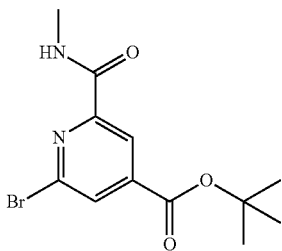

6-Bromo-4-(tert-butoxycarbonyl)picolinic acid (2.03 g, 5.71 mmol, commercially available from, for example, Anichem) was suspended in DCM (18 mL) and oxalyl chloride (1 mL, 11.42 mmol) was added, followed by DMF (0.03 mL, 0.387 mmol). The mixture was stirred for 30 min at rt. The suspension was evaporated in vacuo to give a red/brown oil, this was suspended in THF (18 mL) and methylamine (2M in THF, 4.28 mL, 8.57 mmol) was added dropwise. After 2 h, methylamine (2M in THF, 5.7 mL, 11.40 mmol) was added and the reaction stirred for 30 min. The suspension was concentrated to give a brown oil, this was partitioned between EtOAc (30 mL) and water (30 mL), extracted with EtOAc (2×20 mL), washed with brine (20 mL), dried over a hydrophobic frit and concentrated to give 2.1 g of a dark orange oil. This was purified by chromatography on SiO₂ (Biotage® SNAP 100 g, eluting with 0-60% ethyl acetate/cyclohexane). The desired fractions were concentrated to give tert-butyl 2-bromo-6-(methylcarbamoyl) isonicotinate (1.25 g, 2.97 mmol, 52.1% yield) as an orange solid.

LCMS (2 min Formic): Rt=1.15 min, $[MH]^+$=315.1, 317.0.

Intermediate 15: 2-Bromo-6-(methylcarbamoyl)isonicotinic Acid

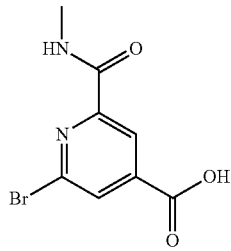

tert-Butyl 2-bromo-6-(methylcarbamoyl)isonicotinate (667 mg, 2.116 mmol), was dissolved in DCM (12 mL) and TFA (3 mL, 38.9 mmol) was added and the reaction stirred at rt for 5 h. The solution was concentrated to give 2-bromo-6-(methylcarbamoyl)isonicotinic acid (648 mg, 2.126 mmol, 100% yield, ~80% purity) which was used crude in further synthesis.

LCMS (2 min Formic): Rt=0.75 min, $[MH]^+$=259.3, 261.3.

Intermediate 16: 6-Bromo-$N^2$-methyl-$N^4$-((1S,2S)-2-methylcyclopropyl)pyridine-2,4-dicarboxamide

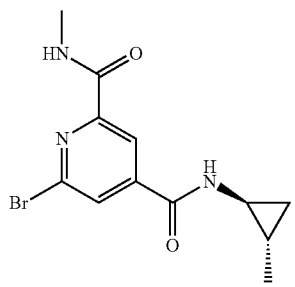 [SMILES: CNC(=O)c1cc(C(=O)N[C@H]2C[C@@H]2C)cc(Br)n1]

2-Bromo-6-(methylcarbamoyl)isonicotinic acid (648 mg, 2.501 mmol), HATU (1422 mg, 3.74 mmol), DIPEA (1.311 mL, 7.50 mmol), (1S,2S)-2-methylcyclopropanamine (183 mg, 2.57 mmol) and DMF (10 mL) were stirred at rt under N₂ for 1.5 h. The solution was partitioned between EtOAc (20 mL) and sat. aq. LiCl solution (20 mL), extracted with EtOAc (2×20 mL), washed with brine (2×20 mL), dried over a hydrophobic frit and concentrated to give 2.08 g of a brown oil. This was purified by chromatography on SiO₂ (Biotage® SNAP 100 g, eluting with 10-60% ethyl acetate/cyclohexane). The desired fractions were concentrated to give 6-bromo-$N^2$-methyl-$N^4$-((1S,2S)-2-methylcyclopropyl)pyridine-2,4-dicarboxamide (464 mg, 1.338 mmol, 53.5% yield) as a pale yellow solid.

LCMS (2 min Formic): Rt=0.83 min, $[MH]^+$=312.3, 314.3.

Intermediate 17: tert-Butyl 2-chloro-6-(methylcarbamoyl)isonicotinate

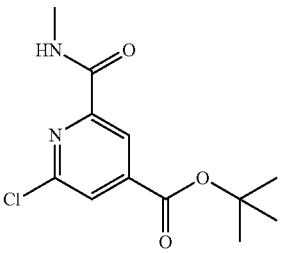 [SMILES: CNC(=O)c1cc(C(=O)OC(C)(C)C)cc(Cl)n1]

2,4,6-Tripropyl-1,3,5,2,4,6-trioxatriphosphinane 2,4,6-trioxide (40.7 g, 64.0 mmol) was added to a solution of 4-(tert-butoxycarbonyl)-6-chloropicolinic acid (15 g, 58.2 mmol, commercially available from, for example, Anichem) and Et₃N (16.23 mL, 116 mmol) in DCM (100 mL) at rt, then the mixture was stirred for 20 min before addition of methanamine (2M in THF, 38.8 mL, 78 mmol). The mixture was stirred for 2 h, then washed with water (100 mL) and saturated sodium bicarbonate solution, then dried and evaporated in vacuo to give a pale yellow gum. This was dissolved in DCM and loaded onto a 340 g silica column, then eluted with 0-40% EtOAc/cyclohexane and the product-containing fractions were evaporated in vacuo to give tert-butyl 2-chloro-6-(methylcarbamoyl)isonicotinate (6.9 g, 25.5 mmol, 43.8% yield) as a pale yellow gum which crystallised on standing.

LCMS (2 min High pH): Rt=1.16 min, [MH]⁺=271.2.
¹H NMR (400 MHz, CDCl₃) δ ppm 8.55 (d, J=1.2 Hz, 1H) 7.95 (d, J=1.2 Hz, 1H) 7.79 (br. s, 1H) 3.05 (d, J=4.9 Hz, 3H) 1.61 (s, 9H)

Intermediate 18: 4-tert-Butyl 2-ethyl 6-(methylcarbamoyl)pyridine-2,4-dicarboxylate

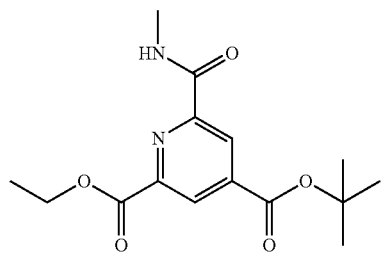 [SMILES: CCOC(=O)c1cc(C(=O)OC(C)(C)C)cc(C(=O)NC)n1]

tert-Butyl 2-chloro-6-(methylcarbamoyl)isonicotinate (4.2 g, 15.51 mmol) was dissolved in a mixture of DMF (50 mL) and ethanol (50 mL), then triethylamine (4.71 g, 46.5 mmol) and [(R)-(+)-2,2'-bis(diphenylphosphino)-1,1'-binaphthyl]palladium(II) chloride (0.621 g, 0.776 mmol) were added and the mixture was purged with carbon monoxide, then sealed and a balloon full of carbon monoxide fitted. The mixture was heated at 70° C. over the weekend, then evaporated in vacuo and the residue was partitioned between water (100 mL) and EtOAc (100 mL). The organic layer was washed with water (100 mL), dried and evaporated in vacuo. The dark brown residue was purified by chromatography on a 100 g silica column eluting with 0-50% EtOAc/cyclohexane to give 4-tert-butyl 2-ethyl 6-(methylcarbamoyl)pyridine-2,4-dicarboxylate (4.2 g, 13.62 mmol, 88% yield) as a pale yellow gum.

LCMS (2 min High pH): Rt=1.11 min, [MH]⁺=309.2.
¹H NMR (400 MHz, CDCl₃) δ ppm 8.80 (d, J=1.5 Hz, 1H) 8.67 (d, J=1.7 Hz, 1H) 8.08 (br. d, J=3.4 Hz, 1H) 4.50 (q, J=7.1 Hz, 2H) 3.08 (d, J=5.1 Hz, 3H) 1.63 (s, 9H) 1.46 (t, J=7.1 Hz, 3H)

Intermediate 19: tert-Butyl 2-(hydroxymethyl)-6-(methylcarbamoyl)isonicotinate

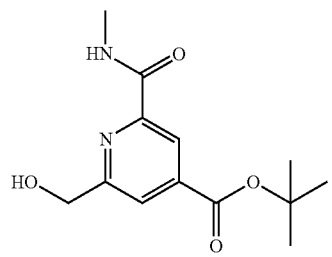 [SMILES: CNC(=O)c1cc(C(=O)OC(C)(C)C)cc(CO)n1]

Calcium chloride (4.54 g, 40.9 mmol) was added to a solution of 4-tert-butyl 2-ethyl 6-(methylcarbamoyl)pyridine-2,4-dicarboxylate (4.2 g, 13.62 mmol) in a mixture of ethanol (50 mL) and 2-MeTHF (50.0 mL) at 0° C., then sodium tetrahydroborate (0.773 g, 20.43 mmol) was added and the resulting red mixture was stirred for 2 h allowing the mixture to warm to rt. The mixture was allowed to stand overnight, then cooled in an ice bath and ammonium chloride solution (100 mL) was added slowly over 20 min. The mixture was extracted with EtOAc (2×150 mL), then the organics were dried and evaporated in vacuo and the residue purified by chromatography on a 50 g silica column to give tert-butyl 2-(hydroxymethyl)-6-(methylcarbamoyl)isonicotinate (2.2 g, 8.26 mmol, 60.6% yield) as a beige solid.

LCMS (2 min High pH): Rt=0.84 min, [MH]⁺=267.3.
¹H NMR (400 MHz, CDCl₃) δ ppm 8.49-8.58 (m, 1H) 7.90-8.02 (m, 2H) 4.87 (s, 2H) 3.05 (d, J=5.1 Hz, 3H) 1.61 (s, 9H). 1 exchangeable proton not observed.

Intermediate 20: tert-Butyl 2-(chloromethyl)-6-(methylcarbamoyl)isonicotinate

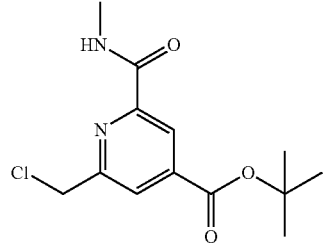 [SMILES: CNC(=O)c1cc(C(=O)OC(C)(C)C)cc(CCl)n1]

tert-Butyl 2-(hydroxymethyl)-6-(methylcarbamoyl)isonicotinate (1.5 g, 5.63 mmol) was dissolved in DCM (5 mL), sulfurous dichloride (1.257 mL, 16.90 mmol) was added and the reaction stirred at rt for 4 h, then the mixture was quenched by the addition of saturated sodium bicarbonate solution and the mixture was stirred for 20 min, then the organic layer was separated, dried and evaporated in vacuo to give tert-butyl 2-(chloromethyl)-6-(methylcarbamoyl)isonicotinate (1.35 g, 4.74 mmol, 84% yield) as a colourless solid.

LCMS (2 min High pH): Rt=1.13 min, [MH]+=285.2.

1H NMR (400 MHz, CDCl3) δ ppm 8.59 (d, J=1.2 Hz, 1H) 8.11 (d, J=1.2 Hz, 1H) 7.95 (br. s., 1H) 4.72 (s, 2H) 3.07 (d, J=5.1 Hz, 3H) 1.62 (s, 9H)

Intermediate 21: tert-Butyl 2-formyl-6-(methylcarbamoyl)isonicotinate

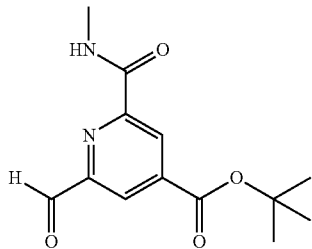 [SMILES: CNC(=O)c1cc(C(=O)OC(C)(C)C)cc(C=O)n1]

tert-Butyl 2-(hydroxymethyl)-6-(methylcarbamoyl)isonicotinate (543 mg, 2.039 mmol) was dissolved in DCM (5 mL). Dess-Martin periodinane (1009 mg, 2.380 mmol) was added and the mixture stirred at rt for 3 h. Sodium thiosulfate was added to the reaction mixture then NaHCO3 was also added. The resultant mixture was stirred for 15 min. The aqueous phase was extracted with DCM three times and the combined organic layers were dried over MgSO4 and evaporated. The crude product was purified by chromatography on SiO2 (Biotage® SNAP 10 g, eluting with 0-50% ethyl acetate/cyclohexane). The desired fractions were concentrated to give tert-butyl 2-formyl-6-(methylcarbamoyl)isonicotinate (501 mg, 1.706 mmol, 84% yield) as a colourless oil.

LCMS (2 min Formic): Rt=0.97 min, [MH]+=265.3.

1H NMR (400 MHz, CDCl3) δ ppm 10.14 (s, 1H) 8.88 (d, J=1.5 Hz, 1H) 8.55 (d, J=1.5 Hz, 1H) 8.00 (br. s., 1H) 3.12 (d, J=4.9 Hz, 3H) 1.62-1.66 (m, 9H)

Intermediate 22: 6-Bromo-N4-cyclopropyl-N2-methylpyridine-2,4-dicarboxamide

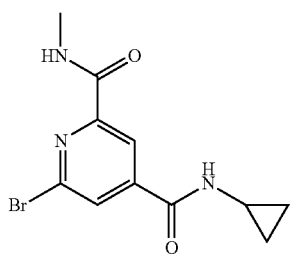 [SMILES: CNC(=O)c1cc(C(=O)NC2CC2)cc(Br)n1]

2-Bromo-6-(methylcarbamoyl)isonicotinic acid (400 mg, 1.544 mmol), HATU (880 mg, 2.314 mmol), DIPEA (0.81 mL, 4.64 mmol), cyclopropanamine (0.21 mL, 3.03 mmol) and DMF (5 mL) were stirred at rt under N2 for 1.5 h. The solution was partitioned between EtOAc (20 mL) and sat. aq. LiCl solution (20 mL), extracted with EtOAc (2×20 mL), washed with brine (2×20 mL), dried through a hydrophobic frit and concentrated to give 1.04 g of an orange oil. This was purified by chromatography on SiO2 (Biotage® SNAP 100 g, eluting with 10-60% ethyl acetate/cyclohexane). The desired fractions were concentrated to give 6-bromo-N4-cyclopropyl-N2-methylpyridine-2,4-dicarboxamide (320 mg, 0.966 mmol, 62.6% yield) as a pale yellow solid.

LCMS (2 min Formic): Rt=0.72 min, [MH]+=298.0, 300.0.

Intermediate 23: Ethyl 4-(cyclopropylcarbamoyl)-6-(methylcarbamoyl)picolinate

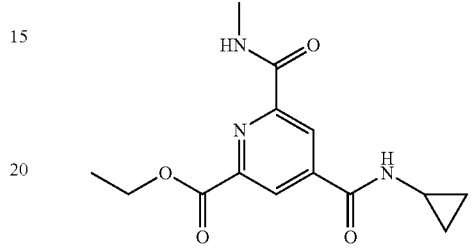

To a solution of 6-bromo-N4-cyclopropyl-N2-methylpyridine-2,4-dicarboxamide (216 mg, 0.725 mmol) in DMF (7.25 mL) in a 20 mL microwave vial was added triethylamine (0.4 mL, 2.87 mmol), palladium(II) acetate (28 mg, 0.125 mmol), dppp (47 mg, 0.114 mmol) and ethanol (0.72 mL, 12.33 mmol). The reaction was purged with CO and heated at 90° C. in the microwave for 2 h. The microwave vial was purged with CO and heated at 90° C. in the microwave for 2 h. The vial was heated for 1.5 h at 90° C.

Separately, to a solution of 6-bromo-N4-cyclopropyl-N2-methylpyridine-2,4-dicarboxamide (50 mg, 0.168 mmol) in DMF (0.56 mL) was added triethylamine (0.1 mL, 0.717 mmol), palladium(II) acetate (7 mg, 0.031 mmol), dppp (12 mg, 0.029 mmol) and ethanol (0.17 mL, 2.91 mmol). The reaction was purged with CO and a septum with a balloon of CO was added and the reaction heated at 70° C. for 21 h. Further triethylamine (0.094 mL, 0.671 mmol), palladium(II) acetate (7.53 mg, 0.034 mmol), ethanol (0.166 mL, 2.85 mmol), dppp (11.76 mg, 0.029 mmol) and DMF (0.560 mL) were added and the reaction purged with CO and a balloon of CO was fitted and the reaction heated at 70° C. for 24 h.

Separately, to a solution of 6-bromo-N4-cyclopropyl-N2-methylpyridine-2,4-dicarboxamide (50 mg, 0.168 mmol) in DMF (2 mL) in a 2 mL microwave vial, was added triethylamine (0.1 mL, 0.717 mmol), palladium(II) acetate (8 mg, 0.036 mmol), dppp (14 mg, 0.034 mmol) and ethanol (0.17 mL, 2.91 mmol). The reaction was purged with CO and heated at 100° C. in the microwave for 1 h. The vial was purged with CO again and heated at 90° C. for 3 h.

The crude reaction mixtures for the three reactions were combined, partitioned between EtOAc (10 mL) and sat. aq. LiCl solution (10 mL), extracted with EtOAc (2×20 mL), washed with brine (2×20 mL), dried over a hydrophobic frit and concentrated to give 470 mg of an orange oil. This was purified by chromatography on SiO2 (Biotage® SNAP 50 g, eluting with 0-100% (25% ethanol in ethyl acetate)/cyclohexane). The desired fractions were concentrated to give ethyl 4-(cyclopropylcarbamoyl)-6-(methylcarbamoyl)picolinate (158 mg, 0.461 mmol) as a yellow solid.

LCMS (2 min Formic): Rt=0.70 min, [MH]+=292.4.

Intermediate 24: N⁴—Cyclopropyl-6-(hydroxymethyl)-N²-methylpyridine-2,4-dicarboxamide

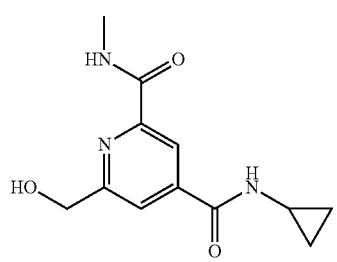 [SMILES: CNC(=O)c1cc(C(=O)NC2CC2)cc(CO)n1]

Ethyl 4-(cyclopropylcarbamoyl)-6-(methylcarbamoyl)picolinate (80 mg, 0.275 mmol) was dissolved in ethanol (3 mL) and THF (1.5 mL). Calcium chloride (67 mg, 0.604 mmol) was added and the reaction cooled to 0° C. in an ice bath and sodium borohydride (10.39 mg, 0.275 mmol) was added. The solution was stirred at 0° C. for 30 min. The solution was quenched with sat. ammonium chloride solution and extracted with EtOAc (2×20 mL). The aqueous layer was acidified to pH 2 with 2 M HCl soln. This was extracted with further EtOAc (2×20 mL). The organic layer was dried over a hydrophobic frit and concentrated to give N⁴-cyclopropyl-6-(hydroxymethyl)-N²-methylpyridine-2,4-dicarboxamide (78 mg, 0.266 mmol, 97% yield) as a white solid.

LCMS (2 min Formic): Rt=0.48 min, [MH]⁺=250.5.

Intermediate 25: 6-(Chloromethyl)-N⁴-cyclopropyl-N²-methylpyridine-2,4-dicarboxamide

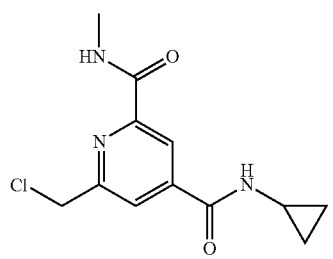 [SMILES: CNC(=O)c1cc(C(=O)NC2CC2)cc(CCl)n1]

N⁴-Cyclopropyl-6-(hydroxymethyl)-N²-methylpyridine-2,4-dicarboxamide (78 mg, 0.313 mmol) was dissolved in DCM (2 mL) and thionyl chloride (0.07 mL, 0.959 mmol) was added and the reaction stirred at rt overnight. Further thionyl chloride (0.05 mL, 0.685 mmol) was added and the reaction stirred for 1 h. The solution was concentrated to give 6-(chloromethyl)-N⁴-cyclopropyl-N²-methylpyridine-2,4-dicarboxamide (66 mg, 0.222 mmol, 70.9% yield) as a cream solid which was used directly in the subsequent step.

LCMS (2 min Formic): Rt=0.70 min, [MH]⁺=268.4.

Intermediate 26: tert-Butyl 2-benzyl-6-(methylcarbamoyl)isonicotinate

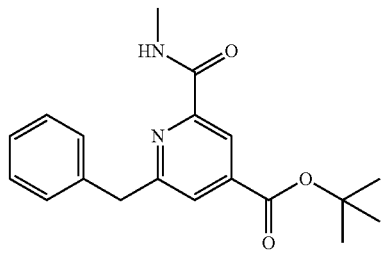 [SMILES: CNC(=O)c1cc(C(=O)OC(C)(C)C)cc(Cc2ccccc2)n1]

tert-Butyl 2-chloro-6-(methylcarbamoyl)isonicotinate (5 g, 18.47 mmol, commercially available from, for example, Anichem) and PdCl₂(PPh₃)₂ (1.296 g, 1.847 mmol) were dissolved in THF (50 mL) and benzylzinc(II) bromide (0.5M in THF, 55.4 mL, 27.7 mmol) was added, then the mixture was heated at 70° C. for 2 h. The solvent was evaporated in vacuo and the residue purified by chromatography on a 100 g silica column eluting with 0-50% EtOAc/cyclohexane to give tert-butyl 2-benzyl-6-(methylcarbamoyl)isonicotinate (5.7 g, 17.46 mmol, 95% yield) as a dark brown oil which was used in the next step without further purification.

LCMS (2 min High pH): Rt=1.30 min, [MH]⁺=327.3.

Intermediate 27: 2-Benzyl-6-(methylcarbamoyl)isonicotinic acid

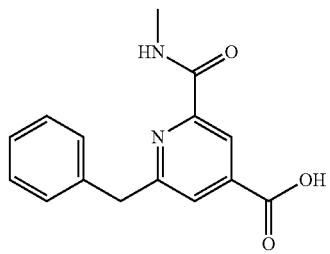 [SMILES: CNC(=O)c1cc(C(=O)O)cc(Cc2ccccc2)n1]

tert-Butyl 2-benzyl-6-(methylcarbamoyl)isonicotinate (2.5 g, 7.66 mmol) was dissolved in DCM (30 mL), then TFA (10 mL, 130 mmol) was added and the mixture was stirred for 3 h at rt. The solvent was evaporated in vacuo to give a pale yellow gum. The crude material was dissolved in DCM (100 mL) and washed with water (100 mL), the organic layer was dried and evaporated in vacuo to give 2-benzyl-6-(methylcarbamoyl)isonicotinic acid (2.0 g, 7.40 mmol, 97% yield) as a pale yellow solid LCMS (2 min High pH): Rt=0.63 min, [MH]⁺=271.3.

Intermediate 28: tert-Butyl 2-(2-fluorobenzyl)-6-(methylcarbamoyl)isonicotinate

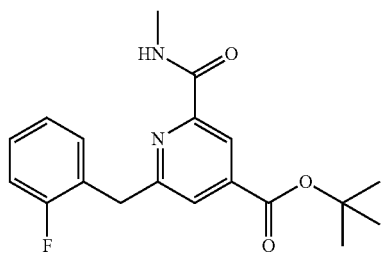 [SMILES: CNC(=O)c1cc(C(=O)OC(C)(C)C)cc(Cc2ccccc2F)n1]

tert-Butyl 2-chloro-6-(methylcarbamoyl)isonicotinate (100 mg, 0.369 mmol), (2-fluorobenzyl)zinc(II) chloride (0.5M in THF, 1.25 mL, 0.625 mmol), PdCl$_2$(PPh$_3$)$_2$ (39 mg, 0.056 mmol) and THF (0.5 mL) were heated at 110° C. for 30 min in the microwave. The reaction mixture was filtered through Celite® (eluent EtOAc) then concentrated to give 453 mg of crude product. This was purified by chromatography on SiO$_2$ (Biotage® SNAP 10 g, eluting with 0-60% ethyl acetate/cyclohexane). The desired fractions were concentrated to give tert-butyl 2-(2-fluorobenzyl)-6-(methylcarbamoyl)isonicotinate (86.5 mg, 0.226 mmol, 61.2% yield) as a colourless oil.

LCMS (2 min Formic): Rt=1.29 min, [MH]$^+$=345.1.

Intermediate 29: 2-(2-Fluorobenzyl)-6-(methylcarbamoyl)isonicotinic acid

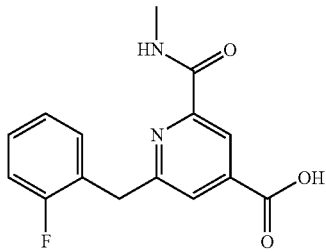

To a solution of tert-butyl 2-(2-fluorobenzyl)-6-(methylcarbamoyl)isonicotinate (86.5 mg, 0.251 mmol) in DCM (1 mL) was added TFA (0.68 mL, 8.83 mmol) and the reaction mixture was stirred at rt overnight. The reaction mixture was concentrated to give 2-(2-fluorobenzyl)-6-(methylcarbamoyl)isonicotinic acid (90.5 mg, 0.251 mmol, 100% yield, ~80% purity) as an orange solid which was used without purification in subsequent chemistry.

LCMS (2 min Formic): Rt=0.95 min, [MH]$^+$=289.0.

Intermediate 30: tert-Butyl 2-(3-methoxybenzyl)-6-(methylcarbamoyl)isonicotinate

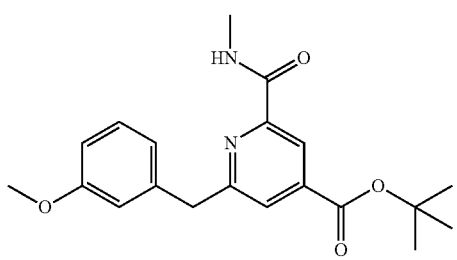 [SMILES: CNC(=O)c1cc(C(=O)OC(C)(C)C)cc(Cc2cccc(OC)c2)n1]

tert-Butyl 2-chloro-6-(methylcarbamoyl)isonicotinate (1.5 g, 5.54 mmol) was dissolved in THF (20 mL) and palladium dichloride bistriphenylphosphine (0.389 g, 0.554 mmol) was added. The solution was sparged with nitrogen for 5 min, then (3-methoxybenzyl)zinc(II) bromide (0.5M in THF, 20 mL, 10.00 mmol) was added and the mixture heated at 70° C. for 2 h. The solution was diluted with EtOAc (100 mL) and washed with water (100 mL), dried and evaporated in vacuo. The residue was purified by chromatography on a 50 g silica column eluting with 0-50% EtOAc/cyclohexane and the product-containing fractions evaporated in vacuo to give tert-butyl 2-(3-methoxybenzyl)-6-(methylcarbamoyl)isonicotinate (1.65 g, 4.63 mmol, 84% yield) as a dark yellow oil.

LCMS (2 min High pH): Rt=1.29 min, [MH]$^+$=357.3.

Intermediate 31: 2-(3-Methoxybenzyl)-6-(methylcarbamoyl)isonicotinic acid

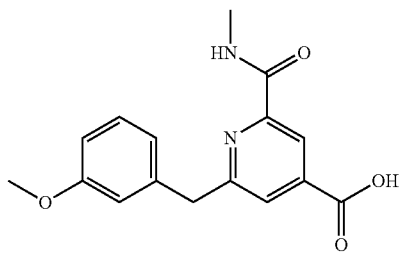 [SMILES: CNC(=O)c1cc(C(=O)O)cc(Cc2cccc(OC)c2)n1]

tert-Butyl 2-(3-methoxybenzyl)-6-(methylcarbamoyl)isonicotinate (2.5 g, 7.01 mmol) was dissolved in DCM (30 mL), then TFA (10 mL, 130 mmol) was added and the mixture was stirred for 18 h at rt. The solvent was evaporated in vacuo to give a pale yellow gum. This was dissolved in DCM (50 mL) and washed with water (50 mL). The organic layer was dried and evaporated in vacuo to give 2-(3-methoxybenzyl)-6-(methylcarbamoyl)isonicotinic acid (1.8 g, 5.99 mmol, 85% yield) as a pale yellow solid.

LCMS (2 min High pH): Rt=0.64 min, [MH]$^+$=301.2.

Intermediate 32: 2-(3-Hydroxybenzyl)-6-(methylcarbamoyl)isonicotinic acid

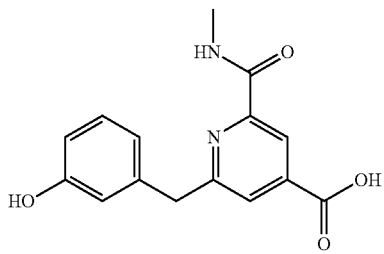 [SMILES: CNC(=O)c1cc(C(=O)O)cc(Cc2cccc(O)c2)n1]

A suspension of 2-(3-methoxybenzyl)-6-(methylcarbamoyl)isonicotinic acid (100 mg, 0.333 mmol) in DCM (3 mL) was cooled to 0° C. under N$_2$ and BBr$_3$ (1M in DCM, 1.665 mL, 1.665 mmol) was added dropwise. The reaction was quenched with water (10 mL) and extracted with ethyl acetate (3×20 mL). The organic extract was then washed with sat. NaHCO$_3$ solution, dried (Na$_2$SO$_4$) and concentrated to give the title compound (109 mg) as a yellow oil which was used without further purification.

LCMS (2 min Formic): Rt=0.76 min, [MH]$^+$=287.1.

Intermediate 33: (S)-2-Hydroxypropyl 2-(3-((S)-2-hydroxypropoxy)benzyl)-6-(methylcarbamoyl)isonicotinate

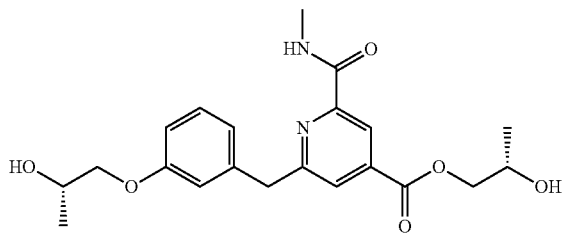 [SMILES: CNC(=O)c1cc(C(=O)OC[C@H](C)O)cc(Cc2cccc(OC[C@H](C)O)c2)n1]

A mixture of 2-(3-hydroxybenzyl)-6-(methylcarbamoyl)isonicotinic acid (54 mg, 0.189 mmol), (S)-2-methyloxirane (0.066 mL, 0.943 mmol) and cesium carbonate (184 mg, 0.566 mmol) were dissolved in DMF (2 mL) and the reaction mixture was heated at 150° C. for 30 min in a 2 mL microwave vial. The crude solution containing (S)-2-(3-(2-hydroxypropoxy)benzyl)-6-(methylcarbamoyl)isonicotinic acid was used directly in the next reaction with an assumed 100% yield. Therefore, to (S)-2-(3-(2-hydroxypropoxy)benzyl)-6-(methylcarbamoyl)isonicotinic acid (65 mg, 0.189 mmol) in DMF (2 mL) was added HATU (108 mg, 0.283 mmol) followed by cyclopropanamine (0.052 mL, 0.753 mmol) and DIPEA (0.132 ml, 0.755 mmol). The resulting reaction mixture was stirred at rt in air for 30 min. LCMS shows a complex mixture including 13% of the starting carboxylic acid and 11% of the title compound, consistent with the acid opening residual (S)-2-methyloxirane, rather than the desired amide coupling. The reaction mixture was left to stir o/n. The reaction mixture was then partitioned between ethyl acetate and water. The aqueous layer was acidified to ~pH 3 and extracted with further ethyl acetate. The combined organic layers were dried (Na$_2$SO$_4$) and concentrated to give impure (S)-2-hydroxypropyl 2-(3-((S)-2-hydroxypropoxy)benzyl)-6-(methylcarbamoyl)isonicotinate (226 mg) as a yellow oil. This was used as is for the subsequent ester hydrolysis step.

LCMS (2 min Formic): Rt=0.82 min, [MH]$^+$=403.2.

Intermediate 34: (S)-2-(3-(2-Hydroxypropoxy)benzyl)-6-(methylcarbamoyl)isonicotinic acid

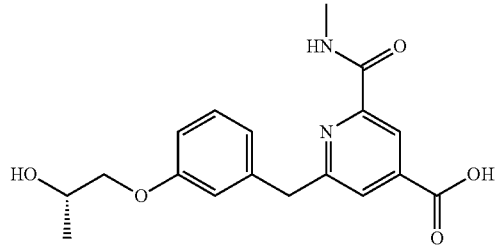 [SMILES: CNC(=O)c1cc(C(=O)O)cc(Cc2cccc(OC[C@H](C)O)c2)n1]

(S)-2-Hydroxypropyl 2-(3-((S)-2-hydroxypropoxy)benzyl)-6-(methylcarbamoyl)isonicotinate (76 mg, 0.189 mmol) (assumed 100% yield from previous step) was dissolved in 1,4-dioxane (2 mL). Water (2 mL) was added followed by LiOH (15 mg, 0.626 mmol) and the reaction mixture stirred at rt for 48 h. The dioxane was removed in vacuo and acetic acid (0.038 mL, 0.666 mmol) was added. The reaction mixture was partitioned between ethyl acetate and water. The organic layer was separated and the aqueous layer extracted with further ethyl acetate (4×20 mL). The combined organic layers were dried (Na$_2$SO$_4$) and concentrated to give (S)-2-(3-(2-hydroxypropoxy)benzyl)-6-(methylcarbamoyl)isonicotinic acid (90 mg, 0.196 mmol, 104% yield) as a pale yellow oil which was ~75% purity and was used as is for subsequent chemistry.

LCMS (2 min Formic): Rt=0.82 min, [MH]$^+$=345.1.

Intermediate 35: tert-Butyl 2-(4-methoxybenzyl)-6-(methylcarbamoyl)isonicotinate

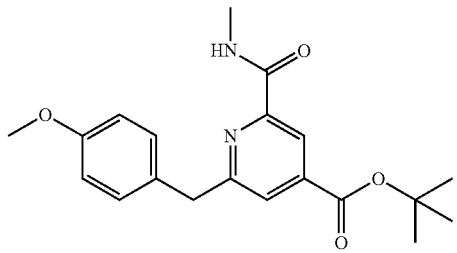 [SMILES: CNC(=O)c1cc(C(=O)OC(C)(C)C)cc(Cc2ccc(OC)cc2)n1]

tert-Butyl 2-chloro-6-(methylcarbamoyl)isonicotinate (100 mg, 0.369 mmol), (4-methoxybenzyl)zinc(II) chloride (0.5M in THF, 1.25 mL, 0.625 mmol), PdCl$_2$(PPh$_3$)$_2$ (38.9 mg, 0.055 mmol) and THF (0.5 mL) were heated at 110° C. for 30 min in the microwave. The reaction mixture was filtered through Celite® (eluent EtOAc) then washed with water, then dried and concentrated to give 387 mg of crude brown solid. This was purified by chromatography on SiO$_2$ (Biotage® SNAP 10 g, eluting with 0-60% ethyl acetate/cyclohexane). The desired fractions were concentrated to give tert-butyl 2-(4-methoxybenzyl)-6-(methylcarbamoyl)isonicotinate (134.6 mg, 0.340 mmol, 92% yield) as a white solid.

LCMS (2 min Formic): Rt=1.26 min, [MH]$^+$=357.2.

Intermediate 36: 2-(4-Methoxybenzyl)-6-(methylcarbamoyl)isonicotinic acid

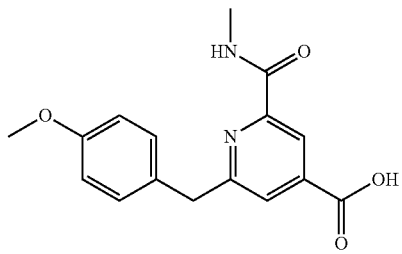 [SMILES: CNC(=O)c1cc(C(=O)O)cc(Cc2ccc(OC)cc2)n1]

To a solution of tert-butyl 2-(4-methoxybenzyl)-6-(methylcarbamoyl)isonicotinate (134.6 mg, 0.378 mmol) in DCM (5 mL) was added TFA (0.873 mL, 11.33 mmol). The resultant mixture was stirred at rt for 2 h and then overnight. The reaction mixture was then concentrated to give 2-(4-methoxybenzyl)-6-(methylcarbamoyl)isonicotinic acid (123.3 mg, 0.322 mmol, 85% yield, ~78.5% purity) as an orange oil.

LCMS (2 min Formic): Rt=0.92 min, [MH]$^+$=301.1.

Intermediate 37: tert-Butyl 2-(2-methylbenzyl)-6-(methylcarbamoyl)isonicotinate

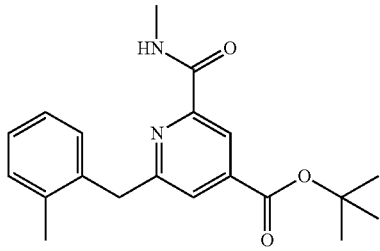 [SMILES: CNC(=O)c1cc(C(=O)OC(C)(C)C)cc(Cc2ccccc2C)n1]

tert-Butyl 2-chloro-6-(methylcarbamoyl)isonicotinate (43 mg, 0.159 mmol), (2-methylbenzyl)zinc(II) chloride (0.5M in THF, 0.538 mL, 0.269 mmol), PdCl$_2$(PPh$_3$)$_2$ (16.72 mg, 0.024 mmol) and THF (1 mL) were heated at 110° C. for 30 min in the microwave. The reaction mixture was filtered through Celite® (eluent EtOAc) then concentrated to give a brown solid. This was purified by chromatography on SiO$_2$ (Biotage® SNAP 10 g cartridge, eluting with 0-60% ethyl acetate/cyclohexane). The desired fractions were concentrated to give the title compound (30 mg) as a colourless oil. This was further purified by chromatography on SiO$_2$ (Biotage® SNAP 10 g, eluting with 0-20% ethyl acetate/cyclohexane). The desired fractions were concentrated to give tert-butyl 2-(2-methylbenzyl)-6-(methylcarbamoyl)isonicotinate (17.2 mg, 0.051 mmol, 31.8% yield) as a colourless oil.

LCMS (2 min Formic): Rt=1.34 min, [MH]$^+$=341.1.

Intermediate 38: 2-(2-Methylbenzyl)-6-(methylcarbamoyl)isonicotinic acid

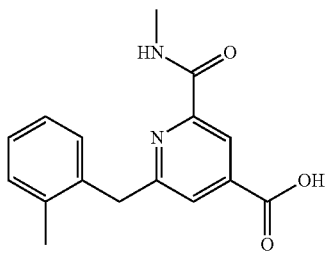 [SMILES: CNC(=O)c1cc(C(=O)O)cc(Cc2ccccc2C)n1]

To a solution of tert-butyl 2-(2-methylbenzyl)-6-(methylcarbamoyl)isonicotinate (17.2 mg, 0.051 mmol) in DCM (1 mL) was added TFA (0.13 mL, 1.687 mmol) and the reaction mixture was stirred at rt for 2 h and then over the weekend. Further TFA (0.13 mL, 1.687 mmol) was added and the reaction mixture stirred for 8 h and then overnight. The reaction mixture was concentrated to give 2-(2-methylbenzyl)-6-(methylcarbamoyl)isonicotinic acid (13.8 mg, 0.043 mmol, 85% yield, ~89% purity) as an orange solid. This was used without purification.

LCMS (2 min Formic): Rt=1.00 min, [MH]$^+$=285.1.

Intermediate 39: tert-Butyl 2-(3-fluorobenzyl)-6-(methylcarbamoyl)isonicotinate

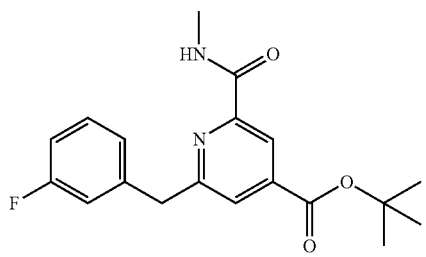 [SMILES: CNC(=O)c1cc(C(=O)OC(C)(C)C)cc(Cc2cccc(F)c2)n1]

tert-Butyl 2-chloro-6-(methylcarbamoyl)isonicotinate (100 mg, 0.369 mmol), (3-fluorobenzyl)zinc(II) chloride (0.5M in THF, 1.25 mL, 0.625 mmol), PdCl$_2$(PPh$_3$)$_2$ (39 mg, 0.056 mmol) and THF (0.5 mL) were heated at 120° C. for 30 min in the microwave. The reaction mixture was filtered through Celite® (eluent EtOAc) then concentrated to give 482 mg of crude product. This was purified by chromatography on SiO$_2$ (Biotage® SNAP 10 g, eluting with 0-25% ethyl acetate/cyclohexane). The desired fractions were concentrated to give tert-butyl 2-(3-fluorobenzyl)-6-(methylcarbamoyl)isonicotinate (52.2 mg, 0.136 mmol, 36.9% yield) as a colourless oil.

LCMS (2 min Formic): Rt=1.28 min, [MH]$^+$=345.2.

Intermediate 40: 2-(3-Fluorobenzyl)-6-(methylcarbamoyl)isonicotinic acid

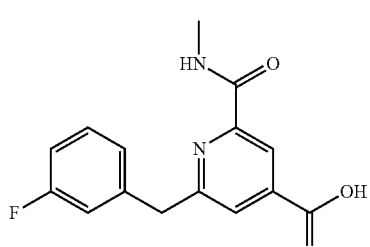

To a solution of tert-butyl 2-(3-fluorobenzyl)-6-(methylcarbamoyl)isonicotinate (52.2 mg, 0.152 mmol) in DCM (2 mL) was added 2,2,2-trifluoroacetic acid (0.700 mL, 9.09 mmol) and the reaction mixture was stirred at rt over the weekend. The reaction mixture was concentrated to 2-(3-fluorobenzyl)-6-(methylcarbamoyl)isonicotinic acid (53 mg, 0.147 mmol, 97% yield, ~80% purity) as an orange solid. This was used without purification in subsequent chemistry.

LCMS (2 min Formic): Rt=0.95 min, [MH]$^+$=289.1.

Intermediate 41: tert-Butyl 2-(3-methylbenzyl)-6-(methylcarbamoyl)isonicotinate

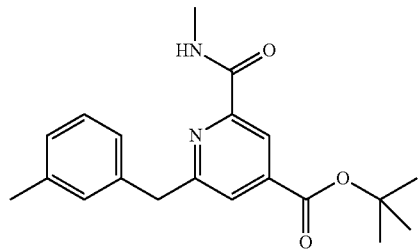 [SMILES: CNC(=O)c1cc(C(=O)OC(C)(C)C)cc(Cc2cccc(C)c2)n1]

tert-Butyl 2-chloro-6-(methylcarbamoyl)isonicotinate (100 mg, 0.369 mmol), (3-methylbenzyl)zinc(II) chloride (0.5M in THF, 1.25 mL, 0.625 mmol), PdCl$_2$(PPh$_3$)$_2$ (38.9 mg, 0.055 mmol) and THF (0.5 mL) were heated at 110° C. for 30 min in the microwave. The reaction mixture was filtered through Celite® (eluent EtOAc) then concentrated to give 393.9 mg of a brown solid. This was purified by chromatography on SiO$_2$ (Biotage® SNAP 10 g, eluting with 0-30% ethyl acetate/cyclohexane). The desired fractions were concentrated to give tert-butyl 2-(3-methylbenzyl)-6-(methylcarbamoyl)isonicotinate (52.2 mg, 0.123 mmol, 33.2% yield) as a colourless oil.

LCMS (2 min Formic): Rt=1.35 min, [MH]+ 341.2.

Intermediate 42: 2-(3-Methylbenzyl)-6-(methylcarbamoyl)isonicotinic acid

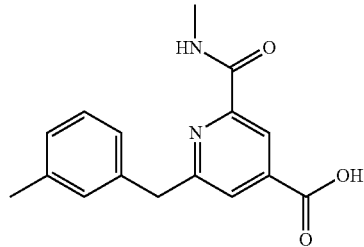 [SMILES: CNC(=O)c1cc(C(=O)O)cc(Cc2cccc(C)c2)n1]

To a solution of tert-butyl 2-(3-methylbenzyl)-6-(methylcarbamoyl)isonicotinate (52.2 mg, 0.153 mmol) in DCM (2 mL) was added 2,2,2-trifluoroacetic acid (0.700 mL, 9.09 mmol) and the reaction mixture was stirred at rt over the weekend. The reaction mixture was concentrated to give 2-(3-methylbenzyl)-6-(methylcarbamoyl)isonicotinic acid (102 mg, 0.144 mmol, 94% yield, ~40% purity) of an orange solid. This was used without purification in the subsequent reaction.

LCMS (2 min Formic): Rt=1.01 min, [MH]+ 285.1.

Intermediate 43: tert-Butyl 2-(methylcarbamoyl)-6-((2-oxoindolin-4-ylmethyl)isonicotinate

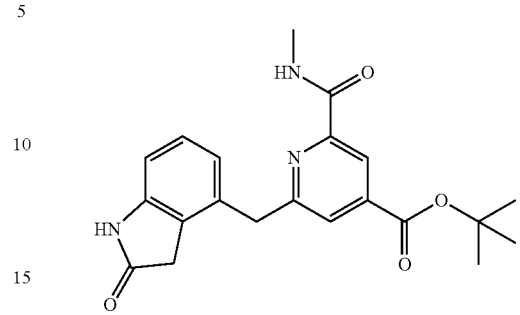

tert-Butyl 2-(chloromethyl)-6-(methylcarbamoyl)isonicotinate (80 mg, 0.281 mmol) was combined with 4-(4,4,5,5-tetramethyl-1,3,2-dioxaborolan-2-yl)indolin-2-one (479 mg, 0.425 mmol, 23% wt.), potassium carbonate (129.9 mg, 0.940 mmol) and PdCl$_2$(dppf) (41.1 mg, 0.056 mmol) in 1,4-dioxane (1 mL) and water (0.5 mL) in a 2 mL microwave vial. This was heated at 120° C. for 40 min. The solution was filtered through Celite® (eluent EtOAc) then concentrated to give 198 mg of a black solid. This was purified by chromatography on SiO$_2$ (Biotage® SNAP 10 g, eluting with 10-50% ethyl acetate/cyclohexane). The desired fractions were concentrated to give tert-butyl 2-(methylcarbamoyl)-6-((2-oxoindolin-4-yl)methyl)isonicotinate (39.7 mg, 0.094 mmol, 33.3% yield) as a colourless oil.

LCMS (2 min Formic): Rt=1.00 min, [MH]+ 382.3.

Intermediate 44: 2-(Methylcarbamoyl)-6-((2-oxoindolin-4-yl)methyl)isonicotinic acid

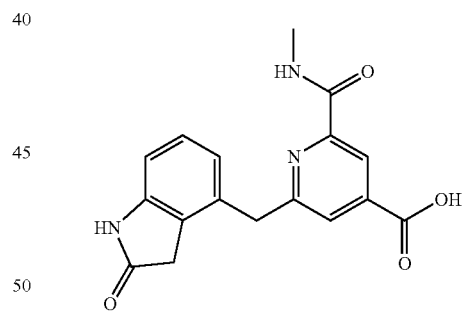

To a solution of tert-butyl 2-(methylcarbamoyl)-6-((2-oxoindolin-4-yl)methyl)isonicotinate (39.7 mg, 0.104 mmol, 78% wt.) in DCM (2 mL) was added 2,2,2-trifluoroacetic acid (0.4 mL, 5.19 mmol) and the reaction mixture was stirred for 6 h. Further 2,2,2-trifluoroacetic acid (0.3 mL, 3.89 mmol) was added and the resultant mixture was stirred over the weekend. The reaction mixture was concentrated to give 2-(methylcarbamoyl)-6-((2-oxoindolin-4-yl)methyl)isonicotinic acid (55.7 mg, 0.080 mmol, 99% yield, ~47% purity) as an orange solid. This was used without purification in subsequent chemistry.

LCMS (2 min Formic): Rt=0.70 min, [MH]+ 326.1.

$^1$H NMR (400 MHz, MeOH-d$_4$) δ ppm 8.33 (d, J=1.5 Hz, 1H) 7.55-7.77 (m, 2H) 7.25-7.45 (m, 5H) 7.11 (t, =7-7.2 Hz, 1H) 6.84 (d, J=7.6 Hz, 1H) 5.21 (br. s., 2H) 4.18 (s, 2H) 3.97 (t, J=8.7 Hz, 2H) 2.92-3.05 (m, 5H) 1.56 (s, 9H). Exchangeable protons not observed Intermediate 45: Benzyl 4-((4-(tert-butoxycarbonyl)-6-(methylcarbamoyl)pyridin-2-yl)methyl)indoline-1-carboxylate

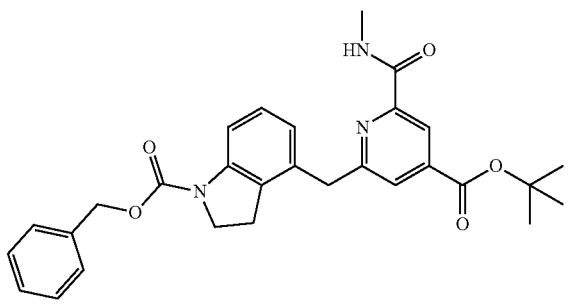 [SMILES: CNC(=O)c1cc(C(=O)OC(C)(C)C)cc(Cc2cccc3c2CCN3C(=O)OCc2ccccc2)n1]

tert-Butyl 2-(chloromethyl)-6-(methylcarbamoyl)isonicotinate (110 mg, 0.386 mmol) was combined with benzyl 4-(4,4,5,5-tetramethyl-1,3,2-dioxaborolan-2-yl)indoline-1-carboxylate (285.5 mg, 0.602 mmol), potassium carbonate (183 mg, 1.321 mmol) and PdCl$_2$(dppf) (56.5 mg, 0.077 mmol) in 1,4-dioxane (1 mL) and water (0.5 mL) in a 2 mL microwave vial. This was heated at 120° C. for 40 min. The solution was then filtered through Celite® (eluent EtOAc), dried and then concentrated. This was purified by chromatography on SiO$_2$ (Biotage® SNAP 10 g, eluting with 0-30% ethyl acetate/cyclohexane). The desired fractions were concentrated to give benzyl 4-((4-(tert-butoxycarbonyl)-6-(methylcarbamoyl)pyridin-2-yl)methyl)indoline-1-carboxylate (138.7 mg, 0.249 mmol, 64.4% yield) as a colourless oil.

LCMS (2 min Formic): Rt=1.44 min, [MH]+ 502.2.

Intermediate 46: 2-((1-((Benzyloxy)carbonyl)indolin-4-yl)methyl)-6-(methylcarbamoyl)isonicotinic acid

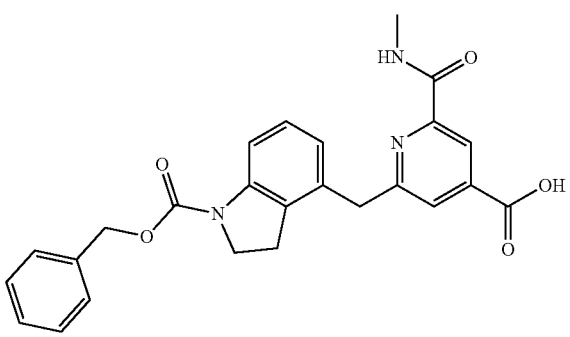 [SMILES: CNC(=O)c1cc(C(=O)O)cc(Cc2cccc3c2CCN3C(=O)OCc2ccccc2)n1]

To a solution of benzyl 4-((4-(tert-butoxycarbonyl)-6-(methylcarbamoyl)pyridin-2-yl)methyl)indoline-1-carboxylate (138.7 mg, 0.221 mmol) in DCM (4 mL) was added 2,2,2-trifluoroacetic acid (0.7 mL, 9.09 mmol) and the reaction mixture was stirred for 4 h. Further 2,2,2-trifluoroacetic acid (1 mL, 12.98 mmol) was added and the resultant mixture was stirred overnight. The reaction mixture was concentrated to give a brown solid. EtOAc (10 mL) was added to the brown solid, then the resulting mixture was base washed 5 times with sodium bicarbonate solution, then the aqueous phase was neutralised with a solution of 2M HCl (10 mL), then it was extracted with EtOAc. The combined organic phases were dried (a solid appeared so the solution was filtered) and then concentrated in vacuo to give a brown oil—2-((1-((benzyloxy)carbonyl)indolin-4-yl)methyl)-6-(methylcarbamoyl)isonicotinic acid (109 mg, 0.196 mmol, 88% yield).

LCMS (2 min Formic): Rt=1.18 min, [MH]+ 446.2.

Intermediate 47: (+/−)-tert-Butyl 2-(methylcarbamoyl)-6-(1-phenylethyl)isonicotinate

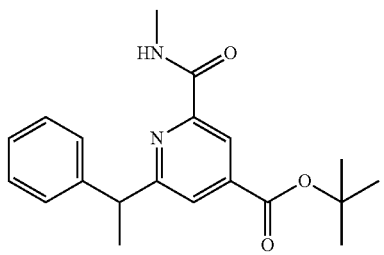 [SMILES: CNC(=O)c1cc(C(=O)OC(C)(C)C)cc(C(C)c2ccccc2)n1]

tert-Butyl 2-chloro-6-(methylcarbamoyl)isonicotinate (0.5 g, 1.847 mmol) was dissolved in THF (20 mL) and palladium dichloride bistriphenylphosphine (0.130 g, 0.185 mmol) was added. The solution was sparged with nitrogen for 5 min, then (1-phenylethyl)zinc(II) bromide (0.5M in THF, 7.39 mL, 3.69 mmol, commercially available from, for example, Sigma Aldrich) was added and the mixture heated at 70° C. for 2 h. The solution was diluted with EtOAc (100 mL) and washed with water (100 mL), dried and evaporated in vacuo. The residue was purified by chromatography on a 25 g silica column eluting with 0-50% EtOAc/cyclohexane and the product-containing fractions evaporated in vacuo to give tert-butyl 2-(methylcarbamoyl)-6-(1-phenylethyl)isonicotinate (0.41 g, 1.204 mmol, 65.2% yield) as a dark yellow oil.

LCMS (2 min High pH): Rt=1.37 min, [MH]$^+$=341.3.
$^1$H NMR (400 MHz, CDCl$_3$) δ ppm 8.45 (d, J=1.5 Hz, 1H) 8.02 (br. s., 1H) 7.81 (d, J=1.2 Hz, 1H) 7.18-7.36 (obs. m, 5H) 4.38 (q, J=7.3 Hz, 1H) 3.07 (d, J=5.1 Hz, 3H) 1.74 (d, J=7.3 Hz, 3H) 1.59 (s, 9H)

Intermediate 48: (+/−)-2-(Methylcarbamoyl)-6-(1-phenylethyl)isonicotinic acid

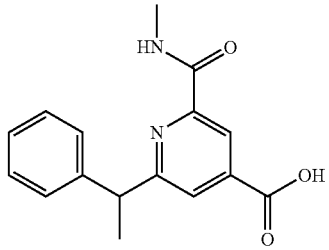

tert-Butyl 2-(methylcarbamoyl)-6-(1-phenylethyl)isonicotinate (0.41 g, 1.204 mmol) was dissolved in TFA (6 mL) and stirred for 3 h at rt, then the mixture was evaporated in vacuo and the residue partitioned between water (20 mL)

and DCM (20 mL). The organic layer was dried and evaporated in vacuo to give 2-(methylcarbamoyl)-6-(1-phenylethyl)isonicotinic acid (305 mg, 1.073 mmol, 89% yield) as a grey foam.

LCMS (2 min High pH): Rt=0.69 min, [MH]+=285.2.

¹H NMR (400 MHz, DMSO-$d_6$) δ ppm 13.74 (br. s., 1H) 8.75 (m, J=4.9 Hz, 1H) 8.21 (d, J=1.5 Hz, 1H) 7.82 (d, J=1.5 Hz, 1H) 7.42 (br. d, J=7.1 Hz, 2H) 7.30 (t, J=7.5 Hz, 2H) 7.16-7.23 (m, 1H) 4.47 (q, J=7.1 Hz, 1H) 2.89 (d, J=4.9 Hz, 3H) 1.72 (d, J=7.3 Hz, 3H)

Intermediate 49: (R*)-tert-Butyl 2-(methylcarbamoyl)-6-(1-phenylethyl)isonicotinate Intermediate 50: (S*)-tert-Butyl 2-(methylcarbamoyl)-6-(1-phenylethyl)isonicotinate

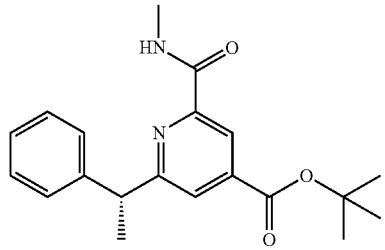

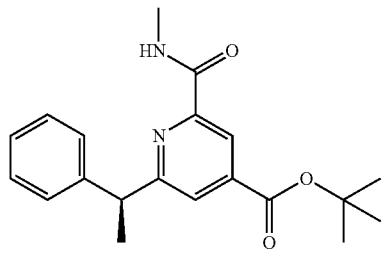

Intermediate 47 (7.777 g) was purified by chiral HPLC. The racemate was dissolved in EtOH (150 mL). Injection: 1.1 mL of the solution was injected via preparative autosampler, onto the column (20% EtOH/heptane+0.2% isopropylamine, flow rate=42.5 mL/min, detection wavelength=280 nm, band width 140 nm, reference 400 nm bandwidth 100 nm, Column 30 mm×25 cm Chiralcel OJ-H. Total number of injections=1). Fractions from 11.2-13.7 min were bulked and labelled peak 1. Fractions from 15.7-19 min were bulked and labelled peak 2. The bulked fractions were concentrated in vacuo and then transferred to weighed flasks.

The fractions corresponding to peak 1 were collected to afford intermediate 49 (2.84 g)

LCMS (2 min High pH): Rt=1.35 min, [MH]+=341.3

The fractions corresponding to peak 2 were collected to afford intermediate 50 (2.80 g)

LCMS (2 min High pH): Rt=1.35 min, [MH]+=341.3

Intermediate 51: (S*)-2-(Methylcarbamoyl)-6-(1-phenylethyl)isonicotinic Acid

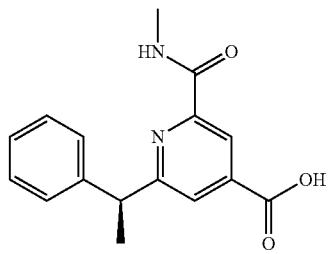 [SMILES: CNC(=O)c1cc(C(=O)O)cc([C@@H](C)c2ccccc2)n1]

A mixture of (S*)-tert-butyl 2-(methylcarbamoyl)-6-(1-phenylethyl)isonicotinate (2.1878 g, 6.43 mmol) and trifluoroacetic acid (10.0 mL, 130 mmol) in DCM (15 mL) was stirred at rt for 19 h. The volatiles were evaporated from the mixture in vacuo and the oily residue redissolved in acetonitrile (ca. 10 mL) and the solvent evaporated in vacuo. The orange oily residue had ether (ca. 10 mL) added and a white solid precipitated. The solid was filtered, washed with ether (2×5 mL) and dried in vacuo to give the desired product as a white solid; (S*)-2-(methylcarbamoyl)-6-(1-phenylethyl)isonicotinic acid (1.1768 g, 4.14 mmol, 64.4% yield)

The solvent from the mother liquor of the second ether wash was evaporated under a stream of nitrogen to give a second batch of the desired product as a white solid; (S*)-2-(methylcarbamoyl)-6-(1-phenylethyl)isonicotinic acid (95.6 mg, 0.336 mmol, 5.23% yield)

The solvent from the combined mother liquors of the initial trituration and first ether wash were evaporated under a stream of nitrogen and the orange viscous oil which resulted was triturated with ether (5 mL). The mother liquor was decanted away and the solid triturated with further ether (3×5 mL), each time decanting the mother liquor. The solid was dried in vacuo to give a third batch of the desired product as a cream solid, yield; (S*)-2-(methylcarbamoyl)-6-(1-phenylethyl)isonicotinic acid (310.8 mg, 1.093 mmol, 17.01% yield)

The combined mother liquors from the isolation of the above batch were evaporated under a stream of nitrogen and the resultant orange semi-crystalline solid was washed with ether (3 mL). The mother liquor was decanted away and the solid triturated with further ether (3×3 mL), each time decanting the mother liquor. The solid was dried in vacuo to give a fourth batch of the desired product as a cream solid (100.4 mg)

Total product isolated summed over the four batches=1.6836 g, 92.2%.

LCMS (2 min Formic): Rt=1.00 min, [MH]+=285.3

Intermediate 52: tert-Butyl 2-((1H-indol-4-yl)methyl)-6-(methylcarbamoyl)isonicotinate

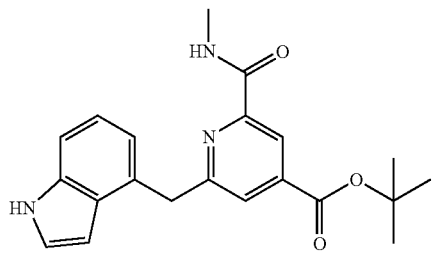 [SMILES: CNC(=O)c1cc(C(=O)OC(C)(C)C)cc(Cc2cccc3[nH]ccc23)n1]

tert-Butyl 2-(chloromethyl)-6-(methylcarbamoyl)isonicotinate (100 mg, 0.351 mmol) was combined with (1H-indol-4-yl)boronic acid (113 mg, 0.702 mmol), potassium carbonate (291 mg, 2.107 mmol) and PdCl$_2$(dppf) (51.4 mg, 0.070 mmol) in 1,4-dioxane (1 mL) and water (0.5 mL) in a 2 mL microwave vial. This was heated at 120° C. for 40 min. The solution was filtered though Celite® eluting with EtOAc (10 mL) then dried and concentrated. The crude product was purified by chromatography on SiO$_2$ (Biotage® SNAP 10 g, eluting with 0-60% ethyl acetate/cyclohexane). The desired fractions were concentrated to give tert-butyl 2-((1H-indol-4-yl)methyl)-6-(methylcarbamoyl)isonicotinate (75.4 mg, 0.165 mmol, 47.0% yield) as a white solid.

LCMS (2 min Formic): Rt=1.20 min, [MH]$^+$=366.2.

$^1$H NMR (400 MHz, MeOH-d$_4$) δ ppm 8.30 (d, J=1.2 Hz, 1H) 7.76 (d, J=1.2 Hz, 1H) 7.31 (d, J=8.3 Hz, 1H) 7.21 (d, J=3.2 Hz, 1H) 7.03-7.11 (m, 1H) 6.91 (br. d, J=7.1 Hz, 1H) 6.47 (dd, J=3.2, 0.7 Hz, 1H) 4.52 (s, 2H) 2.99 (s, 3H) 1.54 (s, 9H). Exchangeables not observed.

Intermediate 53: 2-((1H-Indol-4-yl)methyl)-6-(methylcarbamoyl)isonicotinic acid

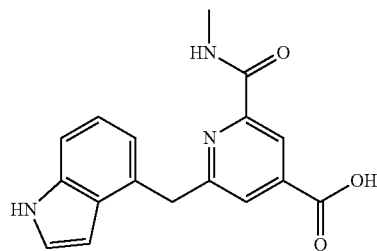 [SMILES: CNC(=O)c1cc(C(=O)O)cc(Cc2cccc3[nH]ccc23)n1]

To a solution of tert-butyl 2-((1H-indol-4-yl)methyl)-6-(methylcarbamoyl)isonicotinate (75.4 mg, 0.165 mmol) in DCM (3 mL) was added TFA (0.60 mL, 7.79 mmol) and the reaction mixture was stirred at rt overnight. Further TFA (0.3 mL, 0.165 mmol) was added and the resultant mixture stirred for 3 h. The reaction mixture was concentrated in vacuo to give 2-((1H-indol-4-yl)methyl)-6-(methylcarbamoyl)isonicotinic acid (184 mg, 0.149 mmol, 90% yield, ~25% purity).

LCMS (2 min Formic): Rt=0.88 min, [MH]$^+$=310.1.

$^1$H NMR (400 MHz, DMSO-d$_6$) δ ppm 11.59-12.89 (m, 1H) 11.11 (br. s., 1H) 8.76 (d, J=4.9 Hz, 1H) 8.19 (d, J=1.2 Hz, 1H) 7.71 (d, J=1.5 Hz, 1H) 7.21-7.39 (m, 2H) 7.05 (t, J=7.6 Hz, 1H) 6.95 (d, J=6.8 Hz, 1H) 6.46-6.56 (m, 1H) 4.48 (s, 2H) 2.88 (d, J=4.9 Hz, 3H).

Intermediate 54: (+/−)-tert-Butyl 2-(hydroxy(phenyl)methyl)-6-(methylcarbamoyl)isonicotinate

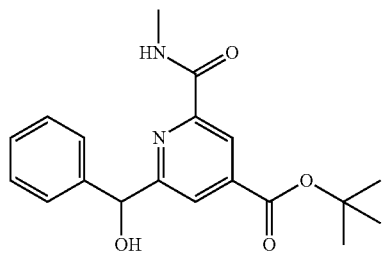

To a solution of tert-butyl 2-formyl-6-(methylcarbamoyl)isonicotinate (118 mg, 0.447 mmol) in THF (1.5 mL) at 0° C., was added dropwise phenylmagnesium bromide (1M in THF, 2 mL, 2 mmol).

The reaction mixture was stirred for 2 h. The reaction mixture was poured onto a saturated ammonium chloride aqueous solution and extracted with EtOAc (20 mL×3). The organic layer was dried over MgSO$_4$ and concentrated in vacuo. The crude product was purified by chromatography on SiO$_2$ (Biotage® SNAP 10 g, eluting with 0-60% ethyl acetate/cyclohexane). The desired fractions were concentrated to give tert-butyl 2-(hydroxy(phenyl)methyl)-6-(methylcarbamoyl)isonicotinate (43 mg, 0.107 mmol, 23.91% yield).

LCMS (2 min Formic): Rt=1.09 min, [MH]$^+$=343.3.

$^1$H NMR (400 MHz, MeOH-d$_4$) δ ppm 8.38 (d, J=1.2 Hz, 1H) 8.05 (d, J=1.2 Hz, 1H) 7.42-7.47 (m, 2H) 7.22-7.36 (m, 3H) 5.95 (s, 1H) 2.99 (s, 3H) 1.60 (s, 9H). Exchangeables not observed.

Intermediate 55: (+/−)-2-(Hydroxy(phenyl)methyl)-6-(methylcarbamoyl)isonicotinic acid

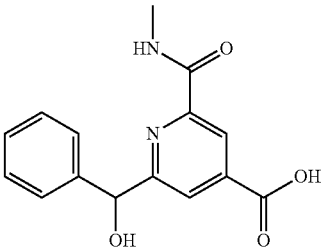 [SMILES: CNC(=O)c1cc(C(=O)O)cc(C(O)c2ccccc2)n1]

To a solution of tert-butyl 2-(hydroxy(phenyl)methyl)-6-(methylcarbamoyl)isonicotinate (43 mg, 0.126 mmol) in DCM (0.5 mL) was added TFA (0.4 mL, 5.19 mmol) and the reaction mixture was stirred for 2 h and then overnight. Further TFA (0.4 mL, 0.126 mmol) was added and the reaction mixture was stirred for 5 h, then the solvent was removed to give 2-(hydroxy(phenyl)methyl)-6-(methylcarbamoyl)isonicotinic acid (47.9 mg, 0.117 mmol, 93% yield, 70% purity) which was used directly in the next step.

LCMS (2 min Formic): Rt=0.74 min, [MH]$^+$=287.1.

$^1$H NMR (400 MHz, MeOH-d$_4$) δ ppm 8.45 (d, J=1.2 Hz, 1H) 8.10 (d, J=1.5 Hz, 1H) 7.41-7.48 (m, 2H) 7.21-7.38 (m, 3H) 5.97 (s, 1H) 2.99 (s, 3H). Exchangeables not observed.

Intermediate 56: (+/−)-tert-Butyl 2-(chloro(phenyl)methyl)-6-(methylcarbamoyl)isonicotinate

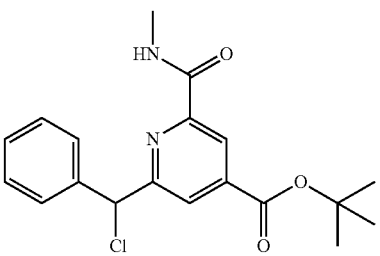 [SMILES: CNC(=O)c1cc(C(=O)OC(C)(C)C)cc(C(Cl)c2ccccc2)n1]

To a solution of tert-butyl 2-(hydroxy(phenyl)methyl)-6-(methylcarbamoyl)isonicotinate (46 mg, 0.134 mmol) in DCM (4 mL) at 0° C., was added dropwise thionyl chloride (30 µL, 0.411 mmol). The reaction mixture was then stirred at rt for 12 h. Further thionyl chloride (50 µL, 0.685 mmol) was added and the resultant mixture was stirred for 5 h then concentrated in vacuo to give tert-butyl 2-(chloro(phenyl)methyl)-6-(methylcarbamoyl)isonicotinate (54 mg) which was used without purification in the subsequent reaction.

LCMS (2 min Formic): Rt=1.33 min, [MH]$^+$=361.1

Intermediate 57: (+/−)-tert-Butyl 2-(methoxy(phenyl)methyl)-6-(methylcarbamoyl)isonicotinate

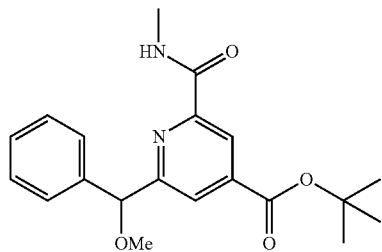 [SMILES: CNC(=O)c1cc(C(=O)OC(C)(C)C)cc(C(OC)c2ccccc2)n1]

A solution of tert-butyl 2-(chloro(phenyl)methyl)-6-(methylcarbamoyl)isonicotinate (54 mg, 0.150 mmol) in methanol (5 mL) was stirred over the weekend. The reaction mixture was then heated under reflux for 1 h initially, then 4 h and finally overnight. The reaction mixture was then concentrated in vacuo. The resultant crude product was purified by flash silica chromatography (SNAP 10 g cartridge, eluent: 0-50% ethyl acetate/cyclohexane). The desired fractions were combined and concentrated in vacuo to give tert-butyl 2-(methoxy(phenyl)methyl)-6-(methylcarbamoyl)isonicotinate (33 mg, 0.083 mmol, 55.7% yield) as a colourless oil.

LCMS (2 min Formic): Rt=1.26 min, [MH]$^+$=357.2.

Intermediate 58: (+/−)-2-(Methoxy(phenyl)methyl)-6-(methylcarbamoyl)isonicotinic acid

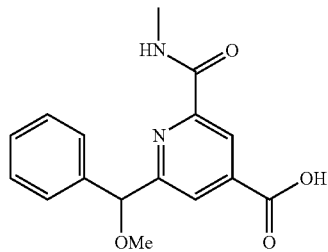 [SMILES: CNC(=O)c1cc(C(=O)O)cc(C(OC)c2ccccc2)n1]

To a solution of tert-butyl 2-(methoxy(phenyl)methyl)-6-(methylcarbamoyl)isonicotinate (33 mg, 0.093 mmol) in DCM (1 mL) was added 2,2,2-trifluoroacetic acid (0.5 mL, 6.49 mmol) and the reaction mixture was stirred overnight. This was then washed with water and extracted with DCM three times, then it was dried. The solvent was removed in vacuo to give 2-(methoxy(phenyl)methyl)-6-(methylcarbamoyl)isonicotinic acid (44.9 mg, 0.090 mmol, 97% yield, ~60% purity) LCMS (2 min Formic): Rt=0.91 min, [MH]$^+$=301.1

Intermediate 59: (+/−)-tert-Butyl 2-(hydroxy(pyridin-2-yl)methyl)-6-(methylcarbamoyl)isonicotinate

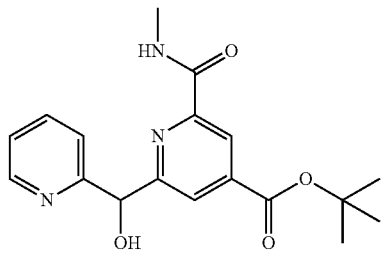 [SMILES: CNC(=O)c1cc(C(=O)OC(C)(C)C)cc(C(O)c2ccccn2)n1]

In a round bottom flask dried and under N$_2$, containing lithium chloride (140 mg, 3.29 mmol), was added 2-bromopyridine (0.400 mL, 4.11 mmol) and THF (4 mL) at rt. The reaction mixture was then stirred at rt for 30 min, then isopropylmagnesium chloride (2M in THF, 2.057 mL, 4.11 mmol) was added (after the addition the solution became yellow/brown) and the resultant mixture was stirred for 30 min to give a suspension of pyridin-2-ylmagnesium chloride (assumed 100% yield: 1.029M suspension in THF 4 mL). To this suspension of pyridin-2-ylmagnesium bromide (1.029M in THF, 4 mL, 2.93 mmol) at 0° C. under nitrogen, was added dropwise tert-butyl 2-formyl-6-(methylcarbamoyl)isonicotinate (344 mg, 1.171 mmol, 90% wt.) in THF (3 mL). The reaction mixture was stirred for 5 h. Ammonium chloride aqueous solution (3 mL) was added. The reaction mixture was stirred for 30 min before being extracted with EtOAc (20 mL×3). The organic layer was dried over MgSO$_4$ and concentrated in vacuo. This was purified by chromatography on SiO$_2$ (Biotage® SNAP 10 g cartridge, eluent 0-50% (25% EtOH in ethylacetate)/cyclohexane). The desired fractions were concentrated to give tert-butyl 2-(hydroxy(pyridin-2-yl)methyl)-6-(methylcarbamoyl)isonicotinate (232 mg, 0.527 mmol, 45.0% yield, ~78% purity).

LCMS (2 min Formic): Rt=0.76 min, [MH]$^+$=344.3.

Intermediate 60: (+/−)-2-(Hydroxy(pyridin-2-yl)methyl)-6-(methylcarbamoyl)isonicotinic acid

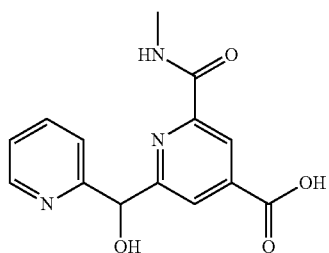 [SMILES: CNC(=O)c1cc(C(=O)O)cc(C(O)c2ccccn2)n1]

To a solution of tert-butyl 2-(hydroxy(pyridin-2-yl)methyl)-6-(methylcarbamoyl)isonicotinate (232 mg, 0.676 mmol) in DCM (0.5 mL) was added 2,2,2-trifluoroacetic acid (1.5 mL, 19.47 mmol) and the reaction mixture was stirred for 4 h. The solvent was removed in vacuo to give 2-(hydroxy(pyridin-2-yl)methyl)-6-(methylcarbamoyl)

isonicotinic acid (289 mg, 0.604 mmol, 89% yield, ~60% purity) which was used without purification in the subsequent reaction.

LCMS (2 min Formic): Rt=0.40 min, [MH]$^+$=288.1.

Intermediate 61: tert-Butyl 2-((1H-indazol-4-yl)methyl)-6-(methylcarbamoyl)isonicotinate

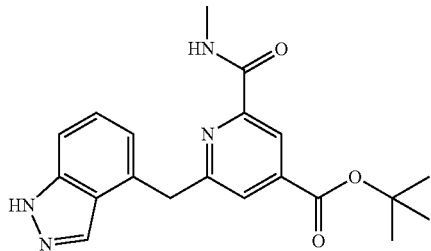 [SMILES: CNC(=O)c1cc(C(=O)OC(C)(C)C)cc(Cc2cccc3[nH]ncc23)n1]

tert-Butyl 2-(chloromethyl)-6-(methylcarbamoyl)isonicotinate (84 mg, 0.295 mmol) was combined with 4-(4,4,5,5-tetramethyl-1,3,2-dioxaborolan-2-yl)-1H-indazole (216 mg, 0.885 mmol, commercially available from, for example, Sigma-Aldrich), potassium carbonate (279 mg, 2.018 mmol) and PdCl$_2$(dppf) (43.2 mg, 0.059 mmol) in 1,4-dioxane (1 mL) and water (0.5 mL) in a 2 mL microwave vial. This was heated at 120° C. for 40 min. The solution was filtered through Celite®, eluent EtOAc (10 mL) then washed with water. The aqueous phase was extracted with EtOAc (3 times). Then the combined organic phase was dried and concentrated in vacuo. This was purified by chromatography on SiO$_2$ (Biotage® SNAP 10 g cartridge, eluting with 0-40% ethyl acetate/cyclohexane). The desired fractions were concentrated to give tert-butyl 2-((1H-indazol-4-yl)methyl)-6-(methylcarbamoyl)isonicotinate (43.8 mg, 0.068 mmol, 23.10% yield, ~57% purity) as a yellow oil.

LCMS (2 min Formic): Rt=1.07 min, [MH]$^+$=367.3.

Intermediate 62: 2-((1H-Indazol-4-yl)methyl)-6-(methylcarbamoyl)isonicotinic acid

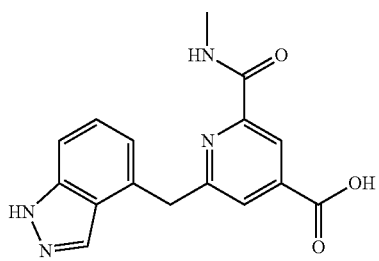 [SMILES: CNC(=O)c1cc(C(=O)O)cc(Cc2cccc3[nH]ncc23)n1]

To a solution of tert-butyl 2-((1H-indazol-4-yl)methyl)-6-(methylcarbamoyl)isonicotinate (43.8 mg, 0.068 mmol, 57% wt.) in DCM (0.5 mL) was added 2,2,2-trifluoroacetic acid (0.4 mL, 5.19 mmol) and the reaction mixture was stirred for 2 h. The solvent was removed in vacuo to give 2-((1H-indazol-4-yl)methyl)-6-(methylcarbamoyl)isonicotinic acid (33.5 mg, 0.054 mmol, 79% yield, ~50% purity).

LCMS (2 min Formic): Rt=0.75 min, [MH]$^+$=311.2.

Intermediate 63: tert-Butyl 4-((4-(tert-butoxycarbonyl)-6-(methylcarbamoyl)pyridin-2-yl)methyl)-2-methyl-1H-benzo[d]imidazole-1-carboxylate

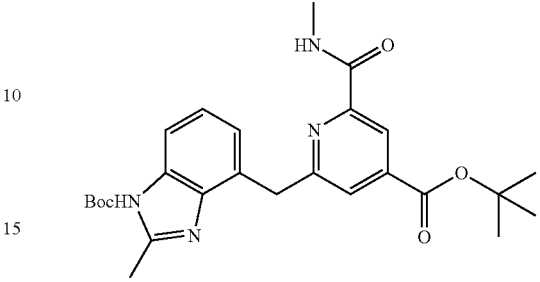

tert-Butyl 2-(chloromethyl)-6-(methylcarbamoyl)isonicotinate (100 mg, 0.351 mmol) was combined with (1-(tert-butoxycarbonyl)-2-methyl-1H-benzo[d]imidazol-4-yl)boronic acid (150 mg, 0.272 mmol, commercially available from, for example, Sigma-Aldrich), potassium carbonate (332 mg, 2.402 mmol) and PdCl$_2$(dppf) (51.4 mg, 0.070 mmol) in 1,4-dioxane (1 mL) and water (0.5 mL) in a 2 mL microwave vial. This was heated at 120° C. for 40 min. The solution was filtered through Celite®, eluent EtOAc (10 mL), then washed with water. The aqueous phase was extracted with EtOAc (3 times). Then the combined organic phase was dried over magnesium sulfate and concentrated in vacuo. The crude product was purified by chromatography on SiO$_2$ (Biotage® SNAP 10 g, eluting with 50-70% ethyl acetate/cyclohexane). The desired fractions were concentrated to give tert-butyl 4-((4-(tert-butoxycarbonyl)-6-(methylcarbamoyl)pyridin-2-yl)methyl)-2-methyl-1H-benzo[d]imidazole-1-carboxylate (24 mg, 0.047 mmol, 17.47% yield) as a yellow oil.

LCMS (2 min Formic): Rt=1.41 min, [MH]$^+$=481.3.

Intermediate 64: 2-((2-Methyl-1H-benzo[d]imidazol-4-yl)methyl)-6-(methylcarbamoyl)isonicotinic acid

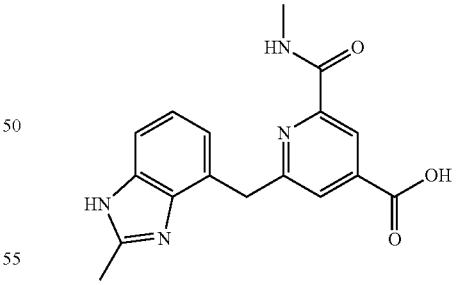

To a solution of tert-butyl 4-((4-(tert-butoxycarbonyl)-6-(methylcarbamoyl)pyridin-2-yl)methyl)-2-methyl-1H-benzo[d]imidazole-1-carboxylate (24 mg, 0.050 mmol) in DCM (0.5 mL) was added 2,2,2-trifluoroacetic acid (0.1 mL, 1.298 mmol) and the reaction mixture was stirred for 1.5 h. Further 2,2,2-trifluoroacetic acid (0.1 mL, 1.298 mmol) was added and the resultant mixture was stirred for 2 h. Further 2,2,2-trifluoroacetic acid (0.2 mL, 0.050 mmol) was added and the resultant mixture was stirred for 1 h. The solvent was removed in vacuo to give 2-((2-methyl-1H-benzo[d]imidazol-4-yl)methyl)-6-(methylcarbamoyl)isonicotinic acid (32.5 mg, 0.045 mmol, 90% yield, ~45% purity) LCMS (2 min Formic): Rt=0.45 min, [MH]⁺=325.2.

Intermediate 65: tert-Butyl 2-((1H-indol-3-yl)methyl)-6-(methylcarbamoyl)isonicotinate

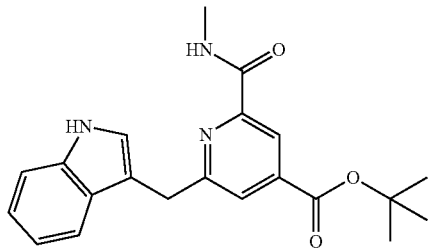 [SMILES: CNC(=O)c1cc(C(=O)OC(C)(C)C)cc(Cc2c[nH]c3ccccc23)n1]

tert-Butyl 2-(chloromethyl)-6-(methylcarbamoyl)isonicotinate (140 mg, 0.492 mmol) was combined with (1-(tert-butoxycarbonyl)-1H-indol-3-yl)boronic acid (250 mg, 0.958 mmol, commercially available from, for example, Fluorochem), potassium carbonate (408 mg, 2.95 mmol) and PdCl₂(dppf) (72.0 mg, 0.098 mmol) in 1,4-dioxane (1 mL) and water (0.5 mL) in a 2 mL microwave vial. This was heated at 110° C. for 40 min. The solution was filtered through Celite®, eluent: EtOAc (10 mL) then washed with water (10 mL). The aqueous phase was extracted 3 times with EtOAc. Then the combined organic phase was dried and concentrated in vacuo. This was purified by chromatography on SiO₂ (Biotage® SNAP 25 g cartridge, eluting with 0-30% ethyl acetate in cyclohexane). The desired fractions were concentrated in vacuo to give tert-butyl 3-((4-(tert-butoxycarbonyl)-6-(methylcarbamoyl)pyridin-2-yl)methyl)-1H-indole-1-carboxylate (100 mg, 0.095 mmol, 19.22% yield) as a yellow oil. The same column was then eluted with 100% ethyl acetate and the desired fractions were concentrated in vacuo to give tert-butyl 2-((1H-indol-3-yl)methyl)-6-(methylcarbamoyl)isonicotinate (10 mg, 0.022 mmol, 4.45% yield) as a yellow oil.

LCMS (2 min Formic): Rt=1.53 min, [MH]⁺=466.4.

Intermediate 66: 2-((1H-Indol-3-yl)methyl)-6-(methylcarbamoyl)isonicotinic acid

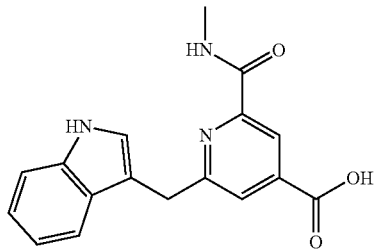 [SMILES: CNC(=O)c1cc(C(=O)O)cc(Cc2c[nH]c3ccccc23)n1]

To a solution of tert-butyl 3-((4-(tert-butoxycarbonyl)-6-(methylcarbamoyl)pyridin-2-yl)methyl)-1H-indole-1-carboxylate (100 mg, 0.215 mmol) in DCM (1 mL) was added 2,2,2-trifluoroacetic acid (0.5 ml, 6.49 mmol) and the reaction mixture was stirred for 20 h. The solvent was removed in vacuo to give 2-((1H-indol-3-yl)methyl)-6-(methylcarbamoyl)isonicotinic acid (200 mg, 0.129 mmol, 60.2% yield, ~20% purity) which was used without purification in the subsequent reaction.

LCMS (2 min Formic): Rt=0.98 min, [MH]⁺=310.2.

Intermediate 67: (+/−)-tert-Butyl 2-(hydroxy(6-methylpyridin-2-yl)methyl)-6-(methylcarbamoyl)isonicotinate

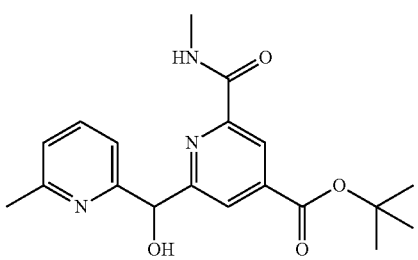 [SMILES: CNC(=O)c1cc(C(=O)OC(C)(C)C)cc(C(O)c2cccc(C)n2)n1]

To a solution of magnesium turnings (24 mg, 0.987 mmol) in dry THF (0.5 mL) at rt under nitrogen, in a dry round bottomed flask, was added 2-bromo-6-methylpyridine (0.124 mL, 1.090 mmol). The reaction mixture was stirred for 45 min, then tert-butyl 2-formyl-6-(methylcarbamoyl)isonicotinate (157 mg, 0.475 mmol) was added in dry THF (0.8 mL) at 0° C. The reaction mixture was stirred for 2 h. Ammonium chloride aqueous solution (3 mL) was added and the reaction mixture was stirred for 5 min before being extracted with EtOAc (20 mL×3). The organic layer was dried over MgSO₄ and concentrated in vacuo. This was purified by chromatography on SiO₂ (Biotage® SNAP 10 g cartridge, eluent: 0-100% ethyl acetate in cyclohexane). The desired fractions were concentrated to give tert-butyl 2-(hydroxy(6-methylpyridin-2-yl)methyl)-6-(methylcarbamoyl)isonicotinate (28 mg, 0.071 mmol, 14.84% yield).

LCMS (2 min Formic): Rt=0.70 min, [MH]⁺=358.3.

Intermediate 68: (+/−)-2-(Hydroxy(6-methylpyridin-2-yl)methyl)-6-(methylcarbamoyl)isonicotinic acid

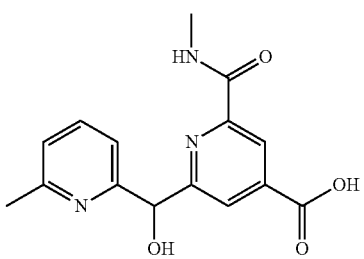 [SMILES: CNC(=O)c1cc(C(=O)O)cc(C(O)c2cccc(C)n2)n1]

To a solution of tert-butyl 2-(hydroxy(6-methylpyridin-2-yl)methyl)-6-(methylcarbamoyl)isonicotinate (28 mg, 0.078 mmol) in DCM (0.5 mL) was added 2,2,2-trifluoroacetic acid (0.5 mL, 6.49 mmol) and the reaction mixture was stirred for 2 h. The solvent was removed in vacuo to give 2-(hydroxy(6-methylpyridin-2-yl)methyl)-6-(methylcarbamoyl)isonicotinic acid (28 mg, 0.074 mmol, 95% yield, ~80% purity) which was used without purification in the subsequent reaction.

LCMS (2 min Formic): Rt=0.39 min, [MH]⁺=302.2.

Intermediate 69: (+/−)-tert-Butyl 2-(hydroxy(1-(phenylsulfonyl)-1H-pyrrolo[3,2-c]pyridin-4-yl)methyl)-6-(methylcarbamoyl)isonicotinate

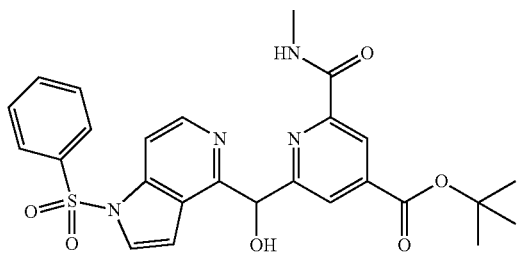 [SMILES: CNC(=O)c1cc(C(=O)OC(C)(C)C)cc(C(O)c2nccc3c2ccn3S(=O)(=O)c2ccccc2)n1]

In a round bottom flask dried and under N$_2$, with lithium chloride (11.32 mg, 0.267 mmol) was added 4-bromo-1-(phenylsulfonyl)-1H-pyrrolo[3,2-c]pyridine (90 mg, 0.267 mmol) and THF (0.5 mL) at rt. The reaction mixture was then stirred at rt for 30 min, then isopropylmagnesium chloride (2M in THF, 0.14 mL, 0.280 mmol) was added at 0° C. (after the addition of the isopropylmagnesium chloride, the solution became yellow/brown) and the resultant mixture was stirred for 30 min at 0° C. to give (1-(phenylsulfonyl)-1H-pyrrolo[3,2-c]pyridin-4-yl)magnesium bromide (assumed 100% yield: 0.417M solution in THF, 0.64 mL, 0.266 mmol). To a solution of (1-(phenylsulfonyl)-1H-pyrrolo[3,2-c]pyridin-4-yl)magnesium bromide (0.417 M solution in THF, 0.64 mL, 0.266 mmol) at 0° C. under nitrogen, was added dropwise tert-butyl 2-formyl-6-(methylcarbamoyl)isonicotinate (60 mg, 0.182 mmol, 80% wt.) in THF (0.5 mL). The reaction mixture was stirred overnight (and allowed to warm to rt). A saturated solution of NH$_4$Cl (2 mL) was added to the reaction mixture. The solution was partitioned between EtOAc and water and the layers were separated and the aqueous phase further extracted with EtOAc (2 times). The combined organic phases were dried over magnesium sulfate then concentrated in vacuo. The crude product was purified by chromatography on SiO$_2$ (Biotage® SNAP 10 g cartridge, eluting with 0-50% ethyl acetate cyclohexane, then 100% (25% EtOH in ethyl acetate). The desired fractions were concentrated in vacuo to give tert-butyl 2-(hydroxy(1-(phenylsulfonyl)-1H-pyrrolo[3,2-c]pyridin-4-yl)methyl)-6-(methylcarbamoyl)isonicotinate (30 mg, 0.029 mmol, 15.80% yield, ~50% purity) as a yellow oil.

LCMS (2 min Formic): Rt=0.97 min, [MH]$^+$=523.3.

Intermediate 70: (+/−)-2-(Hydroxy(1-(phenylsulfonyl)-1H-pyrrolo[3,2-c]pyridin-4-yl)methyl)-6-(methylcarbamoyl)isonicotinic acid

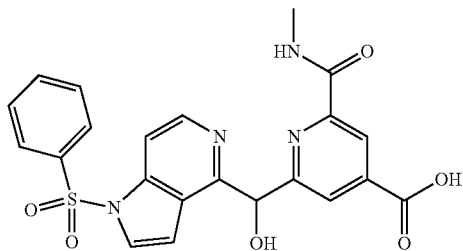 [SMILES: CNC(=O)c1cc(C(=O)O)cc(C(O)c2nccc3c2ccn3S(=O)(=O)c2ccccc2)n1]

To a solution of tert-butyl 2-(hydroxy(1-(phenylsulfonyl)-1H-pyrrolo[3,2-c]pyridin-4-yl)methyl)-6-(methylcarbamoyl)isonicotinate (30 mg, 0.029 mmol, 50% wt.) in DCM (0.5 mL) was added 2,2,2-trifluoroacetic acid (0.2 mL, 2.60 mmol) and the reaction mixture was stirred overnight. This was washed with water and extracted with DCM five times. Then the combined organic phases were dried. The solvent was removed in vacuo to give 2-(hydroxy(1-(phenylsulfonyl)-1H-pyrrolo[3,2-c]pyridin-4-yl)methyl)-6-(methylcarbamoyl)isonicotinic acid (27 mg, 0.021 mmol, 72.6% yield, ~36% purity). This was used without purification in the subsequent reaction.

LCMS (2 min Formic): Rt=0.66 min, [MH]$^+$=467.3.

Intermediate 71: tert-Butyl 2-((1H-pyrrolo[2,3-c]pyridin-4-yl)methyl)-6-(methylcarbamoyl)isonicotinate

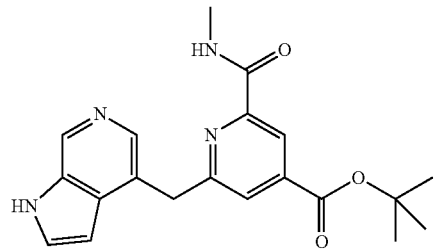 [SMILES: CNC(=O)c1cc(C(=O)OC(C)(C)C)cc(Cc2cncc3[nH]ccc23)n1]

tert-Butyl 2-(chloromethyl)-6-(methylcarbamoyl)isonicotinate (30 mg, 0.105 mmol) was combined with 4-(4,4,5,5-tetramethyl-1,3,2-dioxaborolan-2-yl)-1H-pyrrolo[2,3-c]pyridine (50 mg, 0.205 mmol, commercially available from, for example, Fluorochem), potassium carbonate (50 mg, 0.362 mmol) and PdCl$_2$(dppf) (15.42 mg, 0.021 mmol) in 1,4-dioxane (1 mL) and water (0.5 mL) in a 2 mL microwave vial. This was heated at 110° C. for 40 min. The solution was filtered through Celite®, eluent: EtOAc (10 mL), then washed with water. The aqueous phase was extracted 3 times with EtOAc. Then the combined organic phase was dried and concentrated in vacuo. This was purified by chromatography on SiO$_2$ (Biotage® SNAP 10 g cartridge, eluting with 0-50% ethyl acetate in cyclohexane, then 30 to 100% (25% EtOH in ethyl acetate)). The desired fractions were concentrated in vacuo to give tert-butyl 2-((1H-pyrrolo[2,3-c]pyridin-4-yl)methyl)-6-(methylcarbamoyl)isonicotinate (40 mg, 0.098 mmol, 93% yield) as a yellow oil.

LCMS (2 min Formic): Rt=0.63 min, [MH]$^+$=367.3.

$^1$H NMR (400 MHz, MeOH-d$_4$) δ ppm 8.62 (s, 1H) 8.32 (d, J=1.2 Hz, 1H) 8.04 (s, 1H) 7.81 (d, J=1.5 Hz, 1H) 7.53 (d, J=3.2 Hz, 1H) 6.58 (dd, J=2.9, 0.7 Hz, 1H) 4.54 (s, 2H) 2.99 (s, 3H) 1.54 (s, 9H). Exchangeables not observed.

Intermediate 72: 2-((1H-Pyrrolo[2,3-c]pyridin-4-yl)methyl)-6-(methylcarbamoyl)isonicotinic acid

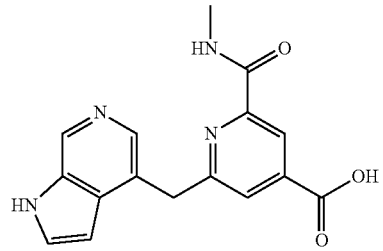 [SMILES: CNC(=O)c1cc(C(=O)O)cc(Cc2cncc3[nH]ccc23)n1]

To a solution of tert-butyl 2-((1H-pyrrolo[2,3-c]pyridin-4-yl)methyl)-6-(methylcarbamoyl)isonicotinate (32.2 mg, 0.088 mmol) in DCM (0.5 mL) was added 2,2,2-trifluoroacetic acid (0.3 mL, 3.89 mmol) and the reaction mixture was stirred overnight. The solvent was removed in vacuo to give 2-((1H-pyrrolo[2,3-c]pyridin-4-yl)methyl)-6-(methylcarbamoyl)isonicotinic acid (54 mg, 0.087 mmol, 99% yield, ~50% purity) which was used without purification in the subsequent reaction.

LCMS (2 min Formic): Rt=0.41 min, [MH]$^+$=311.2.

Intermediate 73: tert-Butyl 4-((4-(tert-butoxycarbonyl)-6-(methylcarbamoyl)pyridin-2-yl)methyl)-1H-pyrrolo[2,3-c]pyridine-1-carboxylate

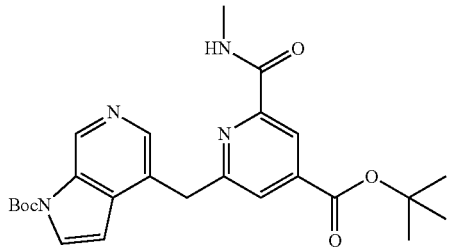 [SMILES: CNC(=O)c1cc(C(=O)OC(C)(C)C)cc(Cc2cncc3c2ccn3C(=O)OC(C)(C)C)n1]

To a solution of tert-butyl 2-((1H-pyrrolo[2,3-c]pyridin-4-yl)methyl)-6-(methylcarbamoyl)isonicotinate (117 mg, 0.319 mmol) in DCM (2 mL) was added di-tert-butyl dicarbonate (77 mg, 0.351 mmol) and pyridine (0.03 mL, 0.371 mmol). The reaction mixture was stirred at rt for 2 h, then HCl (2 mL, 2M aq.) was added. Water (5 mL) and DCM (5 mL) were then added. The organic phase was separated and the aqueous phase was extracted again with DCM (2×10 mL). The combined organic phases were dried over a hydrophobic frit, then concentrated in vacuo to give tert-butyl 4-((4-(tert-butoxycarbonyl)-6-(methylcarbamoyl)pyridin-2-yl)methyl)-1H-pyrrolo[2,3-c]pyridine-1-carboxylate (140 mg, 0.285 mmol, 89% yield) LCMS (2 min Formic): Rt=0.85 min, [MH]$^+$=467.4.

$^1$H NMR (400 MHz, CDCl$_3$) δ ppm 9.43 (s, 1H) 8.48-8.54 (m, 2H) 8.18 (d, J=3.4 Hz, 1H) 7.89 (d, J=1.2 Hz, 1H) 7.72 (br. d, J=3.9 Hz, 1H) 6.87 (d, J=3.7 Hz, 1H) 4.58 (s, 2H) 3.03 (d, J=4.9 Hz, 3H) 1.71 (s, 9H) 1.59 (s, 9H)

Intermediate 74: (+/−)-tert-Butyl 4-(1-(4-(tert-butoxycarbonyl)-6-(methylcarbamoyl)pyridin-2-yl)ethyl)-1H-pyrrolo[2,3-c]pyridine-1-carboxylate

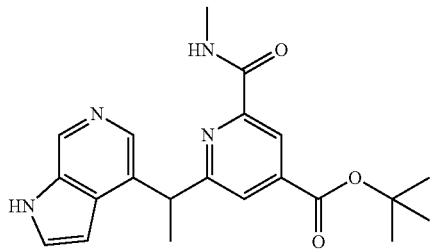 [SMILES: CNC(=O)c1cc(C(=O)OC(C)(C)C)cc(C(C)c2cncc3[nH]ccc23)n1]

tert-Butyl 4-((4-(tert-butoxycarbonyl)-6-(methylcarbamoyl)pyridin-2-yl)methyl)-1H-pyrrolo[2,3-c]pyridine-1-carboxylate (138 mg, 0.281 mmol) was dissolved in THF (1 mL) and cooled to −78° C. under N$_2$. LiHMDS (1M in THF, 1.3 mL, 1.300 mmol) was added dropwise and the reaction mixture left to stir for 1 h. MeI (0.050 mL, 0.800 mmol) was added (colour change dark green to yellow solution) and the resultant mixture was stirred for 30 min. Water (0.5 mL) was added and the reaction mixture was allowed to warm up. The reaction mixture was then diluted with water (10 mL) and extracted with EtOAc (3×10 mL). The combined organic phases were dried through a hydrophobic filter, then the solvent was removed in vacuo. The crude product was purified by flash chromatography (SNAP silica 10 g column, eluent: 0 to 60% (25% EtOH in EtOAc)/cyclohexane). The combined desired fractions were concentrated in vacuo to give tert-butyl 4-(1-(4-(tert-butoxycarbonyl)-6-(methylcarbamoyl)pyridin-2-yl)ethyl)-1H-pyrrolo[2,3-c]pyridine-1-carboxylate (126 mg, 0.236 mmol, 84% yield) as an orange oil.

LCMS (2 min Formic): Rt=0.89 min, [MH]$^+$=481.4.

$^1$H NMR (400 MHz, MeOH-d$_4$) δ ppm 9.22 (s, 1H) 8.37 (s, 1H) 8.33 (d, J=1.2 Hz, 1H) 7.83 (d, J=1.5 Hz, 1H) 7.79 (d, J=3.7 Hz, 1H) 6.73 (d, J=3.7 Hz, 1H) 4.85 (q, J=7.3 Hz, 1H) 3.01 (s, 3H) 1.90 (d, J=7.3 Hz, 3H) 1.66 (s, 9H) 1.54 (s, 9H). Exchangeable proton not observed.

Intermediate 75: (+/−)-2-(1-(1H-Pyrrolo[2,3-c]pyridin-4-yl)ethyl)-6-(methylcarbamoyl)isonicotinic acid

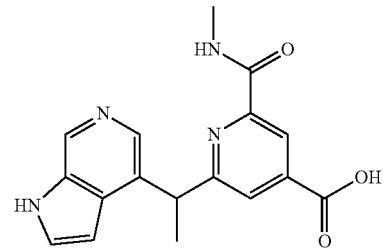 [SMILES: CNC(=O)c1cc(C(=O)O)cc(C(C)c2cncc3[nH]ccc23)n1]

To a solution of tert-butyl 4-(1-(4-(tert-butoxycarbonyl)-6-(methylcarbamoyl)pyridin-2-yl)ethyl)-1H-pyrrolo[2,3-c]pyridine-1-carboxylate (126 mg, 0.262 mmol) in DCM (1 mL) was added 2,2,2-trifluoroacetic acid (1 mL, 12.98 mmol) and the reaction mixture was stirred for 5 h. The solvent was removed in vacuo to give the title compound (110.7 mg, ~75% purity) which was used without purification in the subsequent reaction.

LCMS (2 min Formic): Rt=0.46 min, [MH]$^+$=325.2.

$^1$H NMR (400 MHz, MeOH-d$_4$) δ ppm 8.96 (s, 1H) 8.43 (d, J=1.2 Hz, 1H) 8.36 (s, 1H) 8.11 (d, J=2.9 Hz, 1H) 8.03 (d, J=1.2 Hz, 1H) 6.97 (d, J=2.9 Hz, 1H) 5.06 (q, J=7.3 Hz, 1H) 2.99 (s, 3H) 1.96 (d, J=7.1 Hz, 3H). Exchangeables not observed.

Intermediate 76: 6-(3-Hydroxybenzyl)-N$^2$-methyl-N$^4$-((1S,2S)-2-methylcyclopropyl)pyridine-2,4-dicarboxamide

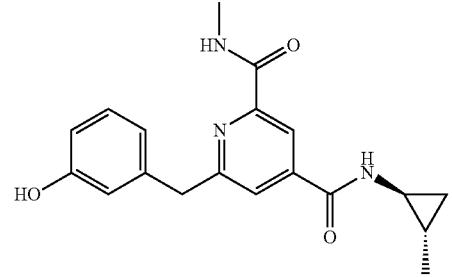 [SMILES: CNC(=O)c1cc(C(=O)N[C@H]2C[C@@H]2C)cc(Cc2cccc(O)c2)n1]

Tribromoborane (0.553 mL, 5.83 mmol) was added dropwise to a solution of 6-(3-methoxybenzyl)-N²-methyl-N⁴-((1S,2S)-2-methylcyclopropyl)pyridine-2,4-dicarboxamide (206 mg, 0.583 mmol) in DCM (4 mL). The reaction mixture was stirred for 10 min after which another equivalent of tribromoborane (0.553 mL, 5.83 mmol) was added. The reaction mixture was left stirring for 30 min after which further tribromoborane (0.553 mL, 5.83 mmol) was added. The reaction mixture was then left to stir for 1 h. The reaction mixture was partitioned between EtOAc and water. The aqueous layer was removed, the organic layer washed (1× water, 2× sat. aq. NaHCO₃), passed through a hydrophobic frit and evaporated in vacuo to a brown oil. The sample was then dissolved in DCM (3 mL) and loaded onto a 25 g Biotage® SNAP column eluting with 20-80% EtOAc/cyclohexane. The product containing fractions were combined and the solvent removed in vacuo. The sample was then dried under a stream of nitrogen for 1 h and was then placed in vacuo at 40° C. for 1 h to afford the desired product (34 mg).

LCMS (2 min Formic): Rt=0.85 min, [MH]⁺=340.4.

Intermediate 77: Benzyl 4-((4-(cyclopropylcarbamoyl)-6-(methylcarbamoyl)pyridin-2-yl)methyl)indoline-1-carboxylate

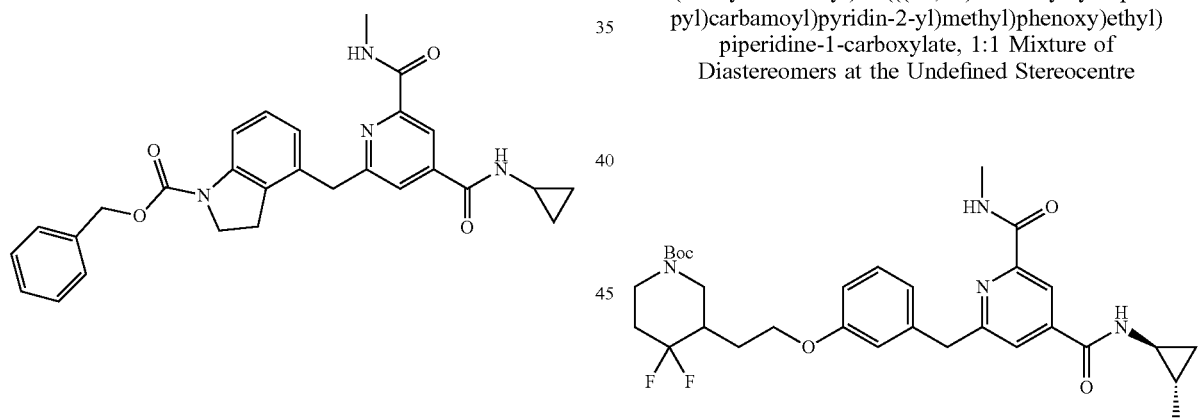

To a solution of 2-((1-((benzyloxy)carbonyl)indolin-4-yl)methyl)-6-(methylcarbamoyl)isonicotinic acid (54.5 mg, 0.098 mmol) in DMF (0.8 mL) was added HATU (55.8 mg, 0.147 mmol) followed by cyclopropanamine (0.014 mL, 0.196 mmol) and DIPEA (0.068 mL, 0.391 mmol). The resulting reaction mixture was stirred at rt over the weekend. The reaction mixture was diluted with DCM then washed with sat. LiCl solution, then 2M HCl. The combined organic phases were dried then concentrated in vacuo to give 256 mg of a brown oil. This was purified by chromatography on SiO₂ (Biotage® SNAP 10 g, eluting with 0-50% ethyl acetate/cyclohexane). The desired fractions were concentrated to give benzyl 4-((4-(cyclopropylcarbamoyl)-6-(methylcarbamoyl)pyridin-2-yl)methyl)indoline-1-carboxylate (31.8 mg, 0.066 mmol, 67.1% yield) as a colourless oil.

LCMS (2 min Formic): Rt=1.17 min, [MH]+ 485.2.

Intermediate 78: 6-(Chloro(pyridin-2-yl)methyl)-N²-methyl-N⁴-((1S,2S)-2-methylcyclopropyl)pyridine-2,4-dicarboxamide. 1:1 Mixture of Diastereomers at the Undefined Stereocentre

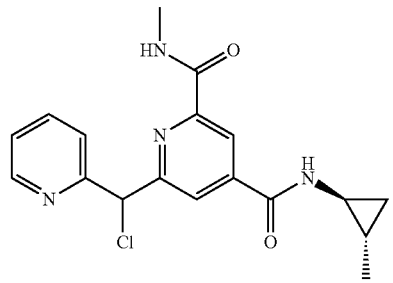 [SMILES: CNC(=O)c1cc(C(=O)N[C@H]2C[C@@H]2C)cc(C(Cl)c2ccccn2)n1]

To a solution of 6-(hydroxy(pyridin-2-yl)methyl)-N²-methyl-N⁴-((1S,2S)-2-methylcyclopropyl)pyridine-2,4-dicarboxamide (19 mg, 0.056 mmol) in DCM (1 mL) at 0° C., was added dropwise thionyl chloride (0.033 mL, 0.447 mmol). The reaction mixture was then stirred at rt for 5 h. The solvent was removed in vacuo to give 6-(chloro(pyridin-2-yl)methyl)-N²-methyl-N⁴-((1 S,2)-2-methylcyclopropyl)pyridine-2,4-dicarboxamide (20 mg, 0.033 mmol, 59.9% yield, ~60% purity) as a colourless oil. This was used without purification in the subsequent reaction.

LCMS (2 min Formic): Rt=0.86 min, [MH]⁺=359.2.

Intermediate 79: tert-Butyl 4,4-difluoro-3-(2-(3-((6-(methylcarbamoyl)-4-(((1S,2S)-2-methylcyclopropyl)carbamoyl)pyridin-2-yl)methyl)phenoxy)ethyl)piperidine-1-carboxylate, 1:1 Mixture of Diastereomers at the Undefined Stereocentre In a microwave vial, 2-(tributylphosphoranylidene)acetonitrile (0.222 mL, 0.848 mmol) was added to a suspension of 6-(3-hydroxybenzyl)-N²-methyl-N⁴-((1S,2S)-2-methylcyclopropyl)pyridine-2,4-dicarboxamide (64.0 mg, 0.188 mmol) and (+/−)-tert-butyl 4,4-difluoro-3-(2-hydroxyethyl)piperidine-1-carboxylate (50 mg, 0.188 mmol) in toluene (4 mL). The reaction mixture was irradiated for 0.5 h at 110° C. The reaction was then irradiated for a further 1 h with the addition of another equivalent of 2-(tributylphosphoranylidene)acetonitrile (0.222 mL, 0.848 mmol) at 120° C. Another equivalent of 2-(tributylphosphoranylidene)acetonitrile (0.222 mL, 0.848 mmol) was added and the reaction mixture was irradiated for 2 h at 120° C. A further equivalent of 2-(tributylphosphoranylidene)acetonitrile (0.222 mL, 0.848 mmol) was added and the reaction irradiated for 1 h at 130° C. The reaction mixture was partitioned between EtOAc and water. The aqueous layer was removed, the organic layer washed (1× water, 2× sat. aq. NaHCO₃), passed through a hydrophobic frit and evaporated in vacuo to a brown oil. The sample was purified using a 10 g Biotage® SNAP column using a gradient of 30-80% EtOAc/cyclohexane. The product containing fractions were combined and the solvent removed in vacuo to a brown oil. The sample was then dried under a stream of nitrogen for 1 h and was further dried in vacuo at 40° C. to afford the desired product (53.9 mg).

LCMS (2 min Formic): Rt=1.33 min, [MH]⁺=587.2.

Intermediate 80: 6-(Hydroxy(1-(phenylsulfonyl)-1H-pyrrolo[3,2-c]pyridin-4-yl)methyl)-N²-methyl-N⁴-((1S,2S)-2-methylcyclopropyl)pyridine-2,4-dicarboxamide, 1:1 Mixture of Diastereomers at the Undefined Stereocentre

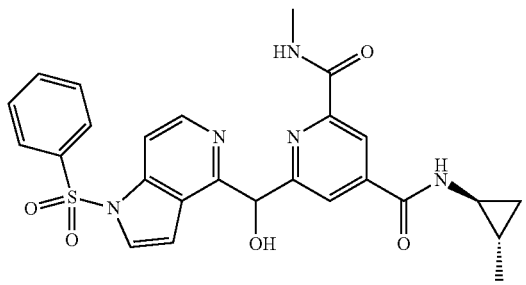 [SMILES: CNC(=O)c1cc(C(=O)N[C@H]2C[C@@H]2C)cc(C(O)c2nccc3c2ccn3S(=O)(=O)c2ccccc2)n1]

To a solution of 2-(hydroxy(1-(phenylsulfonyl)-1H-pyrrolo[3,2-c]pyridin-4-yl)methyl)-6-(methylcarbamoyl)isonicotinic acid (27 mg, 0.021 mmol, 36% wt.) in DMF (0.8 mL) was added DIPEA (0.01 mL, 0.057 mmol) followed by HATU (11.88 mg, 0.031 mmol) and (1S,2S)-2-methylcyclopropanamine, hydrochloride (3.36 mg, 0.031 mmol). The resulting reaction mixture was stirred at rt for 3 h. Further (1S,2S)-2-methylcyclopropanamine, hydrochloride (15 mg, 0.139 mmol), HATU (35 mg, 0.092 mmol) and N-ethyl-N-isopropylpropan-2-amine (0.04 mL, 0.021 mmol) were added and the resultant mixture was stirred for 1 h. The reaction mixture was purified directly by MDAP (high pH). The fractions containing the desired product were concentrated in vacuo to give 6-(hydroxy(1-(phenylsulfonyl)-1H-pyrrolo[3,2-c]pyridin-4-yl)methyl)-N²-methyl-N⁴-((1S,2S)-2-methylcyclopropyl)pyridine-2,4-dicarboxamide (6 mg, 9.82 μmol, 47.1% yield, ~85% purity) as a colourless oil.

LCMS (2 min Formic): Rt=0.78 min, [MH]⁺=520.3.

Intermediate 81: 2-(trans-3-hydroxycyclobutyl)isoindoline-1,3-dione

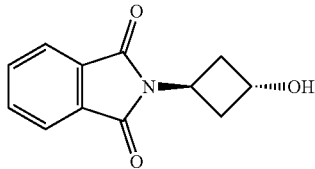 [SMILES: O=C1c2ccccc2C(=O)N1[C@H]1C[C@H](O)C1]

To a mixture of trans-3-aminocyclobutanol hydrochloride (1.0428 g, 8.44 mmol) (commercially available from Activate Scientific) and phthalic anhydride (1.2565 g, 8.48 mmol) in toluene (35 mL) was added triethylamine (2.50 mL, 17.94 mmol). The mixture was stirred and heated at 120° C. for 17 hours. The mixture was allowed to cool to room temperature and the volatiles evaporated in vacuo to give a white solid to which was added ethyl acetate (50 mL) and saturated aqueous sodium bicarbonate (50 mL) and the phases separated. The organic phase was washed with further saturated aqueous sodium bicarbonate (2×50 mL) and filtered through a cartridge fitted with a hydrophobic frit. The filtrate was evaporated in vacuo to give 2-(trans-3-hydroxycyclobutyl)isoindoline-1,3-dione (1.4520 g, 6.68 mmol, 79% yield) as a white solid.

¹H NMR (400 MHz, D6 DMSO) δ ppm 7.83 (s, 4H) 5.12 (d, 1H, J=5.5 Hz) 4.86 (m, 1H) 4.49 (m, 1H) 2.87 (m, 2H) 2.21 (m, 2H).

Intermediate 82: 2-((1r,3r)-3-(2-Hydroxyethoxy)cyclobutyl)isoindoline-1,3-dione

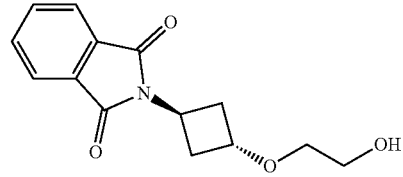 [SMILES: O=C1c2ccccc2C(=O)N1[C@H]1C[C@H](OCCO)C1]

To a stirring solution of 2-((1r,3r)-3-hydroxycyclobutyl)isoindoline-1,3-dione (299.8 mg, 1.380 mmol) and 1,3-dioxolan-2-one (380.4 mg, 4.32 mmol) in DMF (12 mL) at rt was added sodium hydride (60% in mineral oils, 106.7 mg, 2.67 mmol) portionwise. The resulting mixture was heated to 80° C. and stirred for 20.75 h under nitrogen. Further sodium hydride (60% in mineral oils, 56.7 mg, 1.418 mmol) was added after 19.5 h. The reaction mixture was allowed to cool to rt and to it was added water (5 mL) and sat. aqueous NH₄Cl (5 mL) and this mixture stirred at rt for approx. 10 min. To this was added ethyl acetate (20 mL) and the layers separated. The aqueous phase was extracted with further ethyl acetate (3×20 mL). The organic layers were combined and filtered through a cartridge fitted with a hydrophobic frit. The filtrate was evaporated in vacuo to give a brown oil (449.8 mg). This was redissolved in DCM (approx. 2 mL) and directly applied to the top of a 50 g SNAP cartridge and purified by SP4 flash column chromatography. The column was eluted with a gradient of 0%-50% ethyl acetate in cyclohexane. The appropriate fractions were combined and evaporated in vacuo to give a viscous colourless oil (97.1 mg). This was redissolved in DMSO (1 mL) and further purified by MDAP (1 mL injection, formic). The required fraction was evaporated under a stream of nitrogen and the residue dried in vacuo to give the desired product as a viscous colourless oil (54.9 mg, 0.210 mmol, 15% yield).

LCMS (2 min High pH): Rt=0.79 min, does not ionise at correct m/z

Intermediate 83: 2-(trans-3-methoxycyclobutyl)isoindoline-1,3-dionenamine

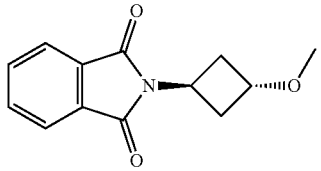 [SMILES: CO[C@H]1C[C@H](N2C(=O)c3ccccc3C2=O)C1]

A solution of 2-(trans-3-hydroxycyclobutyl)isoindoline-1,3-dione (196.3 mg, 0.904 mmol) and methyl iodide (0.085 mL, 1.356 mmol) in tetrahydrofuran (4.5 mL) was stirred at room temperature under nitrogen for approximately 5 minutes. To this mixture was added sodium hydride (60% dispersion in mineral oils) (42.8 mg, 1.070 mmol) portionwise and the resulting cloudy white mixture was stirred at room temperature for 16 hours. The mixture was then heated in a microwave reactor at 60° C. for 30 minutes. Further sodium hydride (60% dispersion in mineral oils) (18.2 mg, 0.455 mmol) was added and the mixture heated in a microwave reactor at 60° C. for a further total of 90 minutes. Further methyl iodide (0.040 mL, 0.640 mmol) was added and the mixture heated in a microwave reactor at 60° C. for a further 30 minutes and then at 70° C. for a further 30 minutes. To the reaction mixture was added water (2 mL) and sat. aqueous ammonium chloride (2 mL) and the mixture was stirred at room temperature for approximately 10 minutes. The phases were separated and the aqueous phase extracted with ethyl acetate (3×4 mL). The organic phases were combined and filtered through a cartridge fitted with a hydrophobic frit. The filtrate was evaporated in vacuo to give a yellow solid which was redissolved in dichloromethane (approximately 3 mL) and directly applied to the top of a 10 g SNAP silica cartridge and was purified by SP4 flash column chromatography. The column was eluted with a gradient of 0-50% ethyl acetate in cyclohexane. The required fractions were combined and evaporated in vacuo to give 2-(trans-3-methoxycyclobutyl)isoindoline-1,3-dione (82.8 mg, 0.358 mmol, 39.6% yield) as a white solid.

$^1$H NMR (400 MHz, CDCl$_3$) δ ppm 7.85 (m, 2H) 7.73 (m, 2H) 5.02 (m, 1H) 4.31 (m, 1H) 3.31 (s, 3H) 2.99 (m, 2H) 2.45 (m, 2H).

Intermediate 84: 2-((1r,3r)-3-Aminocyclobutoxy)ethanol hydrochloride

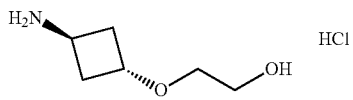

To a solution of 2-((1r,3r)-3-(2-hydroxyethoxy)cyclobutyl)isoindoline-1,3-dione (54.9 mg, 0.21 mmol) in ethanol (2 mL) was added hydrazine hydrate (~80% in water 0.013 mL, 0.268 mmol). The solution was stirred at rt for 49.5 h. Further hydrazine hydrate (80% in water, 0.015 mL, 0.245 mmol) was added after 43 h. The reaction mixture was filtered and the cartridge washed with ethanol (approx. 10 mL). The filtrate was evaporated in vacuo to give a white solid. This was redissolved in methanol (approx. 2 mL) and ethanol (approx. 2 mL) and directly applied to the top of a 2 g Isolute SCX-2 ion exchange column. The column was eluted with ethanol and then 2M aqueous HCl. The acidic fraction was evaporated under a stream of nitrogen and the residue dried in vacuo to give the desired product as a sticky yellow solid (32.8 mg, 0.196 mmol, 93% yield).

$^1$H NMR (400 MHz, DMSO-d) δ ppm 8.17-8.48 (m, 3H) 4.18-4.31 (m, 1H) 3.61-3.77 (m, 1H) 3.48 (t, J=5.3 Hz, 2H) 3.28-3.34 (m, 2H) 2.18-2.38 (m, 4H).

Intermediate 85: tert-Butyl ((1R,5S,6r)-3,3-difluorobicyclo[3.1.0]hexan-6-yl)carbamate

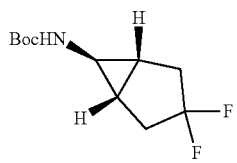 [SMILES: CC(C)(C)OC(=O)N[C@H]1[C@@H]2CC(F)(F)C[C@@H]21]

DPPA (1.462 mL, 6.78 mmol) was added to a solution of (1R,5S,6r)-3,3-difluorobicyclo[3.1.0]hexane-6-carboxylic acid (1 g, 6.17 mmol, commercially available from, for example, Astatech) and Et$_3$N (1.289 mL, 9.25 mmol) in toluene (20 mL) and the solution was stirred for 30 min, then tert-butanol (10 mL) was added and the mixture heated at reflux for 3 h. The mixture was diluted with EtOAc (50 mL) and washed with water (50 mL) and saturated sodium bicarbonate solution, then dried and evaporated in vacuo and the resulting brown gummy solid purified by chromatography on a silica column (25 g) eluting with 0-50% EtOAc/cyclohexane. The product-containing fractions were collected and evaporated in vacuo to give the desired product (0.92 g, 3.94 mmol, 64% yield) as a colourless solid.

$^1$H NMR (400 MHz, CDCl$_3$) δ ppm 4.64 (br. s., 1H) 2.19-2.49 (m, 6H) 1.46 (s, 9H).

Intermediate 86: (1R,5S,6r)-3,3-Difluorobicyclo[3.1.0]hexan-6-amine

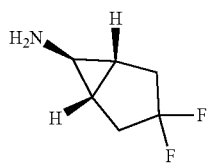

HCl (5 mL, 20.00 mmol, 4M in 1,4-dioxane) was added to a solution of tert-butyl ((1R,5S,6r)-3,3-difluorobicyclo[3.1.0]hexan-6-yl)carbamate (0.92 g, 3.94 mmol) in DCM (10 mL) and the solution was stirred for 3 h at rt, then evaporated in vacuo to give the desired product (620 mg, 3.66 mmol, 93% yield) as a pale yellow solid.

$^1$H NMR (400 MHz, DMSO-d$_6$) δ ppm 8.45 (br. s., 3H) 2.40-2.58 (obs. m, 2H) 2.30 (d, J=2.4 Hz, 1H) 2.16 (ddd, J=18.7, 15.3, 3.2 Hz, 2H) 1.84 (br. s., 2H)

Intermediate 87: tert-Butyl 2-(methylcarbamoyl)-6-(1-phenylvinyl)isonicotinate

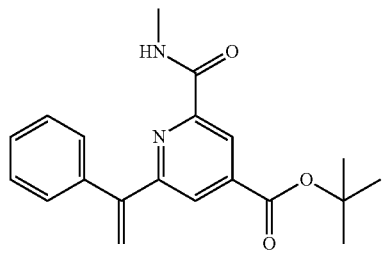 [SMILES: C=C(c1ccccc1)c1cc(C(=O)OC(C)(C)C)cc(C(=O)NC)n1]

(1-Phenylvinyl)boronic acid (2.62 g, 17.73 mmol, commercially available from, for example, Sigma-Aldrich), tert-butyl 2-chloro-6-(methylcarbamoyl)isonicotinate (4 g, 14.78 mmol, commercially available from, for example, Anichem), tripotassium phosphate (9.41 g, 44.3 mmol) and PEPPSI iPr (1.004 g, 1.478 mmol) were dissolved in 1,4-dioxane (24 mL) and water (12 mL) at rt and degassed under nitrogen. The resulting solution was stirred at 70° C. for 2 h. The reaction was cooled to rt, diluted with water (20 mL), extracting with DCM (3×25 mL). The combined organics were passed through a hydrophobic frit and concentrated in vacuo to give a yellow foam. This was purified by flash chromatography on $SiO_2$ (Biotage SNAP 100 g cartridge, eluting with 0-60% ethyl acetate/cyclohexane) to give tert-butyl 2-(methylcarbamoyl)-6-(1-phenylvinyl)isonicotinate (4.06 g, 11.40 mmol, 77% yield, 95% purity) as a pale yellow foam.

LCMS (2 min Formic): Rt=1.35 min, $[MH]^+$=339.2.

Intermediate 88: tert-Butyl 2-(2-hydroxy-1-phenylethyl)-6-(methylcarbamoyl)isonicotinate

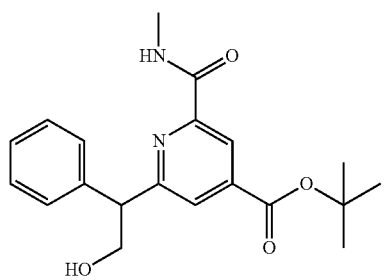 [SMILES: CNC(=O)c1cc(C(=O)OC(C)(C)C)cc(C(CO)c2ccccc2)n1]

(2,3-Dimethylbutan-2-yl)borane (0.66 M in THF, 30.0 mL, 19.80 mmol, preparation of which is described in the literature: For example H. C. Brown and E. Negishi, *J. Am. Chem. Soc.*, 94, 3567 (1972) was added to tert-butyl 2-(methylcarbamoyl)-6-(1-phenylvinyl)isonicotinate (3.94 g, 9.90 mmol) under nitrogen at 0° C. in a round bottomed flask. The reaction mixture was stirred for 1.5 h at rt then water (30 mL) was added, followed by hydrogen peroxide (35% w/w in water, 24.26 mL, 277 mmol) and sodium hydroxide (2M, 24.74 mL, 49.5 mmol) was added at 0° C. The reaction mixture was stirred at 0° C. for 25 min then allowed to warm up. The reaction mixture was then stirred for 2 h. Citric acid (10%, 30 mL) and EtOAc (30 mL) were added. The organic layer was separated and the aqueous layer was extracted with further portions of EtOAc (3×50 mL). The combined organic phases were dried over a hydrophobic frit then concentrated in vacuo. This was purified by chromatography on $SiO_2$ (Biotage SNAP 50 g, eluent 0 to 100% EtOAc/cyclohexane). The combined desired fractions were concentrated in vacuo to give the desired product (1.15 g, 3.07 mmol, 31% yield, 95% purity).

LCMS (2 min Formic): Rt=1.08 min, $[MH]^+$=357.3.

Intermediate 89: (+/−)-tert-Butyl 2-(2-((tert-butyldimethylsilyl)oxy)-1-phenylethyl)-6-(methylcarbamoyl)isonicotinate

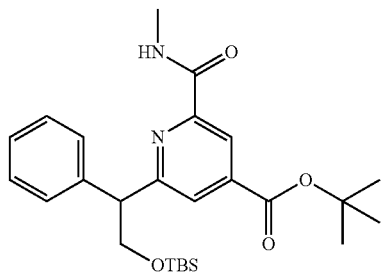 [SMILES: CNC(=O)c1cc(C(=O)OC(C)(C)C)cc(C(CO[Si](C)(C)C(C)(C)C)c2ccccc2)n1]

To a round bottomed flask was added tert-butyl 2-(2-hydroxy-1-phenylethyl)-6-(methylcarbamoyl)isonicotinate (994 mg, 2.79 mmol) which was dissolved in DCM (10 mL) and DIPEA (0.98 mL, 5.61 mmol) was added. Then, tert-butyldimethylsilyl chloride (670 mg, 4.45 mmol) was added slowly with stirring. The reaction mixture was stirred overnight. The reaction was diluted with DCM (10 mL) and washed with water (30 mL). The layers were separated and the aqueous phase was extracted with further portions of DCM (2×20 mL). The combined organic phase was passed over a hydrophobic frit and concentrated in vacuo. The residue was loaded onto a SNAP (50 g) silica column which was eluted using two successive gradients of 0-8% EtOAc in cyclohexane and then 7-40% EtOAc in cyclohexane. The relevant fractions were combined and concentrated in-vacuo to give tert-butyl 2-(2-((tert-butyldimethylsilyl)oxy)-1-phenylethyl)-6-(methylcarbamoyl)isonicotinate (1.29 g, 2.60 mmol, 93% yield) as a colourless oil.

LCMS (2 min Formic): Rt=1.65 min, $[MH]^+$=471.5.

Intermediate 90: (+/−)-2-(2-Hydroxy-1-phenylethyl)-6-(methylcarbamoyl)isonicotinic acid

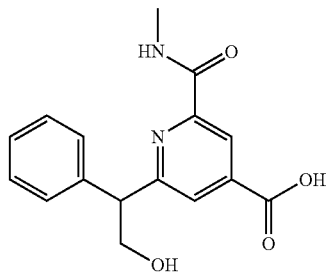 [SMILES: CNC(=O)c1cc(C(=O)O)cc(C(CO)c2ccccc2)n1]

To a solution of tert-butyl 2-(2-((tert-butyldimethylsilyl)oxy)-1-phenylethyl)-6-(methylcarbamoyl)isonicotinate (1.29 g, 2.60 mmol) in DCM (1 mL) was added TFA (3 mL, 38.9 mmol) and reaction mixture was stirred at rt overnight. DCM (5 mL) was added, then the reaction mixture was concentrated in vacuo. Ether (5 mL) was added and the reaction mixture was concentrated in vacuo (×4) to give the crude product as a white foam, which also contains a TFA adduct by-product. THF (5 mL) and a solution of LiOH (1M, 5 mL) were added and the resultant mixture was stirred for 1 h. The reaction mixture was concentrated in vacuo to give 2-(2-hydroxy-1-phenylethyl)-6-(methylcarbamoyl)isonicotinic acid (981 mg, 2.287 mmol, 88% yield, 70% purity) as a white foam.

LCMS (2 min Formic): Rt=0.75 min, [MH]$^+$=301.2.

Intermediate 91: tert-Butyl 2-(3-methoxybenzyl)-6-(methylcarbamoyl)isonicotinate

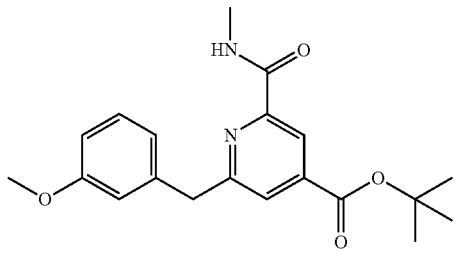 [SMILES: CNC(=O)c1cc(C(=O)OC(C)(C)C)cc(Cc2cccc(OC)c2)n1]

tert-Butyl 2-chloro-6-(methylcarbamoyl)isonicotinate (1.5 g, 5.54 mmol) was dissolved in THF (20 mL) and palladium dichloride bistriphenylphosphine (0.389 g, 0.554 mmol) was added. The solution was sparged with nitrogen for 5 min, then (3-methoxybenzyl)zinc(II) bromide (0.5M in THF, 20 mL, 10.00 mmol) was added and the mixture heated at 70° C. for 2 h. The solution was diluted with EtOAc (100 mL) and washed with water (100 mL), dried and evaporated in vacuo. The residue was purified by chromatography on a 50 g silica column eluting with 0-50% EtOAc/cyclohexane and the product-containing fractions evaporated in vacuo to give tert-butyl 2-(3-methoxybenzyl)-6-(methylcarbamoyl)isonicotinate (1.65 g, 4.63 mmol, 84% yield) as a dark yellow oil.

LCMS (2 min High pH): Rt=1.29 min, [MH]$^+$=357.3.

Intermediate 92: tert-Butyl 2-(1-(3-methoxyphenyl)ethyl)-6-(methylcarbamoyl)isonicotinate

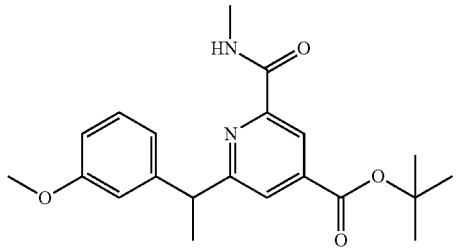 [SMILES: CNC(=O)c1cc(C(=O)OC(C)(C)C)cc(C(C)c2cccc(OC)c2)n1]

tert-Butyl 2-(3-methoxybenzyl)-6-(methylcarbamoyl)isonicotinate (110 mg, 0.31 mmol) and palladium(II) acetate (62.4 mg, 0.28 mmol) were dissolved in THF (1 mL) and cooled to −78° C. in a cardice/acetone bath under N$_2$. LiHMDS (1M in THF, 0.95 mL, 0.950 mmol) was added dropwise and the reaction mixture left to stir for 45 min. MeI (0.03 mL, 0.480 mmol) was added and the resultant mixture was stirred for 2 h. Further MeI (0.01 mL, 0.160 mmol) was added and the resultant mixture was stirred for 1 h. MeI (0.02 mL, 0.320 mmol) was added to the reaction mixture and the resultant mixture was stirred for 1.5 h. Then the solution was allowed to warm up and water (2 mL) was added to give a first batch of reaction mixture.

In a separate flask, tert-butyl 2-(3-methoxybenzyl)-6-(methylcarbamoyl)isonicotinate (39 mg, 0.11 mmol) was dissolved in THF (0.35 mL) and cooled to −78° C. in a cardice/acetone bath under N$_2$. LiHMDS (1M in THF, 0.33 mL, 0.330 mmol) was added dropwise and the reaction mixture left to stir for 45 min (colour change: colourless to yellow to dark green). MeI (0.06 mL, 0.320 mmol, from a stock solution of 0.03 mL MeI in 0.06 mL THF) was added (colour change: dark green to yellow solution) and the resultant mixture was stirred for 1 h to give a second batch of reaction mixture.

The reaction mixtures were combined and extracted with water (10 mL) and EtOAc (3×10 mL). The combined organic phases were dried over a hydrophobic filter then the solvent was removed in vacuo. The crude product was purified by chromatography on SiO$_2$ (Biotage SNAP column (10 g), eluent 0 to 40% ethyl acetate/cyclohexane). The combined desired fractions were concentrated in vacuo to give tert-butyl 2-(1-(3-methoxyphenyl)ethyl)-6-(methylcarbamoyl)isonicotinate (57.3 mg, 0.15 mmol, 32% yield) as an orange oil.

LCMS (2 min Formic): Rt=1.31 min, [MH]$^+$=371.3.

Intermediate 93: (+/−)-2-(1-(3-Hydroxyphenyl)ethyl)-6-(methylcarbamoyl)isonicotinic acid

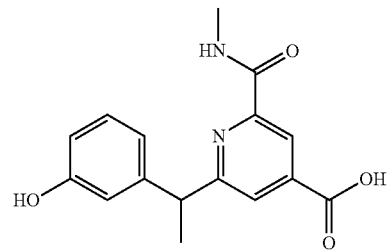 [SMILES: CNC(=O)c1cc(C(=O)O)cc(C(C)c2cccc(O)c2)n1]

tert-Butyl 2-(1-(3-methoxyphenyl)ethyl)-6-(methylcarbamoyl)isonicotinate (950 mg, 1.923 mmol, 75% wt.) was dissolved in DMF (10 mL) and iodocyclohexane (6.3 mL, 48.7 mmol) was added. The resultant reaction mixture was heated to 140° C. for 6 h then stopped. Then heated again at 140° C. for 1 h. The reaction mixture was left to cool to rt and was then partitioned between ethyl acetate (40 mL) and washed (×3) with 5% acetic acid in water (40 mL). The organic layer was separated, then the aqueous layer was extracted three more times. The combined organic layers were dried through a hydrophobic frit and concentrated to give a red oil, 2-(1-(3-hydroxyphenyl)ethyl)-6-(methylcarbamoyl)isonicotinic acid (537 mg, 1.162 mmol, 60% yield, 65% purity).

LCMS (2 min Formic): Rt=0.81 min, [MH]$^+$=301.2.

Intermediate 94: 6-(1-(3-Hydroxyphenyl)ethyl)-N²-methyl-N⁴-((1S,2S)-2-methylcyclopropyl)pyridine-2,4-dicarboxamide, mixture of diastereomers

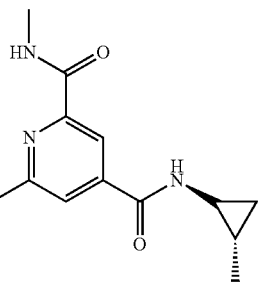

To a solution of 2-(1-(3-hydroxyphenyl)ethyl)-6-(methylcarbamoyl)isonicotinic acid (537 mg, 1.162 mmol, 65% wt.) in DMF (0.7 mL) was added DIPEA (0.61 mL, 3.49 mmol) followed by HATU (663 mg, 1.743 mmol) and (1S,2S)-2-methylcyclopropanamine hydrochloride (188 mg, 1.743 mmol).

The resulting reaction mixture was stirred at rt for 2 h. The reaction mixture was partitioned between sat LiCl (10 mL) and EtOAc (10 mL). The organic layer was separated and the aqueous layer was extracted with further portions of EtOAc. Water (10 mL) was added to the combined organic layers, then the organic layer was separated and the aqueous layer was extracted with further portions of EtOAc (2×10 mL). The combined organic phases were dried over a hydrophobic frit then concentrated in vacuo. The crude product was purified by silica flash column (10 g) chromatography, eluting with 40-100% EtOAc/cyclohexane. The fractions containing the desired product were concentrated in vacuo to give 6-(1-(3-hydroxyphenyl)ethyl)-1M-methyl-N⁴-((1S,2S)-2-methylcyclopropyl)pyridine-2,4-dicarboxamide (425 mg, 0.842 mmol, 72% yield, 70% purity) as a yellow oil.

LCMS (2 min Formic): Rt=0.91 min, [MH]⁺=354.3.

Intermediate 95: tert-Butyl 2-(1H-indole-4-carbonyl)-6-(methylcarbamoyl)isonicotinate

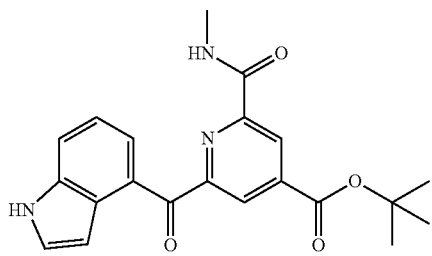 [SMILES: CNC(=O)c1cc(C(=O)OC(C)(C)C)cc(C(=O)c2cccc3[nH]ccc23)n1]

tert-Butyl 2-chloro-6-(methylcarbamoyl)isonicotinate (1 g, 3.69 mmol, commercially available, from, for example Anichem), cesium carbonate (2.407 g, 7.39 mmol), palladium(II) acetate (0.050 g, 0.222 mmol) and 1,3-dimesityl-1H-imidazol-3-ium chloride (0.151 g, 0.443 mmol) were added to a steel Parr vessel, which was purged with nitrogen, then 1,4-dioxane (10 mL) was added and the mixture was heated to 80° C. under 4 bar of nitrogen pressure. The vessel was cooled to 20° C. and vented, then the top was removed and (1H-indol-4-yl)boronic acid (0.714 g, 4.43 mmol) was added, the vessel was sealed and charged with carbon monoxide to 4 bar and heated at 120° C. overnight. The vessel was vented and purged with nitrogen three times, then the mixture was evaporated in vacuo and the residue partitioned between water (20 mL) and EtOAc (2×20 mL). The combined organics were dried and evaporated in vacuo and the residue purified by chromatography on a 50 g SNAP ultra column eluting with 0-100% EtOAc/cyclohexane. The product-containing fractions were evaporated in vacuo to give tert-butyl 2-(1H-indole-4-carbonyl)-6-(methylcarbamoyl)isonicotinate (45 mg, 0.119 mmol, 3% yield) as a yellow gum.

LCMS (2 min High pH): Rt=1.15 min, [MH]⁺=380.4

Also isolated was tert-butyl 2-(1H-indol-4-yl)-6-(methylcarbamoyl)isonicotinate (165 mg, 0.470 mmol, 13% yield) as a yellow glass.

Intermediate 96: (+/−)-tert-Butyl 2-(hydroxy(1H-indol-4-yl)methyl)-6-(methylcarbamoyl)isonicotinate

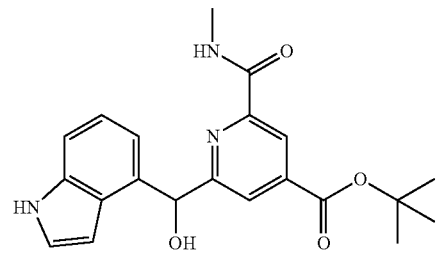 [SMILES: CNC(=O)c1cc(C(=O)OC(C)(C)C)cc(C(O)c2cccc3[nH]ccc23)n1]

tert-Butyl 2-(1H-indole-4-carbonyl)-6-(methylcarbamoyl)isonicotinate (40 mg, 0.105 mmol) was taken up in ethanol (1 mL) and the reaction purged with nitrogen for 30 min. NaBH₄ (4.39 mg, 0.116 mmol) in ethanol (1 mL) was added to the reaction at 0° C. and left to stir warming to rt for 1 h. The reaction was quenched with saturated Rochelle salt solution (10 mL) and left to stir for a further 10 min. The reaction was extracted using DCM (3×15 mL) and the organic phase filtered through a hydrophobic frit and concentrated in vacuo to afford the desired product, tert-butyl 2-(hydroxy(1H-indol-4-yl)methyl)-6-(methylcarbamoyl)isonicotinate (40 mg, 0.105 mmol, 99% yield).

LCMS (2 min High pH): Rt=1.02 min, [MH]⁺=382.4

Intermediate 97: (+/−)-2-(Hydroxy(1H-indol-4-yl)methyl)-6-(methylcarbamoyl)isonicotinic acid

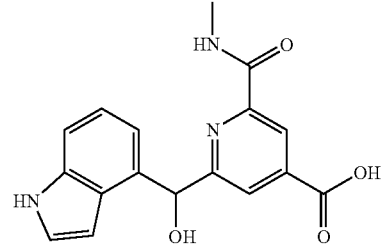 [SMILES: CNC(=O)c1cc(C(=O)O)cc(C(O)c2cccc3[nH]ccc23)n1]

tert-Butyl 2-(hydroxy(1H-indol-4-yl)methyl)-6-(methylcarbamoyl)isonicotinate (40 mg, 0.105 mmol) was taken up in methanol (1 mL) and THF (1 mL). NaOH (0.524 mL, 1.049 mmol, 2M) was added and the reaction left to stir at rt for 1 h. The reaction was concentrated in vacuo. The residue was taken up in water (5 mL) and acidified to pH 2 using 2M HCl. The precipitate was filtered off and retained. The aqueous filtrate was investigated and found to have the desired product present. The filtrate was concentrated in vacuo. The residues were combined and concentrated in vacuo. The residue was taken up in ethyl acetate (15 mL) and washed with water (15 mL). The organic phase was dried over sodium sulphate, filtered through a hydrophobic frit and concentrated in vacuo. to afford 2-(hydroxy(1H-indol-4-yl)methyl)-6-(methylcarbamoyl)isonicotinic acid (15 mg, 0.046 mmol, 44% yield).

LCMS (2 min High pH): Rt=0.47 min, [MH]$^+$=326.2

Intermediate 98: $N^4$-Cyclopropyl-6-(3-hydroxybenzyl)-$N^2$-methylpyridine-2,4-dicarboxamide

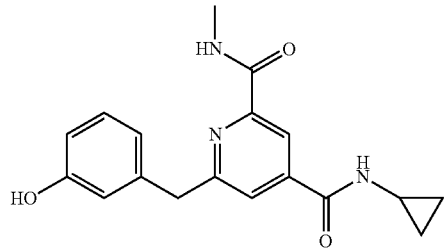 [SMILES: CNC(=O)c1cc(C(=O)NC2CC2)cc(Cc2cccc(O)c2)n1]

$N^4$-Cyclopropyl-6-(3-methoxybenzyl)-$N^2$-methylpyridine-2,4-dicarboxamide (100 mg, 0.295 mmol, example 12) was taken up in DCM (2 mL). The reaction was cooled to 0° C. before BBr$_3$ (0.295 mL, 0.295 mmol, 1M in DCM) was added. The reaction was left to stir for 1 h. Further BBr$_3$ (3 eq.) was added and the reaction left to stir for a further 1 h. The reaction was quenched with water and left to stir for 15 min, before being taken up in DCM (10 mL) and then washed with water (3×15 mL). The organic phase was dried over sodium sulphate, filtered through a hydrophobic frit and concentrated in vacuo to afford $N^4$-cyclopropyl-6-(3-hydroxybenzyl)-$N^2$-methylpyridine-2,4-dicarboxamide (40 mg, 0.123 mmol, 42% yield).

LCMS (2 min Formic): Rt=0.76 min, [MH]$^+$=326.3

Intermediate 99: (1-(tert-Butoxycarbonyl)-1H-pyrrolo[2,3-b]pyridin-4-yl)boronic acid

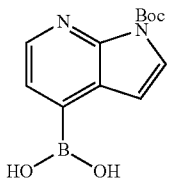

To a stirred solution of tert-butyl 4-bromo-1H-pyrrolo[2,3-b]pyridine-1-carboxylate (340 mg, 0.973 mmol, 85% wt.), potassium acetate (432 mg, 4.40 mmol) and PdCl$_2$(dppf) (215 mg, 0.294 mmol) in 1,4-dioxane (2.5 mL) was added 4,4,4',4',5,5,5',5'-octamethyl-2,2'-bi(1,3,2-dioxaborolane) (745 mg, 2.93 mmol). The reaction mixture was purged with N$_2$ and stirred at 100° C. for 20 hours. The reaction mixture was partitioned between EtOAc (15 mL) and water (15 mL). The layers were separated and the aqueous layer was extracted with further portions of EtOAc (15×2 mL). The combined organic phases were dried (hydrophobic frit) then concentrated in vacuo to give (1-(tert-butoxycarbonyl)-1H-pyrrolo[2,3-b]pyridin-4-yl)boronic acid (204 mg, 0.195 mmol, 20.01% yield, ~25% purity) as a black oil.

LCMS (2 min Formic): Rt=0.77 min, [MH]$^+$=263.3.

Intermediate 100: tert-Butyl 4-((4-(tert-butoxycarbonyl)-6-(methylcarbamoyl)pyridin-2-yl)methyl)-1H-pyrrolo[2,3-b]pyridine-1-carboxylate

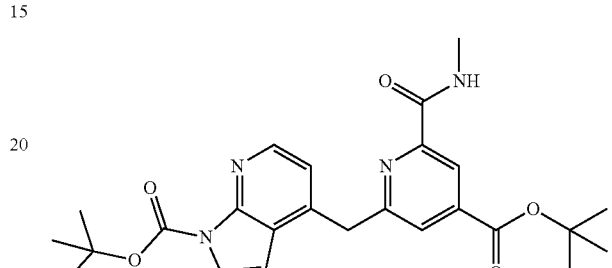

Potassium carbonate (65.5 mg, 0.474 mmol) was combined with tert-butyl 4-(4,4,5,5-tetramethyl-1,3,2-dioxaborolan-2-yl)-H-pyrrolo[2,3-b]pyridine-1-carboxylate (204 mg, 0.148 mmol, 25% wt.), PdCl$_2$(dppf) (23.13 mg, 0.032 mmol) and tert-butyl 2-(chloromethyl)-6-(methylcarbamoyl)isonicotinate (50 mg, 0.158 mmol, 90% wt.) in 1,4-dioxane (1 mL) and water (0.5 mL). This was heated at 100° C. for 30 minutes in a microwave vial. The reaction mixture was partioned between water (10 mL) and EtOAc (10 mL). The organic layer was separated and the aqueous layer was extracted with further portions of EtOAc (3×10 mL). The combined organic phases were dried (hydrophobic frit) then concentrated in vacuo. This was purified by MDAP (high pH). The combined desired fractions were concentrated in vacuo to give tert-butyl 4-((4-(tert-butoxycarbonyl)-6-(methylcarbamoyl)pyridin-2-yl)methyl)-1H-pyrrolo[2,3-b]pyridine-1-carboxylate (15 mg, 0.024 mmol, 15.26% yield, ~75% purity) as yellow oil.

LCMS (2 min Formic): Rt=1.28 min, [MH]$^+$=467.4.

Intermediate 101: tert-Butyl 2-(methylcarbamoyl)-6-((1-tosyl-1H-pyrrolo[2,3-b]pyridin-4-yl)methyl)isonicotinate

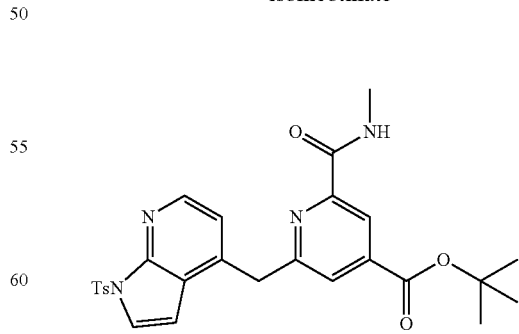

To a mixture of potassium carbonate (1182.9 mg, 8.56 mmol), tert-butyl 2-(chloromethyl)-6-(methylcarbamoyl) isonicotinate (824.7 mg, 2.90 mmol) and PdCl$_2$(dppf)-CH$_2$Cl$_2$ adduct (239 mg, 0.293 mmol) and 4-(4,4,5,5-tetramethyl-1,3,2-dioxaborolan-2-yl)-1-tosyl-1H-pyrrolo[2,3-b]pyridine (1239.3 mg, 3.11 mmol, commercially available from, for example, Peakdale) in a microwave vial was added 1,4-dioxane (6 mL). Water (3 mL) was added to the mixture, the mixture was de-gassed with nitrogen, re-sealed and the mixture heated at 90° C. for 30 min in a microwave reactor. The mixture was diluted with ethyl acetate (20 mL) and filtered through a 2.5 g Celite cartridge. The cartridge was washed through with further ethyl acetate (2×20 mL) and the combined organics were washed with water (60 mL). The organic phase was washed with further water (60 mL) and saturated brine (20 mL), the phases were separated and the organic phase dried by filtration through a cartridge fitted with a hydrophobic frit. The solvent was evaporated from the organic phase in vacuo to give a golden brown crunchy foam which was redissolved in dichloromethane (ca. ~6 mL) and was purified by SP4 flash column chromatography (100 g Silica cartridge) eluting with a gradient of 10-60% ethyl acetate in cyclohexane. The required fractions were combined, the solvent was evaporated in vacuo, the residue was dissolved in DCM, transferred to a tarred vial then dried under a stream of nitrogen before being dried in vacuo to give the desired product as a crunchy yellow foam; tert-butyl 2-(methylcarbamoyl)-6-((1-tosyl-1H-pyrrolo[2,3-b]pyridin-4-yl)methyl)isonicotinate (1.055 g, 2.027 mmol, 70% yield).

LCMS (2 min Formic): Rt=1.31 min, [MH]$^+$=521.3.

$^1$H NMR (400 MHz, DMSO-d$_6$) δ ppm 8.68 (q, J=4.2 Hz, 1H) 8.29 (d, J=4.9 Hz, 1H) 8.17 (d, J=1.5 Hz, 1H) 7.99 (d, J=8.3 Hz, 2H) 7.85-7.92 (m, 2H) 7.40 (d, J=8.1 Hz, 2H) 7.27 (d, J=4.9 Hz, 1H) 7.09 (d, J=4.2 Hz, 1H) 4.52 (s, 2H) 2.85 (d, J=4.9 Hz, 3H) 2.33 (s, 3H) 1.53 (s, 9H)

Intermediate 102: (+/−)-tert-Butyl 2-(1-(1H-pyrrolo[2,3-b]pyridin-4-yl)ethyl)-6-(methylcarbamoyl)isonicotinate

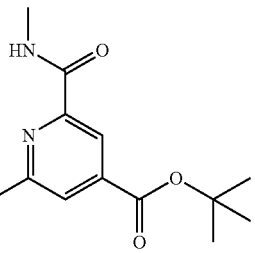

tert-Butyl 4-((4-(tert-butoxycarbonyl)-6-(methylcarbamoyl)pyridin-2-yl)methyl)-1-pyrrolo[2,3-b]pyridine-1-carboxylate (110 mg, 0.189 mmol, 80% wt.) was dissolved in THF (1 mL) and cooled to −78° C. in a cardice/acetone bath under N$_2$. LiHMDS (0.75 mL, 0.750 mmol, 1M in THF) was added dropwise and the reaction mixture left to stir for 45 min. MeI (0.02 mL, 0.320 mmol) was added and the resultant mixture was stirred for 30 min. Water (1 mL) was added and the reaction mixture was allowed to warm up. The reaction mixture was partitioned between water (10 mL) and EtOAc (10 mL). The organic layer was separated and the aqueous layer was extracted with further portions of EtOAc (3×10 mL). The combined organic phases were dried over a hydrophobic frit and then concentrated in vacuo. The crude product was purified on a SNAP silica column (10 g) eluting with 0-70% EtOAc/cyclohexane, then 0 to 50% (25% EtOH in EtOAc)/cyclohexane. The combined desired fractions were concentrated in vacuo to give tert-butyl 2-(1-(1H-pyrrolo[2,3-b]pyridin-4-yl)ethyl)-6-(methylcarbamoyl)isonicotinate (20 mg, 0.021 mmol, 11% yield, 40% wt.) as a yellow oil.

LCMS (2 min Formic): Rt=0.90 min, [MH]$^+$=381.4

Intermediate 103: (+/−)-2-(1-(1H-Pyrrolo[2,3-b]pyridin-4-yl)ethyl)-6-(methylcarbamoyl)isonicotinic acid

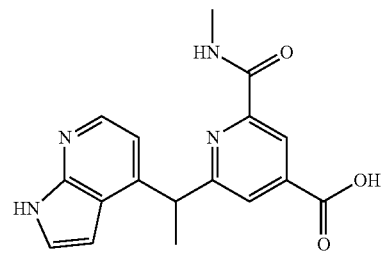 [SMILES: CNC(=O)c1cc(C(=O)O)cc(C(C)c2ccnc3[nH]ccc23)n1]

To a solution of tert-butyl 4-((4-(tert-butoxycarbonyl)-6-(methylcarbamoyl)pyridin-2-yl)methyl)-1H-pyrrolo[2,3-b]pyridine-1-carboxylate (20 mg, 0.021 mmol, 40% wt) in DCM (1 mL) was added TFA (0.5 mL, 6.49 mmol) and reaction mixture was stirred at rt for 3 h. DCM (5 mL) was added, then the reaction mixture was concentrated in vacuo. Ether (5 mL) was added and the reaction mixture was concentrated in vacuo (×4) to give 2-(1-(1H-pyrrolo[2,3-b]pyridin-4-yl)ethyl)-6-(methylcarbamoyl)isonicotinic acid (14 mg, 0.015 mmol, 72% yield, 35% purity) as a yellow oil which was used without further purification.

LCMS (2 min Formic): Rt=0.56 min, [MH]$^+$=325.2

Intermediate 104: tert-Butyl 2-(2-hydroxy-1-phenylpropyl)-6-(methylcarbamoyl)isonicotinate

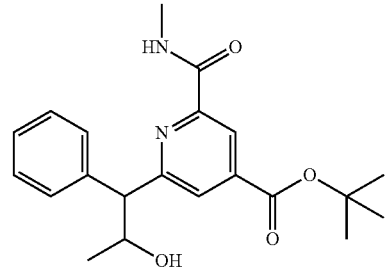 [SMILES: CNC(=O)c1cc(C(=O)OC(C)(C)C)cc(C(c2ccccc2)C(C)O)n1]

tert-Butyl 2-benzyl-6-(methylcarbamoyl)isonicotinate (375 mg, 1.149 mmol) was dissolved in tetrahydrofuran (1 mL) and cooled to −78° C. in a cardice/acetone bath under N$_2$. LiHMDS (1 M in THF, 4.60 mL, 4.60 mmol) was added dropwise and reaction mixture left to stir for 30 min. Acetaldehyde (0.2 mL, 3.54 mmol) was added and the resultant mixture was stirred for 3 hours at −78° C. Then the reaction was allowed to warm up and when the reaction mixture was at rt the reaction mixture was quenched with water (1 mL). The reaction mixture was partitioned between EtOAc and water.

The organic layer was separated then the aqueous layer was extracted three more times. The combined organic layer was dried (hydrophobic frit) and concentrated to give an orange oil. This was purified on a SNAP column 10 g, eluent 0-40% EtOAc/cyclohexane. The combined desired fractions were concentrated in vacuo to give tert-butyl 2-(2-hydroxy-1-phenylpropyl)-6-(methylcarbamoyl)isonicotinate (293 mg, 0.554 mmol, 48.2% yield, ~70% purity) as a yellow oil.

LCMS (2 min Formic): Rt=1.10 min, [MH]$^+$=371.3.

Intermediate 105: 2-(2-Hydroxy-1-phenylpropyl)-6-(methylcarbamoyl)isonicotinic acid

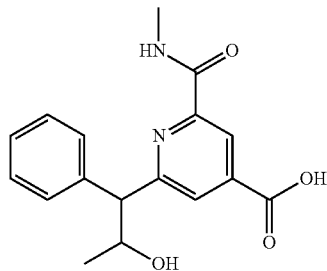 [SMILES: CNC(=O)c1cc(C(=O)O)cc(C(c2ccccc2)C(C)O)n1]

To a solution of tert-butyl 2-(2-hydroxy-1-phenylpropyl)-6-(methylcarbamoyl)isonicotinate (293 mg, 0.554 mmol, 70% wt.) in dichloromethane (2 mL) was added TFA (0.8 mL, 10.38 mmol) and reaction mixture was stirred for 3 hours. The reaction mixture was concentrated in vacuo then ether (5 mL) was added and the reaction mixture was concentrated in vacuo (four times) to give 2-(2-hydroxy-1-phenylpropyl)-6-(methylcarbamoyl)isonicotinic acid (318 mg, 0.405 mmol, 73.1% yield, ~40% purity) as a yellow oil.

LCMS (2 min Formic): Rt=0.76 min, [MH]$^+$=315.2.

Intermediate 106: tert-Butyl 2-(methylcarbamoyl)-6-vinylisonicotinate

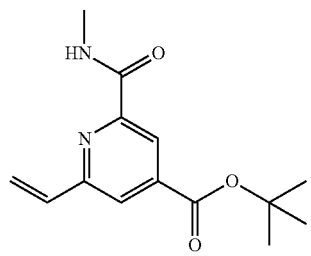 [SMILES: C=Cc1cc(C(=O)OC(C)(C)C)cc(C(=O)NC)n1]

A suspension of tert-butyl 2-chloro-6-(methylcarbamoyl) isonicotinate (0.8010 g, 2.96 mmol, commercially available from, for example, Anichem), 2,4,6-trivinylcyclotriboroxane pyridine complex (1.0627 g, 4.42 mmol), [1,1'-bis (diphenylphosphino)ferrocene]dichloropalladium(II) (0.1040 g, 0.142 mmol) and potassium carbonate (1.2526 g, 9.06 mmol) in ethanol (5.0 mL) and toluene (5.0 mL) in a sealed microwave vial was heated in a microwave reactor at 120° C. for 40 minutes. The vial was resealed and the mixture heated in a microwave reactor for a further 20 minutes. The reaction mixture was filtered through a 10 g Celite® cartridge and the cartridge washed with ethyl acetate (approx 30 mL). The filtrate was evaporated in vacuo to give a viscous dark red oil. This was redissolved in dichloromethane (approx 3 mL) and directly applied to the top of a 50 g SNAP cartridge and purified by flash column chromatography, eluent 0-40% ethyl acetate/cyclohexane. The appropriate fractions were combined and evaporated in vacuo to give a viscous dark brown oil. This was redissolved in dichloromethane (approx 3 mL) and directly applied to the top of a 50 g SNAP cartridge and further purified by flash column chromatography, eluent 15-40% ethyl acetate/cyclohexane. The appropriate fractions were combined and evaporated in vacuo to give tert-butyl 2-(methylcarbamoyl)-6-vinylisonicotinate (738.1 mg, 2.81 mmol, 95% yield) as a viscous light yellow oil.

LCMS (2 min High pH): Rt=1.14 min, [MH]$^+$=263.3.

Intermediate 107: tert-Butyl 2-(1-bromovinyl)-6-(methylcarbamoyl)isonicotinate

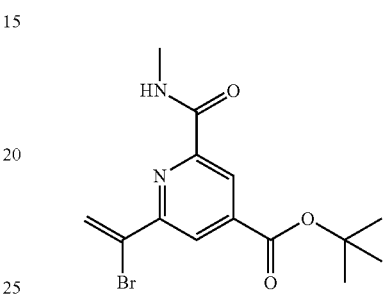

Bromine (0.11 mL, 2.147 mmol) was added to tert-butyl 2-(methylcarbamoyl)-6-vinylisonicotinate (400 mg, 1.525 mmol) in dichloromethane (3 mL). The resulting solution was stirred at rt for 2 h. The solvent was removed in vacuo then EtOH (4 mL) at 50° C. and KOH (171 mg, 3.05 mmol) were added and the reaction mixture was stirred for 2 min. The reaction mixture was partioned between water (10 mL), brine (2 mL) and EtOAc (10 mL). The organic layer was separated and the aqueous layer was extracted with further portions of EtOAc (2×10 mL). The combined organic phases were dried (hydrophobic frit) then concentrated in vacuo to give tert-butyl 2-(1-bromovinyl)-6-(methylcarbamoyl)isonicotinate (600 mg, 1.495 mmol, 98% yield, ~85% purity).

LCMS (2 min Formic): Rt=1.27 min, [MH]$^+$=341.1, 343.0.

Intermediate 108: (+/−)-tert-Butyl 2-(hydroxy(o-tolyl)methyl)-6-(methylcarbamoyl)isonicotinate

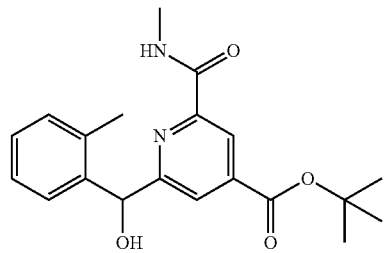 [SMILES: CNC(=O)c1cc(C(=O)OC(C)(C)C)cc(C(O)c2ccccc2C)n1]

o-Tolylmagnesium bromide (2M in ether, 4.73 mL, 9.46 mmol) was added to a solution of tert-butyl 2-formyl-6-(methylcarbamoyl)isonicotinate (1000 mg, 3.78 mmol) in THF at −78° C. and the mixture was stirred for 30 min at −78° C., then allowed to warm to rt. Ammonium chloride solution (5 mL) was added dropwise, then the mixture was diluted with water (20 mL) and extracted with EtOAc (2×20 mL). The combined organics were washed with brine, dried and evaporated in vacuo. The crude product was purified by chromatography on a 50 g silica column eluting with 0-100% EtOAc/cyclohexane and the product-containing fractions were evaporated in vacuo to give (+/−)-tert-butyl 2-(hydroxy(o-tolyl)methyl)-6-(methylcarbamoyl)isonicotinate (80 wt % purity, 0.74 g, 1.66 mmol, 44% yield) as a colourless gum.

LCMS (2 min High pH): Rt=1.14. min, [MH]⁺=357.3.

Intermediate 109: (+/−)-2-(Hydroxy(o-tolyl)methyl)-6-(methylcarbamoyl)isonicotinic acid

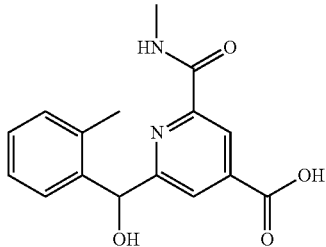 [SMILES: CNC(=O)c1cc(C(=O)O)cc(C(O)c2ccccc2C)n1]

NaOH (2M, 2.491 mL, 4.98 mmol) was added to a solution of (+/−)-tert-butyl 2-(hydroxy(o-tolyl)methyl)-6-(methylcarbamoyl)isonicotinate (80 wt %, 0.74 g, 1.66 mmol) in methanol (10 mL) at rt and the solution was stirred for 2 h, then evaporated in vacuo and the residue partitioned between water (20 mL) and ether (20 mL). The aqueous layer was acidified with 2M HCl to pH 4, then extracted with EtOAc (2×20 mL). The mixture included solid at the interface, which was collected by filtration, washed with EtOAc and dried in the vacuum oven to give (+/−)-2-(hydroxy(o-tolyl)methyl)-6-(methylcarbamoyl)isonicotinic acid (220 mg, 0.73 mmol, 44% yield) as a colourless solid.

LCMS (2 min High pH): Rt=0.54 min, [MH]⁺=301.2.

Intermediate 110: 4-Bromo-1-(phenylsulfonyl)-1H-pyrrolo[2,3-c]pyridine

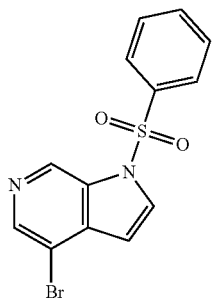 [SMILES: O=S(=O)(c1ccccc1)n1ccc2c(Br)cncc21]

To a suspension of 4-bromo-1H-pyrrolo[2,3-c]pyridine (310 mg, 1.573 mmol, commercially available from, for example, Aldrich) in THF (10 mL) under nitrogen at 0° C. was added sodium hydride (94 mg, 2.360 mmol). The reaction mixture was stirred for 20 min at rt, then cooled to 0° C. and benzenesulfonyl chloride (0.27 mL, 1.573 mmol) was added slowly. The mixture was stirred at 0° C. for 3 hours. Water (2 mL) was added and this was extracted with EtOAc three times. This was dried (magnesium sulfate) then concentrated in vacuo to give 4-bromo-1-(phenylsulfonyl)-1H-pyrrolo[2,3-c]pyridine (600 mg, 1.548 mmol, 98% yield, ~87% purity) a white solid.

LCMS (2 min Formic): Rt=1.15 min, [MH]⁺=337.0, 339.0.

Intermediate 111: (1-(Phenylsulfonyl)-1H-pyrrolo[2,3-c]pyridin-4-yl)boronic acid

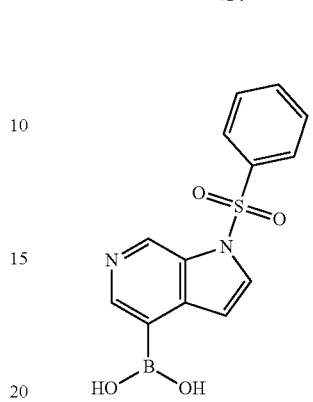

To a stirred solution of 4,4,4',4',5,5,5',5'-octamethyl-2,2'-bi(1,3,2-dioxaborolane) (2.4 g, 9.45 mmol), potassium acetate (2.140 g, 21.81 mmol) and PdCl₂(dppf) (1.064 g, 1.454 mmol) in dioxane was added 4-bromo-1-(phenylsulfonyl)-1H-pyrrolo[2,3-c]pyridine (2.58 g, 7.27 mmol). The reaction mixture was purged with N₂ and stirred at 100° C. for 20 hours. The reaction mixture was filtered through Celite® (eluent EtOAc). The liquid obtained was partitioned between EtOAc (10 mL) and water (10 mL). The organic phase was separated and the aqueous phase was extracted with EtOAc (2×10 mL). The combined organic phases were dried (hydrophobic frit) then concentrated in vacuo to give (1-(phenylsulfonyl)-1H-pyrrolo[2,3-c]pyridin-4-yl)boronic acid (4.58 g, 6.06 mmol, 83% yield, ~40% purity) as a black oil.

LCMS (2 min Formic): Rt=0.53 min, [MH]⁺=303.0.

Intermediate 112: tert-Butyl 2-(methylcarbamoyl)-6-(1-(1-(phenylsulfonyl)-1H-pyrrolo[2,3-c]pyridin-4-yl)vinyl)isonicotinate

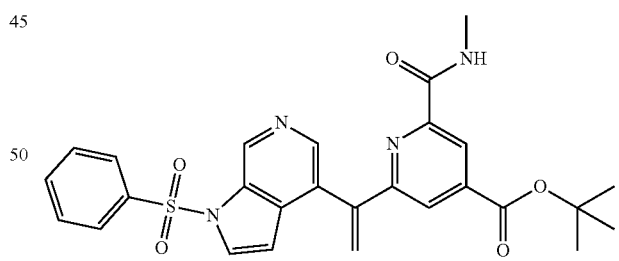

A mixture of tert-butyl 2-(1-bromovinyl)-6-(methylcarbamoyl)isonicotinate (600 mg, 1.495 mmol, 85% wt.), (1-(phenylsulfonyl)-1H-pyrrolo[2,3-c]pyridin-4-yl)boronic acid (2258 mg, 2.99 mmol, 40% wt.), Chloro(2-dicyclohexylphosphino-2',4',6'-triisopropyl-1,1'-biphenyl)[2-(2'-amino-1,1'-biphenyl)]palladium(II) (51.7 mg, 0.066 mmol) and tripotassium phosphate (952 mg, 4.48 mmol) in water (4 mL) and 1,4-dioxane (8 mL) was stirred at 50° C. for 20 hours. The reaction mixture was filtered through Celite® (eluent EtOAc). Water (10 mL) was added and the organic phase was separated. The aqueous phase was extracted with further portions of EtOAc (2×20 mL). The combined organic phases were concentrated in vacuo. This was purified by chromatography on SiO$_2$ (Biotage SNAP 25 g cartridge, eluting with 0-100% ethyl acetate/cyclohexane). The combined desired fractions were concentrated in vacuo to give tert-butyl 2-(methylcarbamoyl)-6-(1-(1-(phenylsulfonyl)-1H-pyrrolo[2,3-c]pyridin-4-yl)vinyl)isonicotinate (340 mg, 0.459 mmol, 30.7% yield, ~70% purity) as a green oil.

LCMS (2 min Formic): Rt=1.11 min, [MH]$^+$=519.3.

Intermediate 113: 2-(Methylcarbamoyl)-6-(1-(1-(phenylsulfonyl)-1H-pyrrolo[2,3-c]pyridin-4-yl)vinyl)isonicotinic acid

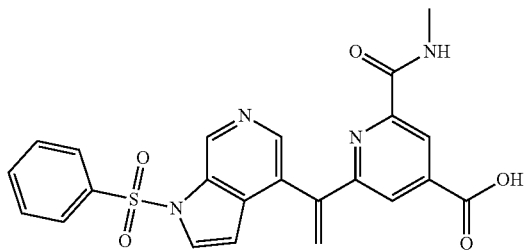 [SMILES: C=C(c1cc(C(=O)O)cc(C(=O)NC)n1)c1cncc2c1ccn2S(=O)(=O)c1ccccc1]

To a solution of tert-butyl 2-(methylcarbamoyl)-6-(1-(1-(phenylsulfonyl)-1H-pyrrolo[2,3-c]pyridin-4-yl)vinyl)isonicotinate (340 mg, 0.459 mmol, 70% wt.) in dichloromethane (1 mL) was added TFA (1 mL, 12.98 mmol) and reaction mixture was stirred at rt overnight. The reaction mixture was concentrated in vacuo then DCM (5 mL) was added and the reaction mixture was concentrated in vacuo. Ether (5 mL) was added and the reaction mixture was concentrated in vacuo four times to give 2-(methylcarbamoyl)-6-(1-(1-(phenylsulfonyl)-1H-pyrrolo[2,3-c]pyridin-4-yl)vinyl)isonicotinic acid (496 mg, 0.429 mmol, 93% yield, ~40% purity) as a yellow oil.

LCMS (2 min Formic): Rt=0.78 min, [MH]$^+$=463.2.

Intermediate 114: N$^2$-Methyl-N$^4$-((1S,2S)-2-methylcyclopropyl)-6-(1-(1-(phenylsulfonyl)-1H-pyrrolo[2,3-c]pyridin-4-yl)vinyl)pyridine-2,4-dicarboxamide

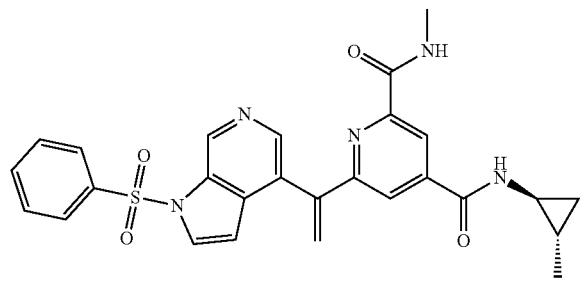 [SMILES: C=C(c1cc(C(=O)N[C@H]2C[C@@H]2C)cc(C(=O)NC)n1)c1cncc2c1ccn2S(=O)(=O)c1ccccc1]

To a solution of 2-(methylcarbamoyl)-6-(1-(1-(phenylsulfonyl)-1H-pyrrolo[2,3-c]pyridin-4-yl)vinyl)isonicotinic acid (496 mg, 0.429 mmol, 40% wt.) in N,N-dimethylformamide (0.7 mL) was added DIPEA (0.17 mL, 0.973 mmol) followed by HATU (245 mg, 0.643 mmol) and (1S,2S)-2-methylcyclopropanamine hydrochloride (69.2 mg, 0.643 mmol). The resulting reaction mixture was stirred at rt for 2 hours. The reaction mixture was partioned between sat. LiCl (10 mL) and EtOAc (10 mL). The organic layer was separated and the aqueous layer was extracted with further portions of EtOAc. Water (10 mL) was added to the combined organic layers then the organic layer was separated and the aqueous layer was extracted with further portions of EtOAc (2×10 mL). The combined organic phases was dried (hydrophobic frit) then concentrated in vacuo. This was purified by silica gel column 25 g, eluent 40-100% EtOAc/cyclohexane. The appropriate fractions were concentrated in vacuo to give N$^4$-methyl-N$^4$-((1S,2S)-2-methylcyclopropyl)-6-(1-(1-(phenylsulfonyl)-1H-pyrrolo[2,3-c]pyridin-4-yl)vinyl)pyridine-2,4-dicarboxamide (220 mg, 0.375 mmol, 88% yield, ~88% purity) as a yellow oil.

LCMS (2 min Formic): Rt=0.88 min, [MH]$^+$=516.3.

Intermediate 115: N$^4$-Methyl-N$^4$-((1S,2S)-2-methylcyclopropyl)-6-(1-(1-(phenylsulfonyl)-1H-pyrrolo[2,3-c]pyridin-4-yl)ethyl)pyridine-2,4-dicarboxamide 1:1 Mixture of Diastereomers at the Undefined Stereocentre

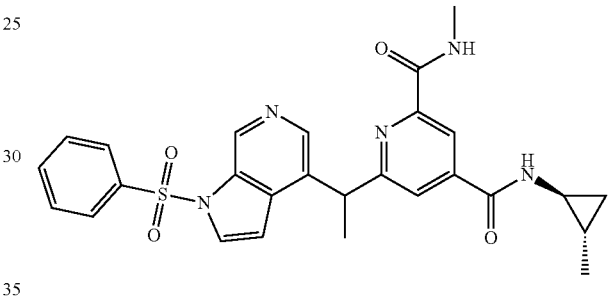

To a hydrogenation flask was added N$^4$-methyl-N$^4$-((1S,2S)-2-methylcyclopropyl)-6-(1-(1-(phenylsulfonyl)-1H-pyrrolo[2,3-c]pyridin-4-yl)vinyl)pyridine-2,4-dicarboxamide (50 mg, 0.097 mmol) and palladium on carbon (20.64 mg, 9.70 µmol) in ethanol (10 mL). The flask was evacuated and refilled with nitrogen (three times) and then evacuated and refilled with hydrogen (three times). The mixture was stirred under a hydrogen atmosphere at room temperature for 5 hours. The reaction mixture was filtered through Celite (eluent EtOAc) then the liquid was concentrated in vacuo to afford a mixture of N$^2$-methyl-N$^4$-((1S,2S)-2-methylcyclopropyl)-6-(1-(1-(phenylsulfonyl)-1H-pyrrolo[2,3-c]pyridin-4-yl)ethyl)pyridine-2,4-dicarboxamide and N$^4$-methyl-N$^4$-((1S,2S)-2-methylcyclopropyl)-6-(1-(1-(phenylsulfonyl)-1H-pyrrolo[2,3-c]pyridin-4-yl)vinyl)pyridine-2,4-dicarboxamide in a ratio of approximately 8:2. This material was combined with additional N$^4$-methyl-N$^4$-((1S,2)-2-methylcyclopropyl)-6-(1-(1-(phenylsulfonyl)-1-pyrrolo[2,3-c]pyridin-4-yl)vinyl)pyridine-2,4-dicarboxamide (170 mg, 0.330 mmol) and palladium on carbon (91 mg, 0.043 mmol) in ethanol (20 mL). The flask was evacuated and refilled with nitrogen (three times) and then evacuated and refilled with hydrogen (three times). The mixture was stirred under a hydrogen atmosphere and stirred at room temperature for 20 hours. The reaction mixture was filtered through Celite® (eluent EtOAc). The solvent was removed in vacuo. This was purified on a SNAP column 10 g, eluent 0-50% 25% ethanol in EtOAc/cyclohexane. The combined desired fractions were concentrated in vacuo to give N$^2$-methyl-N$^4$-((1S,2S)-2-methylcyclopropyl)-6-(1-(1-(phenylsulfonyl)-1H-pyrrolo[2,3-c]pyridin-4-yl)ethyl)pyridine-2,4-dicarboxamide (140 mg, 0.243 mmol, 57.0% yield, ~90% purity) as a colourless oil LCMS (2 min Formic): Rt=0.79 min, [MH]+=518.3.

Intermediate 116: tert-Butyl 4-bromo-1H-pyrrolo[2,3-b]pyridine-1-carboxylate

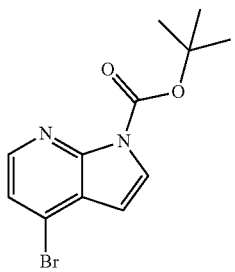 [SMILES: CC(C)(C)OC(=O)n1ccc2c(Br)ccnc21]

To a solution of pyridine (0.1 mL, 1.236 mmol) in dichloromethane (3 mL) under nitrogen was added 4-bromo-1H-pyrrolo[2,3-b]pyridine (220 mg, 1.117 mmol, commercially available from, for example, Aldrich) and di-tert-butyl dicarbonate (268 mg, 1.228 mmol). The reaction mixture was stirred at rt overnight. Further pyridine (0.1 mL, 1.236 mmol) and di-tert-butyl dicarbonate (268 mg, 1.228 mmol) were added and the reaction mixture was stirred for 3 hours. Citric acid (1M, 5 mL) was added and the organic phase was separated. The aqueous phase was extracted with further portions of DCM (2×5 mL). The combined organic phases were dried (hydrophobic frit) then concentrated in vacuo to give tert-butyl 4-bromo-1H-pyrrolo[2,3-b]pyridine-1-carboxylate (340 mg, 0.973 mmol, 87% yield, ~85% purity).

LCMS (2 min Formic): Rt=1.25 min, [MH]+=297.1, 299.1.

Intermediate 117: 2-((1H-Pyrrolo[2,3-b]pyridin-4-yl)methyl)-6-(methylcarbamoyl)isonicotinic acid

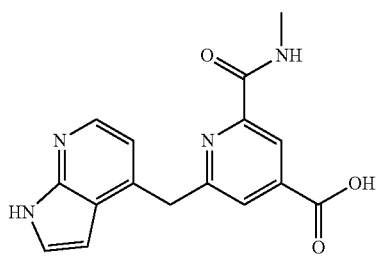 [SMILES: CNC(=O)c1cc(C(=O)O)cc(Cc2ccnc3[nH]ccc23)n1]

To a solution of tert-butyl 4-((4-(tert-butoxycarbonyl)-6-(methylcarbamoyl)pyridin-2-yl)methyl)-pyrrolo[2,3-b]pyridine-1-carboxylate (15 mg, 0.024 mmol) in dichloromethane (1 mL) was added TFA (0.2 mL, 2.60 mmol) and reaction mixture was stirred at rt overnight. DCM (5 mL) was added then the reaction mixture was concentrated in vacuo. Ether (5 mL) was added and the reaction mixture was concentrated in vacuo (four times) to give 2-((1H-pyrrolo[2,3-b]pyridin-4-yl)methyl)-6-(methylcarbamoyl)isonicotinic acid (13 mg, 0.021 mmol, 87% yield, ~50% purity) as a yellow oil.

LCMS (2 min Formic): Rt=0.50 min, [MH]+=311.2.

Alternate procedure:

A solution of tert-butyl 2-(methylcarbamoyl)-6-((1-tosyl-1H-pyrrolo[2,3-b]pyridin-4-yl)methyl)isonicotinate (1.044 g, 2.006 mmol) and sodium hydroxide (0.6779 g, 16.95 mmol) in methanol (5 mL) and THF (5 mL) was stirred at rt for 70 min. The volatiles were evaporated in vacuo to give a green solid. This was redissolved in water (20 mL) and this solution was acidified to pH 2 with 2M aqueous HCl (approx. 15 mL) to afford a light yellow precipitate. This was isolated by filtration and the solid washed with 2M aqueous HCl (approx. 20 mL) and diethyl ether (approx 3×20 mL) and dried in vacuo to give the desired product as a peach solid; 2-((1H-pyrrolo[2,3-b]pyridin-4-yl)methyl)-6-(methylcarbamoyl)isonicotinic acid (0.564 g, 1.817 mmol, 91% yield).

LCMS (2 min Formic): Rt=0.50 min, [MH]+=311.2.

$^1$H NMR (400 MHz, DMSO-d) δ ppm 12.47 (br. s., 1H) 8.73 (q, J=4.5 Hz, 1H) 8.32 (d, J=5.6 Hz, 1H) 8.25 (d, J=1.2 Hz, 1H) 7.99 (d, J=1.5 Hz, 1H) 7.60-7.66 (m, 1H) 7.38 (d, J=5.4 Hz, 1H) 6.91 (d, J=2.0 Hz, 1H) 4.69 (s, 2H) 2.87 (d, J=4.6 Hz, 3H). One exchangeable proton not observed Intermediate 118: 2-((1-((Benzyloxy)carbonyl)indolin-4-yl)methyl)-6-(methylcarbamoyl)isonicotinic acid

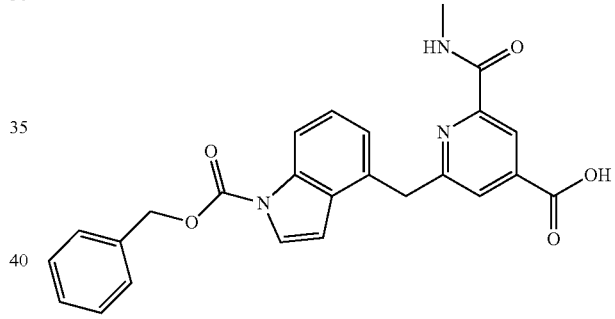

To a solution of benzyl 4-((4-(tert-butoxycarbonyl)-6-(methylcarbamoyl)pyridin-2-yl)methyl)indoline-1-carboxylate (138.7 mg, 0.221 mmol) in DCM (4 mL) was added 2,2,2-trifluoroacetic acid (0.7 mL, 9.09 mmol) and the reaction mixture was stirred for 4 h. Further 2,2,2-trifluoroacetic acid (1 mL, 12.98 mmol) was added and the resultant mixture was stirred overnight. The reaction mixture was concentrated to give a brown solid. EtOAc (10 mL) was added to the brown solid, then the resulting mixture was base washed 5 times with sodium bicarbonate solution, then the aqueous phase was neutralised with a solution of 2M HCl (10 mL), then it was extracted with EtOAc. The combined organic phases were dried (a solid appeared so the solution was filtered) and then concentrated in vacuo to give a brown oil—2-((1-((benzyloxy)carbonyl)indolin-4-yl)methyl)-6-(methylcarbamoyl)isonicotinic acid (109 mg, 0.196 mmol, 88% yield).

LCMS (2 min Formic): Rt=1.18 min, [MH]+ 446.2.

$^1$H NMR (400 MHz, MeOH-d) δ ppm 8.40 (d, J=1.0 Hz, 1H) 7.78 (d, J=1.2 Hz, 1H) 7.68 (br. s., 1H) 7.25-7.44 (m, 5H) 7.12 (br. t, J=7.0, 7.0 Hz, 1H) 6.86 (d, 7-=7.8 Hz, 1H) 5.22 (br. s., 2H) 4.20 (s, 2H) 3.99 (t, J=8.7 Hz, 2H) 2.93-3.06 (m, 5H), exchangeable protons not observed

Intermediate 119: Benzyl 4-((6-(methylcarbamoyl)-4-(((1S,2S)-2-methylcyclopropyl)carbamoyl)pyridin-2-yl)methyl)indoline-1-carboxylate

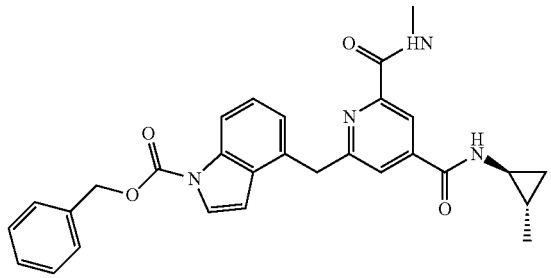 [SMILES: CNC(=O)c1cc(C(=O)N[C@H]2C[C@@H]2C)cc(Cc2cccc3c2ccn3C(=O)OCc2ccccc2)n1]

To a mixture of 2-((1-((benzyloxy)carbonyl)indolin-4-yl)methyl)-6-(methylcarbamoyl)isonicotinic acid (155.7 mg, 0.350 mmol), (1S,2S)-2-methylcyclopropan-1-amine hydrochloride (57.4 mg, 0.534 mmol) and HATU (199.6 mg, 0.525 mmol) was added DIPEA (0.214 mL, 1.223 mmol) and N,N-dimethylformamide (3 mL). The mixture was stirred at room temperature for 3 h. The mixture was concentrated under a stream of nitrogen and the volume made up to 3 mL with acetonitrile before being directly purified by MDAP (high pH). The required fractions were evaporated under a stream of nitrogen, the residues were redissolved in dichloromethane (approx 4 mL) before being combined and transferred to a tared vial. The solvent was evaporated under a stream of nitrogen and dried in vacuo to give benzyl 4-((6-(methylcarbamoyl)-4-(((1S,2S)-2-methylcyclopropyl)carbamoyl)pyridin-2-yl)methyl)indoline-1-carboxylate (152.4 mg, 0.306 mmol, 87% yield) as a white powder.

LCMS (2 min Formic): Rt=1.23 min, [MH]$^+$=499.4.

$^1$H NMR (400 MHz, CDCl$_3$) δ ppm 8.14 (br. s, 1H) 7.91-8.01 (m, 1H) 7.83 (br. s., 1H) 7.74 (br. s, 1H) 7.32-7.48 (m, 5H) 7.08-7.23 (m, 1H) 6.83 (br. d, J=7.1 Hz, 1H) 6.50 (br. s., 1H) 5.29 (br. s., 2H) 4.15 (s, 2H) 4.06 (t, J=8.6 Hz, 2H) 2.96-3.09 (m, 5H) 2.55-2.64 (m, 1H) 1.16 (d, J=5.9 Hz, 3H) 0.93-1.07 (m, 1H) 0.75-0.84 (m, 1H) 0.62-0.71 (m, 1H)

Intermediate 120: 2-(6-(Methylcarbamoyl)-4-(((1S,2S)-2-methylcyclopropyl)carbamoyl)pyridin-2-yl)-2-phenylethyl methanesulfonate 1:1 Mixture of Diastereomers at the Undefined Stereocentre

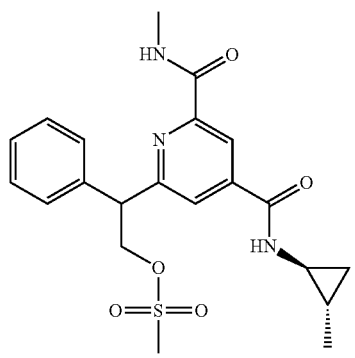 [SMILES: CNC(=O)c1cc(C(=O)N[C@H]2C[C@@H]2C)cc(C(COS(C)(=O)=O)c2ccccc2)n1]

To a solution of 6-(2-hydroxy-1-phenylethyl)-N$^2$-methyl-N$^4$-((1S,2S)-2-methylcyclopropyl)pyridine-2,4-dicarboxamide (39 mg, 0.110 mmol) in dichloromethane (1 mL) under nitrogen was added mesyl-C$_1$ (0.02 mL, 0.257 mmol) and Et$_3$N (0.05 mL, 0.359 mmol). The reaction mixture was stirred at rt for 45 minutes. Water (5 mL) and DCM (5 mL) were added. The layers were separated and the aqueous phase was extracted with further portions of DCM (2×10 mL). The combined organic phases were passed through a hydrophobic frit and concentrated in vacuo to give 2-(6-(methylcarbamoyl)-4-(((1S,2S)-2-methylcyclopropyl)carbamoyl)pyridin-2-yl)-2-phenylethyl methanesulfonate (58 mg, 0.108 mmol, 97% yield, ~80% purity) as a white foam.

LCMS (2 min Formic): Rt=0.96 min, [MH]$^+$=432.4.

Intermediate 121: (±)-tert-butyl 2-(hydroxy(pyridin-2-yl)methyl)-6-(methylcarbamoyl)isonicotinate

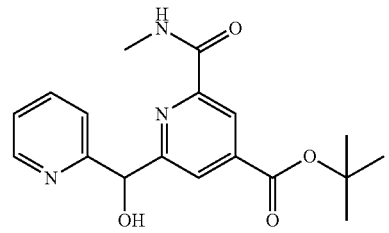 [SMILES: CNC(=O)c1cc(C(=O)OC(C)(C)C)cc(C(O)c2ccccn2)n1]

To a solution of pyridin-2-ylmagnesium bromide (1100 mg, 6.03 mmol) in THF (commercially available from Matrix Scientific) at 0° C. under nitrogen, was added dropwise tert-butyl 2-formyl-6-(methylcarbamoyl)isonicotinate (650 mg, 2.091 mmol) 4 mL of THF. The reaction mixture was stirred at 0° C. for 2 hours. 5 mL of a solution of saturated ammonium chloride was added followed by 10 mL of ethyl acetate and 5 mL of water. The organic layer was separated and the aqueous layer was extracted with further portions of ethyl acetate (3×20 mL). The combined organic phases were dried by filtering through a hydrophobic frit then concentrated in vacuo. The residue was purified by SNAP column chromatography (25 g column eluting with 40 to 80% EtOAc/cyclohexane then 100%). The combined desired fractions were concentrated in vacuo to give (±)-tert-butyl 2-(hydroxy(pyridin-2-yl)methyl)-6-(methylcarbamoyl)isonicotinate (432 mg, 1.006 mmol, 48.1% yield) in approximately 80% purity.

LCMS (2 mins formic) Peak R$_f$=0.75 minutes, m/z=344 for [MH]

Intermediate 122: (±)-tert-butyl 2-(chloro(pyridin-2-yl)methyl)-6-(methylcarbamoyl)isonicotinate

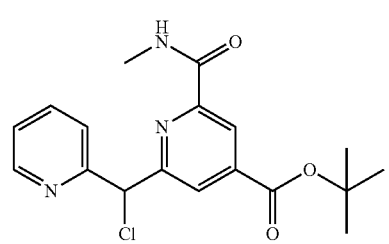 [SMILES: CNC(=O)c1cc(C(=O)OC(C)(C)C)cc(C(Cl)c2ccccn2)n1]

To a solution of (±)-tert-butyl 2-(hydroxy(pyridin-2-yl) methyl)-6-(methylcarbamoyl)isonicotinate (432 mg, 1.258 mmol) in dichloromethane (1 mL) at 0° C., was added dropwise thionyl chloride (0.73 mL, 10.00 mmol). The reaction mixture was then stirred at room temperature for 2 hours.

The solvent was removed in vacuo to give (±)-tert-butyl 2-(chloro(pyridin-2-yl)methyl)-6-(methylcarbamoyl)isonicotinate (598 mg, 0.909 mmol, 72.3% yield) as a yellow oil which was used in the subsequent step without further purification.

LCMS (2 mins formic) Peak $R_f$=1.13 minutes, m/z=362 for [MH]

Intermediate 123: tert-butyl 2-(methylcarbamoyl)-6-(pyridin-2-ylmethyl)isonicotinate

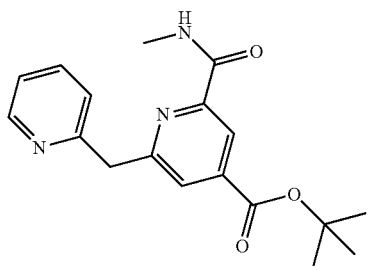 [SMILES: CNC(=O)c1cc(C(=O)OC(C)(C)C)cc(Cc2ccccn2)n1]

To a solution of the crude (±)-tert-butyl 2-(chloro(pyridin-2-yl)methyl)-6-(methylcarbamoyl)isonicotinate (598 mg, 0.909 mmol) in acetic acid (5 mL) at room temperature was added zinc powder (178 mg, 2.73 mmol) in portions. The reaction mixture was then stirred at room temperature overnight. Further of zinc powder (60 mg, 0.92 mmol) was added and the resultant mixture was stirred for 1 hour. 7 mL of 2M NaOH solution and 10 mL of water were added to the mixture followed by 10 mL of DCM. The aqueous and organic layers were separated and the aqueous phase was extracted two more times with DCM.

The combined organic phases was dried by filtering through a hydrophobic frit and then concentrated in vacuo. The residue was purified by column chromatography (SNAP 25 g eluenting with 40-100% EtOAc/cyclohexane). The desired fractions were combined and concentrated in vacuo to give tert-butyl 2-(methylcarbamoyl)-6-(pyridin-2-ylmethyl)isonicotinate (175 mg, 0.481 mmol, 52.9% yield).

LCMS (2 mins formic) Peak $R_f$=0.72 minutes, m/z=328 for [MH]

Intermediate 124: (±)-tert-butyl 2-(methylcarbamoyl)-6-(1-(pyridin-2-ylethyl)isonicotinate

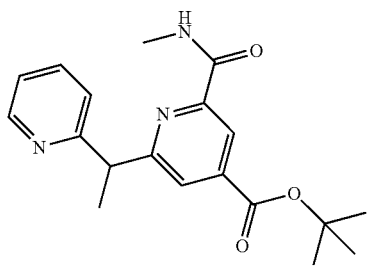 [SMILES: CNC(=O)c1cc(C(=O)OC(C)(C)C)cc(C(C)c2ccccn2)n1]

tert-butyl 2-(methylcarbamoyl)-6-(pyridin-2-ylmethyl) isonicotinate (175 mg, 0.481 mmol) was dissolved in tetrahydrofuran (1 mL) and cooled to −78° C. in a CO$_2$/acetone bath under nitrogen. Lithiumhexamethyldisilazide (1M in THF) (1.4 mL, 1.400 mmol) was added dropwise and the reaction mixture left to stir for 45 minutes. Methyl iodide (0.050 mL, 0.800 mmol) was added and the resultant mixture was stirred for 30 minutes. 1 mL of water was added and the reaction mixture was allowed to warm up. Water 10 mL was added to the mixture which was extracted with ethyl acetate (3×10 mL). The combined organic phases were dried by filtering through a hydrophobic filter and the solvent was removed in vacuo to give (±)-tert-butyl 2-(methylcarbamoyl)-6-(1-(pyridin-2-yl)ethyl)isonicotinate (190 mg, 0.473 mmol, 98% yield) as an orange oil.

LCMS (2 mins formic) Peak $R_f$=0.81 minutes, m/z=342 for [MH]

Intermediate 125: (±)-2-(methylcarbamoyl)-6-(1-(pyridin-2-yl)ethyl)isonicotinic acid

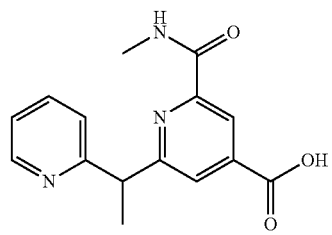 [SMILES: CNC(=O)c1cc(C(=O)O)cc(C(C)c2ccccn2)n1]

To a solution of (±)-tert-butyl 2-(methylcarbamoyl)-6-(1-(pyridin-2-yl)ethyl)isonicotinate (190 mg, 0.473 mmol) in dichloromethane (1 mL) was added TFA (1 mL, 12.98 mmol) and the reaction mixture was stirred at room temperature over the weekend. The reaction mixture was concentrated in vacuo then 5 mL of DCM was added and the reaction mixture was concentrated in vacuo. 5 mL of ether were added and the reaction mixture was concentrated in vacuo (procedure repeated 4 times) to give (+)-2-(methylcarbamoyl)-6-(1-(pyridin-2-yl)ethyl)isonicotinic acid (330 mg, 0.463 mmol, 98% yield) as a yellow oil in approximately 40% purity (impurities being solvent related).

LCMS (2 mins formic) Peak $R_f$=0.44 minutes, m/z=286 for [MH]

Intermediate 126: 2-((3-Fluorophenyl)(hydroxy) methyl)-6-(methylcarbamoyl)isonicotinic acid

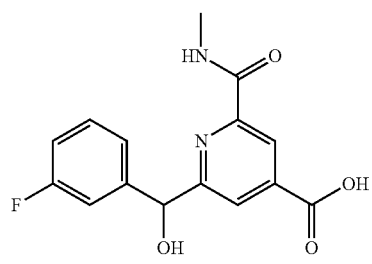 [SMILES: CNC(=O)c1cc(C(=O)O)cc(C(O)c2cccc(F)c2)n1]

(3-Fluorophenyl)magnesium bromide (10.41 mL, 10.41 mmol, 1M in THF) was added dropwise to a solution of tert-butyl 2-formyl-6-(methylcarbamoyl)isonicotinate (1.1 g, 4.16 mmol) in THF at −78° C. and the mixture was stirred for 30 min, then allowed to warm to −20° C. and the mixture was then quenched with saturated ammonium chloride solution (10 mL) and extracted with EtOAc (20 mL). The organic layer was dried and evaporated in vacuo to give an orange gum, which was purified by flash chromatography on a silica column (50 g) eluting with 0-100% EtOAc/cyclohexane. The product-containing fractions were evaporated in vacuo to give tert-butyl 2-((3-fluorophenyl)(hydroxy)methyl)-6-(methylcarbamoyl)isonicotinate (1.25 g, 3.47 mmol, 83% yield) as a colourless gum. The impure product was dissolved in methanol and NaOH (6 mL, 12.00 mmol, 2M aq.) was added, then the mixture was allowed to stand at rt over the weekend. The solvent was evaporated to half its original volume and the resulting solution was acidified to pH 3 with 2M HCl, then allowed to stand for 2 h, giving a dense precipitate. This was collected by filtration and washed with water, the solid then dried in the vacuum oven to give 2-((3-fluorophenyl)(hydroxy)methyl)-6-(methylcarbamoyl)isonicotinic acid (0.71 g, 2.33 mmol, 56% yield) as a colourless solid.

LCMS (2 min High pH): Rt=0.52 min, [MH]$^+$=305.4.

Intermediate 127: (±)-tert-butyl 2-((2-fluorophenyl)(hydroxy)methyl)-6-(methylcarbamoyl)isonicotinate

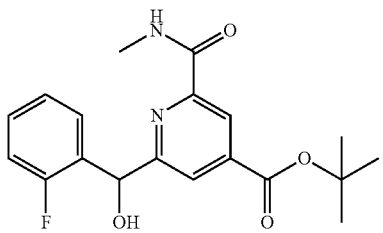 [SMILES: CNC(=O)c1cc(C(=O)OC(C)(C)C)cc(C(O)c2ccccc2F)n1]

To a solution of (2-fluorophenyl)magnesium bromide (184 mg, 0.923 mmol) (for a preparation see WO 2012/138734) in THF at 0° C. under nitrogen, was added dropwise (±)-tert-butyl 2-formyl-6-(methylcarbamoyl)isonicotinate (110 mg, 0.375 mmol) in 0.5 ml of THF. The reaction mixture was stirred during 2 hours. Aqueous ammonium chloride solution (1 mL) was added and the reaction mixture was partioned between water (10 mL) and ethyl acetate (10 mL). The organic layer was separated and the aqueous layer was extracted with further portions of ethyl acetate (3×10 mL). The combined organic phases were dried by filtering through a hydrophobic frit then concentrated in vacuo. The residue was purified by chromatography on silica (Biotage SNAP 10 g cartridge, eluting with 0-80% ethyl acetate/cyclohexane). The desired fractions were concentrated to give (±)-tert-butyl 2-((2-fluorophenyl)(hydroxy)methyl)-6-(methylcarbamoyl)isonicotinate (99 mg, 0.192 mmol, 51.3% yield).

LCMS (2 mins formic) Peak R$_t$=1.10 minutes, m/z=361 for [MH]$^+$

Intermediate 128: (±)-2-((2-fluorophenyl)(hydroxy)methyl)-6-(methylcarbamoyl)isonicotinic acid

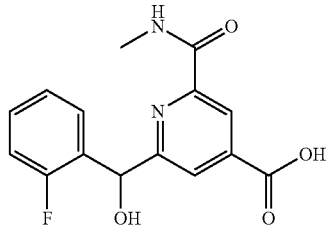 [SMILES: CNC(=O)c1cc(C(=O)O)cc(C(O)c2ccccc2F)n1]

(±)-tert-butyl 2-((2-fluorophenyl)(hydroxy)methyl)-6-(methylcarbamoyl)isonicotinate (144 mg, 0.400 mmol) was taken up in methanol (1.00 mL) and tetrahydrofuran (1 mL). 2M Sodium hydroxide (1.998 mL, 4.00 mmol) was added and the reaction left to stir at room temperature for 1 hour. The reaction was concentrated in vacuo. The residue was taken up in water (5 ml) and acidified to pH 2. The precipitate was filtered off and dried to give crude (+)-2-((2-fluorophenyl)(hydroxy)methyl)-6-(methylcarbamoyl) isonicotinic acid (68 mg, 0.223 mmol, 55.9% yield) which was used in the subsequent step without further purification.

LCMS (2 mins high pH) Peak R$_t$=0.52 minutes, m/z=305 for [MH]$^+$

Intermediate 129: 4-(4,4,5,5-tetramethyl-1,3,2-dioxaborolan-2-yl)indolin-2-one

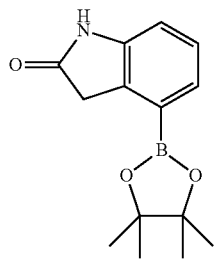 [SMILES: CC1(C)OB(c2cccc3c2CC(=O)N3)OC1(C)C]

A mixture of 4,4,4',4',5,5,5',5'-octamethyl-2,2'-bi(1,3,2-dioxaborolane) (1.9025 g, 7.49 mmol), 4-bromoindolin-2-one (1.0383 g, 4.90 mmol), [1,1'-Bis(diphenylphosphino)ferrocene]dichloropalladium(II), complex with dichloromethane (0.6005 g, 0.734 mmol) and potassium acetate (1.4802 g, 15.08 mmol) in 1,4-Dioxane (30 mL) was stirred at 110° C. for 2 hr. The mixture was allowed to cool to room temperature before being filtered through a 10 g celite cartridge. The cartridge was washed through with ethyl acetate (3×30 mL) and the combined filtrates were evaporated in vacuo to give to give a brown liquid, which was redissolved in dichloromethane (ca. 10 mL), loaded onto a 100 g SNAP silica cartridge and purified by Biotage SP4 semi-automated flash column chromatography eluting with a gradient of 20 to 50% ethyl acetate in cyclohexane. The required fractions were combined and evaporated in vacuo, the residue (which was on the verge of crystallisation) was re-dissolved in dichloromethane (ca. 10 mL), transferred to a tared vial, the solvent evaporated under a stream of nitrogen. The residue was triturated with ether (5×5 mL), decanting away the mother liquor each time, and the residue dried under a stream of nitrogen and in vacuo to give the desired product as a cream solid (941.8 mg, 3.63 mmol, 74.2% yield) LCMS (2 min Formic): Rt=0.93 min, [MH]⁺=260

Intermediate 130: tert-butyl 2-(methylcarbamoyl)-6-(1-(2-oxoindolin-4-yl)vinyl)isonicotinate

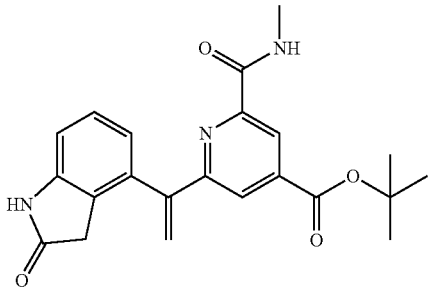 [SMILES: C=C(c1cc(C(=O)OC(C)(C)C)cc(C(=O)NC)n1)c1cccc2c1CC(=O)N2]

A solution of tert-butyl 2-(1-bromovinyl)-6-(methylcarbamoyl)isonicotinate (380 mg, 0.724 mmol), 4-(4,4,5,5-tetramethyl-1,3,2-dioxaborolan-2-yl)indolin-2-one (250.3 mg, 0.966 mmol), [1,3-Bis(2,6-Diisopropylphenyl)imidazol-2-ylidene](3-chloropyridyl)palladium(II) dichloride (51.9 mg, 0.076 mmol) and tripotassium phosphate (492.6 mg, 2.321 mmol) in 1,4-Dioxane (4.0 mL) and Water (2.0 mL) was stirred at room temperature under nitrogen in the dark for 22.5 hours. To the reaction mixture was added ethyl acetate (15 mL), water (10 mL) and brine (5 mL) and the layers separated. The aqueous layer was extracted with further ethyl acetate (2×15 mL) and the organic phases were combined and filtered through a cartridge fitted with a hydrophobic frit. The filtrate was evaporated in vacuo to give a sticky light brown solid (415.0 mg). This was redissolved in DMSO (4 mL) and methanol (2 mL) and directly purified by (MDAP) (2×3 mL injection, high pH). The required fractions were combined and evaporated in vacuo to give the desired product as a yellow solid (103.2 mg, 0.262 mmol, 36.2% yield).

LCMS (2 min High pH): Rt=1.05 min, [MH]⁺=394

Intermediate 131: tert-butyl 2-(methylcarbamoyl)-6-(1-(2-oxoindolin-4-yl)ethyl)isonicotinate

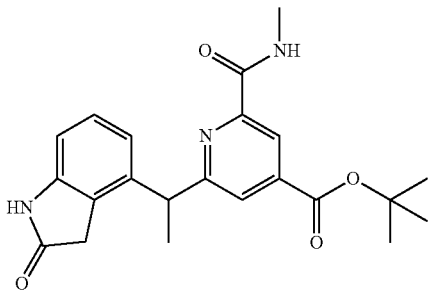 [SMILES: CNC(=O)c1cc(C(=O)OC(C)(C)C)cc(C(C)c2cccc3c2CC(=O)N3)n1]

A solution of tert-butyl 2-(methylcarbamoyl)-6-(1-(2-oxoindolin-4-yl)vinyl)isonicotinate (260 mg, 0.661 mmol) in Ethyl acetate (20 mL) and Ethanol (20 mL) was hydrogenated using a Thales H-Cube apparatus at 20° C. in full H2 mode over a 10% palladium on carbon catalyst cartridge. The solution was evaporated in vacuo to give the desired product as a yellow gum (257.1 mg, 0.650 mmol, 98% yield).

LCMS (2 mins high pH) Peak R$_t$=1.05 minutes, m/z=396 for [MH]

Intermediate 132: 2-(methylcarbamoyl)-6-(1-(2-oxoindolin-4-yl)ethyl)isonicotinic acid

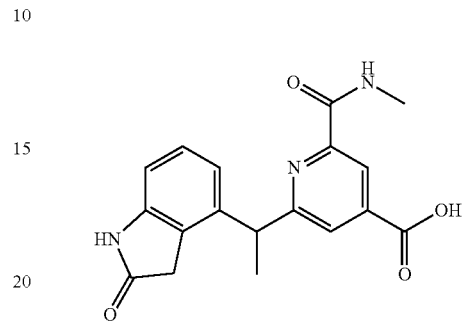

To a solution of (±)-tert-butyl 2-(methylcarbamoyl)-6-(1-(2-oxoindolin-4-yl)ethyl)isonicotinate (257 mg, 0.650 mmol) in DCM (8.0 mL) was added trifluoroacetic acid (1.0 mL, 12.98 mmol) dropwise. The resulting orange solution was stirred at room temperature under nitrogen for a total of 2 days, during which further DCM (4.0 mL, after 7.5 hours) and trifluoroacetic acid (0.5 mL, 6.49 mmol, after 23.75 hours) were added. The volatiles were evaporated in vacuo to give a dark red gum, which was azeotroped with acetonitrile (3×5 mL) and the volatiles evaporated in vacuo to give a sticky pink solid. To this was added water (5 mL) and dichloromethane (5 mL) and the layers separated using a cartridge fitted with a hydrophobic frit. The aqueous layer was washed with further dichloromethane (2×5 mL) and evaporated in vacuo to give a brown gum. This was azeotroped with diethyl ether (5 mL) and the volatiles evaporated in vacuo to give the desired product as a brown solid (158.9 mg, 0.398 mmol, 61.2% yield).

LCMS (2 mins high pH) Peak R$_t$=0.54 minutes, m/z=340 for [MH]⁺

Intermediate 133: N⁴-methyl-N⁴-((1S,2S)-2-methylcyclopropyl)-6-(1-(2-oxoindolin-4-yl)ethyl)pyridine-2,4-dicarboxamide

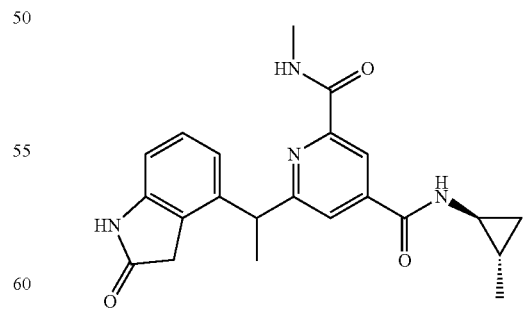

(+)-2-(methylcarbamoyl)-6-(1-(2-oxoindolin-4-yl)ethyl) isonicotinic acid (74 mg, 0.218 mmol) was dissolved in DMF (0.8 mL). DIPEA (0.190 mL, 1.090 mmol) was added followed by HATU (120 mg, 0.316 mmol) and (1S,2S)-2-methylcyclopropan-1-amine hydrochloride (47 mg, 0.437 mmol) and the reaction mixture was stirred under nitrogen for 16.5 hrs. The reaction mixture was purified by MDAP (formic acid method). Fractions containing the desired product were partitioned between sat. aq. NaHCO₃ solution and DCM. The organic layer was extracted (2×20 mL), dried (Na₂SO₄) and concentrated in vacuo to give/M-methyl-N⁴-((1S,2S)-2-methylcyclopropyl)-6-(1-(2-oxoindolin-4-yl)ethyl)pyridine-2,4-dicarboxamide (39 mg, 0.089 mmol, 41.0% yield).

LCMS (2 mins formic) Peak $R_f$=0.85 minutes, m/z=393 for [MH]⁺

Intermediate 134: tert-butyl 2-(imidazo[1,2-a]pyridin-5-ylmethyl)-6-(methylcarbamoyl)isonicotinate

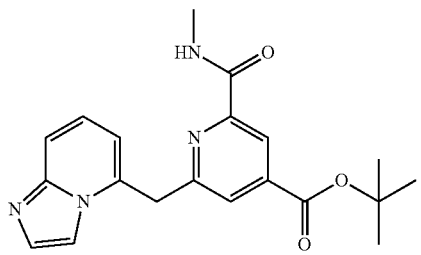 [SMILES: CNC(=O)c1cc(C(=O)OC(C)(C)C)cc(Cc2cccc3nccn23)n1]

5-Bromoimidazo[1,2-a]pyridine (500 mg, 2.54 mmol) (commercially available from Fluorochem) and triisopropyl borate (0.589 mL, 2.54 mmol) were dissolved in a mixture of toluene (6 mL) and tetrahydrofuran (1.5 mL). The resulting solution was cooled to −78° C. and n-butyl lithium (1.6M in hexanes) (1.586 mL, 2.54 mmol) was added dropwise. The reaction mixture was allowed to slowly warm to 0° C. and was quenched with isopropanol (1 mL) and left to stir at room temperature overnight. The reaction mixture was concentrated in vacuo and the residue re-suspended in acetone (20 mL). The resulting cream suspension was filtered and dried in a vacuum oven to give lithium imidazo[1,2-a]pyridin-5-yltriisopropoxyborate (371 mg) in approximately 50% purity and which was used in the subsequent step without further purification. A mixture of tert-butyl 2-(chloromethyl)-6-(methylcarbamoyl)isonicotinate (100 mg, 0.351 mmol), the crude triisopropyl imidazo[1,2-a]pyridin-5-ylborate, lithium salt, prepared as described above (200 mg, approximately 0.320 mmol), Chloro(2-dicyclohexylphosphino-2',4',6'-triisopropyl-1,1'-biphenyl)[2-(2'-amino-1,1'-biphenyl)]palladium(II) ligand (41 mg, 0.052 mmol) (commercially available from Aldrich) and tripotassium phosphate (149 mg, 0.702 mmol) in 1,4-dioxane (2 mL) and water (0.500 mL) was heated in a 5 mL microwave vial at 70° C. in a microwave reactor for 30 mins. The reaction mixture was combined with a previous reaction mixture batch (approximately 50% of the scale of this batch) and was filtered through celite and concentrated to give a crude brown oil. This was purified by chromatography on silica (Biotage SNAP 25 g cartridge, eluting with 10-80% of 20% 2M NH₃ in MeOH/DCM over 330 mls) to give tert-butyl 2-(imidazo[1,2-a]pyridin-5-ylmethyl)-6-(methylcarbamoyl)isonicotinate (141 mg, 0.308 mmol, 88% yield) as an orange oil and in >80% purity.

LCMS (2 mins formic) Peak $R_f$=0.61 minutes, m/z=367 for [MH]⁺

Intermediate 135: 2-(imidazo[1,2-a]pyridin-5-ylmethyl)-6-(methylcarbamoyl)isonicotinic acid

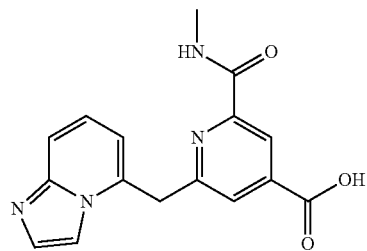 [SMILES: CNC(=O)c1cc(C(=O)O)cc(Cc2cccc3nccn23)n1]

To a solution of tert-butyl 2-(imidazo[1,2-a]pyridin-5-ylmethyl)-6-(methylcarbamoyl)isonicotinate (140 mg, 0.382 mmol) in 1,4-dioxane (2 mL) and water (2 mL) was added lithium hydroxide (23 mg, 0.960 mmol) and reaction mixture was stirred at room temperature for 1 hr. HCl (2M aqueous solution) (0.480 mL, 0.959 mmol) was added and the reaction mixture concentrated in vacuo to give as a pale yellow solid the crude 2-(imidazo[1,2-a]pyridin-5-ylmethyl)-6-(methylcarbamoyl)isonicotinic acid (260 mg, 0.293 mmol, 77% yield) as a mixture with lithium chloride.

LCMS (2 mins High pH) Peak $R_f$=0.48 minutes, m/z=311 for [MH]⁺

Intermediate 136: tert-butyl 4-bromo-1H-pyrrolo[2,3-c]pyridine-1-carboxylate

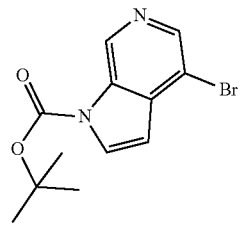 [SMILES: CC(C)(C)OC(=O)n1ccc2c(Br)cncc21]

To a solution of pyridine (1.210 mL, 14.96 mmol) in dichloromethane (5 mL) under nitrogen was added 4-bromo-1H-pyrrolo[2,3-c]pyridine (2.68 g, 13.60 mmol) (commercially available from Aldrich) and di-tert-butyl dicarbonate (3.27 g, 14.96 mmol). The reaction mixture was stirred at room temperature for 3 hours. 5 mL of 2M HCl was added and the organic phase was separated. The aqueous phase was extracted with further portions of DCM (2×5 mL). The combined organic phases were dried by filtering through a hydrophobic frit and then concentrated in vacuo to give tert-butyl 4-bromo-1H-pyrrolo[2,3-c]pyridine-1-carboxylate (4.19 g, 12.69 mmol, 93% yield) LCMS (2 mins Formic) Peak $R_f$=1.15 minutes, m/z=297, 299 for [MH]

Intermediate 137: (1-(tert-butoxycarbonyl)-1H-pyrrolo[2,3-c]pyridin-4-yl)boronic acid

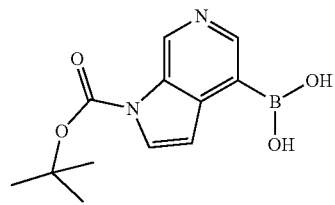 [SMILES: CC(C)(C)OC(=O)n1ccc2c(B(O)O)cncc21]

To a stirred solution of 4,4,4',4',5,5,5',5'-octamethyl-2,2'-bi(1,3,2-dioxaborolane) (3.22 g, 12.68 mmol), potassium acetate (1.899 g, 19.35 mmol) and tert-butyl 4-bromo-1H-pyrrolo[2,3-c]pyridine-1-carboxylate (2.13 g, 6.45 mmol) in 1,4-dioxane (10 mL) was added [1,1'-bis(diphenylphosphino)ferrocene]dichloropalladium(II) (0.944 g, 1.290 mmol). The reaction mixture was purged with nitrogen and stirred at 80° C. for 18 hours, then for 4 hours at 100° C. The reaction mixture was partioned between water (30 mL) brine (10 mL) and ethyl acetate (30 mL). The organic layer was separated and the aqueous layer was extracted with further portions of ethyl acetate (3×10 mL). The combined organic phases was dried by filtering through a hydrophobic frit then concentrated in vacuo. To the residue 20 mL of ether was added and the mixture was filtrated. The filtrate was concentrated in vacuo to give (1-(tert-butoxycarbonyl)-1H-pyrrolo[2,3-c]pyridin-4-yl)boronic acid (4.49 g, 6.00 mmol, 93% yield) in approximately 60% purity.

LCMS (2 mins Formic) Peak $R_t$=0.51 minutes, m/z=263 for [MH]$^+$

Intermediate 138: tert-butyl 4-((4-(tert-butoxycarbonyl)-6-(methylcarbamoyl)pyridin-2-yl)methyl)-1H-pyrrolo[2,3-c]pyridine-1-carboxylate

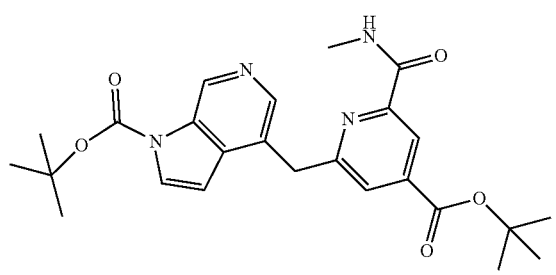 [SMILES: CNC(=O)c1cc(C(=O)OC(C)(C)C)cc(Cc2cncc3c2ccn3C(=O)OC(C)(C)C)n1]

Potassium carbonate (568 mg, 4.11 mmol) was combined with the impure (1-(tert-butoxycarbonyl)-1H-pyrrolo[2,3-c]pyridin-4-yl)boronic acid (4 g, 5.34 mmol), [1,1'-bis(diphenylphosphino)ferrocene]dichloropalladium(II) (0.785 g, 1.073 mmol) and tert-butyl 2-(chloromethyl)-6-(methylcarbamoyl)isonicotinate (1.698 g, 5.37 mmol) in 1,4-dioxane (20 mL) and water (10 mL). The mixture was heated at 100° C. for 2 hours before being partioned between water (30 mL) brine (10 mL) and ethyl acetate (30 mL). The organic layer was separated and the aqueous phase was extracted with further portions of ethyl acetate (3×30 mL). The combined organic phases were dried by filtering through a hydrophobic frit then concentrated in vacuo. The residue was purified by chromatography on silica (Biotage SNAP 100 g column, eluting with 0 to 60% ethyl acetate in cyclohexane then 60 to 100%). The desired fractions were concentrated in vacuo to give tert-butyl 4-((4-(tert-butoxycarbonyl)-6-(methylcarbamoyl)pyridin-2-yl)methyl)-1H-pyrrolo[2,3-c]pyridine-1-carboxylate (760 mg, 1.548 mmol, 28.8% yield) as yellow oil.

LCMS (2 mins Formic) Peak $R_t$=0.85 minutes, m/z=467 for [MH]

Intermediate 139: (±)-tert-butyl 4-(1-(4-(tert-butoxycarbonyl)-6-(methylcarbamoyl)pyridin-2-yl)propyl-1H-pyrrolo[2,3-c]pyridine-1-carboxylate

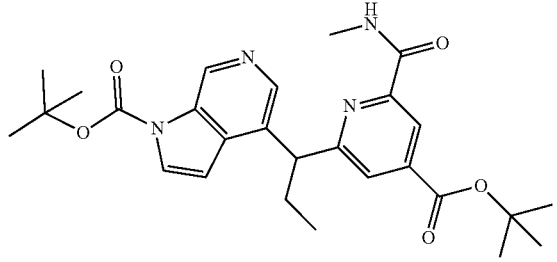 [SMILES: CCC(c1cc(C(=O)OC(C)(C)C)cc(C(=O)NC)n1)c1cncc2c1ccn2C(=O)OC(C)(C)C]

tert-butyl 4-((4-(tert-butoxycarbonyl)-6-(methylcarbamoyl)pyridin-2-yl)methyl)-1H-pyrrolo[2,3-c]pyridine-1-carboxylate (370 mg, 0.753 mmol) was dissolved in tetrahydrofuran (2.5 mL) and cooled to −78° C. in a $CO_2$/acetone bath under nitrogen. Lithiumhexamethyldisilazide (1M in THF) (3.0 mL, 3.00 mmol) was added dropwise and the reaction mixture left to stir for 45 mins. Iodoethane (0.13 mL, 1.617 mmol) was added and the resultant mixture was stirred for 45 minutes. 1 mL of water was added and the reaction mixture was allowed to warm up. The reaction mixture was partioned between water (10 mL) and ethyl acetate (10 mL). The organic layer was separated and the aqueous layer was extracted with further portions of ethyl acetate (3×10 mL). The combined organic phases was dried by filtering through a hydrophobic frit and then concentrated in vacuo. The residue was purified by Snap column chromatography 10 g column, eluenting with 0-80% EtOAc/cyclohexane.

The combined desired fractions were concentrated in vacuo to give (±)-tert-butyl 4-(1-(4-(tert-butoxycarbonyl)-6-(methylcarbamoyl)pyridin-2-yl)propyl)-1H-pyrrolo[2,3-c]pyridine-1-carboxylate (222 mg, 0.404 mmol, 53.6% yield) as an orange oil.

LCMS (2 mins Formic) Peak $R_t$=0.92 minutes, m/z=495 for [MH]$^+$

Intermediate 140: (±)-2-(1-(1H-pyrrolo[2,3-c]pyridin-4-yl)propyl)-6-(methylcarbamoyl)isonicotinic acid

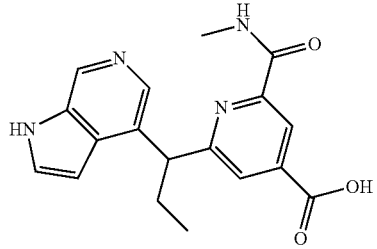 [SMILES: CCC(c1cc(C(=O)O)cc(C(=O)NC)n1)c1cncc2[nH]ccc12]

To a solution of (±)-tert-butyl 4-(1-(4-(tert-butoxycarbonyl)-6-(methylcarbamoyl)pyridin-2-yl)propyl)-1H-pyrrolo[2,3-c]pyridine-1-carboxylate (222 mg, 0.404 mmol) in dichloromethane (1 mL) was added 2,2,2-trifluoroacetic acid (1.00 mL, 12.98 mmol) and the reaction mixture was stirred overnight. The reaction mixture was concentrated in vacuo then 5 mL of ether was added and the reaction mixture was concentrated in vacuo (procedure repeated ×4) to give (+)-2-(1-(1H-pyrrolo[2,3-c]pyridin-4-yl)propyl)-6-(methylcarbamoyl)isonicotinic acid (224 mg, 0.331 mmol, 82% yield) as a yellow oil.

LCMS (2 mins Formic) Peak $R_t$=0.49 minutes, m/z=339 for [MH]$^+$

Intermediate 141: 4-bromo-7-methyl-1-tosyl-1H-pyrrolo[2,3-c]pyridine

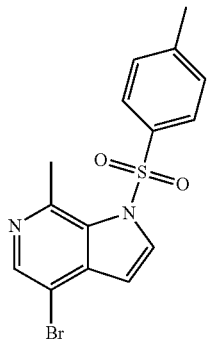 [SMILES: Cc1ccc(S(=O)(=O)n2ccc3c(Br)cnc(C)c32)cc1]

4-bromo-7-methyl-1H-pyrrolo[2,3-c]pyridine (Commercially available from e.g. Pharmablocks, 500 mg, 2.369 mmol) was taken up in DMF (5 mL) under nitrogen and cooled in an ice-bath. NaH (a 60% suspension in mineral oil, 114 mg, 2.84 mmol) was added and the reaction stirred for 15 mins. Tosyl chloride (542 mg, 2.84 mmol) was added and the reaction left to warm up to room temperature overnight. The reaction mixture was diluted with water (20 mL) and extracted with EtOAc (2×25 mL). The combined organics were dried with Na$_2$SO$_4$, filtered through a hydrophobic frit and concentrated in vacuo to yield a brown oil. The crude product was applied to a 25 g silica cartridge in the minimum of DCM and eluted with 0% Ethyl Acetate in cyclohexane for 2CV then 0-25% Ethyl Acetate over 10CV then held at % for 5CV. The appropriate fractions were concentrated in vacuo to give the desired product (447 mg, 1.163 mmol, 49.1% yield) as a cream solid.

LCMS (2 mins Formic) Peak $R_t$=0.49 minutes, m/z=339 for [MH]

Intermediate 142: 7-methyl-4-(4,4,5,5-tetramethyl-1,3,2-dioxaborolan-2-yl)-1-tosyl-1H-pyrrolo[2,3-c]pyridine

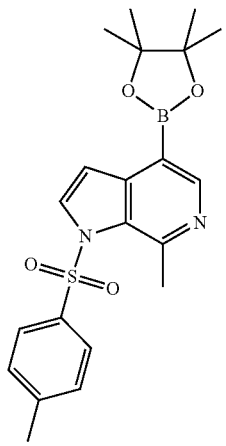 [SMILES: Cc1ccc(S(=O)(=O)n2ccc3c(B4OC(C)(C)C(C)(C)O4)cnc(C)c32)cc1]

4-bromo-7-methyl-1-tosyl-1H-pyrrolo[2,3-c]pyridine (440 mg, 1.205 mmol), bis(pinacolato)diboron (459 mg, 1.807 mmol) and potassium acetate (355 mg, 3.61 mmol) were combined in 1,4-Dioxane (10 mL) and nitrogen blown through the mixture for 10 mins. PdCl$_2$(dppf) (176 mg, 0.241 mmol) was added and the reaction heated to 50° C. under nitrogen over the weekend. An additional portion of PdCl$_2$(dppf) (176 mg, 0.241 mmol) was added and heating increased to 65° C. overnight. The reaction was cooled and filtered through celite. The filter cake was washed with EtOAc (20 mL). The filtrate was washed with water (25 mL) then dried with Na$_2$SO$_4$, filtered through a hydrophobic frit and concentrated in vacuo to yield the crude desired product (1.0688 g, 0.259 mmol, 21.52% yield) as a brown oil, which was used without further purification.

LCMS (2 mins High pH) Peak $R_t$=1.30 minutes, m/z=413.6 for [MH]

Intermediate 143: tert-butyl 2-((7-methyl-1-tosyl-1H-pyrrolo[2,3-c]pyridin-4-yl)methyl)-6-(methylcarbamoyl)isonicotinate

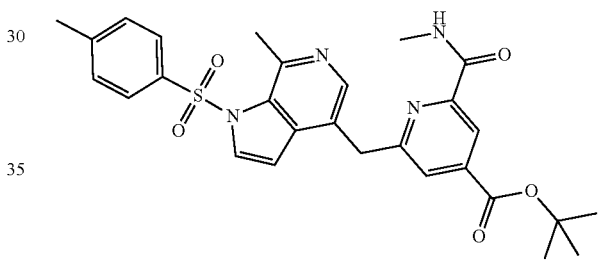

7-methyl-4-(4,4,5,5-tetramethyl-1,3,2-dioxaborolan-2-yl)-1-tosyl-1H-pyrrolo[2,3-c]pyridine (1.0688 g, 0.259 mmol) was taken up in 1,4-Dioxane (3 mL) and Water (1.5 mL). tert-butyl 2-(chloromethyl)-6-(methylcarbamoyl)isonicotinate (0.066 g, 0.233 mmol) and tripotassium phosphate (0.165 g, 0.778 mmol) were added and nitrogen bubbled through the solution for 10 mins. [1,3-Bis(2,6-Diisopropylphenyl)imidazol-2-ylidene](3-chloropyridyl)palladium(II) dichloride (0.018 g, 0.026 mmol) was added and the reaction stirred at room temperature overnight. The reaction was then heated to 80° C. for 5 h, then the reaction was left to cool and stand over the weekend. The reaction was concentrated in vacuo and the residue partitioned between EtOAc and water (25 mL each). The aqueous layer was reextracted with EtOAc (25 mL). The combined organics were dried with Na$_2$SO$_4$, filtered and concentrated in vacuo to yield a brown oil. The crude product was purified by MDAP (High pH method). The appropriate fractions were concentrated in vacuo to give the desired product (44.2 mg, 0.079 mmol, 30.3% yield) as a brown oil.

LCMS (2 mins High pH) Peak $R_t$=1.29 minutes, m/z=533.5 for [MH]

Intermediate 144: 2-((7-methyl-1H-pyrrolo[2,3-c]pyridin-4-yl)methyl)-6-(methylcarbamoyl)isonicotinic acid

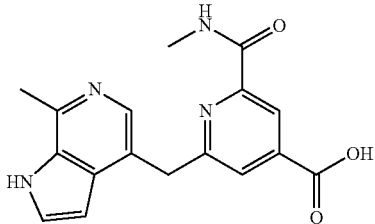 [SMILES: CNC(=O)c1cc(C(=O)O)cc(Cc2cnc(C)c3[nH]ccc23)n1]

Tert-butyl 2-((7-methyl-1-tosyl-1H-pyrrolo[2,3-c]pyridin-4-yl)methyl)-6-(methylcarbamoyl)isonicotinate (44.2 mg, 0.083 mmol) was taken up in methanol (2 mL) and THF (2.0 mL). 1M LiOH (0.413 mL, 0.413 mmol) was added and the reaction heated to 60° C. overnight.

The reaction was cooled and concentrated in vacuo to give the crude product as a brown oil which was used without further purification.

LCMS (2 mins High pH) Peak $R_t$=0.51 minutes, m/z=325.4 for [MH]

Intermediate 145: 1-(tert-Butyldimethylsilyl)-4-iodo-1H-pyrrolo[2,3-b]pyridine

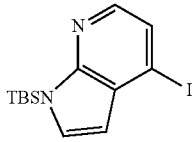

To a solution of 4-iodo-1H-pyrrolo[2,3-b]pyridine (1 g, 4.10 mmol) in THF (16 mL) cooled to 0° C., was added NaHMDS (1M in THF, 4.51 mL, 4.51 mmol) dropwise. After 15 min, TBDMS-Cl (0.803 g, 5.33 mmol) was added. The reaction was stirred for 30 min at 0° C. and 30 min at rt. Water (75 mL) and DCM (75 mL) were added and the layers were separated (a small amount of MeOH was added to aid separation). The aqueous layer was further extracted with DCM (2×50 mL). The combined organics were dried ($Na_2SO_4$), filtered and concentrated in vacuo to afford the desired crude product as a brown oil. This was taken up in cyclohexane and purified by flash SP4 chromatography using a 50 g SNAP silica cartridge and eluting with 100% cyclohexane. The appropriate fractions were collected and concentrated in vacuo, redissolved in toluene and concentrated again to remove any residual waster, to afford the desired product as a clear oil—1-(tert-butyldimethylsilyl)-4-iodo-1H-pyrrolo[2,3-b]pyridine (1.41 g, 3.94 mmol, 96% yield) LCMS (2 min High pH): Rt=1.71 min, [MH]⁺=359.1.

$^1$H NMR (400 MHz, DMSO-d) δ ppm 7.91 (d, J=5.0 Hz, 1H) 7.56 (d, J=3.5 Hz, 1H) 7.53 (d, J=5.0 Hz, 1H) 6.42 (d, J=3.5 Hz, 1H) 0.87 (s, 9H) 0.62 (s, 6H)

Intermediate 146: (+/−)-tert-Butyl 2-((1-(tert-butyldimethylsilyl)-1H-pyrrolo[2,3-b]pyridin-4-yl)(hydroxy)methyl)-6-(methylcarbamoyl)isonicotinate

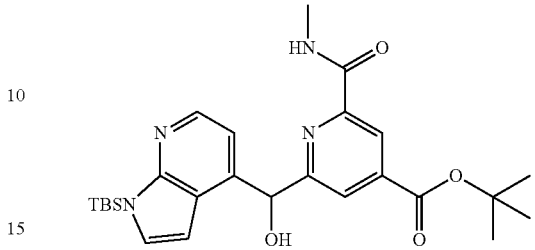

To a solution of 1-(tert-butyldimethylsilyl)-4-iodo-pyrrolo[2,3-b]pyridine (305 mg, 0.851 mmol) in THF (4 mL) cooled to 0° C., was added isopropylmagnesium chloride (1.89M in THF, 0.480 mL, 0.908 mmol) dropwise and the reaction stirred for 30 min at 0° C. tert-Butyl 2-formyl-6-(methylcarbamoyl)isonicotinate (150 mg, 0.568 mmol) was then added in THF (4 mL). The reaction was stirred for 1 h at 0° C. The reaction was allowed to stir at 0° C. for a further 30 min and was then quenched with sat. aq. NH₄Cl solution (20 mL) and EtOAc (20 mL) then added. The layers were separated and the aqueous layer further extracted with EtOAc (2×20 mL). The combined organics were dried ($Na_2SO_4$) and concentrated in vacuo to afford the crude product as an orange oil. This was taken up in cyclohexane (with a few drops of DCM) and added to a SNAP silica 25 g cartridge. This was purified by flash SP4 chromatography, eluting with 0-60% EtOAc/cyclohexane. The appropriate fractions were collected and concentrated in vacuo to afford the desired product as a yellow oil—tert-butyl 2-((1-(tert-butyldimethylsilyl)-1H-pyrrolo[2,3-b]pyridin-4-yl)(hydroxy)methyl)-6-(methylcarbamoyl)isonicotinate (160 mg, 0.322 mmol, 57% yield) LCMS (2 min High pH): Rt=1.49 min, [MH]⁺=497.3.

$^1$H NMR (400 MHz, DMSO-d₆) δ ppm 8.94 (q, J=4.5 Hz, 1H) 8.22 (d, J=4.8 Hz, 1H) 8.20 (d, J=1.5 Hz, 1H) 8.04 (d, J=1.5 Hz, 1H) 7.43 (d, J=3.5 Hz, 1H) 7.25 (d, J=5.3 Hz, 1H) 6.87 (d, J=3.5 Hz, 1H) 6.54 (d, J=5.0 Hz, 1H) 6.24 (d, J=4.8 Hz, 1H) 2.88 (d, J=4.8 Hz, 3H) 1.54 (s, 9H) 0.87 (s, 9H) 0.59 (d, J=4.0 Hz, 6H)

Intermediate 147: (+/−)-tert-Butyl 2-((1-(tert-butyldimethylsilyl)-1H-pyrrolo[2,3-b]pyridin-4-yl)(methoxy)methyl)-6-(methylcarbamoyl)isonicotinate

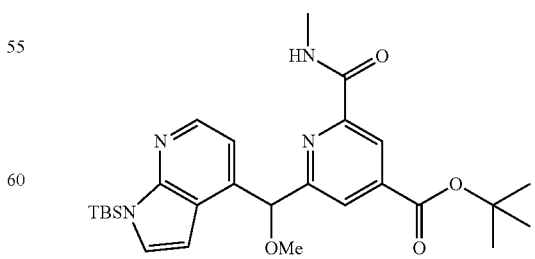

Trimethyloxonium tetrafluoroborate (143 mg, 0.966 mmol) was added to a mixture of tert-butyl 2-((1-(tert-butyldimethylsilyl)-1H-pyrrolo[2,3-b]pyridin-4-yl)(hydroxy)methyl)-6-(methylcarbamoyl)isonicotinate (160 mg, 0.322 mmol) and N¹,N¹,N³,N³-tetramethylnaphthalene-1,8-diamine (221 mg, 1.031 mmol) in DCM (1 mL) at rt and the mixture was stirred for 3 h. Further portions of Proton Sponge (74 mg) and trimethyloxonium tetrafluoroborate (48 mg) were added sequentially and the reaction stirred for a further 2 h. The reaction was diluted with EtOAc (20 mL) and saturated sodium bicarbonate solution (20 mL) was added. The layers were separated and the aqueous layer was further extracted with EtOAc (2×20 mL). The combined organics were washed with NH₄Cl (2×10 mL) and the organic layer then dried (Na₂SO₄) and evaporated in vacuo. The residue was taken up in cyclohexane and added to a SNAP 10 g silica cartridge. This was purified by flash SP4 chromatography eluting with 0-60% EtOAc/cyclohexane. The product-containing fractions were collected and concentrated in vacuo to afford the product, TLC showed this product still contained residual proton sponge. Therefore the crude product was taken up in cyclohexane and added to a SNAP 10 g silica cartridge. This was re-purified by flash SP4 chromatography eluting with 0-40% EtOAc/cyclohexane. The product-containing fractions were collected and concentrated in vacuo to afford the product, TLC showed this product still contained residual proton sponge. Therefore the crude product was taken up in cyclohexane and added to a SNAP 25 g silica cartridge. This was re-purified by flash SP4 chromatography eluting with 0-50% EtOAc/cyclohexane. The product-containing fractions were collected and concentrated in vacuo to afford the desired pure product as a pale-yellow oil—tert-butyl 2-((1-(tert-butyldimethylsilyl)-1H-pyrrolo[2,3-b]pyridin-4-yl)(methoxy)methyl)-6-(methylcarbamoyl)isonicotinate (99 mg, 0.194 mmol, 60% yield).

LCMS (2 min High pH): Rt=1.63 min, [MH]⁺=511.3.

¹H NMR (400 MHz, DMSO-d₆) δ ppm 8.70 (q, J=4.9 Hz, 1H) 8.24 (d, J=4.8 Hz, 1H) 8.22 (d, J=1.5 Hz, 1H) 8.06 (d, J=1.5 Hz, 1H) 7.46 (d, J=3.5 Hz, 1H) 7.26 (d, J=5.0 Hz, 1H) 6.87 (d, J=3.5 Hz, 1H) 5.89 (s, 1H) 3.44 (s, 3H) 2.87 (d, J=4.8 Hz, 3H) 1.55 (s, 9H) 0.86 (s, 9H) 0.59 (s, 6H)

Intermediate 148: (+/−)-2-(Methoxy(1H-pyrrolo[2,3-b]pyridin-4-yl)methyl)-6-(methylcarbamoyl)isonicotinic acid

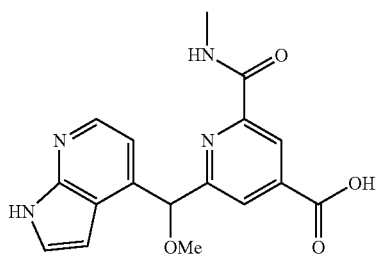 [SMILES: CNC(=O)c1cc(C(=O)O)cc(C(OC)c2ccnc3[nH]ccc23)n1]

To a flask containing tert-butyl 2-((1-(tert-butyldimethylsilyl)-1H-pyrrolo[2,3-b]pyridin-4-yl)(methoxy)methyl)-6-(methylcarbamoyl)isonicotinate (99 mg, 0.194 mmol) in methanol (1.2 mL) was added sodium hydroxide (2M in H₂O, 500 μL, 1.00 mmol) at rt and the reaction mixture was stirred for 3 h. HCl (2M in H₂O, 500 μL, 1.00 mmol) was added (pH ~4) and the reaction concentrated in vacuo to afford the crude product as a cream solid—2-(methoxy(1H-pyrrolo[2,3-b]pyridin-4-yl)methyl)-6-(methylcarbamoyl) isonicotinic acid (128 mg, 0.188 mmol, 97% yield, ~50% purity) which was used without further purification in the next reaction.

LCMS (2 min Formic): Rt=0.58 min, [MH]⁺=341.1.

¹H NMR (400 MHz, DMSO-d₆) δ ppm 11.66 (br. s., 1H) 8.61 (q, J=4.5 Hz, 1H) 8.24 (d, J=1.3 Hz, 1H) 8.21 (d, J=4.8 Hz, 1H) 8.01 (d, J=1.5 Hz, 1H) 7.40-7.44 (m, 1H) 7.24 (d, J=5.0 Hz, 1H) 6.65 (dd, J=3.4, 1.9 Hz, 1H) 5.82 (s, 1H) 3.41 (s, 3H) 2.87 (d, J=4.8 Hz, 3H). One exchangeable proton not observed.

Intermediate 149: 6-(Methoxy(1H-pyrrolo[2,3-b]pyridin-4-yl)methyl)-N²-methyl-N⁴-((1S,2S)-2-methylcyclopropyl)pyridine-2,4-dicarboxamide, Mixture of Diastereomers

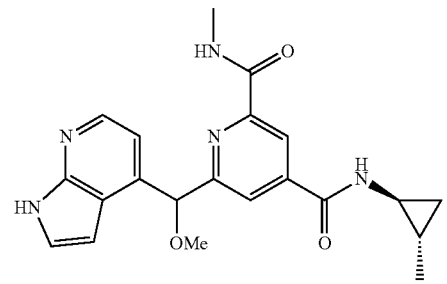 [SMILES: CNC(=O)c1cc(C(=O)N[C@H]2C[C@@H]2C)cc(C(OC)c2ccnc3[nH]ccc23)n1]

To a solution of 2-(methoxy(1H-pyrrolo[2,3-b]pyridin-4-yl)methyl)-6-(methylcarbamoyl)isonicotinic acid (50% wt., 128 mg, 0.188 mmol) in DMF (0.9 mL) was added sequentially, HATU (107 mg, 0.282 mmol) and DIPEA (0.099 mL, 0.564 mmol). The reaction was stirred for 1 min then (1S,2S)-2-methylcyclopropan-1-amine, hydrochloride (30.3 mg, 0.282 mmol) was added. The reaction was stirred for 1 h. The DMF solution was added directly to two MDAP vials and diluted with MeOH/DMSO to (2×0.9 mL). These were purified by MDAP (high pH). The appropriate fractions were collected and concentrated in vacuo to afford the product as an off white solid (43 mg, 0.109 mmol, 58% yield) LCMS (2 min High pH): Rt=0.81 min, [MH]⁺=394.3.

¹H NMR (400 MHz, DMSO-d) δ ppm 11.67 (br. s., 1H) 8.94 (d, J=4.3 Hz, 1H) 8.62-8.69 (m, 1H) 8.29 (d, 7-=1.0 Hz, 1H) 8.22 (d, J=5.0 Hz, 1H) 8.07 (d, 7-=1.5 Hz, 1H) 7.44 (dd, J=3.1, 1.9 Hz, 1H) 7.25 (d, J=4.8 Hz, 1H) 6.69 (br. d, J=2.8 Hz, 1H) 5.85 (s, 1H) 3.42 (s, 3H) 2.87 (d, J=4.8 Hz, 3H) 2.56 (dq, J=7.4, 3.8 Hz, 1H) 1.03-1.08 (m, 3H) 0.92-1.02 (m, 1H) 0.74-0.82 (m, 1H)

Intermediate 150: tert-butyl(cyclopent-3-en-1-yloxy)dimethylsilane

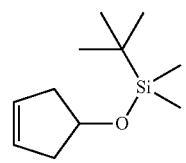

Cyclopent-3-en-1-ol (5 g, 59.4 mmol, commercially available from, for example, Astatech) was dissolved in DCM (100 mL) and TBDMS-Cl (8.96 g, 59.4 mmol) and imidazole (4.86 g, 71.3 mmol) were added, then the resulting suspension was stirred at room temperature over the weekend. The mixture was washed with water (2×100 mL), dried and evaporated in vacuo to give tert-butyl(cyclopent-3-en-1-yloxy)dimethylsilane (12.05 g, 60.7 mmol, 102% yield) as a pale yellow liquid.

$^1$H NMR (400 MHz, CHLOROFORM-d) ppm 5.68 (s, 2H) 4.50-4.62 (m, 1H) 2.59 (dd, J=14.9, 6.8 Hz, 2H) 2.23-2.37 (m, 2H) 0.91 (s, 9H) 0.09 (s, 6H).

Intermediate 151: (1R,5S,6r)-ethyl 3-((tert-butyldimethylsilyl)oxy)bicyclo[3.1.0]hexane-6-carboxylate

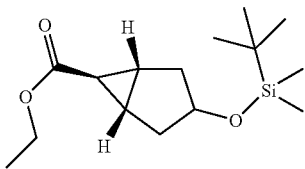 [SMILES: CCOC(=O)[C@H]1[C@@H]2CC(O[Si](C)(C)C(C)(C)C)C[C@@H]21]

Ethyl diazoacetate (6.90 mL, 66.5 mmol, commercially available from, for example, Sigma Aldrich) was dissolved in DCM (150 mL) and added dropwise over ~5 h to a mixture of rhodium(II) acetate dimer (1 g, 2.263 mmol, commercially available from, for example, Sigma Aldrich) and tert-butyl(cyclopent-3-en-1-yloxy)dimethylsilane (12 g, 60.5 mmol) in DCM (150 mL) at room temperature. The resulting green solution was stirred overnight, then evaporated in vacuo to give a green liquid. This was loaded onto a 340 g silica column and eluted with 0-40% EtOAc/cyclohexane. Appropriate fractions were evaporated in vacuo to give ethyl (1R,5S,6r)-3-((tert-butyldimethylsilyl)oxy)bicyclo[3.1.0]hexane-6-carboxylate (5.5 g, 19.33 mmol, 32.0% yield) as a colourless liquid—NMR appears to be consistent with the desired product as a mixture of isomers at the silyl ether position in about 3:1 ratio and this was carried through crude to the next step.

LCMS (2 min High pH): Rt=0.96 min, [MH]$^+$=not present.

Intermediate 152: benzyl ((1R,5S,6r)-3-((tert-butyldimethylsilyl)oxy)bicyclo[3.1.0]hexan-6-yl)carbamate

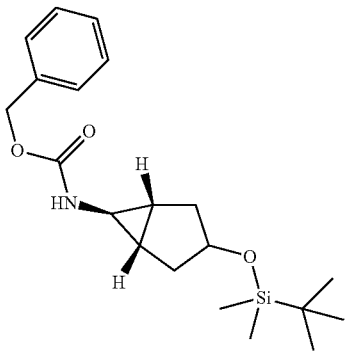 [SMILES: CC(C)(C)[Si](C)(C)OC1C[C@@H]2[C@H](C1)[C@H]2NC(=O)OCc1ccccc1]

Step 1: Sodium hydroxide (20 mL, 40.0 mmol) was added to a solution of ethyl (1R*,5S*,6r*)-3-((tert-butyldimethylsilyl)oxy)bicyclo[3.1.0]hexane-6-carboxylate (5.0 g, 17.58 mmol) in ethanol (50 mL) at room temperature and the mixture was stirred for 3 h. TLC suggested that all the starting material had been consumed and the mixture was evaporated in vacuo to about 30 mL volume, then diluted with water (30 mL) and washed with ether (50 mL). The ether washings from the workup were dried and evaporated in vacuo to give recovered starting material (3.85 g) ethyl (1R*,5S*,6r*)-3-((tert-butyldimethylsilyl)oxy)bicyclo[3.1.0]hexane-6-carboxylate. This was dissolved in ethanol (30 mL) and 2M aqueous NaOH solution (20 mL) was added, then the mixture was heated at 70° C. for 3 h, then evaporated in vacuo. The residue was dissolved in water (50 mL) and washed with ether (50 mL), then the aqueous layer was acidified with 2M HCl (20 mL) and extracted with EtOAc (2×50 mL). The combined organics were dried and evaporated in vacuo to give (1R,5S,6r)-3-((tert-butyldimethylsilyl)oxy)bicyclo[3.1.0]hexane-6-carboxylic acid (1.9 g, 7.41 mmol, 42.2% yield) as a pale yellow solid. The product was carried through to the next step without purification.

Step 2: (1R,5S,6r)-3-((tert-butyldimethylsilyl)oxy)bicyclo[3.1.0]hexane-6-carboxylic acid (1.8 g, 7.02 mmol) was dissolved in a mixture of toluene (20 mL) and Et$_3$N (1.957 mL, 14.04 mmol), then DPPA (1.815 mL, 8.42 mmol) was added and the mixture was stirred for 30 min at room temperature.

Benzyl alcohol (1.095 mL, 10.53 mmol) was added and the mixture heated at 100° C. for 4 h, then cooled to room temperature. Ethyl acetate (100 mL) was added and the solution was washed with water (2×100 mL), then dried over sodium sulphate, filtered and the filtrate evaporated in vacuo to give a pale yellow oil. This was dissolved in DCM (10 mL) and loaded onto a 50 g silica column, then eluted with 0-30% EtOAc/cyclohexane and product-containing fractions (detected by permanganate dip) were collected and evaporated in vacuo to give benzyl ((1R,5S,6r)-3-((tert-butyldimethylsilyl)oxy)bicyclo[3.1.0]hexan-6-yl)carbamate (1.90 g, 5.26 mmol, 74.9% yield) as a pale yellow oil, NMR consistent with desired product as a mixture of isomers in approximately 2:1 ratio. The compound was taken through to the next step without further purification.

LCMS (2 min Formic): Rt=1.56 min, [MH]$^+$=362.6.

Intermediate 153: (1R,5S,6r)-3-((tert-butyldimethylsilyl)oxy)bicyclo[3.1.0]hexan-6-amine

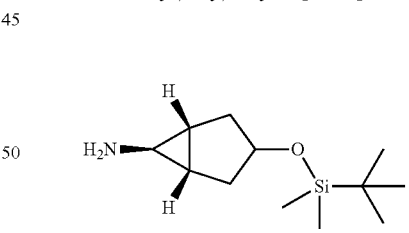

Benzyl ((1R,5S,6r)-3-((tert-butyldimethylsilyl)oxy)bicyclo[3.1.0]hexan-6-yl)carbamate (1.9 g, 5.26 mmol) was dissolved in ethanol (100 mL) and hydrogenated in the H-Cube at atmospheric pressure and 1 mL/min flow rate. The eluant was evaporated in vacuo to give the desired product (1.12 g, 4.92 mmol, 84% yield) as a pale yellow oil, NMR consistent with desired product as an approximately equal mixture of isomers at the silyl ether position.

$^1$H NMR (400 MHz, CHLOROFORM-d) ppm 4.23 (t, J=1.0 Hz, 1H) 3.81 (q, J=1.0 Hz, 1H) 3.48 (s, 2H) 2.49 (s, 1H) 1.93-2.08 (m, 5H) 1.63 (d, J=13.0 Hz, 3H) 1.25-1.33 (m, 1H) 1.13-1.25 (m, 3H) 0.80-0.92 (m, 18H) −0.04-0.06 (m, 12H).

Intermediate 154: N⁴-((1R,5S,6r)-3-((tert-butyldimethylsilyl)oxy)bicyclo[3.1.0]hexan-6-yl)-N²-methyl-6-((S)-1-phenylethyl)pyridine-2,4-dicarboxamide

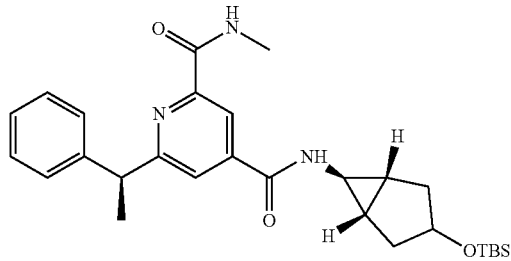 [SMILES: CNC(=O)c1cc(C(=O)N[C@H]2[C@@H]3CC(O[Si](C)(C)C(C)(C)C)C[C@@H]32)cc([C@@H](C)c2ccccc2)n1]

(S)-2-(methylcarbamoyl)-6-(1-phenylethyl)isonicotinic acid (100 mg, 0.352 mmol), HATU (160 mg, 0.422 mmol), DMF (2 mL) and DIPEA (0.184 mL, 1.055 mmol) were mixed into a flask and stirred for 5 minutes. Then (1R,5S,6r)-3-((tert-butyldimethylsilyl)oxy)bicyclo[3.1.0]hexan-6-amine (96 mg, 0.422 mmol) was added and the reaction was stirred 2 h at room temperature. The reaction mixture was diluted with water and extracted 3 times with EtOAc, the combined organics were washed with a 10% aqueous LiCl solution, dried using a hydrophobic frit and concentrated in vacuo to a yellow oil. It was then purified by silica gel column chromatography eluting with a gradient of 0 to 32% of (25% EtOH in AcOEt) in cyclohexane to give the desired product (156.7 mg, 0.279 mmol, 82% yield) as a yellow gum.

LCMS (2 min Formic): Rt=1.53 min, [MH]⁺=494.4

Intermediate 155: 6-benzyl-N-((1R,5S,6r)-3-((tert-butyldimethylsilyl)oxy)bicyclo[3.1.0]hexan-6-yl)-N²-methylpyridine-2,4-dicarboxamide

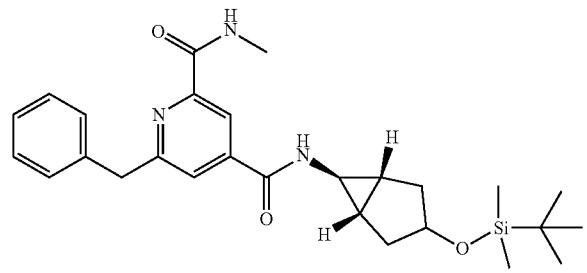 [SMILES: CNC(=O)c1cc(C(=O)N[C@H]2[C@@H]3CC(O[Si](C)(C)C(C)(C)C)C[C@@H]32)cc(Cc2ccccc2)n1]

2-benzyl-6-(methylcarbamoyl)isonicotinic acid (35 mg, 0.129 mmol), HATU (59.1 mg, 0.155 mmol), DMF (1.2 mL) and DIPEA (0.068 mL, 0.388 mmol) were mixed into a flask and stirred for 5 minutes. Then (1R,5S,6r)-3-((tert-butyldimethylsilyl)oxy)bicyclo[3.1.0]hexan-6-amine (35.3 mg, 0.155 mmol) was added and the reaction was stirred 1.5 h at room temperature. The reaction mixture was diluted with water (30 mL) and extracted with EtOAc (3×30 mL), the combined organics were washed with a 10% aqueous LiCl solution (20 mL), dried using a hydrophobic frit and concentrated in vacuo to a yellow oil. It was then purified by silica gel column chromatography eluting with a gradient of 0 to 40% of (25% EtOH in EtOAc) in cyclohexane (10CVs) to give the desired product (113.5 mg, 0.208 mmol, 59.3% yield) as an orange gum.

LCMS (2 min Formic): Rt=1.49 min, [MH]⁺=480.4

Intermediate 156: N⁴-((1R,5S,6r)-3-((tert-butyldimethylsilyl)oxy)bicyclo[3.1.0]hexan-6-yl)-6-(methoxy(phenyl)methyl)-N²-methylpyridine-2,4-dicarboxamide

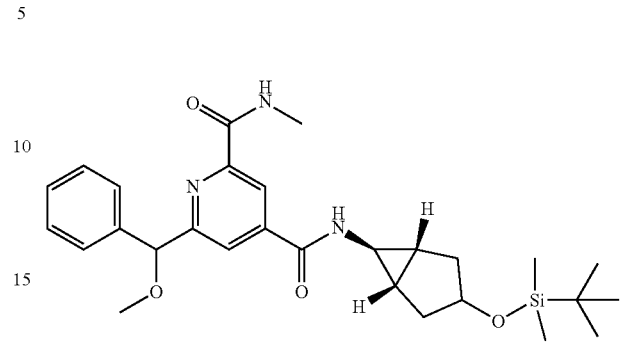

2-(methoxy(phenyl)methyl)-6-(methylcarbamoyl)isonicotinic acid (185 mg, 0.578 mmol), HATU (264 mg, 0.693 mmol), DMF (4 mL) and DIPEA (0.303 mL, 1.733 mmol) were mixed into a flask and stirred for 5 minutes. Then (1R,5S,6r)-3-((tert-butyldimethylsilyl)oxy)bicyclo[3.1.0]hexan-6-amine (158 mg, 0.693 mmol) was added and the reaction was stirred 1.5 h at room temperature. DIPEA (0.303 mL, 1.733 mmol) was added and the reaction mixture was stirred at 45° C. for 2 h. A further portion of HATU (264 mg, 0.693 mmol) was added and the reaction was stirred at 45° C. for 2 h. The reaction mixture was diluted with water (40 mL) and extracted with EtOAc (3×40 mL), the combined organics were washed with a 10% aqueous LiCl solution (20 mL), with a saturated NaHCO₃ solution (20 mL), dried using a hydrophobic frit and concentrated in vacuo to an orange oil. It was purified firstly by silica column chromatography, eluting with a gradient of 0 to 32% of (25% EtOH in AcOEt) in cyclohexane (10 CVs), and then a second time by silica column chromatography, eluting with a gradient of 20 to 80% of AcOEt in cyclohexane (10 CVs). The appropriate fractions were combined and evaporated under reduced pressure to give the desired product (168.3 mg, 0.147 mmol, 44.7% yield) as an orange gum.

LCMS (2 min Formic): Rt=1.52 min, [MH]⁺=510.4

EXAMPLES

Example 1: (+/−)-N⁴-Cyclopropyl-N²-methyl-6-(1-phenylethyl)pyridine-2,4-dicarboxamide

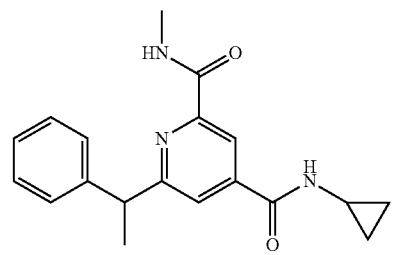 [SMILES: CNC(=O)c1cc(C(=O)NC2CC2)cc(C(C)c2ccccc2)n1]

2-(Methylcarbamoyl)-6-(1-phenylethyl)isonicotinic acid (100 mg, 0.352 mmol), HATU (204 mg, 0.537 mmol), DIPEA (0.19 mL, 1.088 mmol), cyclopropanamine (0.05 mL, 0.722 mmol) and DMF (3 mL) were stirred at rt under N$_2$ for 1 h. The solution was concentrated to give 750 mg of an orange oil. This was purified by chromatography on SiO$_2$ (Biotage® SNAP 25 g cartridge, eluting with 0-100% ethyl acetate/cyclohexane. The appropriate fractions were concentrated to give 83 mg of a yellow oil. The sample was dissolved in 1:1 MeOH:DMSO (1 mL) and purified by MDAP (Formic). The appropriate fractions were concentrated to give N$^4$-cyclopropyl-N$^2$-methyl-6-(1-phenylethyl)pyridine-2,4-dicarboxamide (58 mg, 0.161 mmol, 45.9% yield) as a colourless oil.

LCMS (2 min Formic): Rt=0.98 min, [MH]$^+$=324.0.

Example 2: 6-Benzyl-N$^4$-cyclopropyl-N$^2$-methylpyridine-2,4-dicarboxamide

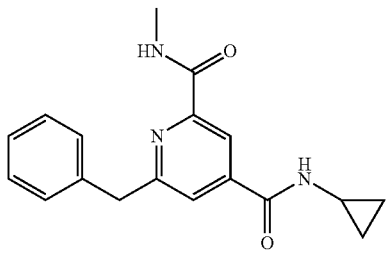 [SMILES: CNC(=O)c1cc(C(=O)NC2CC2)cc(Cc2ccccc2)n1]

2-Benzyl-6-(methylcarbamoyl)isonicotinic acid (130 mg, 0.481 mmol), HATU (267 mg, 0.702 mmol), DIPEA (0.25 mL, 1.431 mmol), cyclopropanamine (0.07 mL, 1.010 mmol) and DMF (3 mL) were stirred at rt under N$_2$ for 45 min. The solution was concentrated to give 60 mg of an orange oil. This was purified by chromatography on SiO$_2$ (Biotage® SNAP 25 g cartridge, eluting with 0-100% ethyl acetate/cyclohexane. The appropriate fractions were concentrated to give 139 mg of a yellow oil. This was purified by chromatography on SiO$_2$ (Biotage® SNAP 25 g cartridge, eluting with 50-100% ethyl acetate/cyclohexane. The appropriate fractions were concentrated to give 83 mg of a yellow oil. This was taken up in DMF (1 mL) and further purified by MDAP (Formic). Fractions containing the desired product were concentrated to give 6-benzyl-N$^4$-cyclopropyl-N$^2$-methylpyridine-2,4-dicarboxamide (66 mg, 0.192 mmol, 39.9% yield) as a white solid.

LCMS (2 min Formic): Rt=0.91 min, [MH]$^+$=310.0.

Example 3: 6-Benzyl-N$^4$-cyclobutyl-N$^2$-methylpyridine-2,4-dicarboxamide

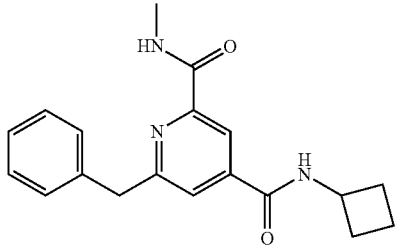 [SMILES: CNC(=O)c1cc(C(=O)NC2CCC2)cc(Cc2ccccc2)n1]

6-Bromo-N$^4$-cyclobutyl-N$^2$-methylpyridine-2,4-dicarboxamide (46 mg, 0.147 mmol), benzylzinc(II) bromide (0.5M in THF, 0.5 mL, 0.250 mmol), PdCl$_2$(PPh$_3$)$_2$ (12 mg, 0.017 mmol) and THF (1.5 mL) were heated at 110° C. for 30 min in the microwave. The black solution was filtered over Celite®, partitioned between EtOAc and water, extracted with EtOAc (3×30 mL), dried over a hydrophobic frit and concentrated to give 70 mg of a brown solid. The sample was dissolved in 1:1 MeOH:DMSO, (1 mL) and purified by MDAP (Formic). The solution was concentrated to give 6-benzyl-N$^4$-cyclobutyl-N$^2$-methylpyridine-2,4-dicarboxamide (23 mg, 0.064 mmol, 43.4% yield) as a colourless oil.

LCMS (2 min Formic): Rt=1.02 min, [MH]$^+$=324.0.

Example 4: (+/−)-N$^4$-Cyclobutyl-N$^2$-methyl-6-(1-phenylethyl)pyridine-2,4-dicarboxamide

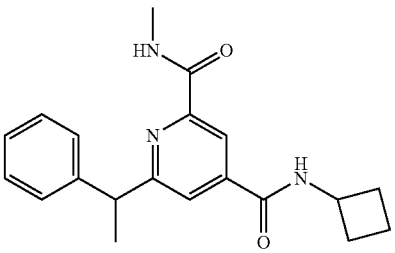 [SMILES: CNC(=O)c1cc(C(=O)NC2CCC2)cc(C(C)c2ccccc2)n1]

6-Bromo-N$^4$-cyclobutyl-N$^2$-methylpyridine-2,4-dicarboxamide (46 mg, 0.147 mmol), (1-phenylethyl)zinc(II) bromide (0.5M in THF, 0.147 mL, 0.074 mmol), PdCl$_2$(PPh$_3$)$_2$ (16 mg, 0.023 mmol) and THF (1 mL) were heated at 110° C. for 30 min in the microwave. The reaction was heated at 110° C. for another 30 min in the microwave. (1-Phenylethyl)zinc(II) bromide (0.5M in THF, 0.3 mL, 0.150 mmol), PdCl$_2$(PPh$_3$)$_2$ (11 mg, 0.016 mmol) and THF (0.5 mL) were added and the reaction was heated at 110° C. for 30 min in the microwave. The reaction mixture was partitioned between EtOAc and water, the aqueous layer was further extracted with EtOAc (3×30 mL), and the combined organics dried over a hydrophobic frit and concentrated to give 120 mg of a brown solid. This was purified by chromatography on SiO$_2$ (Biotage® SNAP 10 g cartridge, eluting with 0-100% ethyl acetate/cyclohexane). The desired fractions were concentrated to give 31 mg of a brown solid. The sample was dissolved in 1:1 MeOH:DMSO (1 mL) and purified by MDAP (Formic). The solution was concentrated to give N$^4$-cyclobutyl-N$^2$-methyl-6-(1-phenylethyl)pyridine-2,4-dicarboxamide (21 mg, 0.056 mmol, 38.0% yield) as a white solid.

LCMS (2 min Formic): Rt=1.08 min, [MH]$^+$=338.0.

Example 5: (S*)—N$^4$-Cyclopropyl-N$^2$-methyl-6-(1-phenylethyl)pyridine-2,4-dicarboxamide Example 6: (R*)—N$^4$-Cyclopropyl-N$^2$-methyl-6-(1-phenylethyl)pyridine-2,4-dicarboxamide

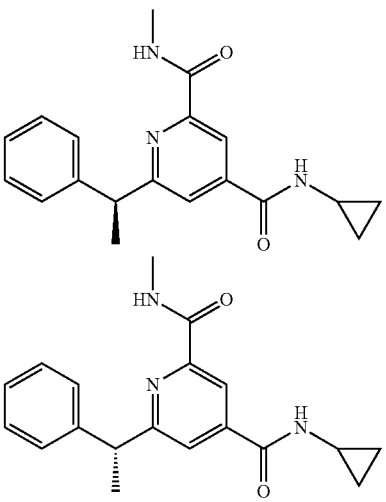

Example 1 (53 mg) was purified by chiral HPLC. The racemate was dissolved in EtOH (1 mL). Injection: 0.5 mL of the solution was injected onto the column (20% EtOH (+0.2% isopropylamine)/heptane (+0.2% isopropylamine), flow rate=30 mL/min, detection wavelength=215 nm, Column 30 mm×25 cm Chiralpak IC). Total number of injections=2. Fractions from 21-23.5 min were bulked and labelled peak 1. Fractions from 25-28 min were bulked and labelled peak 2. The bulked fractions were concentrated in vacuo and then transferred to weighed flasks.

The fractions corresponding to peak 1 were collected to afford example 5 (26 mg)

LCMS (2 min Formic): Rt=0.98 min, $[MH]^+$=324.2.

The fractions corresponding to peak 2 were collected to afford example 6 (20 mg)

LCMS (2 min Formic): Rt=0.98 min, $[MH]^+$=324.1.

Example 7: 6-Benzyl-$N^2$-methyl-$N^4$-((1S,2S)-2-methylcyclopropyl)pyridine-2,4-dicarboxamide

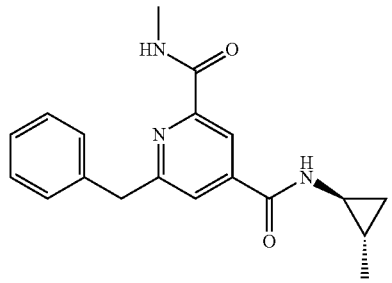 [SMILES: CNC(=O)c1cc(C(=O)N[C@H]2C[C@@H]2C)cc(Cc2ccccc2)n1]

6-Bromo-$N^2$-methyl-$N^4$-((1S,2S)-2-methylcyclopropyl)pyridine-2,4-dicarboxamide (80 mg, 0.256 mmol), benzylzinc(II) bromide (0.5 M in THF, 0.871 mL, 0.436 mmol), $PdCl_2(PPh_3)_2$ (27 mg, 0.038 mmol) and THF (1.5 mL) were heated at 110° C. for 30 min in the microwave. The black solution was filtered over Celite®, partitioned between EtOAc and water, extracted with EtOAc (3×30 mL), dried over a hydrophobic frit and concentrated to give ~149 mg of crude product as a brown oil. This was purified by chromatography on $SiO_2$ (Biotage® SNAP 10 g cartridge, eluting with 10-70% ethyl acetate/cyclohexane) to give 86 mg of a brown oil. This was taken up in 1:1 DMSO:MeOH (1 mL) and further purified by MDAP (Formic). The fractions containing the desired product were partitioned between sat. $NaHCO_3$ solution and DCM. The organic layer was extracted (2×50 mL), dried ($Na_2SO_4$) and concentrated in vacuo to give 6-benzyl-$N^2$-methyl-$N^4$-((1S,2S)-2-methylcyclopropyl)pyridine-2,4-dicarboxamide (58 mg, 0.161 mmol, 63.0% yield) as a white solid.

LCMS (2 min Formic): Rt=1.00 min, $[MH]^+$=324.4.

Example 8: 6-((1H-Indazol-7-yl)methyl)-$N^4$-cyclopropyl-$N^2$-methylpyridine-2,4-dicarboxamide

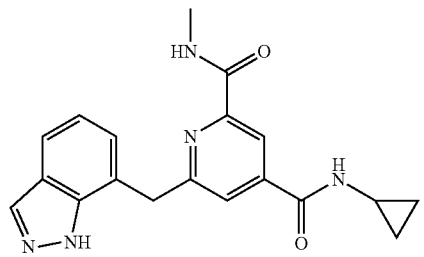 [SMILES: CNC(=O)c1cc(C(=O)NC2CC2)cc(Cc2cccc3cn[nH]c23)n1]

6-(Chloromethyl)-$N^4$-cyclopropyl-$N^2$-methylpyridine-2,4-dicarboxamide (66 mg, 0.247 mmol) was combined with 7-(4,4,5,5-tetramethyl-1,3,2-dioxaborolan-2-yl)-1H-indazole (68 mg, 0.279 mmol), potassium carbonate (104 mg, 0.753 mmol) and $PdCl_2$(dppf) (34 mg, 0.046 mmol) in 1,4-dioxane (2 mL) and water (1 mL) in a 2 mL microwave vial. This was heated at 120° C. for 40 min. The solution was filtered through Celite®, partitioned between EtOAc (10 mL) and water (10 mL), extracted with further EtOAc (2×10 mL), dried through a hydrophobic frit and concentrated to give 240 mg of a brown oil. This was purified by chromatography on $SiO_2$ (Biotage® SNAP 25 g, eluting with 0-100% ethyl acetate/cyclohexane). The desired fractions were concentrated to give 6-((1H-indazol-7-yl)methyl)-$N^4$-cyclopropyl-$N^2$-methylpyridine-2,4-dicarboxamide (43 mg, 0.111 mmol, 44.9% yield) as a pale brown solid.

LCMS (2 min Formic): Rt=0.80 min, $[MH]^+$=350.5.

Example 9: 6-(3-(2-Hydroxyethoxy)benzyl-$N^2$-methyl-$N^4$-((1S,2S)-2-methylcyclopropyl)pyridine-2,4-dicarboxamide

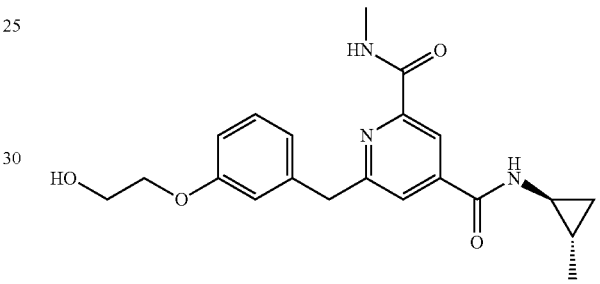

1,3-Dioxolan-2-one (11.47 mg, 0.130 mmol) was added to a solution of 6-(3-hydroxybenzyl)-$N^2$-methyl-$N^4$-((1S,2S)-2-methylcyclopropyl)pyridine-2,4-dicarboxamide (34 mg, 0.100 mmol) and $K_2CO_3$ (27.7 mg, 0.200 mmol) in DMF (4 mL). The reaction mixture was stirred for 1 h and an additional equivalent of 1,3-dioxolan-2-one (11.47 mg, 0.130 mmol) was added. The reaction mixture was left stirring for another 2 h and an additional equivalent of 1,3-dioxolan-2-one (11.47 mg, 0.130 mmol) was once again added. The reaction mixture was stirred for 2 h and further 1,3-dioxolan-2-one (11.47 mg, 0.130 mmol) was added. A final equivalent of 1,3-dioxolan-2-one (11.47 mg, 0.130 mmol) was added and the reaction mixture was left stirring for 15 h. The reaction mixture was partitioned between EtOAc and water. The aqueous layer was removed, the organic layer washed (1× water, 2× sat. aq. $NaHCO_3$), passed through a hydrophobic frit and evaporated in vacuo to a clear oil. The sample was then purified using a 10 g Biotage® SNAP column using a gradient of 30-100% EtOAc/cyclohexane.

The product containing fractions were combined and the solvent removed in vacuo to give a clear oil.

The sample was then dried under a stream of nitrogen for 2 h and was then placed in the vacuum oven at 40° C. for 1 h. The sample was further purified via MDAP (Formic). The product containing fractions were combined and the solvent removed in vacuo to give a white solid. The sample was then dried under a stream of nitrogen for 16 h and was then placed in vacuo at 40° C. for 1 h to afford the desired product (12 mg).

LCMS (2 min Formic): Rt=0.84 min, $[MH]^+$=384.4.

Example 10: N⁴—Cyclopropyl-6-(2-fluorobenzyl)-N²-methylpyridine-2,4-dicarboxamide

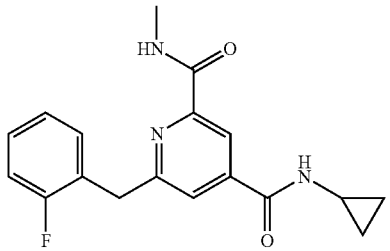

To a solution of 2-(2-fluorobenzyl)-6-(methylcarbamoyl)isonicotinic acid (45.2 mg, 0.125 mmol, 80% wt.) in DMF (0.8 mL) was added HATU (64.2 mg, 0.169 mmol) followed by cyclopropanamine (0.02 mL, 0.289 mmol) and DIPEA (0.1 mL, 0.573 mmol). The resulting reaction mixture was stirred at rt overnight. The reaction mixture was purified directly by MDAP (Formic). The fractions containing the desired product were partitioned between sat. sodium bicarbonate solution and DCM. The organic layer was extracted (2×20 mL) then dried and concentrated in vacuo to give N⁴-cyclopropyl-6-(2-fluorobenzyl)-N²-methylpyridine-2,4-dicarboxamide (23.4 mg, 0.068 mmol, 60.3% yield) as a colourless oil.

LCMS (2 min Formic): Rt=0.94 min, [MH]⁺=328.2.

Example 11: N⁴-((1S,2S)-2-(Hydroxymethyl)cyclopropyl)-6-(3-methoxybenzyl)-N²-methylpyridine-2,4-dicarboxamide

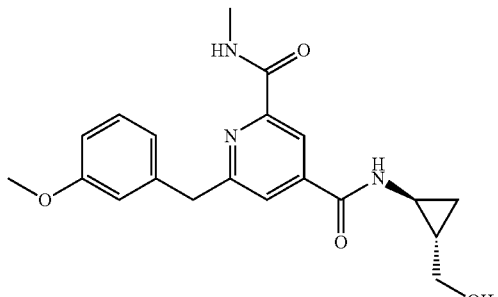

2-(3-Methoxybenzyl)-6-(methylcarbamoyl)isonicotinic acid (30 mg, 0.100 mmol) was suspended in DCM (10 mL), and Et₃N (0.028 mL, 0.200 mmol) and HATU (49.4 mg, 0.130 mmol) were added, then the mixture was stirred for 20 min before the addition of ((1S,2S)-2-aminocyclopropyl)methanol, hydrochloride (18.52 mg, 0.150 mmol). The resulting yellow solution was stirred for 2 h, then washed with water (10 mL), dried and evaporated in vacuo and the residue purified by MDAP (High pH) to give N⁴-((1S,2S)-2-(hydroxymethyl)cyclopropyl)-6-(3-methoxybenzyl)-N²-methylpyridine-2,4-dicarboxamide (25 mg, 0.068 mmol, 67.7% yield) as a colourless solid.

LCMS (2 min High pH): Rt=0.85 min, [MH]⁺=370.3.

Example 12: N⁴—Cyclopropyl-6-(3-methoxybenzyl)-N²-methylpyridine-2,4-dicarboxamide

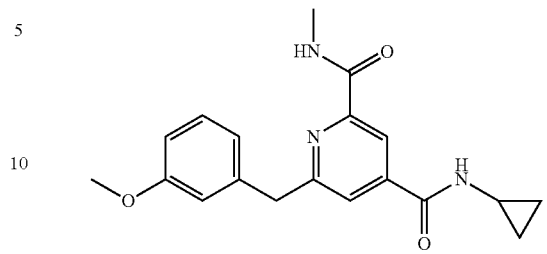

2-(3-Methoxybenzyl)-6-(methylcarbamoyl)isonicotinic acid (40 mg, 0.133 mmol) was suspended in DCM (10 mL), and Et₃N (0.037 mL, 0.266 mmol) and HATU (65.8 mg, 0.173 mmol) were added, then the mixture was stirred for 20 min before the addition of cyclopropylamine (0.028 mL, 0.400 mmol). The resulting yellow solution was stirred for 2 h, then washed with water (10 mL), dried and evaporated in vacuo and the residue purified by MDAP (High pH) to give N⁴-cyclopropyl-6-(3-methoxybenzyl)-N²-methylpyridine-2,4-dicarboxamide (25 mg, 55.3% yield) as a colourless solid.

LCMS (2 min Formic): Rt=0.95 min, [MH]⁺=340.2.

Example 13: 6-(3-Methoxybenzyl)-N²-methyl-N⁴-((1S,2S)-2-methylcyclopropyl)pyridine-2,4-dicarboxamide

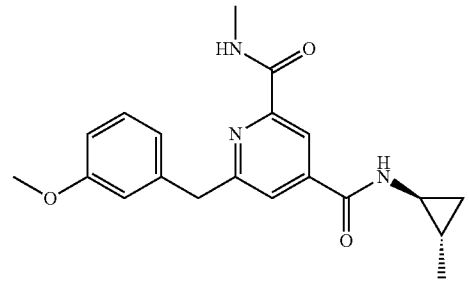 [SMILES: CNC(=O)c1cc(C(=O)N[C@H]2C[C@@H]2C)cc(Cc2cccc(OC)c2)n1]

HATU (425 mg, 1.119 mmol) was added to a solution of 2-(3-methoxybenzyl)-6-(methylcarbamoyl)isonicotinic acid (210 mg, 0.699 mmol), (1S,2S)-2-methylcyclopropanamine hydrochloride (90 mg, 0.839 mmol) and DIPEA (0.366 mL, 2.098 mmol) in DMF (4 mL). The reaction mixture was stirred for 15 min. The reaction mixture was partitioned between EtOAc and water. The aqueous layer was removed, the organic layer washed (1× water, 2× sat. aq. NaHCO₃), passed through a hydrophobic frit and evaporated in vacuo to a brown oil. The sample was then purified using a 10 g Biotage® SNAP column, eluting with 0-80% EtOAc/cyclohexane. The product containing fractions were combined and the solvent removed in vacuo. The sample was then dried under a stream of nitrogen for 1 h and was then placed in vacuo at 40° C. for 1 h to afford the desired product (206 mg).

LCMS (2 min Formic): Rt=1.01 min, [MH]⁺=354.3.

Example 14: Amide array of 2-benzyl-6-(methylcarbamoyl)isonicotinic Acid Monomers

| Ex No. | Reagent Name | Structure | MW | Reagent Mass (g) | Reagent Volume (mL) | mmol |
|---|---|---|---|---|---|---|
| 14 | (+/−)-(trans)-2-Aminocyclobutanol | 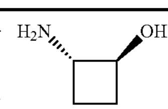 | 87.12 | 0.010 | — | 0.120 |

A stock solution prepared of 2-benzyl-6-(methylcarbamoyl)isonicotinic acid (162 mg) plus HATU (228 mg) was dissolved together in DMF (3 mL). DIPEA (330 μL) was added and the vial capped and shaken to aid dissolution. An aliquot of this reaction mixture (0.5 mL, 0.1 mmol) was added to the preweighed amine with the structure shown above (0.120 mmol) in a matrix vial (1.2 mL). This was capped and shaken to disperse the contents and then stood at rt for 18 h. To the reaction mixture was then added T3P (50% in EtOAc, 120 μL) plus DIPEA (55 μL) and further starting amine (+/−)-(trans)-2-aminocyclobutanol (20 mg) was added. The vial was shaken and left to stand at rt for 1 h. The sample was injected as is and purified by MDAP (High pH). The solvent was then dried under a stream of nitrogen to give the required product as listed in the table below Examples

| Ex No. | Name | Structure | Mass (mg) | Yield (%) | [MH]+ | Rt (min)* |
|---|---|---|---|---|---|---|
| 14 | (+/−)-6-Benzyl-$N^4$-((trans)-2-hydroxycyclobutyl)-$N^2$-methylpyridine-2,4-dicarboxamide | 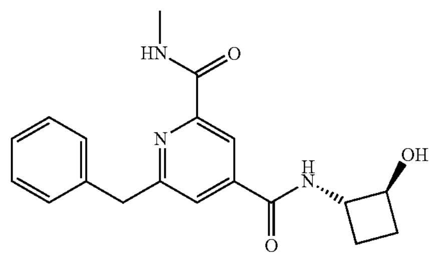 | 2.3 | 6 | 340 | 0.86 |

*All LCMS were conducted using 2 min High pH.

Example 15: Amide array of 2-benzyl-6-(methylcarbamoyl)isonicotinic acid

| Ex No. | Reagent Name | Structure | MW | Reagent Mass (g) | Reagent Volume (mL) | mmol |
|---|---|---|---|---|---|---|
| 15 | (1r,4r)-4-Aminocyclohexanol | 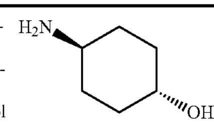 | 115.17 | 0.012 | — | 0.100 |

2-Benzyl-6-(methylcarbamoyl)isonicotinic acid was added to HATU (0.038 g, 0.100 mmol) and DIPEA (0.052 mL, 0.300 mmol) and the mixture dissolved in DMF (0.5 mL) and left for 5 min. This solution was dispensed to the amine (0.100 mmol) and the reaction left for 24 h at 22° C. T3P (0.2 mmol) was then added to the reaction and progression analysed by LCMS. The sample in DMF was then purified by MDAP (High pH). The solvent was dried under a stream of nitrogen to give the required product as shown in the table below.

Examples

| Ex No. | Name | Structure | Mass (mg) | Yield (%) | [MH]+ | Rt (min)* |
|---|---|---|---|---|---|---|
| 15 | 6-Benzyl-$N^4$-((1r,4r)-4-hydroxycyclohexyl)-$N^2$-methylpyridine-2,4-dicarboxamide | 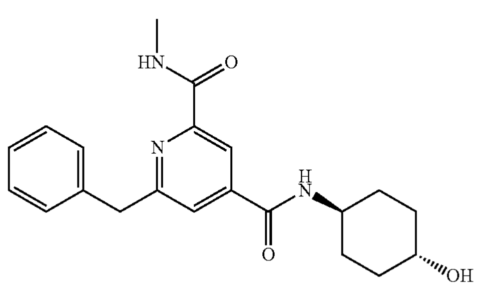 [SMILES: CNC(=O)c1cc(C(=O)N[C@H]2CC[C@H](O)CC2)cc(Cc2ccccc2)n1] | 13.8 | 34 | 368 | 0.84 |

*All LCMS were conducted using 2 min High pH.

Example 16: (S)—N⁴-Cyclopropyl-6-(3-(2-hydroxypropoxy)benzyl)-N²-methylpyridine-2,4-dicarboxamide

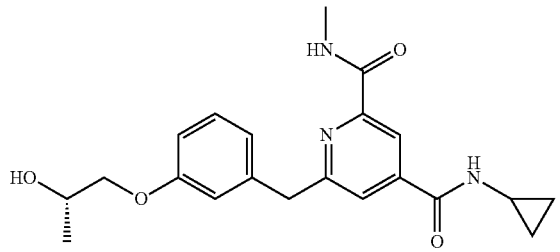 [SMILES: CNC(=O)c1cc(C(=O)NC2CC2)cc(Cc2cccc(OC[C@H](C)O)c2)n1]

To a solution of (S)-2-(3-(2-hydroxypropoxy)benzyl)-6-(methylcarbamoyl)isonicotinic acid (82 mg, 0.238 mmol) in DMF (2 mL) was added HATU (136 mg, 0.357 mmol) followed by cyclopropanamine (0.035 mL, 0.505 mmol) and DIPEA (0.166 ml, 0.952 mmol). The resulting reaction mixture was stirred at rt in air. Further portions of HATU (136 mg, 0.357 mmol) and cyclopropanamine (0.035 mL, 0.505 mmol) were added and reaction mixture stirred overnight at rt. The reaction mixture was purified directly by MDAP (Formic). The fractions containing the desired product were partitioned between sat. NaHCO₃ solution and DCM. The organic layer was dried (Na₂SO₄) and concentrated in vacuo to give (S)—N⁴-cyclopropyl-6-(3-(2-hydroxypropoxy)benzyl)-N²-methylpyridine-2,4-dicarboxamide (17 mg, 0.040 mmol, 16.76% yield) as a white solid.

LCMS (2 min Formic): Rt=0.83 min, [MH]⁺=384.2.

Example 17: N⁴—Cyclopropyl-6-(3-(2-hydroxyethoxy)benzyl)-N²-methylpyridine-2,4-dicarboxamide

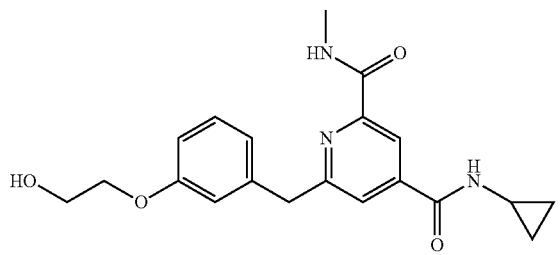 [SMILES: CNC(=O)c1cc(C(=O)NC2CC2)cc(Cc2cccc(OCCO)c2)n1]

To a solution of 2-(3-(2-hydroxyethoxy)benzyl)-6-(methylcarbamoyl)isonicotinic acid (98 mg, 0.297 mmol) in DMF (1 mL) was added HATU (169 mg, 0.445 mmol) followed by cyclopropanamine (33.9 mg, 0.593 mmol) and DIPEA (0.207 ml, 1.187 mmol). The resulting reaction mixture was stirred at rt for 4 h (The yellow solution became brown after addition of the amine). The reaction mixture was purified directly by MDAP (Formic). The fractions containing the desired product were partitioned between sat. NaHCO₃ solution and DCM. The organic layer was concentrated in vacuo to give N⁴-cyclopropyl-6-(3-(2-hydroxyethoxy)benzyl)-N²-methylpyridine-2,4-dicarboxamide (17.6 mg, 0.048 mmol, 16.06% yield) as a yellow oil.

LCMS (2 min Formic): Rt=0.77 min, [MH]⁺=370.2.

Example 18: 6-((1H-Indol-4-yl)methyl)-N²-methyl-N⁴-((1S,2S)-2-methylcyclopropyl)pyridine-2,4-dicarboxamide

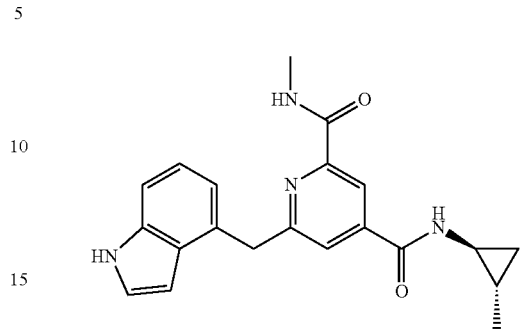

To a solution of 2-((1H-indol-4-yl)methyl)-6-(methylcarbamoyl)isonicotinic acid (27 mg, 0.052 mmol, 59% wt.) in DMF (0.8 mL) was added HATU (49.8 mg, 0.131 mmol) followed by (1S,2S)-2-methylcyclopropanamine, hydrochloride (18.78 mg, 0.175 mmol) and DIPEA (0.076 mL, 0.435 mmol). The resulting reaction mixture was stirred at rt overnight. The yellow solution became brown after addition of the amine. The reaction mixture was purified directly by MDAP (Formic). The fractions containing the desired product were partitioned between sat. NaHCO₃ solution and DCM. The organic layer was extracted and then dried and concentrated in vacuo to give 6-((1H-indol-4-yl)methyl)-N²-methyl-N⁴-((1S,2S)-2-methylcyclopropyl)pyridine-2,4-dicarboxamide (12.4 mg, 0.031 mmol, 59.8% yield) as a colourless oil.

LCMS (2 min Formic): Rt=0.96 min, [MH]⁺=363.2.

Example 19: N⁴—Cyclopropyl-6-(4-methoxybenzyl)-N²-methylpyridine-2,4-dicarboxamide

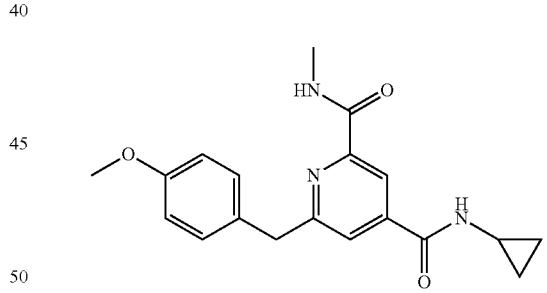

To a solution of 2-(4-methoxybenzyl)-6-(methylcarbamoyl)isonicotinic acid (62 mg, 0.162 mmol, 78.5% wt.) in DMF (0.7 mL) was added HATU (118 mg, 0.310 mmol) followed by cyclopropanamine (0.029 mL, 0.419 mmol) and DIPEA (0.180 mL, 1.031 mmol). The resulting reaction mixture was stirred at rt overnight. The yellow solution became brown after addition of the amine. The reaction mixture was purified directly by MDAP (Formic). The fractions containing the desired product were partitioned between sat. NaHCO₃ solution and DCM. The organic layer was extracted (2×20 mL) then dried and concentrated in vacuo to give N⁴-cyclopropyl-6-(4-methoxybenzyl)-N²-methylpyridine-2,4-dicarboxamide (38 mg, 0.106 mmol, 65.6% yield) as a colourless oil.

LCMS (2 min Formic): Rt=0.92 min, [MH]⁺=340.1.

Example 20: N⁴—Cyclopropyl-N²-methyl-6-(2-methylbenzyl)pyridine-2,4-dicarboxamide

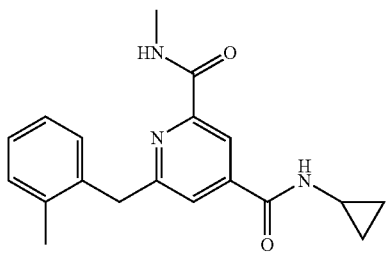

To a solution of 2-(2-methylbenzyl)-6-(methylcarbamoyl)isonicotinic acid (13.8 mg, 0.043 mmol, 89% wt.) in DMF (0.9 mL) was added HATU (27.7 mg, 0.073 mmol) followed by cyclopropanamine (0.01 mL, 0.144 mmol) and DIPEA (0.040 mL, 0.229 mmol). The resulting reaction mixture was stirred at rt overnight. The yellow solution became brown after addition of the amine. The reaction mixture was purified directly by MDAP (Formic). The fractions containing the desired product were partitioned between sat. NaHCO₃ solution and DCM. The organic layer was then dried and concentrated in vacuo to give N⁴-cyclopropyl-N²-methyl-6-(2-methylbenzyl)pyridine-2,4-dicarboxamide (4.2 mg, 0.012 mmol, 27.1% yield) as a colourless oil.

LCMS (2 min Formic): Rt=0.99 min, [MH]⁺=324.3.

Example 21: 6-((1H-Indol-4-yl)methyl)-N⁴-cyclopropyl-N²-methylpyridine-2,4-dicarboxamide

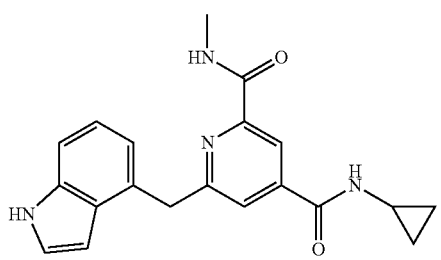

2-((1H-Indol-4-yl)methyl)-6-(methylcarbamoyl)isonicotinic acid (200 mg, 0.647 mmol) was taken up in DMF (5 mL). DIPEA (0.339 mL, 1.940 mmol) and HATU (369 mg, 0.970 mmol) were added and the reaction left to stir at rt for 10 min. Cyclopropanamine (0.090 mL, 1.293 mmol) was added and the reaction left to stir for a further 1 h. The reaction was concentrated in vacuo and the residue taken up in ethyl acetate (10 mL) and extracted using sodium bicarbonate solution (10 mL). The organic phase was washed with brine (10 mL) before being dried over sodium sulfate, filtered through a hydrophobic frit and concentrated in vacuo. The samples were dissolved in 1:1 MeCN:DMSO (1 mL) and purified by MDAP (High pH). The solvent was evaporated in vacuo to give the required product (23 mg) as a cream solid.

LCMS (2 min High pH): Rt=0.89 min, [MH]⁺=349.3.

Example 22: N⁴—Cyclopropyl-6-(3-fluorobenzyl)-N²-methylpyridine-2,4-dicarboxamide

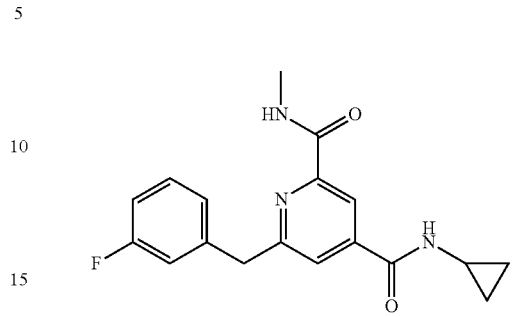

To a solution of 2-(3-fluorobenzyl)-6-(methylcarbamoyl)isonicotinic acid (53 mg, 0.147 mmol, 80% wt.) in DMF (0.8 mL) was added HATU (105 mg, 0.276 mmol) followed by cyclopropanamine (0.03 mL, 0.433 mmol) and DIPEA (0.161 mL, 0.922 mmol). The resulting reaction mixture was stirred at rt overnight. The reaction mixture was purified directly by MDAP (Formic). The fractions containing the desired product were partitioned between sat. sodium bicarbonate solution and DCM. The organic layer was then dried and concentrated in vacuo to give N⁴-cyclopropyl-6-(3-fluorobenzyl)-N²-methylpyridine-2,4-dicarboxamide (26.6 mg, 0.081 mmol, 55.2% yield) as a colourless oil.

LCMS (2 min Formic): Rt=0.95 min, [MH]⁺=328.2.

Example 23: N⁴—Cyclopropyl-N²-methyl-6-(3-methylbenzyl)pyridine-2,4-dicarboxamide

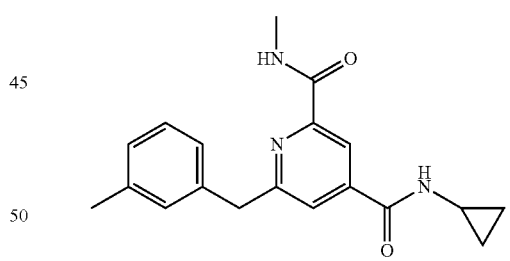

To a solution of 2-(3-methylbenzyl)-6-(methylcarbamoyl)isonicotinic acid (102 mg, 0.359 mmol) in DMF (0.8 mL) was added HATU (205 mg, 0.538 mmol) followed by cyclopropanamine (0.070 mL, 1.010 mmol) and DIPEA (0.2 mL, 1.145 mmol). The resulting reaction mixture was stirred at rt overnight. The reaction mixture was purified directly by MDAP (Formic). The fractions containing the desired product were partitioned between sat. sodium bicarbonate solution and DCM. The organic layer was then dried and concentrated in vacuo to give N⁴-cyclopropyl-N²-methyl-6-(3-methylbenzyl)pyridine-2,4-dicarboxamide (25.1 mg, 0.078 mmol, 21.63% yield) as a colourless oil.

LCMS (2 min Formic): Rt=1.00 min, [MH]⁺=324.2.

Example 24: N²-Methyl-N⁴-((1S,2S)-2-methylcyclopropyl)-6-((2-oxoindolin-4-yl)methyl)pyridine-2,4-dicarboxamide

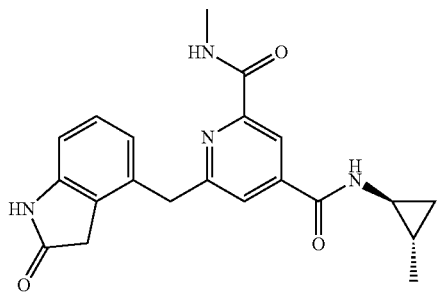 [SMILES: CNC(=O)c1cc(C(=O)N[C@H]2C[C@@H]2C)cc(Cc2cccc3c2CC(=O)N3)n1]

To a solution of 2-(methylcarbamoyl)-6-((2-oxoindolin-4-yl)methyl)isonicotinic acid (55.7 mg, 0.080 mmol, 47% wt.) in DMF (0.8 mL) was added HATU (78 mg, 0.205 mmol) followed by (1S,2S)-2-methylcyclopropanamine, hydrochloride (20 mg, 0.186 mmol) and DIPEA (0.120 mL, 0.689 mmol). The resulting reaction mixture was stirred at rt over the weekend. The reaction mixture was purified directly by MDAP (Formic). The fractions containing the desired product were partitioned between sat. sodium bicarbonate solution and DCM. The organic layer was then dried and concentrated in vacuo to give N²-methyl-N⁴-((1S2S)-2-methylcyclopropyl)-6-((2-oxoindolin-4-yl)methyl)pyridine-2,4-dicarboxamide (22 mg, 0.052 mmol, 65.0% yield) as a colourless oil.

LCMS (2 min Formic): Rt=0.79 min, [MH]+ 379.3.

Example 25: N⁴—Cyclopropyl-6-(indolin-4-ylmethyl)-N²-methylpyridine-2,4-dicarboxamide

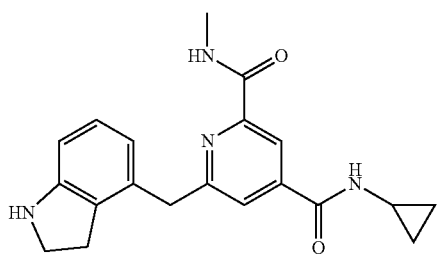 [SMILES: CNC(=O)c1cc(C(=O)NC2CC2)cc(Cc2cccc3c2CCN3)n1]

Benzyl 4-((4-(cyclopropylcarbamoyl)-6-(methylcarbamoyl)pyridin-2-yl)methyl)indoline-1-carboxylate (31.8 mg, 0.066 mmol) was dissolved in methanol (10 mL) and hydrogenated in the H-Cube over a Pd/C cat. cart. on full H2 mode for 1 h. The eluant was evaporated in vacuo to give the crude product. This was purified by chromatography on SiO₂ (Biotage® SNAP 10 g, eluting with 0-100% ethyl acetate/cyclohexane). The desired fractions were concentrated to give N₄-cyclopropyl-6-(indolin-4-ylmethyl)-N₂-methylpyridine-2,4-dicarboxamide (2.3 mg, 6.24 μmol, 9.50% yield).

LCMS (2 min Formic): Rt=0.48 min, [MH]+ 351.2.

Example 26: N⁴—Cyclopropyl-6-(3-hydroxybenzyl)-N²-methylpyridine-2,4-dicarboxamide

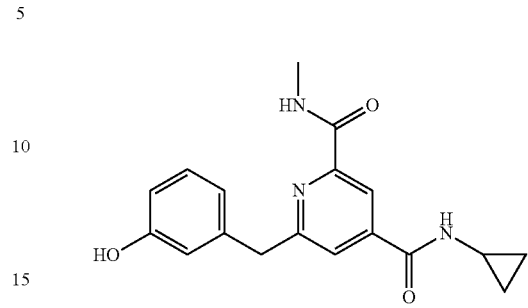

A suspension of N⁴-cyclopropyl-6-(3-methoxybenzyl)-N²-methylpyridine-2,4-dicarboxamide (120 mg, 0.354 mmol) in DCM (3 mL) was cooled to 0° C. under N₂ and BBr₃ (1M in DCM, 1.76 mL, 1.760 mmol) was added dropwise. The reaction was quenched with water (10 mL) and extracted with ethyl acetate (3×20 mL). The organic extract was then washed with sat. NaHCO₃ solution, dried (Na₂SO₄) and concentrated to give a yellow oil—N⁴-cyclopropyl-6-(3-hydroxybenzyl)-N²-methylpyridine-2,4-dicarboxamide (117.3 mg, 0.288 mmol, 82% yield, ~80% purity). 12 mg of this sample was purified by MDAP (Formic). The fractions containing the desired product were partitioned between sat. sodium bicarbonate solution and DCM. The organic layer was then dried and concentrated in vacuo to give N⁴-cyclopropyl-6-(3-hydroxybenzyl)-N²-methylpyridine-2,4-dicarboxamide (3.3 mg, 9.13 μmol, 2.58% yield) as a colourless oil.

LCMS (2 min Formic): Rt=0.77 min, [MH]+ 326.2.

Example 27: (R)—N⁴-Cyclopropyl-6-(3-(2-hydroxypropoxy)benzyl)-N²-methylpyridine-2,4-dicarboxamide

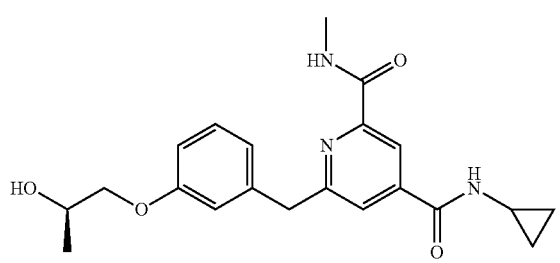 [SMILES: CNC(=O)c1cc(C(=O)NC2CC2)cc(Cc2cccc(OC[C@@H](C)O)c2)n1]

A mixture of N⁴-cyclopropyl-6-(3-hydroxybenzyl)-N²-methylpyridine-2,4-dicarboxamide (53 mg, 0.163 mmol), (R)-2-methyloxirane (0.06 mL, 0.856 mmol) and cesium carbonate (159 mg, 0.489 mmol) were dissolved in DMF (1.5 mL) and the reaction mixture was heated at 150° C. for 30 min in a 2 mL microwave vial. The reaction mixture was washed with water (10 mL) and extracted with EtOAc (3×10 mL), then washed with sat. LiCl solution. The combined organic phases were dried and concentrated to give 300 mg of an oil. This was purified by chromatography on SiO$_2$ (Biotage® SNAP 10 g, eluting with 60-100% ethyl acetate/cyclohexane). The desired fractions were concentrated to give the desired product which was still impure. This was purified further by MDAP (Formic). The fractions containing the desired product were partitioned between sat. sodium bicarbonate solution and DCM. The organic layer was then dried and concentrated in vacuo to give (R)—N$^4$-cyclopropyl-6-(3-(2-hydroxypropoxy)benzyl)-N$^2$-methylpyridine-2,4-dicarboxamide (19.9 mg, 0.049 mmol, 30.3% yield) as a colourless oil.

LCMS (2 min Formic): Rt=0.83 min, [MH]+ 384.2.

Example 28: 6-(Hydroxy(phenyl)methyl)-N$^2$-methyl-N$^4$-((1S,2S)-2-methylcyclopropyl)pyridine-2,4-dicarboxamide, 1:1 Mixture of Diastereomers at Undefined Stereocentre

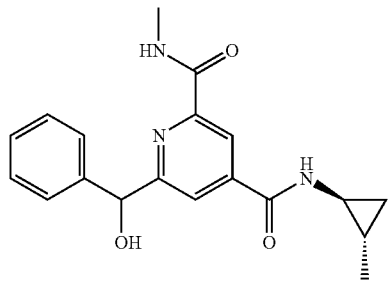

To a solution of (+/−)-2-(hydroxy(phenyl)methyl)-6-(methylcarbamoyl)isonicotinic acid (500 mg, 1.747 mmol) in DMF (3 mL) was added DIPEA (0.915 mL, 5.24 mmol), followed by HATU (996 mg, 2.62 mmol) and (1S,2S)-2-methylcyclopropanamine, hydrochloride (282 mg, 2.62 mmol). The resulting reaction mixture was stirred at rt for 2 h. The reaction mixture was partitioned between a sat. solution of LiCl (10 mL) and EtOAc (10 mL) then the aqueous phase was extracted two more times with EtOAc. The combined organic phases were washed with water (20 mL) and the aqueous phase was extracted two more times with EtOAc. The combined organic phases were dried through a hydrophobic frit. This was purified by flash silica chromatography (SNAP silica 10 g cartridge, eluent 40 to 100% EtOAc/cyclohexane). The combined desired fractions were concentrated in vacuo to give 6-(hydroxy(phenyl)methyl)-N$^2$-methyl-N$^4$-((1S,2S)-2-methylcyclopropyl)pyridine-2,4-dicarboxamide (229 mg, 0.607 mmol, 34.8% yield) as a yellow oil.

LCMS (2 min Formic): Rt=0.85 min, [MH]+ 340.2.

$^1$H NMR (400 MHz, MeOH-d$_4$) δ ppm 8.27 (d, J=1.5 Hz, 1H) 7.95 (d, J=1.5 Hz, 1H) 7.44 (br. d, J=7.3 Hz, 2H) 7.29 (br. t, J=7.5, 7.5 Hz, 2H) 7.18-7.24 (m, 1H) 5.92 (s, 1H) 2.96 (s, 3H) 2.54 (dt, J=7.3, 3.7 Hz, 1H) 1.10 (d, J=6.1 Hz, 3H) 0.95-1.05 (m, 1H) 0.81 (ddd, J=9.2, 5.1, 4.0 Hz, 1H) 0.56 (dt, J=7.3, 5.7 Hz, 1H). Exchangeables not observed.

Example 29: 6-((R)-Hydroxy(phenyl)methyl)-N$^2$-methyl-N$^4$-((1S,2S)-2-methylcyclopropyl)pyridine-2,4-dicarboxamide Example 30: 6-((S)-Hydroxy(phenyl)methyl)-N$^2$-methyl-N$^4$-((1S,2S)-2-methylcyclopropyl)pyridine-2,4-dicarboxamide

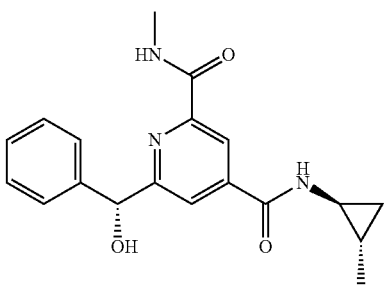 [SMILES: CNC(=O)c1cc(C(=O)N[C@H]2C[C@@H]2C)cc(C(O)c2ccccc2)n1]

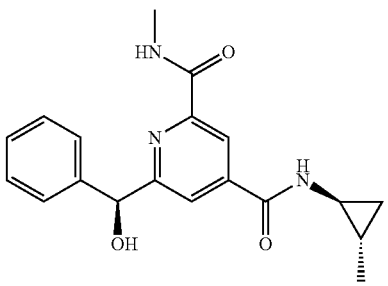

Example 28 (210 mg) was purified by chiral HPLC. The diastereomeric mixture was dissolved in EtOH (3 mL). Injection: 1.5 mL of the solution was injected onto the column (20% EtOH (+0.2% isopropylamine)/heptane (+0.2% isopropylamine), flow rate=30 mL/min, detection wavelength=215 nm, Column 30 mm×25 cm Chiralpak AD-H (5 μm)). Total number of injections=2. Fractions from 10-12.5 min were bulked and labelled peak 1. Fractions from 15-20 min were bulked and labelled peak 2. The bulked fractions were concentrated in vacuo and then transferred to weighed flasks.

The fractions corresponding to peak 1 were collected to afford example 30 (73 mg)

LCMS (2 min Formic): Rt=0.84 min, [MH]$^+$=340.3

$^1$H NMR (400 MHz, MeOH-d) δ ppm 8.26 (d, =7-1.7 Hz, 1H) 7.95 (d, =7-1.2 Hz, 1H) 7.46 (br. d, J=7.3 Hz, 2H) 7.33 (br. t, 7-=7.5, 7.5 Hz, 2H) 7.22-7.28 (m, 1H) 5.94 (s, 1H) 2.98 (s, 3H) 2.54 (dt, J=7.3, 3.6 Hz, 1H) 1.13 (d, J=5.9 Hz, 3H) 0.96-1.06 (m, 1H) 0.82 (ddd, J=9.2, 5.3, 4.0 Hz, 1H) 0.59 (dt, 7-7.5, 5.7 Hz, 1H). Exchangeables not observed.

The fractions corresponding to peak 2 were collected to afford example 29 (92 mg)

LCMS (2 min Formic): Rt=0.84 min, [MH]$^+$=340.2

Example 31: 6-(Methoxy(phenyl)methyl)-N$^2$-methyl-N$^4$-((1S,2S)-2-methylcyclopropyl)pyridine-2,4-dicarboxamide. 1:1 Mixture of Diastereomers at Undefined Stereocentre

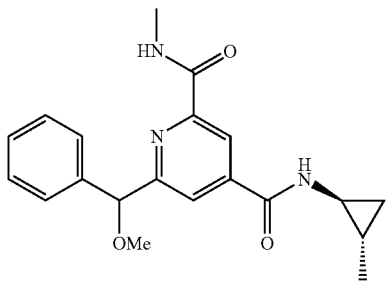 [SMILES: CNC(=O)c1cc(C(=O)N[C@H]2C[C@@H]2C)cc(C(OC)c2ccccc2)n1]

To a solution of 2-(methoxy(phenyl)methyl)-6-(methylcarbamoyl)isonicotinic acid (44.9 mg, 0.090 mmol, 60% wt.) in DMF (0.7 mL) was added HATU (85 mg, 0.224 mmol) followed by (1S,2S)-2-methylcyclopropanamine, hydrochloride (24.13 mg, 0.224 mmol) and DIPEA (0.1 mL, 0.573 mmol). The resulting reaction mixture was stirred at rt for 3 h (The orange solution became yellow after addition of the amine). The reaction mixture was purified directly by MDAP (High pH). The fractions containing the desired product were concentrated in vacuo to give 6-(methoxy (phenyl)methyl)-N$^2$-methyl-N$^4$-((1S,2S)-2-methylcyclopropyl)pyridine-2,4-dicarboxamide (24 mg, 0.061 mmol, 68.1% yield) as a colourless oil.

LCMS (2 min Formic): Rt=1.00 min, [MH]$^+$=354.2

Example 32: 6-(Hydroxy(pyridin-2-yl)methyl)-N$^2$-methyl-N$^4$-((1S,2S)-2-methylcyclopropyl)pyridine-2,4-dicarboxamide. 1:1 Mixture of Diastereomers at Undefined Stereocentre

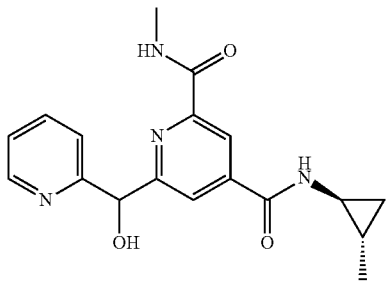 [SMILES: CNC(=O)c1cc(C(=O)N[C@H]2C[C@@H]2C)cc(C(O)c2ccccn2)n1]

To a solution of 2-(hydroxy(pyridin-2-yl)methyl)-6-(methylcarbamoyl)isonicotinic acid (289 mg, 0.604 mmol, 60% wt.) in DMF (1 mL) was added HATU (612 mg, 1.610 mmol) followed by (1S,2S)-2-methylcyclopropanamine, hydrochloride (173 mg, 1.608 mmol) and N-ethyl-N-isopropylpropan-2-amine (0.615 mL, 3.52 mmol). The resulting reaction mixture was stirred at rt overnight. The reaction mixture was purified directly by MDAP (high pH). The fractions containing desired product were concentrated in vacuo to give 6-(hydroxy(pyridin-2-yl)methyl)-N$^2$-methyl-N$^4$-((1S,2S)-2-methylcyclopropyl)pyridine-2,4-dicarboxamide (62 mg, 0.164 mmol, 27.2% yield) as a colourless oil.

LCMS (2 min Formic): Rt=0.55 min, [MH]$^+$=341.2.

Example 33: 6-((1H-Indazol-4-yl)methyl)-N$^2$-methyl-N$^4$-((1S,2S)-2-methylcyclopropyl)pyridine-2,4-dicarboxamide

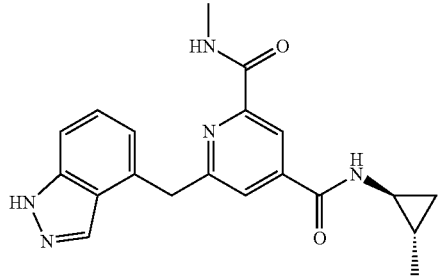 [SMILES: CNC(=O)c1cc(C(=O)N[C@H]2C[C@@H]2C)cc(Cc2cccc3[nH]ncc23)n1]

To a solution of 2-((1H-indazol-4-yl)methyl)-6-(methylcarbamoyl)isonicotinic acid (33.5 mg, 0.054 mmol, 50% wt.) in DMF (0.7 mL) was added HATU (65.7 mg, 0.173 mmol) followed by (1S,2S)-2-methylcyclopropanamine, hydrochloride (18.58 mg, 0.173 mmol) and N-ethyl-N-isopropylpropan-2-amine (0.07 mL, 0.401 mmol). The resulting reaction mixture was stirred at rt overnight. The reaction mixture was purified directly by MDAP (high pH). The fractions containing the desired product were concentrated in vacuo to give 12.6 mg of crude product. This was purified by flash silica chromatography (eluent: 40% ethyl acetate in cyclohexane; followed by 100% (25% EtOH in EtOAc). The fractions containing the desired product were concentrated in vacuo to give 6-((1H-indazol-4-yl)methyl)-N$^2$-methyl-N$^4$-((1 S,2S)-2-methylcyclopropyl)pyridine-2,4-dicarboxamide (3 mg, 8.26 μmol, 15.29% yield)

LCMS (2 min Formic): Rt=0.83 min, [MH]$^+$=364.3.

Example 34: N$^2$-Methyl-N$^4$-((1S,2S)-2-methylcyclopropyl)-6-(pyridin-2-ylmethyl)pyridine-2,4-dicarboxamide

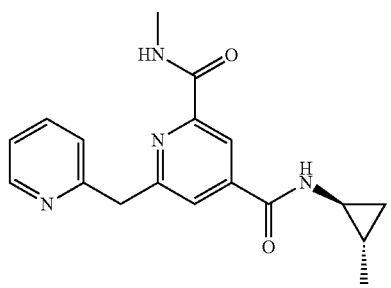

To a solution of 6-(chloro(pyridin-2-yl)methyl)-N$^2$-methyl-N$^4$-((1S,2S)-2-methylcyclopropyl)pyridine-2,4-dicarboxamide (20 mg, 0.033 mmol, 60% wt.) in acetic acid (1 mL) at rt was slowly added zinc powder (6.56 mg, 0.100 mmol). The reaction mixture was then stirred at rt overnight. NaOH (5M, 3 mL) and DCM (5 mL) were added. The aqueous and organic layers were separated and the aqueous phase was extracted with DCM (2 times). The combined organic phases were dried over magnesium sulfate then concentrated in vacuo. 1:1 MeOH:DMSO (0.95 mL) was added and the reaction mixture was purified by MDAP (High pH). The desired fractions were combined and concentrated in vacuo to give N$^2$-methyl-N$^4$-((1S,2S)-2-methylcyclopropyl)-6-(pyridin-2-ylmethyl)pyridine-2,4-dicarboxamide (5.2 mg, 0.015 mmol, 45.5% yield).

LCMS (2 min Formic): Rt=0.51 min, [MH]⁺=325.3.

Example 35: 6-((S)-Fluoro(phenyl)methyl)-$N^2$-methyl-$N^4$-((1S,2S)-2-methylcyclopropyl)pyridine-2,4-dicarboxamide

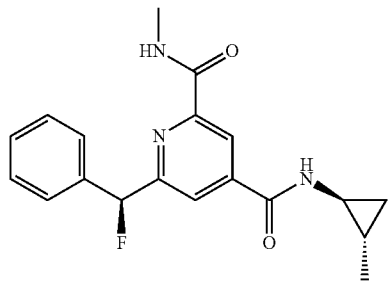 [SMILES: CNC(=O)c1cc(C(=O)N[C@H]2C[C@@H]2C)cc([C@@H](F)c2ccccc2)n1]

6-((R)-Hydroxy(phenyl)methyl)-$N^2$-methyl-$N^4$-((1S,2S)-2-methylcyclopropyl)pyridine-2,4-dicarboxamide (6 mg, 0.018 mmol) was dissolved in DCM (1 mL) and cooled in an ice bath under nitrogen, then deoxofluor (0.04 mL, 0.108 mmol) was added dropwise and the mixture was stirred at 0° C. for 2 h, then allowed to warm to rt and stirred overnight. Sodium carbonate solution (1 mL) and DCM (5 mL) were added. The aqueous and organic layers were separated and the aqueous phase was extracted with DCM (two times). The combined organic phases were dried over magnesium sulfate then concentrated in vacuo. 1:1 MeOH:DMSO (0.95 mL) was added and the reaction mixture was purified by MDAP (high pH). The combined desired fractions were concentrated in vacuo to give 6-((S)-fluoro(phenyl)methyl)-$N^2$-methyl-$N^4$-((1S,2S)-2-methylcyclopropyl)pyridine-2,4-dicarboxamide (2 mg, 5.57 μmol, 31.5% yield) as a colourless oil.

LCMS (2 min Formic): Rt=1.02 min, [MH]⁺=342.2.

Example 36: $N^2$-Methyl-6-((2-methyl-1H-benzo[d]imidazol-4-ylmethyl)-$N^4$-((1S,2S)-2-methylcyclopropyl)pyridine-2,4-dicarboxamide

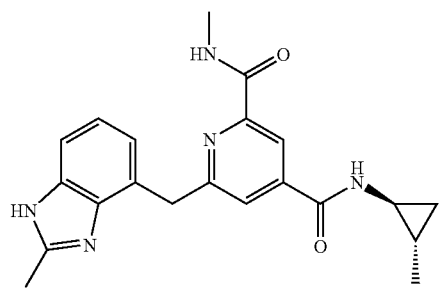 [SMILES: CNC(=O)c1cc(C(=O)N[C@H]2C[C@@H]2C)cc(Cc2cccc3[nH]c(C)nc23)n1]

To a solution of 2-((2-methyl-1H-benzo[d]imidazol-4-yl)methyl)-6-(methylcarbamoyl)isonicotinic acid (32.5 mg, 0.045 mmol, 45% wt.) in DMF (0.8 mL) was added HATU (61 mg, 0.160 mmol) followed by (1S,2S)-2-methylcyclopropanamine, hydrochloride (17.25 mg, 0.160 mmol) and N-ethyl-N-isopropylpropan-2-amine (0.07 mL, 0.401 mmol). The resulting reaction mixture was stirred at rt overnight. The reaction mixture was purified directly by MDAP (High pH). The fractions containing the desired product were concentrated in vacuo to give the desired product (6 mg), with an impurity putatively corresponding to the Me ester. THF (2 mL) and water (2 mL) were added, then lithium hydroxide (1.62 mg, 0.068 mmol) was added and the reaction mixture was stirred for 25 min. The solvent was then removed in vacuo, then DMF (0.8 mL) was added, followed by HATU (75 mg, 0.197 mmol), DIPEA (0.07 mL, 0.401 mmol), (1S,2S)-2-methylcyclopropanamine, hydrochloride (13 mg, 0.121 mmol) and the resultant mixture was stirred for 2 h. The reaction mixture was purified directly by MDAP (High pH). The fractions containing the desired product were concentrated in vacuo to give the desired product (6 mg).

LCMS (2 min Formic): Rt=0.53 min, [MH]⁺=378.2.

Example 37: 6-(3-(2-(4,4-Difluoropiperidin-3-yl)ethoxy)benzyl)-$N^2$-methyl-$N^4$-((1S,2S)-2-methylcyclopropyl)pyridine-2,4-dicarboxamide. 1:1 mixture of diastereomers at the undefined stereocentre

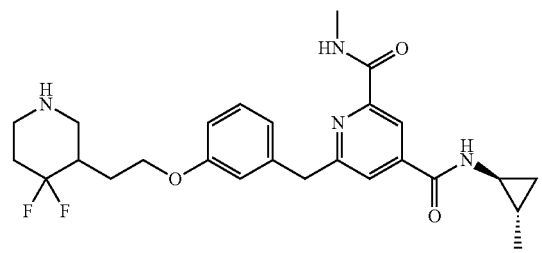 [SMILES: CNC(=O)c1cc(C(=O)N[C@H]2C[C@@H]2C)cc(Cc2cccc(OCCC3CNCCC3(F)F)c2)n1]

TFA (0.5 mL, 6.49 mmol) was added to a solution of tert-butyl 4,4-difluoro-3-(2-(3-((6-(methylcarbamoyl)-4-(((1S,2S)-2-methylcyclopropyl)carbamoyl)pyridin-2-yl)methyl)phenoxy)ethyl)piperidine-1-carboxylate (51 mg, 0.087 mmol) in DCM (4 mL). The reaction mixture was stirred for 15 min. The reaction mixture was then concentrated in vacuo to a brown oil and was then prepared for flash chromatographic purification on a 10 g Biotage® SNAP column using a gradient of DCM:methanolic ammonia (0-50%). However, no obvious peaks obtained suggested separation of product. The column was additionally run using a gradient of EtOAc:Ethanol (0-40%) and again no obvious fractions contained product. Thus, all fractions were combined and concentrated in vacuo. The sample was then prepared for purification using MDAP (high pH). The product containing fractions were combined and the solvent removed in vacuo. The sample was then dried under a stream of nitrogen for 1 h and was then placed in vacuo for 1 h. The sample was then further purified using a 10 g Biotage® SNAP column using a gradient of DCM:methanolic ammonia (0-16%). The product containing fractions were combined and the solvent removed in vacuo. The sample was then dried under a stream of nitrogen and placed in vacuo oven 16 h at 40° C. The sample was then prepared for MDAP (high pH). The product containing fractions were combined and the solvent removed in vacuo to a white solid. The white solid was then dried under a stream of nitrogen for 2 h and was then dried further in vacuo at 40° C. for 1 h to afford the title compound (11 mg).

LCMS (2 min High pH): Rt=1.05 min, [MH]⁺=487.2.

Example 38: 6-Benzyl-N⁴-((1r,3r)-3-hydroxycyclobutyl)-N²-methylpyridine-2,4-dicarboxamide

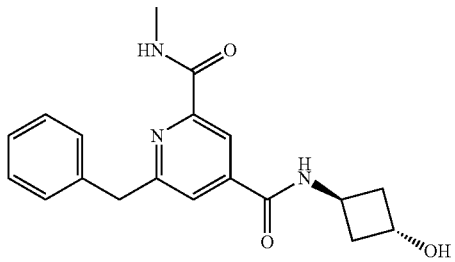 [SMILES: CNC(=O)c1cc(C(=O)N[C@H]2C[C@H](O)C2)cc(Cc2ccccc2)n1]

To a mixture of 2-benzyl-6-(methylcarbamoyl)isonicotinic acid (98.4 mg, 0.364 mmol) and HATU (194.7 mg, 0.512 mmol) was added a solution of trans-3-aminocyclobutanol hydrochloride (64.6 mg, 0.523 mmol) in DMF (1.8 mL). DIPEA (0.191 mL, 1.092 mmol) was added and the mixture was stirred at rt for 50 min. The reaction mixture was concentrated under a stream of nitrogen and diluted with acetonitrile to a total volume of 2 mL and directly purified by MDAP (2×1 mL injection; Formic) and the required fractions were evaporated under a stream of nitrogen. The residues were suspended in DCM and methanol (1:1), transferred to a tarred vial and the solvent evaporated under a stream of nitrogen to give the desired product as a white solid; 6-benzyl-N⁴-(trans-3-hydroxycyclobutyl)-N²-methylpyridine-2,4-dicarboxamide (111.0 mg, 0.327 mmol, 90% yield) LCMS (2 min Formic): Rt=0.80 min, [MH]⁺=340.3.

Example 39: 6-((1H-Indol-3-ylmethyl)-N²-methyl-N⁴-((1S,2S)-2-methylcyclopropyl)pyridine-2,4-dicarboxamide

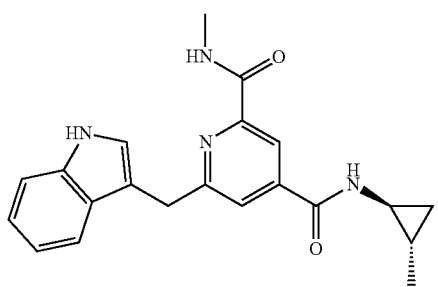 [SMILES: CNC(=O)c1cc(C(=O)N[C@H]2C[C@@H]2C)cc(Cc2c[nH]c3ccccc23)n1]

To a solution of 2-((1H-indol-3-yl)methyl)-6-(methylcarbamoyl)isonicotinic acid (200 mg, 0.129 mmol, 20% wt.) in DMF (0.8 mL) was added DIPEA (0.15 mL, 0.859 mmol) followed by HATU (148 mg, 0.389 mmol) and (1S,2S)-2-methylcyclopropanamine, hydrochloride (41.7 mg, 0.388 mmol). The resulting reaction mixture was stirred at rt for 2 h. The reaction mixture was purified directly by MDAP (high pH). The fractions containing the desired product were concentrated in vacuo to give 6-((1H-indol-3-yl)methyl)-N²-methyl-N⁴-((1S,2S)-2-methylcyclopropyl)pyridine-2,4-dicarboxamide (5 mg, 0.013 mmol, 10.13% yield) as a colourless oil.

LCMS (2 min Formic): Rt=0.98 min, [MH]⁺=363.4.

Example 40: 6-(Hydroxy(6-methylpyridin-2-yl)methyl)-N²-methyl-N⁴-((1S,2S)-2-methylcyclopropyl)pyridine-2,4-dicarboxamide, 1:1 Mixture of Diastereomers at Undefined Stereocentre

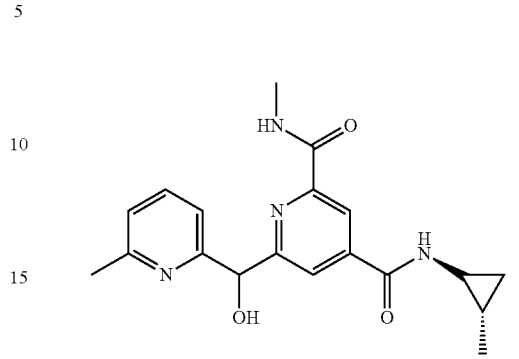

To a solution of 2-(hydroxy(6-methylpyridin-2-yl)methyl)-6-(methylcarbamoyl)isonicotinic acid (28 mg, 0.074 mmol, 80% wt.) in DMF (0.8 mL) was added DIPEA (0.05 mL, 0.286 mmol) followed by HATU (53.0 mg, 0.139 mmol) and (1S,2S)-2-methylcyclopropanamine, hydrochloride (15 mg, 0.139 mmol). The resulting reaction mixture was stirred at rt for 2 h. The reaction mixture was purified directly by MDAP (High pH). The fractions containing the desired product were concentrated in vacuo to give the desired product which was still impure. The residue was dissolved in 1:1 MeOH:DMSO (1 mL) and purified by MDAP (TFA). Sodium bicarbonate solution (5 mL) was added to the desired fraction then the resultant mixture was extracted with DCM three times. The combined organic phase was dried on a hydrophobic filter then concentrated in vacuo to give 6-(hydroxy(6-methylpyridin-2-yl)methyl)-N²-methyl-N⁴-((1S,2S)-2-methylcyclopropyl)pyridine-2,4-dicarboxamide (2 mg, 5.36 µmol, 7.21% yield) as a colourless oil.

LCMS (2 min Formic): Rt=0.52 min, [MH]⁺=355.3.

Example 41: 6-Benzyl-N²-methyl-N⁴-((1r,3r)-3-(methylsulfonyl)cyclobutyl)pyridine-2,4-dicarboxamide

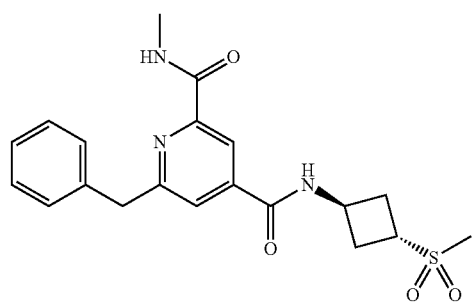 [SMILES: CNC(=O)c1cc(C(=O)N[C@H]2C[C@H](S(C)(=O)=O)C2)cc(Cc2ccccc2)n1]

To a mixture of 2-benzyl-6-(methylcarbamoyl)isonicotinic acid (65.0 mg, 0.240 mmol) and HATU (128.6 mg, 0.338 mmol) was added a solution of trans-3-(methylsulfonyl)cyclobutanamine, hydrochloride (48.0 mg, 0.259 mmol) in DMF (1.8 mL). DIPEA (0.126 mL, 0.721 mmol) was added and the mixture was stirred at rt for 2 h. The reaction mixture was concentrated under a stream of nitrogen and diluted with acetonitrile to a total volume of 2 mL and directly purified by MDAP (2×1 mL injection; Formic) and the required fractions were evaporated under a stream of nitrogen. The residues were suspended in DCM and methanol (1:1, ~10 mL), combined and transferred to a tarred vial and the solvent evaporated under a stream of nitrogen to give the desired product as a white solid; 6-benzyl-$N^2$-methyl-$N^4$-(trans-(methylsulfonyl)cyclobutyl)pyridine-2,4-dicarboxamide (89.7 mg, 0.223 mmol, 93% yield) LCMS (2 min Formic): Rt=0.84 min, [MH]$^+$=402.4.

Example 42: 6-Benzyl-$N^4$-cyclopentyl-$N^2$-methylpyridine-2,4-dicarboxamide

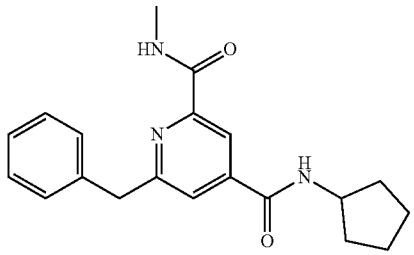 [SMILES: CNC(=O)c1cc(C(=O)NC2CCCC2)cc(Cc2ccccc2)n1]

To a solution of 2-benzyl-6-(methylcarbamoyl)isonicotinic acid (48.3 mg, 0.179 mmol) and HATU (86.9 mg, 0.229 mmol) in DMF (1 mL) was added cyclopentanamine (0.021 mL, 0.214 mmol) and DIPEA (0.094 mL, 0.536 mmol). The resulting solution was stirred at rt for 3 h, after which the volatiles were evaporated under a stream of nitrogen to give a sticky dark brown solid. This was redissolved in DMSO (2 mL) and directly purified by MDAP (2×1 mL injection, High pH). The required fractions were evaporated under a stream of nitrogen, redissolved in methanol (approx 2 mL each) and combined. This solution was evaporated under a stream of nitrogen and the residue dried in vacuo to give the desired product as a white solid; 6-benzyl-$N^4$-cyclopentyl-$N^2$-methylpyridine-2,4-dicarboxamide (50.6 mg, 0.150 mmol, 84% yield).

LCMS (2 min High pH): Rt=1.09 min, [MH]$^+$=338.3.

Example 43: 6-Benzyl-$N^4$-(cyclopropylmethyl)-$N^2$-methylpyridine-2,4-dicarboxamide

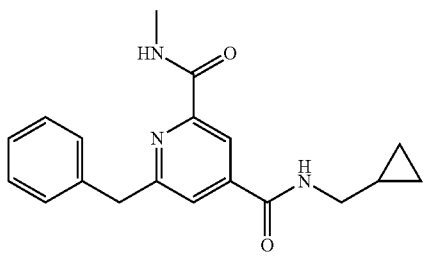 [SMILES: CNC(=O)c1cc(C(=O)NCC2CC2)cc(Cc2ccccc2)n1]

To a solution of 2-benzyl-6-(methylcarbamoyl)isonicotinic acid (49.2 mg, 0.182 mmol) and HATU (85.9 mg, 0.226 mmol) in DMF (1 mL) was added cyclopropylmethanamine (0.019 mL, 0.218 mmol) and DIPEA (0.095 mL, 0.546 mmol). The solution was stirred at rt for 6 h, after which it was diluted with DMSO (1 mL) and directly purified by MDAP (2×1 mL injection, High pH). The required fractions were evaporated under a stream of nitrogen, redissolved in methanol (approx. 2 mL each) and DCM (approx. 1 mL each) and combined. This solution was evaporated under a stream of nitrogen and the residue dried in vacuo to give the desired product as a yellow gum; 6-benzyl-$N^4$-(cyclopropylmethyl)-$N^2$-methylpyridine-2,4-dicarboxamide (49.9 mg, 0.154 mmol, 85% yield).

LCMS (2 min High pH): Rt=1.02 min, [MH]$^+$=324.3.

Example 44: 6-((1H-Indol-4-yl)methyl)-$N^4$-((1r,3r)-3-hydroxycyclobutyl)-$N^2$-methylpyridine-2,4-dicarboxamide

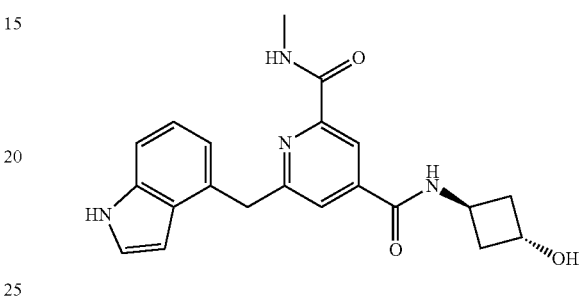

To a mixture of 2-((1H-indol-4-yl)methyl)-6-(methylcarbamoyl)isonicotinic acid (53.3 mg, 0.172 mmol) and HATU (105.6 mg, 0.278 mmol) was added a solution of trans-3-aminocyclobutanol hydrochloride (40.7 mg, 0.329 mmol) in DMF (1.5 mL). DIPEA (0.120 mL, 0.689 mmol) was added and the mixture was stirred at rt for 85 min. The reaction mixture was concentrated under a stream of nitrogen and diluted with acetonitrile to a total volume of 2 mL and directly purified by MDAP (2×1 mL injection; Formic) and the required fractions were combined and evaporated in vacuo. The residues were suspended in DCM and methanol (1:1, ~6 mL), transferred to a tarred vial and the solvent evaporated under a stream of nitrogen to give the desired product as a cream solid; 6-((1H-indol-4-yl)methyl)-$N^4$-(trans-3-hydroxycyclobutyl)-$N^2$-methylpyridine-2,4-dicarboxamide (36.4 mg, 0.096 mmol, 55.8% yield)

LCMS (2 min Formic): Rt=0.75 min, [MH]$^+$=379.3.

Example 45: 6-(hydroxy(1H-pyrrolo[3,2-c]pyridin-4-ylmethyl)-$N^2$-methyl-$N^4$-((1S,2S)-2-methylcyclopropyl)pyridine-2,4-dicarboxamide. 1:1 mixture of diastereomers at the undefined stereocentre

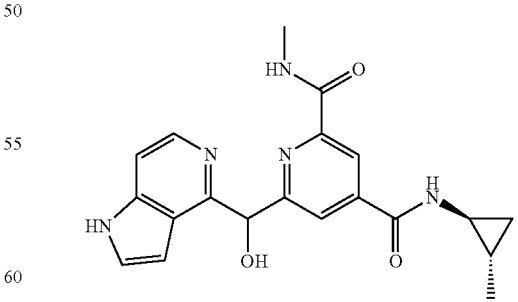

Methanol (0.2 mL) was added to 6-(hydroxy(1-(phenylsulfonyl)-1H-pyrrolo[3,2-c]pyridin-4-yl)methyl)-$N_2$-methyl-$N_4$-((1S,2S)-2-methylcyclopropyl)pyridine-2,4-dicarboxamide (6 mg, 0.018 mmol, 85% wt.). Then KOH (1 mg, 0.018 mmol) and water (0.05 mL) were added and the resultant mixture was stirred at 60° C. for 2 h. Further KOH (0.7 mg, 0.012 mmol) was added and the resultant mixture was stirred for 45 min at 60° C. The MeOH was removed under a stream of nitrogen, then water (1 mL) and DCM (1 mL) were added. The aqueous phase was extracted two more times then the combined organic phases were dried over a hydrophobic filter then concentrated in vacuo to give 6-(hydroxy(1H-pyrrolo[3,2-c]pyridin-4-yl)methyl)-$N^2$-methyl-$N^4$-((1S,2S)-2-methylcyclopropyl)pyridine-2,4-dicarboxamide (4.1 mg, 9.73 μmol, 99% yield) as a yellow solid.

LCMS (2 min Formic): Rt=0.44 min, [MH]$^+$=380.3.

Example 46: 6-((1H-Pyrrolo[2,3-c]pyridin-4-yl)methyl)-$N^2$-methyl-$N^4$-((1S,2S)-2-methylcyclopropyl)pyridine-2,4-dicarboxamide

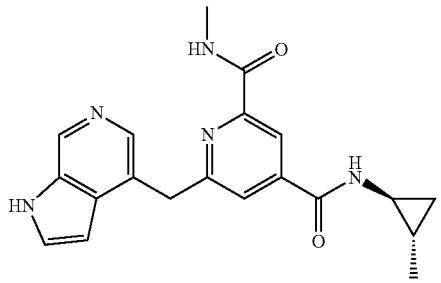 [SMILES: CNC(=O)c1cc(C(=O)N[C@H]2C[C@@H]2C)cc(Cc2cncc3[nH]ccc23)n1]

To a solution of 2-((1H-pyrrolo[2,3-c]pyridin-4-yl)methyl)-6-(methylcarbamoyl)isonicotinic acid (54 mg, 0.087 mmol, 50% wt.) in DMF (0.8 mL) was added DIPEA (0.05 mL, 0.286 mmol), followed by HATU (44 mg, 0.116 mmol) and (1S,2S)-2-methylcyclopropanamine, hydrochloride (12.45 mg, 0.116 mmol). The resulting reaction mixture was stirred at rt for 3 h. The reaction mixture was purified directly by MDAP (high pH). The fractions containing the desired product were concentrated in vacuo to give 6-((1H-pyrrolo[2,3-c]pyridin-4-yl)methyl)-$N^2$-methyl-$N^4$-((1S,2S)-2-methylcyclopropyl)pyridine-2,4-dicarboxamide (10.2 mg, 0.025 mmol, 29.0% yield) as a colourless oil.

LCMS (2 min Formic): Rt=0.52 min, [MH]$^+$=364.3.

$^1$H NMR (400 MHz, MeOH-d$_4$) δ ppm 8.62 (s, 1H) 8.21 (s, 1H) 8.04 (s, 1H) 7.72 (s, 1H) 7.53 (br. d, J=2.9 Hz, 1H) 6.59 (d, J=2.9 Hz, 1H) 4.54 (s, 2H) 2.98 (s, 3H) 2.49 (dt, J=7.3, 3.7 Hz, 1H) 1.10 (d, J=5.9 Hz, 3H) 0.91-1.02 (m, 1H) 0.78 (ddd, J=9.2, 5.3, 4.2 Hz, 1H) 0.52-0.59 (m, 1H). Exchangeables not observed.

Example 47: (+/−)-$N^4$-Cyclopropyl-6-(hydroxy(phenyl)methyl)-$N^2$-methylpyridine-2,4-dicarboxamide

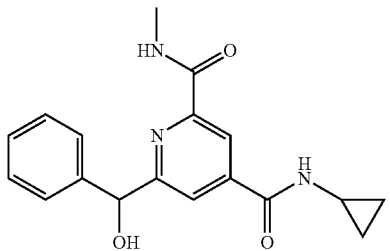 [SMILES: CNC(=O)c1cc(C(=O)NC2CC2)cc(C(O)c2ccccc2)n1]

To a solution of (+/−)-2-(hydroxy(phenyl)methyl)-6-(methylcarbamoyl)isonicotinic acid (105 mg, 0.330 mmol, ~90% wt.) in DMF (0.6 mL) was added HATU (188 mg, 0.495 mmol) followed by DIPEA (0.15 mL, 0.859 mmol) and cyclopropylamine (0.04 mL, 0.577 mmol). The resulting reaction mixture was stirred at rt for 20 h. The reaction mixture was purified directly by MDAP (High pH). The fractions containing the desired product were concentrated in vacuo to give $N^4$-cyclopropyl-6-(hydroxy(phenyl)methyl)-$N^2$-methylpyridine-2,4-dicarboxamide (8 mg, 0.023 mmol, 7.08% yield) as a colourless oil.

LCMS (2 min Formic): Rt=0.76 min, [MH]$^+$=326.2.

$^1$H NMR (400 MHz, MeOH-d$_4$) δ ppm 9.08 (br. d, J=4.2 Hz, 1H) 8.27 (d, J=1.5 Hz, 1H) 7.96 (d, J=1.5 Hz, 1H) 7.46 (br. d, J=7.1 Hz, 2H) 7.29-7.36 (m, 2H) 7.22-7.28 (m, 1H) 5.94 (s, 1H) 2.99 (d, J=4.9 Hz, 3H) 2.87 (tt, J=7.3, 3.8 Hz, 1H) 0.78-0.84 (m, 2H) 0.62-0.68 (m, 2H). Exchangeable proton not observed.

Example 48: 6-(1-(1H-Pyrrolo[2,3-c]pyridin-4-yl)ethyl)-$N^2$-methyl-$N^4$-((1S,2S)-2-methylcyclopropyl)pyridine-2,4-dicarboxamide, 1:1 Mixture of Diastereomers at Undefined Stereocentre

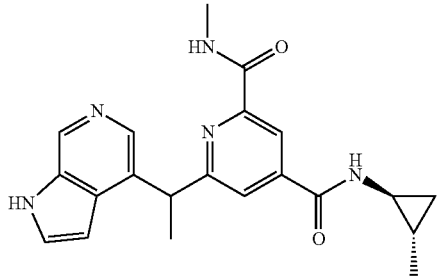

To a solution of (+/−)-2-(1-(1H-pyrrolo[2,3-c]pyridin-4-yl)ethyl)-6-(methylcarbamoyl)isonicotinic acid (110.7 mg, 0.256 mmol, 75% wt.) in DMF (0.7 mL) was added DIPEA (0.17 mL, 0.973 mmol) followed by HATU (146 mg, 0.384 mmol) and (1S,2S)-2-methylcyclopropanamine, hydrochloride (41.3 mg, 0.384 mmol). The resulting reaction mixture was stirred at rt for 2 h. The reaction was washed with a saturated LiCl solution (10 mL) and extracted with EtOAc (3×15 mL), then the combined organic phases were dried over a hydrophobic frit and concentrated in vacuo. The crude product was purified by flash silica chromatography (10 g silica cartridge, eluent: 40-100% (25% EtOH in EtOAc)/cyclohexane). All the fractions with product were concentrated in vacuo. The yellow oil obtained was purified by MDAP (high pH). The fractions containing the desired product were concentrated in vacuo to give 6-(1-(1H-pyrrolo[2,3-c]pyridin-4-yl)ethyl)-$N^2$-methyl-$N^4$-((1S,2S)-2-methylcyclopropyl)pyridine-2,4-dicarboxamide (29 mg, 0.073 mmol, 28.5% yield) as a colourless oil.

LCMS (2 min Formic): Rt=0.57 min, [MH]$^+$=378.3.

$^1$H NMR (400 MHz, MeOH-d$_4$) δ ppm 8.67 (s, 1H) 8.23 (d, J=1.2 Hz, 1H) 8.14 (s, 1H) 7.76 (d, J=1.5 Hz, 1H) 7.60 (d, J=3.2 Hz, 1H) 6.60 (d, J=2.7 Hz, 1H) 4.82-4.90 (obs. m, 1H) 3.00 (s, 3H) 2.50 (dt, J=7.3, 3.7 Hz, 1H) 1.91 (d, J=7.3 Hz, 3H) 1.10 (d, J=6.1 Hz, 3H) 0.91-1.02 (m, 1H) 0.78 (ddd, J=9.2, 5.3, 4.0 Hz, 1H) 0.55 (dt, J=7.3, 5.8 Hz, 1H). Exchangeables not observed.

Example 49: 6-((S*-1-(1H-Pyrrolo[2,3-c]pyridin-4-yl)ethyl)-N²-methyl-N⁴ ((1S,2S)-2-methylcyclopropyl)pyridine-2,4-dicarboxamide Example 50: 6-((R*-1-(1H-Pyrrolo[2,3-c]pyridin-4-yl)ethyl)-N²-methyl-N⁴ ((1S,2S)-2-methylcyclopropyl)pyridine-2,4-dicarboxamide Example 51: (S*)—N⁴-Cyclopropyl-6-(hydroxy(phenyl)methyl)-N²-methylpyridine-2,4-dicarboxamide Example 52: R*—N⁴-Cyclopropyl-6-(hydroxy(phenyl)methyl)-N²-methylpyridine-2,4-dicarboxamide

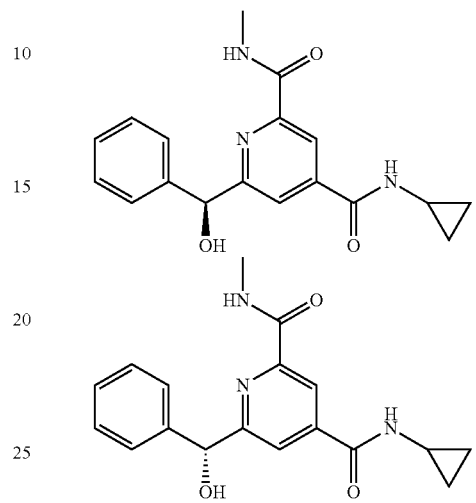

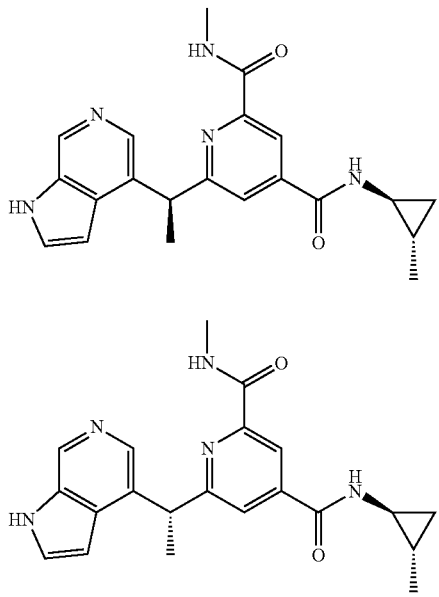

Example 48 (26 mg) was purified by chiral HPLC. The diastereomeric mixture was dissolved in EtOH (1 mL). Injection: 1 mL of the solution was injected onto the column (20% EtOH (+0.2% isopropylamine)/heptane (+0.2% isopropylamine), flow rate=30 mL/min, detection wavelength=215 nm, Column 30 mm×25 cm Chiralpak AD-H (5 µm)). Total number of injections=1. Fractions from 10-12 min were bulked and labelled peak 1. Fractions from 14-17 min were bulked and labelled peak 2. The bulked fractions were concentrated in vacuo and then transferred to weighed flasks.

The fractions corresponding to peak 1 were collected to afford example 49 (15 mg)

LCMS (2 min Formic): Rt=0.53 min, [MH]⁺=378.4

¹H NMR (400 MHz, MeOH-d₄) δ ppm 8.60 (s, 1H) 8.22 (d, J=1.5 Hz, 1H) 8.10 (s, 1H) 7.74 (d, J=1.5 Hz, 1H) 7.48 (d, J=3.2 Hz, 1H) 6.51 (dd, J=3.2, 0.7 Hz, 1H) 4.82 (q, J=7.3 Hz, 1H) 3.01 (s, 3H) 2.49 (dt, J=7.3, 3.7 Hz, 1H) 1.91 (d, J=7.1 Hz, 3H) 1.10 (d, J=6.1 Hz, 3H) 0.92-1.02 (m, 1H) 0.78 (ddd, J=9.2, 5.3, 3.9 Hz, 1H) 0.55 (dt, J=7.3, 5.7 Hz, 1H). Exchangeables not observed.

The fractions corresponding to peak 2 were collected to afford example 50 (16 mg) which contained impurities and was therefore further purified by MDAP (High pH). The combined desired fractions were concentrated in vacuo to give example 50 (8 mg) as a colourless oil.

LCMS (2 min Formic): Rt=0.53 min, [MH]⁺=378.3

Example 47 (13 mg) was purified by chiral HPLC. The racemate was dissolved in EtOH (1 mL). Injection: 1 mL of the solution was injected onto the column (15% EtOH (+0.2% isopropylamine)/heptane (+0.2% isopropylamine), flow rate=30 mL/min, detection wavelength=215 nm, Column 30 mm×25 cm Chiralcel OJ-H (5 µm)). Total number of injections=1. Fractions from 12.5-14.5 min were bulked and labelled peak 1. Fractions from 16.5-20 min were bulked and labelled peak 2. The bulked fractions were concentrated in vacuo and then transferred to weighed flasks.

The fractions corresponding to peak 1 were collected to afford example 51 (7 mg)

LCMS (2 min Formic): Rt=0.76 min, [MH]⁺=326.2

The fractions corresponding to peak 2 were collected to afford example 52 (5 mg)

LCMS (2 min Formic): Rt=0.75 min, [MH]⁺=326.2 ¹H NMR (400 MHz, MeOH-d₄) δ ppm 8.27 (d, J=1.7 Hz, 1H) 7.96 (d, J=1.5 Hz, 1H) 7.46 (br. d, J=7.1 Hz, 2H) 7.29-7.36 (m, 2H) 7.22-7.28 (m, 1H) 5.94 (s, 1H) 2.99 (s, 3H) 2.87 (tt, J=7.4, 3.9 Hz, 1H) 0.78-0.85 (m, 2H) 0.62-0.68 (m, 2H). Exchangeables not observed.

Example 53: N⁴-((1r,3S)-3-Hydroxycyclobutyl)-N²-methyl-6-((S*-1-phenylethyl)pyridine-2,4-dicarboxamide

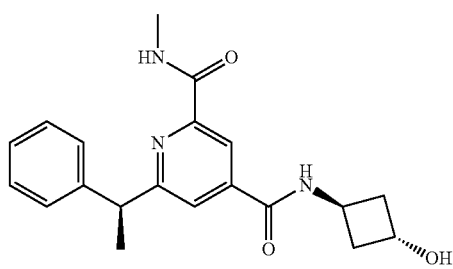 [SMILES: CNC(=O)c1cc(C(=O)N[C@H]2C[C@H](O)C2)cc([C@@H](C)c2ccccc2)n1]

To a mixture of 2-(methylcarbamoyl)-6-(1-phenylethyl) isonicotinic acid (47.9 mg, 0.168 mmol) and HATU (106.1 mg, 0.279 mmol), was added a solution of trans-3-amino-cyclobutanol hydrochloride (28.1 mg, 0.227 mmol) in DMF (0.8 mL). DIPEA (90.0 µL, 0.515 mmol) was added and the mixture was stirred at rt for 50 min. The mixture which was then concentrated under a stream of nitrogen and diluted with acetonitrile to a total volume of 1 mL and directly purified by MDAP (1×1 mL injection; high pH) and the required fraction was evaporated under a stream of nitrogen. The residue was redissolved in 2:1 methanol/DCM (~8 mL) and transferred to a tarred vial, the solvent evaporated under a stream of nitrogen and the residue dried in vacuo to give the desired product as a white solid; $N^4$-((1r,3r)-3-hydroxy-cyclobutyl)-$N^2$-methyl-6-(1-phenylethyl)pyridine-2,4-dicarboxamide (52.8 mg, 0.149 mmol, 89% yield)

LCMS (2 min High pH): Rt=0.89 min, $[MH]^+$=354.3

Examples 54-55

Examples 54-55 were prepared in an analogous manner to the previous examples

To a solution of crude 2-(trans-3-methoxycyclobutyl) isoindoline-1,3-dione (76.2 mg, 0.330 mmol) in ethanol (5 mL) was added hydrazine hydrate (0.030 mL, 0.618 mmol) and the solution stirred at room temperature for 94 hours under nitrogen. The reaction mixture was filtered to remove precipitated by-product and this precipitate was washed with ethanol (approx 10 mL). The combined filtrates were evaporated in vacuo to give a residue which was suspended in ethanol (approx 5 mL) and directly applied to the top of a 1 g Isolute SCX-2 ion exchange column. The column was eluted with 5 column volumes of ethanol and 5 column volumes of 2M aqueous HCl. The acidic fraction was evaporated under a stream of nitrogen and the residue dried in vacuo to give trans-3-methoxycyclobutanamine hydrochloride (24.2 mg, 0.176 mmol, 53.4% yield) as a yellow solid which was used without further purification in the subsequent step. To a mixture of 2-benzyl-6-(methylcarbamoyl)isonicotinic acid (50.1 mg, 0.185 mmol), trans-3-methoxycyclobutanamine hydrochloride (24.2 mg, 0.141 mmol) and 2-(3H-[1,2,3]triazolo[4,5-b]pyridin-3-yl)-1,1,3,3-tetramethylisouronium hexafluorophosphate(V) (HATU)

| Ex No. | Name | Structure | $[MH]^+$ | Rt (min)* |
|---|---|---|---|---|
| 54 | $N^2$-Methyl-$N^4$-((1S,2S)-2-methylcyclopropyl)-6-((2-oxopyridin-1(2H)-yl)methyl)pyridine-2,4-dicarboxamide | 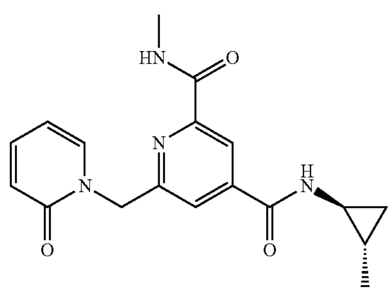 [SMILES: CNC(=O)c1cc(C(=O)N[C@H]2C[C@@H]2C)cc(Cn2ccccc2=O)n1] | 341.3 (Formic) | 0.65 |
| 55 | 6-Benzyl-$N^4$-((1S,2S)-2-(hydroxymethyl)cyclopropyl)-$N^2$-methylpyridine-2,4-dicarboxamide | 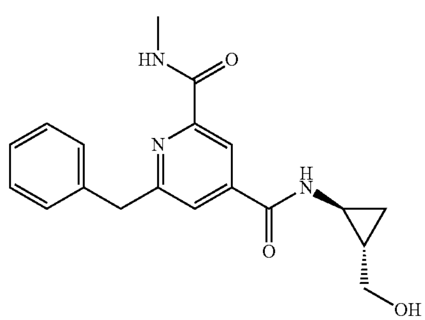 [SMILES: CNC(=O)c1cc(C(=O)N[C@H]2C[C@@H]2CO)cc(Cc2ccccc2)n1] | 340.2 (High pH) | 0.84 |

Example 56: 6-benzyl-$N^4$-(trans-3-methoxycyclobutyl)-$N^2$-methylpyridine-2,4-dicarboxamide

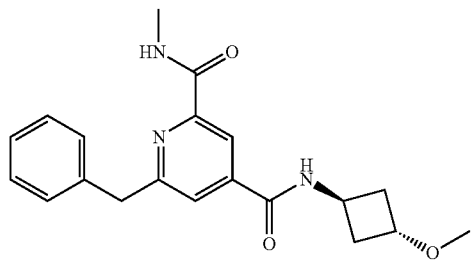 [SMILES: CNC(=O)c1cc(C(=O)N[C@H]2C[C@H](OC)C2)cc(Cc2ccccc2)n1]

(89.0 mg, 0.234 mmol) in DMF (1 mL) was added DIPEA (0.100 mL, 0.573 mmol). The solution was stirred at room temperature for 4 hours. The reaction mixture was diluted with DMSO (1 mL) and directly purified by Mass Directed Auto Preparative Reverse Phase Chromatography (MDAP) (2×1 mL injection, high pH). The required fractions were combined and evaporated in vacuo to give 6-benzyl-$N^4$-(trans-3-methoxycyclobutyl)-$N^2$-methylpyridine-2,4-dicarboxamide (21.6 mg, 0.061 mmol, 43.4% yield) as a yellow gum.

LCMS (2 min high pH) Peak $R_t$=0.95 minutes, m/z=354 for $[MH]^+$

Example 57: 6-Benzyl-N⁴-((1r,3r)-3-(2-hydroxyethoxy)cyclobutyl)-N²-methylpyridine-2,4-dicarboxamide

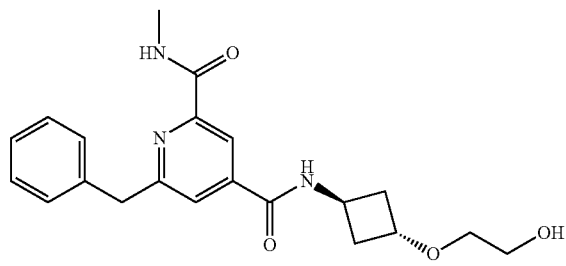 [SMILES: CNC(=O)c1cc(C(=O)N[C@H]2C[C@H](OCCO)C2)cc(Cc2ccccc2)n1]

To a mixture of 2-benzyl-6-(methylcarbamoyl)isonicotinic acid (53.5 mg, 0.198 mmol), HATU (92.0 mg, 0.242 mmol) and 2-((1r,3r)-3-aminocyclobutoxy)ethanol, hydrochloride (30.2 mg, 0.18 mmol) in DMF (1 mL) was added DIPEA (0.138 mL, 0.792 mmol). The resulting dark orange solution was stirred at rt for 3 h, after which the volatiles were evaporated under a stream of nitrogen to give a brown gum. This was redissolved in DMSO (2 mL) and directly purified by MDAP (2×1 mL injection, formic). The required fractions were evaporated under a stream of nitrogen, redissolved in methanol (approx. 2 mL each) and combined. This solution was evaporated under a stream of nitrogen to give the desired product as a sticky white solid (44.7 mg). 6-benzyl-N⁴-((1r,3r)-3-(2-hydroxyethoxy)cyclobutyl)-N²-methylpyridine-2,4-dicarboxamide (44.7 mg, 0.117 mmol, 59% yield).

LCMS (2 min High pH): Rt=0.84 min, [MH]⁺=384.4.

Example 58: 6-(2-Hydroxy-1-phenylethyl)-N²-methyl-N⁴-((1S,2S)-2-methylcyclopropyl)pyridine-2,4-dicarboxamide, mixture of diastereomers

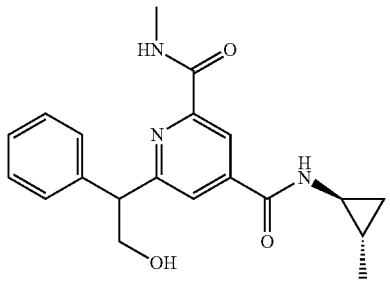 [SMILES: CNC(=O)c1cc(C(=O)N[C@H]2C[C@@H]2C)cc(C(CO)c2ccccc2)n1]

To a solution of 2-(2-hydroxy-1-phenylethyl)-6-(methylcarbamoyl)isonicotinic acid (1.715 g, 2.284 mmol, 40% wt) in DMF (0.7 mL) was added DIPEA (3.05 mL, 17.48 mmol) followed by HATU (1.329 g, 3.50 mmol) and (1S,2S)-2-methylcyclopropan-1-amine, hydrochloride (1.881 g, 17.48 mmol). The resulting reaction mixture was stirred at rt for 1 h. Further HATU (1.2 g) was added. The reaction was stirred for 1 h. Further HATU (600 mg) was added, the reaction was stirred for 1 h.

Further HATU (300 mg) was added and the reaction was stirred for 1 h 20 min. The reaction mixture was partitioned between sat LiCl (10 mL) and EtOAc (10 mL). The organic layer was separated and the aqueous layer was extracted with further portions of EtOAc (3×10 mL). Water (20 mL) was added to the combined organic phases. The organic layer was separated and the aqueous layer was extracted with further portions of EtOAc (3×10 mL). The combined organic phases were dried over a hydrophobic frit and then concentrated in vacuo. The crude product was added to a SNAP silica cartridge (25 g) and purified by flash column chromatography, eluting with 0 to 50% (25% EtOH in EtOAc)/cyclohexane. The desired fraction was concentrated in vacuo to give 6-(2-hydroxy-1-phenylethyl)-N²-methyl-N⁴-((1S,2S)-2-methylcyclopropyl)pyridine-2,4-dicarboxamide (554 mg, 1.489 mmol, 65% yield) as a colourless oil LCMS (2 min Formic): Rt=0.84 min, [MH]⁺=354.3.

Example 59: 6-(Chloro(phenyl)methyl)-N²-methyl-N⁴-((1S,2S)-2-methylcyclopropyl)pyridine-2,4-dicarboxamide Unknown Mixture of Diastereomers at Undefined Stereocentre

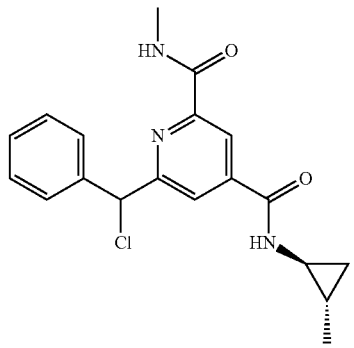 [SMILES: CNC(=O)c1cc(C(=O)N[C@H]2C[C@@H]2C)cc(C(Cl)c2ccccc2)n1]

To a solution of 6-((R)-hydroxy(phenyl)methyl)-N²-methyl-N⁴-((1S,2S)-2-methylcyclopropyl)pyridine-2,4-dicarboxamide (54 mg, 0.151 mmol) in dichloromethane (1 mL) at 0° C., was added dropwise thionyl chloride (0.11 mL, 1.507 mmol). The reaction mixture was then stirred at rt for 30 minutes. Water (5 mL) and DCM (5 mL) was added. The organic phase was separated and the aqueous phase was extracted with further portions of DCM (2×5 mL). The combined organic phase was dried (hydrophobic frit) then concentrated in vacuo. This was purified on a SNAP column, eluent 0-60% EtOAc/cyclohexane. The combined desired fractions were concentrated in vacuo to give 6-(chloro(phenyl)methyl)-N²-methyl-N⁴-((1S,2S)-2-methylcyclopropyl)pyridine-2,4-dicarboxamide (53 mg, 0.133 mmol, 88% yield, ~90% purity) as a white oil.

LCMS (2 min Formic): Rt=1.07 min, [MH]⁺=358.2.

Example 60: N₂-methyl-N₄-((1S,2S)-2-methylcyclopropyl-6-(1-(pyridin-2-yl)ethyl)pyridine-2,4-dicarboxamide

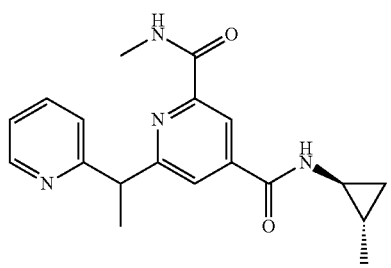 [SMILES: CNC(=O)c1cc(C(=O)N[C@H]2C[C@@H]2C)cc(C(C)c2ccccn2)n1]

To a solution of (±)-2-(methylcarbamoyl)-6-(1-phenylvinyl)isonicotinic acid (330 mg, 0.468 mmol) (approximately 40% purity) in N,N-dimethylformamide (6 mL) was added HATU (356 mg, 0.935 mmol) followed by DIPEA (0.24 mL, 1.374 mmol) and (1S,2S)-2-methylcyclopropanamine hydrochloride (101 mg, 0.935 mmol). The resulting reaction mixture was stirred over the weekend before being partioned between saturated lithium chloride solution (10 mL) and ethyl acetate (10 mL). The organic layer was separated and the aqueous layer was extracted with further portions of ethyl acetate (3×10 mL). The combined organic layers were washed with 10 mL of water and the aqueous layer was extracted with further portions of ethyl acetate (2×10 mL). The combined organic phases were dried by filtering through a hydrophobic frit and then concentrated in vacuo. The residue was purified by SNAP column chromatography (10 g eluenting with 0 to 60% EtOAc/cyclohexane). The combined desired fractions were concentrated in vacuo to give a residue, to which was added 10 mL of DCM and 5 mL of 5M NaOH. The layers were separated and the aqueous phase was extracted with further portions of DCM (2×10 mL). The combined organic phase was dried by filtering through a hydrophobic frit then concentrated in vacuo to give $N_2$-methyl-$N_4$-((1S,2S)-2-methylcyclopropyl)-6-(1-(pyridin-2-yl)ethyl)pyridine-2,4-dicarboxamide (42 mg, 0.112 mmol, 23.89% yield) as a yellow oil.

LCMS (2 mins formic) Peak $R_f$=0.57 minutes, m/z=339 for $[MH]^+$

Example 61: 6-(2-Hydroxy-1-phenylpropyl)-$N^2$-methyl-$N^4$-((1S,2S)-2-methylcyclopropyl)pyridine-2,4-dicarboxamide Unknown Mixture of Diastereomers at Undefined Stereocentres

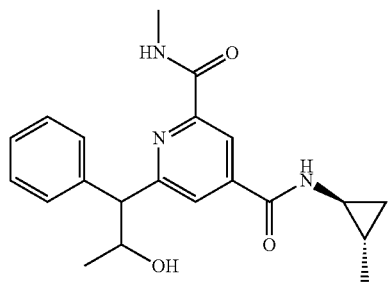 [SMILES: CNC(=O)c1cc(C(=O)N[C@H]2C[C@@H]2C)cc(C(c2ccccc2)C(C)O)n1]

To a solution of 2-(2-hydroxy-1-phenylpropyl)-6-(methylcarbamoyl)isonicotinic acid (40% purity, 318 mg, 0.405 mmol) in N,N-dimethylformamide (1 mL) was added DIPEA (0.22 mL, 1.260 mmol) followed by HATU (169 mg, 0.445 mmol) and (1S,2S)-2-methylcyclopropanamine hydrochloride (47.9 mg, 0.445 mmol). The resulting reaction mixture was stirred overnight. The reaction mixture was partioned between sat. LiCl (10 mL) and EtOAc (10 mL). The organic layer was separated and the aqueous layer was extracted with further portions of EtOAc. The combined organic phases were dried over an hydrophobic frit then concentrated in vacuo. The residue was purified by silica gel column 10 g, eluent 40-100% EtOAc/cyclohexane. The fractions containing desired product were concentrated in vacuo. The residue was purified by column 10 g, eluent 40-80% EtOAc/cyclohexane. The fractions containing the minor diastereomer mixture were concentrated in vacuo and were then purified by MDAP (high pH). The desired fraction was concentrated in vacuo to give 6-(2-hydroxy-1-phenylpropyl)-$N^2$-methyl-$N^4$-((1S,2S)-2-methylcyclopropyl)pyridine-2,4-dicarboxamide (9.8 mg, 0.025 mmol, 6.26% yield) as a white solid.

LCMS (2 min Formic): Rt=0.92 min, $[MH]^+$=368.4.

Example 62: 6-(1-(3-(2-Hydroxyethoxy)phenyl)ethyl-$N^2$-methyl-$N^4$-((1S,2S)-2-methylcyclopropyl)pyridine-2,4-dicarboxamide, Mixture of Diastereomers

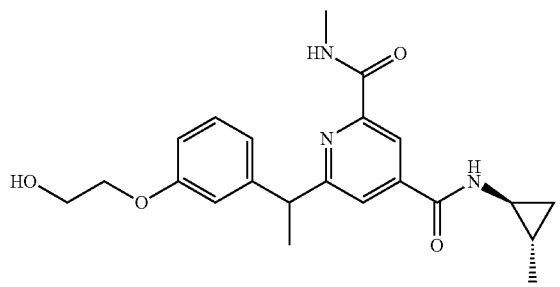 [SMILES: CNC(=O)c1cc(C(=O)N[C@H]2C[C@@H]2C)cc(C(C)c2cccc(OCCO)c2)n1]

Potassium carbonate (465 mg, 3.37 mmol, 70% wt.) was added to a mixture of 6-(1-(3-hydroxyphenyl)ethyl)-$N^2$-methyl-$N^4$-((1S,2S)-2-methylcyclopropyl)pyridine-2,4-dicarboxamide (425 mg, 0.842 mmol) and 1,3-dioxolan-2-one (0.23 mL, 3.45 mmol) in DMF (6 mL). The reaction mixture was stirred at 100° C. under nitrogen for 3 h. The reaction mixture was then cooled to rt and partitioned between ethyl acetate (10 mL) and water (10 mL). The layers were separated and the aqueous layer was extracted with further portions of EtOAc (2×10 mL). The combined organic phases were dried over a hydrophobic frit and then concentrated in vacuo. The resulting oil was dissolved in DCM and purified on a Biotage SNAP (10 g) column using a gradient of 100% cyclohexane followed by 40 to 80% ethyl acetate/cyclohexane. The product-containing fractions were combined and the solvent removed in vacuo to give the desired product with some residual DMF. sat. LiCl solution (10 mL) and EtOAc (10 mL) were added. The layers were separated and the aqueous layer was extracted with further portions of EtOAc (2×10 mL). The combined organic phases were dried over a hydrophobic frit then concentrated in vacuo to give 6-(1-(3-(2-hydroxyethoxy)phenyl)ethyl)-A-methyl-$N^4$-((1S,2S)-2-methylcyclopropyl)pyridine-2,4-dicarboxamide (192 mg, 0.435 mmol, 52% yield, 90% purity) as a colourless oil.

LCMS (2 min Formic): Rt=0.90 min, $[MH]^+$=398.4.

Example 63: 6-(2-hydroxy-1-phenylethyl)-$N^2$-methyl-$N^4$-((1S,2S)-2-methylcyclopropyl)pyridine-2,4-dicarboxamide Isomer 1

Example 64: 6-(2-hydroxy-1-phenylethyl)-$N^2$-methyl-$N^4$-((1S,2S)-2-methylcyclopropyl)pyridine-2,4-dicarboxamide Isomer 2

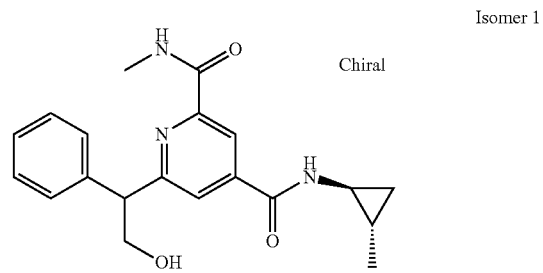

Isomer 1
Chiral

Isomer 2

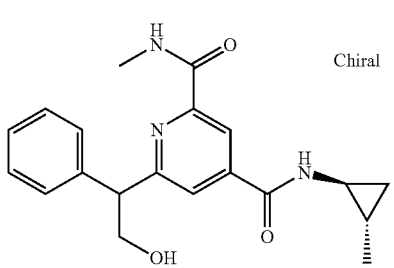

Example 58 (220 mg) was purified by chiral HPLC. The racemate was dissolved in EtOH (3 mL). Injection: 1 mL of the solution was injected onto the column [10% EtOH (+0.2% isopropylamine)/Heptane (+0.2% isopropylamine), flow rate=30 mL/min, detection wavelength=215 nm, 4. Ref 550, 100, Column 30 mm×25 cm Chiralcel OJ-H (5 μm), lot no. OJH10027-01]. Total number of injections=4. Fractions from 9 to 10.5 mins were bulked and labelled peak 1. Fractions from 13 to 16.5 mins were bulked and labelled peak 2. Fractions from 10.5 to 13 mins were bulked and labelled mixed fractions. The mixed fractions were evaporated in vacuo and the residue re-purified as above. Each set of the bulked pure fractions were concentrated in vacuo and then transferred to tarred vials and dried in vacuo. The second eluting isomer was re-purified as above to enhance its purity. The fractions corresponding to peak 1 were collected to afford 6-(2-hydroxy-1-phenylethyl)-$N^2$-methyl-$N^4$-((1S,2S)-2-methylcyclopropyl)pyridine-2,4-dicarboxamide Isomer 1 (92.2 mg).

LCMS (2 min Formic): Rt=0.86 minutes, m/z=354 for [MH]

The fractions corresponding to peak 2 were collected to afford 6-(2-hydroxy-1-phenylethyl)-$N^2$-methyl-$N^4$-((1S,2S)-2-methylcyclopropyl)pyridine-2,4-dicarboxamide Isomer 2 (79.1 mg).

LCMS (2 min Formic): Rt=0.86 minutes, m/z=354 for [MH]$^+$

Example 65: (+/−)-$N^4$-((1R,5S,6r)-3,3-difluorobicyclo[3.1.0]hexan-6-yl)-6-(hydroxy(o-tolyl)methyl)-$N^2$-methylpyridine-2,4-dicarboxamide

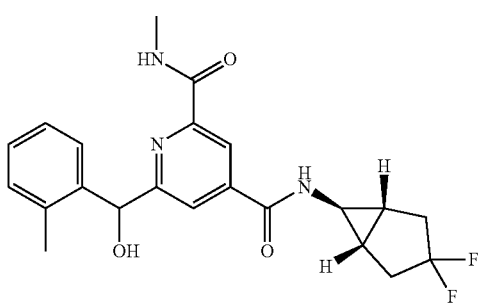 [SMILES: CNC(=O)c1cc(C(=O)N[C@H]2[C@@H]3CC(F)(F)C[C@@H]32)cc(C(O)c2ccccc2C)n1]

2-(Hydroxy(o-tolyl)methyl)-6-(methylcarbamoyl)isonicotinic acid (30 mg, 0.100 mmol) was taken up in DMF (5 mL). DIPEA (0.052 mL, 0.300 mmol), HATU (57.0 mg, 0.150 mmol) and (1R,5S,6r)-3,3-difluorobicyclo[3.1.0]hexan-6-amine (19.95 mg, 0.150 mmol) were added and the reaction left to stir for 1 h. The reaction was concentrated in vacuo. The residue was taken up in ethyl acetate (10 mL) and washed with sodium bicarbonate solution (10 mL) and brine (10 mL). The organic phase was dried over sodium sulphate, filtered through a hydrophobic frit and concentrated in vacuo. The samples were dissolved in 1:1 MeCN:DMSO (1 mL) and purified by MDAP (high pH). The solvent was evaporated in vacuo. The samples were dissolved in 1:1 DMSO:MeCN (1 mL) and re-purified by MDAP (high pH). The solvent was evaporated in vacuo to give the desired product, $N^4$-((1R,5S,6r)-3,3-difluorobicyclo[3.1.0]hexan-6-yl)-6-(hydroxy(o-tolyl)methyl)-$N^2$-methylpyridine-2,4-dicarboxamide (12 mg, 0.029 mmol, 29% yield).

LCMS (2 min High pH): Rt=0.98 min, [MH]$^+$=416.4

Example 66: 6-(Hydroxy(o-tolyl)methyl)-$N^2$-methyl-$N^4$-((1S,2S)-2-methylcyclopropyl)pyridine-2,4-dicarboxamide, mixture of diastereomers

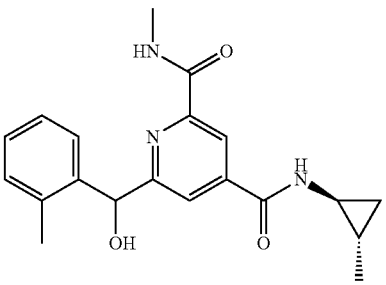

2-(Hydroxy(o-tolyl)methyl)-6-(methylcarbamoyl)isonicotinic acid (30 mg, 0.100 mmol) was taken up in DMF (5 mL). DIPEA (0.052 mL, 0.300 mmol), HATU (57.0 mg, 0.150 mmol) and (1S,2S)-2-methylcyclopropanamine, hydrochloride (16.12 mg, 0.150 mmol) were added and the reaction left to stir for 1 h. The reaction mixture was then concentrated in vacuo. The residue was taken up in ethyl acetate (10 mL) and washed with sodium bicarbonate solution (10 mL) and brine (10 mL). The organic phase was dried over sodium sulphate, filtered through a hydrophobic frit and concentrated in vacuo. The samples were dissolved in 1:1 MeCN:DMSO (1 mL) and purified by MDAP (high pH). The solvent was evaporated in vacuo to give the required product, 6-(hydroxy(o-tolyl)methyl)-$N^2$-methyl-$N^4$-((1S,2S)-2-methylcyclopropyl)pyridine-2,4-dicarboxamide (18 mg, 0.051 mmol, 51% yield).

LCMS (2 min High pH): Rt=0.91 min, [MH]$^+$=354.2

Example 67: 6-((1H-Indol-4-yl)methyl)-$N^4$-((1R,5S,6r)-3,3-difluorobicyclo[3.1.0]hexan-6-yl)-$N^2$-methylpyridine-2,4-dicarboxamide

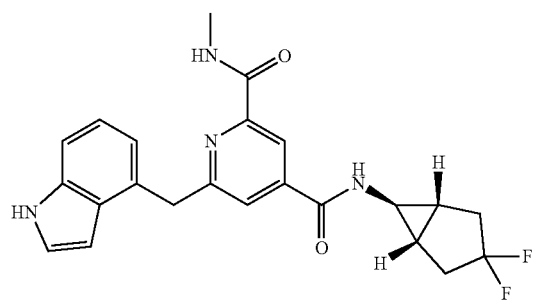 [SMILES: CNC(=O)c1cc(C(=O)N[C@H]2[C@@H]3CC(F)(F)C[C@@H]32)cc(Cc2cccc3[nH]ccc23)n1]

2-((1H-Indol-4-yl)methyl)-6-(methylcarbamoyl)isonicotinic acid (40 mg, 0.129 mmol) was taken up in DMF (5 mL). (1R,5S,6r)-3,3-difluorobicyclo[3.1.0]hexan-6-amine (25.8 mg, 0.194 mmol), HATU (73.8 mg, 0.194 mmol) and DIPEA (0.068 mL, 0.388 mmol) were added and the reaction left to stir at rt for 3 h. The reaction was concentrated in vacuo. The residue was taken up in ethyl acetate (10 mL) and washed with sodium bicarbonate solution (10 mL) and brine (10 mL). The organic phase was dried over sodium sulphate, filtered through a hydrophobic frit and concentrated in vacuo. The samples were dissolved in 1:1 MeCN:DMSO (1 mL) and purified by MDAP (high pH). The solvent was evaporated in vacuo to give, 6-((1H-indol-4-yl)methyl)-$N^4$-((1R,5S,6r)-3,3-difluorobicyclo[3.1.0]hexan-6-yl)-$N^2$-methylpyridine-2,4-dicarboxamide (31 mg, 0.073 mmol, 57% yield).

LCMS (2 min High pH): Rt=1.03 min, [MH]$^+$=425.4

Example 68: 6-(Hydroxy(1H-indol-4-yl)methyl)-$N^2$-methyl-$N^4$-((1S,2S)-2-methylcyclopropyl)pyridine-2,4-dicarboxamide, mixture of diastereomers

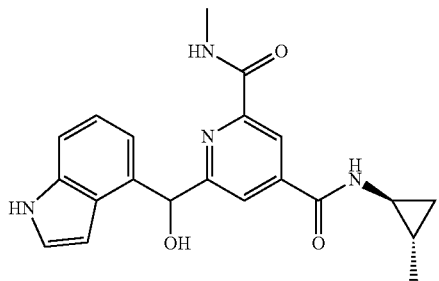 [SMILES: CNC(=O)c1cc(C(=O)N[C@H]2C[C@@H]2C)cc(C(O)c2cccc3[nH]ccc23)n1]

2-(Hydroxy(1H-indol-4-yl)methyl)-6-(methylcarbamoyl)isonicotinic acid (15 mg, 0.046 mmol) was taken up in DMF (5 mL). (1S,2S)-2-Methylcyclopropanamine, hydrochloride (7.44 mg, 0.069 mmol), HATU (26.3 mg, 0.069 mmol) and DIPEA (0.024 mL, 0.138 mmol) were added and the reaction left to stir at rt for 1 h. The reaction mixture was then concentrated in vacuo. The samples were dissolved in 1:1 MeCN:DMSO (1 mL) and purified by MDAP (High pH). The solvent was evaporated in vacuo to afford the crude product (2 mg). This was purified by preparative HPLC: The sample was dissolved in DMSO (3.5 mL). 3.5 mL injection was made onto a CSH C18 150×30 mm, 5 μm column at rt. The flow and gradient was provided by two pumps with a reduced flow passing through the injector during injection. The residual flow is introduced at the head of the column so the overall flow remains constant. Fractionation was determined by mixture of diode array & mass spec signal. A gradient of solvent A and solvent B was utilised as defined below:

Solvent A: 10 mM ammonium bicarbonate in water adjusted to pH 10 with ammonia solution.
Solvent B: acetonitrile

| Time (min) | Flow rate (mL/min) | % B | % A |
|---|---|---|---|
| 0 | 40 | 18 | 82 |
| 3.5 | 40 | 18 | 82 |
| 5 | 40 | 18 | 82 |
| 20 | 40 | 25 | 75 |
| 32 | 40 | 30 | 70 |
| 35 | 40 | 99 | 1 |
| 41 | 40 | 99 | 1 |

The UV detection was a summed signal from wavelength of 210 nm to 350 nm.

MS conditions

MS: Waters ZQ

Ionisation mode: Positive Electrospray

Scan range: 300 to 1200 AMU

Scan time: 0.5 sec

Inter scan delay: 0.1 sec

The fractions were combined and dried under a stream of nitrogen blowdown at 40° C. to afford the title compound (1 mg).

LCMS (2 min High pH): Rt=0.81 min, [MH]$^+$=379.4

Example 69: 6-(hydroxy(o-tolyl)methyl)-$N^2$-methyl-$N^4$-((1S,2S)-2-methylcyclopropyl)pyridine-2,4-dicarboxamide Isomer 1

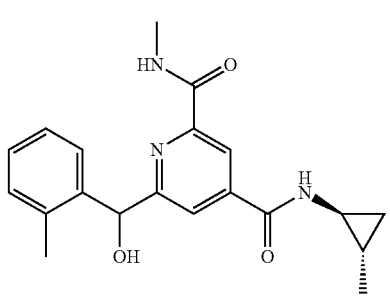

Isomer 1

Example 66 (330 mg) was purified by chiral HPLC. The racemate was dissolved in EtOH (3 mL). Injection: 1 mL of the solution was injected onto the column [20% EtOH/Heptane, flow rate=30 mL/min, detection wavelength=215 nm, 4. Ref 550, 100, Column 30 mm×25 cm Chiralcel OD-H (5 μm), lot no. ODH11158-01]. Total number of injections=3. Fractions from 8 to 10 mins were bulked and labelled peak 1. Fractions from 13 to 17 mins were bulked and labelled peak 2. Each set of the bulked pure fractions were concentrated in vacuo and then transferred to tarred vials and dried in vacuo.

The fractions corresponding to peak 1 were collected to afford 6-(hydroxy(o-tolyl)methyl)-$N^2$-methyl-$N^4$-((1S,2S)-2-methylcyclopropyl)pyridine-2,4-dicarboxamide Isomer 1 (131 mg).

LCMS (2 min Formic): Rt=0.90 minutes, m/z=354 for [MH]$^+$

Example 70: 6-((2-fluorophenyl)(hydroxy)methyl)-N²-methyl-N⁴-((1S,2S)-2-methylcyclopropyl)pyridine-2,4-dicarboxamide

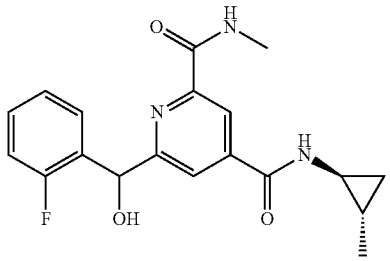 [SMILES: CNC(=O)c1cc(C(=O)N[C@H]2C[C@@H]2C)cc(C(O)c2ccccc2F)n1]

2-((2-fluorophenyl)(hydroxy)methyl)-6-(methylcarbamoyl)isonicotinic acid (68 mg, 0.223 mmol) was taken up in DMF (5 mL). DIPEA (0.117 mL, 0.670 mmol), HATU (127 mg, 0.335 mmol) and (1S,2S)-2-methylcyclopropanamine hydrochloride (36.1 mg, 0.335 mmol) were added and the reaction left to stir at room temperature overnight. The reaction was concentrated in vacuo and the residue was taken up in ethyl acetate (10 ml) and washed with sodium bicarbonate (10 ml) and brine (10 ml). The organic phase was dried over sodium sulphate, filtered through a hydrophobic frit and concentrated in vacuo. The residue was dissolved in 1:1 MeCN:DMSO (1 mL) and purified by Mass Directed AutoPrep on Xselect column using acetonitrile water with an ammonium carbonate modifier (High pH). The solvent was evaporated in vacuo to give 6-((2-fluorophenyl)(hydroxy)methyl)-N₂-methyl-N₄-((1S,2S)-2-methylcyclopropyl)pyridine-2,4-dicarboxamide (4.5 mg, 0.013 mmol, 5.63% yield).

LCMS (2 min High pH) Peak $R_t$=0.88 minutes, m/z=358 for [MH]⁺

Example 71: 6-((S*)-1-(3-(2-Hydroxyethoxy)phenyl)ethyl)-N²-methyl-N⁴-((1S,2S)-2-methylcyclopropyl)pyridine-2,4-dicarboxamide

Example 72: 6-((R)-1-(3-(2-Hydroxyethoxy)phenyl)ethyl)-N²-methyl-N⁴-((1S,2S)-2-methylcyclopropyl)pyridine-2,4-dicarboxamide

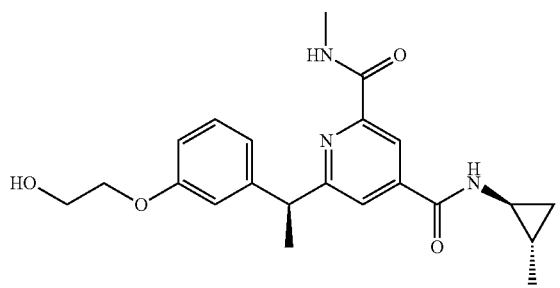

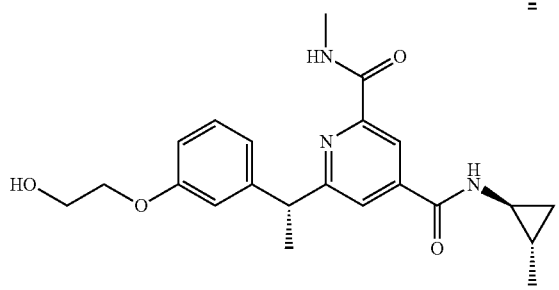

Example 62 (185 mg) was purified by chiral HPLC. The diastereomeric mixture was dissolved in EtOH (ca. 15 mL). Injections: 0.4 mL of the solution was injected onto the column via a rheodyne valve (30% EtOH/heptane, flow rate=20 mL/min, detection: UV diode array at 280 nm (Band width 140 nm, reference 400 nm, bandwidth 100 nm, Column 20 mm×25 cm Regis Whelk-O1 [R,R] (5 μm)). Fractions from 17.5-20.5 min were bulked and labelled peak 1. Fractions from 21.5-26 min were bulked and labelled peak 2. The bulked fractions were transferred in EtOH concentrated in vacuo into weighed flasks.

The fractions corresponding to peak 1 were collected to afford example 71 (51 mg)

LCMS (2 min Formic): Rt=0.90 min, [MH]⁺=398.4

The fractions corresponding to peak 2 were collected to afford example 72 (57 mg)

LCMS (2 min Formic): Rt=0.90 min, [MH]⁺=398.4

Example 73: (+/−)-N⁴-((1R,5S,6r)-3,3-Difluorobicyclo[3.1.0]hexan-6-yl)-6-(hydroxy(phenyl)methyl)-N²-methylpyridine-2,4-dicarboxamide

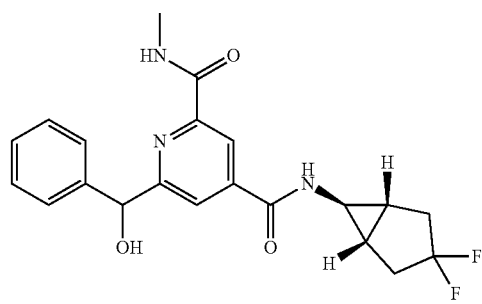 [SMILES: CNC(=O)c1cc(C(=O)N[C@H]2[C@@H]3CC(F)(F)C[C@@H]32)cc(C(O)c2ccccc2)n1]

To a solution of (1R,5S,6r)-3,3-difluorobicyclo[3.1.0]hexan-6-amine hydrochloride (41.2 mg, 0.194 mmol), (+/−)-2-(hydroxy(phenyl)methyl)-6-(methylcarbamoyl)isonicotinic acid (44.2 mg, 0.154 mmol) and HATU (86.9 mg, 0.229 mmol) in N,N-dimethylformamide (1.0 mL) was added N,N diisopropylethylamine (0.108 mL, 0.618 mmol). The resulting orange solution was stirred at room temperature for 2 hours, after which the volatiles were evaporated under a stream of nitrogen to give a sticky dark orange gum. This was redissolved in DMSO (3 mL) and purified by MDAP (high pH). The required fraction was evaporated under a stream of nitrogen, transferred in methanol (approx 2 mL), this solution evaporated under a stream of nitrogen and the residue dried in vacuo to give the desired product (+/−)-N⁴-((1R,5S,6r)-3,3-difluorobicyclo[3.1.0]hexan-6-yl)-6-(hydroxy(phenyl)methyl)-AP-methyl pyridine-2,4-dicarboxamide (39.9 mg, 0.099 mmol, 64.4% yield) as a white solid.

LCMS (2 min High pH): Rt=0.91 min, [MH]⁺=402.4.

Example 74: 6-((R*)-1-(3-Fluoro-1H-pyrrolo[2,3-c]pyridin-4-yl)ethyl)-N²-methyl-N⁴-((1S,2S)-2-methylcyclopropyl)pyridine-2,4-dicarboxamide

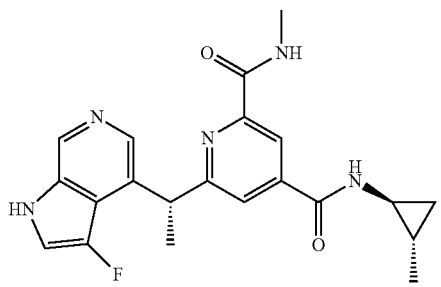 [SMILES: CNC(=O)c1cc(C(=O)N[C@H]2C[C@@H]2C)cc([C@H](C)c2cncc3[nH]cc(F)c23)n1]

6-((R*)-1-(1H-Pyrrolo[2,3-c]pyridin-4-yl)ethyl)-N²-methyl-N⁴-((1S,2S)-2-methylcyclopropyl)pyridine-2,4-dicarboxamide (Example 50, 20 mg, 0.050 mmol) was added in acetonitrile (0.5 mL), then acetic acid (0.01 mL, 0.175 mmol) and Selectfluor® (26.7 mg, 0.076 mmol) were added at 0° C. slowly. This was allowed to warm up and stirred 2 h at rt. Selectfluor® (20 mg, 0.056 mmol) was added and the resultant mixture was stirred 2 h at rt. A further portion of Selectfluor® (20 mg, 0.056 mmol) was added and the resultant mixture was stirred 4 h at rt. Additional Selectfluor® (20 mg, 0.056 mmol) and acetic acid (0.01 mL, 0.175 mmol) were added the resultant mixture was stirred 18 h at rt. A further portion of Selectfluor® (20 mg, 0.056 mmol) was added and the resultant mixture was at 40° C. for 1 h. Additional Selectfluor® (20 mg, 0.056 mmol) and acetic acid (0.01 mL, 0.175 mmol) was added and the resultant mixture was at 40° C. for 1 h. A further portion of Selectfluor® (20 mg, 0.056 mmol) and acetic acid (0.01 mmol, 0.175 mmol) was added and the resultant mixture was at 50° C. for 1 h.

The reaction mixture was purified directly by MDAP (high pH). The desired fractions were concentrated in vacuo to give 6-((R*)-1-(3-fluoro-1H-pyrrolo[2,3-c]pyridin-4-yl)ethyl)-A-methyl-N⁴-((1S,2S)-2-methylcyclopropyl)pyridine-2,4-dicarboxamide (5.4 mg, 0.012 mmol, 24.42% yield, ~90% purity).

LCMS (2 min Formic): Rt=0.53 min, [MH]⁺=396.4.

Example 75: NP-Cyclopropyl-N²-methyl-6-(3-((1-methyl-1H-pyrazol-3-yl)methoxy)benzyl)pyridine-2,4-dicarboxamide

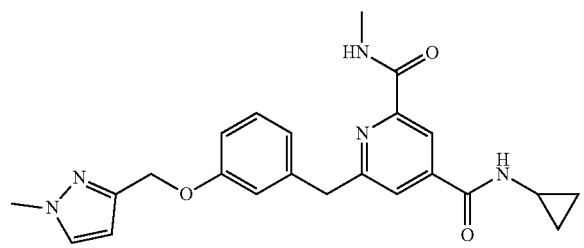 [SMILES: CNC(=O)c1cc(C(=O)NC2CC2)cc(Cc2cccc(OCc3ccn(C)n3)c2)n1]

N⁴-Cyclopropyl-6-(3-hydroxybenzyl)-N²-methylpyridine-2,4-dicarboxamide (40 mg, 0.123 mmol) was taken up in acetone (1 mL). Potassium carbonate (25.5 mg, 0.184 mmol) and 3-(chloromethyl)-1-methyl-1H-pyrazole (24.08 mg, 0.184 mmol, commercially available from, for example, Maybridge) were added and the reaction left to stir at rt for 1 h. The reaction was heated to 50° C. overnight. Further 3-(chloromethyl)-1-methyl-1H-pyrazole (24.08 mg, 0.184 mmol) was added again and the reaction left to stir for a further 1 h. The reaction was concentrated in vacuo. The residue was taken up in 10% methanol/DCM (10 mL) and washed with water (10 mL) and brine (10 mL). The organic phase was dried over sodium sulphate, filtered through a hydrophobic frit and concentrated in vacuo. The samples were dissolved in 1:1 MeCN:DMSO (1 mL) and purified by MDAP (high pH). The solvent was evaporated in vacuo to give the required product, N⁴-cyclopropyl-N²-methyl-6-(3-((1-methyl-1H pyrazol-3-yl)methoxy)benzyl)pyridine-2,4-dicarboxamide (7 mg, 0.017 mmol, 14% yield).

LCMS (2 min High pH): Rt=0.91 min, [MH]⁺=420.3

Example 76: 6-((3-fluorophenyl)(hydroxy)methyl)-N²-methyl-N⁴-((1S,2S)-2-methylcyclopropyl)pyridine-2,4-dicarboxamide

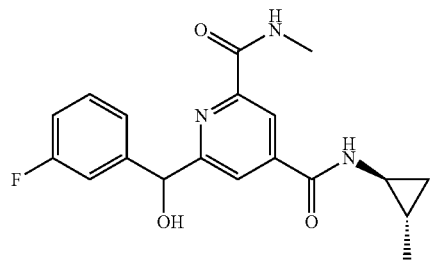 [SMILES: CNC(=O)c1cc(C(=O)N[C@H]2C[C@@H]2C)cc(C(O)c2cccc(F)c2)n1]

2-((3-Fluorophenyl)(hydroxy)methyl)-6-(methylcarbamoyl)isonicotinic acid (380 mg, 1.249 mmol) was suspended in DCM (20 ml), then triethylamine (0.522 ml, 3.75 mmol), HATU (570 mg, 1.499 mmol) and (1S,2S)-2-methylcyclopropan-1-amine hydrochloride (175 mg, 1.624 mmol) were added and the mixture was stirred at room temperature for 2 h. The mixture was diluted with ethyl acetate (30 ml) and washed with water (2×50 ml) and brine, then dried and evaporated in vacuo to give a pale yellow gum. The crude material was dissolved in DCM and loaded onto a 25 g silica column, then eluted with 0-100% EtOAc/cyclohexane and product-containing fractions were evaporated in vacuo to give 6-((3-fluorophenyl)(hydroxy)methyl)-N²-methyl-N⁴-((1S,2S)-2-methylcyclopropyl)pyridine-2,4-dicarboxamide (330 mg, 0.923 mmol, 73.9% yield) as a colourless foam.

LCMS (2 min Formic) Peak R_t=0.89 minutes, m/z=358 for [MH]

Example 77: 6-((S*)-2-Cyano-1-phenylethyl)-N²-methyl-N⁴-((1S,2S)-2-methylcyclopropyl)pyridine-2,4-dicarboxamide

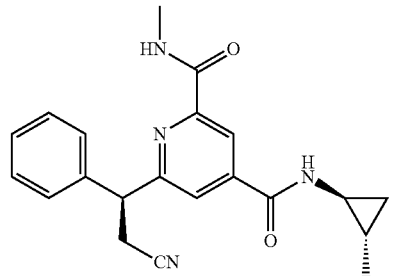

Acetonitrile (0.33 mL, 6.35 mmol) was dissolved in THF (1 mL) and cooled to −78° C. in a cardice/acetone bath under N₂. BuLi (2.5M in hexanes, 2.61 mL, 6.51 mmol) was added dropwise and reaction mixture left to stir for 30 min. 6-(Chloro(phenyl)methyl)-N²-methyl-N⁴-((1S,2S)-2-methylcyclopropyl)pyridine-2,4-dicarboxamide (370 mg, 0.931 mmol) was added and the resultant mixture was stirred for 30 min at −78° C. then allowed to warm up. The reaction mixture was stirred for 30 min at rt. MeOH (0.5 mL) was added and the mixture was purified directly by MDAP (high pH). The combined desired fractions were concentrated in vacuo to give the crude product (12 mg). This was further purified by silica chromatography using a glass pipette column and eluting with 30% EtOAc/cyclohexane. The pure fractions were concentrated in vacuo to give 6-((S*)-2-cyano-1-phenylethyl)-N²-methyl-N⁴-((1S,2S)-2-methylcyclopropyl)pyridine-2,4-dicarboxamide (3.3 mg, 8.19 μmol, 1% yield) as a colourless oil.

LCMS (2 min Formic): Rt=0.95 min, [MH]⁺=363.4

Example 78: 6-(1-(1H-pyrrolo[2,3-c]pyridin-4-yl)propyl)-N2-methyl-N4-((1S,2S)-2-methylcyclopropyl)pyridine-2,4-dicarboxamide Isomer 1

Example 79: 6-(1-(1H-pyrrolo[2,3-c]pyridin-4-yl)propyl)-N2-methyl-N4-((1S,2S)-2-methylcyclopropyl)pyridine-2,4-dicarboxamide Isomer 2

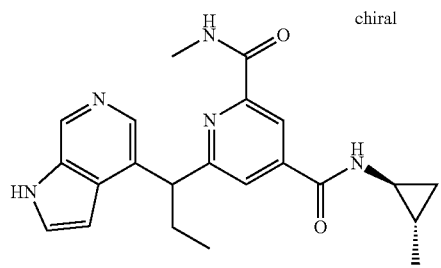

Isomer 1

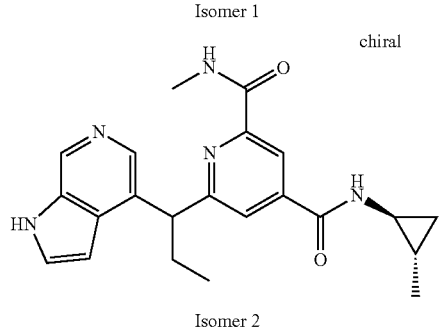

Isomer 2

To a solution of (±)-2-(1-(1H-pyrrolo[2,3-c]pyridin-4-yl)propyl)-6-(methylcarbamoyl)isonicotinic acid (224 mg, 0.331 mmol) in N,N-dimethylformamide (0.7 ml) was added DIPEA (0.2 mL, 1.145 mmol) followed by HATU (189 mg, 0.497 mmol) and (1S,2S)-2-methylcyclopropanamine hydrochloride (53.4 mg, 0.497 mmol). The resulting reaction mixture was stirred at room temperature for 2 hours. The mixture was washed with solution saturated lithium chloride solution (10 mL) and extracted with ethyl acetate (3×15 mL) before the combined organic phases were dried by filtering through a hydrophobic frit and concentrated in vacuo. The residue was purified by column chromatography 10 g column, eluting with 0 to 100% of 25% EtOH in EtOAc/cyclohexane. All the fractions containing the product were concentrated in vacuo. The residue had saturated lithium chloride solution (10 mL) added and was extracted with ethyl acetate (3×15 mL) before the combined organic phases were dried by filtering through a hydrophobic frit and concentrated in vacuo to give 6-(1-(1H-pyrrolo[2,3-c]pyridin-4-yl)propyl)-N²-methyl-N⁴-((1S,2S)-2-methylcyclopropyl)pyridine-2,4-dicarboxamide (207 mg, 0.317 mmol, 96% yield) as a colorless oil in approximately 60% purity.

LCMS (2 min Formic) Peak R_f=0.57 minutes, m/z=392 for [MH]⁺

The second aqueous phase (after column) was concentrated in vacuo, 0.9 mL of MeOH was added and the dissolved material was purified by MDAP. The desired fraction was concentrated in vacuo to give 6-(1-(1H-pyrrolo[2,3-c]pyridin-4-yl)propyl)-N²-methyl-N⁴-((1S,2S)-2-methylcyclopropyl)pyridine-2,4-dicarboxamide (1 mg, 2.299 μmol, 0.695% yield) as a yellow oil.

LCMS (2 min Formic) Peak R_f=0.58 minutes, m/z=392 for [MH]⁺

This racemate was dissolved in EtOH (3 mL). Injection: 1.5 mL of the solution was injected onto the column [20% EtOH (+0.2% isopropylamine)/Heptane (+0.2% isopropylamine), flow rate=30 mL/min, detection wavelength=215 nm, 4. Ref 550, 100, Column 30 mm×25 cm Chiralpak AD-H (5 μm), lot no. ADH13231]. Total number of injections=2. Fractions from 7 to 9 mins were bulked and labelled peak 1. Fractions from 11.5 to 15 mins were bulked and labelled peak 2. Each set of the bulked pure fractions were concentrated in vacuo and then transferred to tarred vials and dried in vacuo.

The fractions corresponding to peak 1 were collected to afford 6-(1-(1H-pyrrolo[2,3-c]pyridin-4-yl)propyl)-N²-methyl-N⁴-((1S,2S)-2-methylcyclopropyl)pyridine-2,4-dicarboxamide, Isomer 1 (44 mg).

LCMS (2 mins formic) Peak R_t=0.55 minutes, m/z=392 for [MH]⁺

The fractions corresponding to peak 2 were collected to afford 6-(1-(1H-pyrrolo[2,3-c]pyridin-4-yl)propyl)-N₂-methyl-N₄-((1S,2S)-2-methylcyclopropyl)pyridine-2,4-dicarboxamide, Isomer 2 (40 mg).

LCMS (2 mins formic) Peak R_t=0.55 minutes, m/z=392 for [MH]

Example 80: 6-((1H-Pyrrolo[2,3-b]pyridin-4-yl)methyl)-N²-methyl-N⁴-((1S,2S)-2-methylcyclopropyl)pyridine-2,4-dicarboxamide

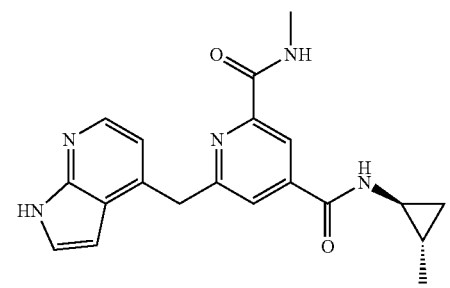 [SMILES: CNC(=O)c1cc(C(=O)N[C@H]2C[C@@H]2C)cc(Cc2ccnc3[nH]ccc23)n1]

To a mixture of 2-((1H-pyrrolo[2,3-b]pyridin-4-yl)methyl)-6-(methylcarbamoyl)isonicotinic acid (583.2 mg, 1.879 mmol), (1S,2S)-2-Methylcyclopropan-1-amine, hydrochloride (302.4 mg, 2.81 mmol) and HATU (1055 mg, 2.77 mmol) was added DIPEA (1.149 mL, 6.58 mmol) and DMF (10 mL). The mixture was stirred at rt for 4 h. The solvent was evaporated in vacuo to give a brown oil which was dissolved in ethyl acetate (50 mL) and washed with 2M aqueous sodium carbonate (2×50 mL), water (1×50 mL) and saturated brine solution (1×50 mL). The organic phase was filtered through a cartridge fitted with a hydrophobic frit and the solvent evaporated in vacuo. The residue was redissolved in ethyl acetate (ca. ~15 mL) and the solution applied to a 25 g SNAP Silica cartridge. The sample was purified by Biotage SP4 flash column chromatography eluting with a gradient of 0-5% ethanol in ethyl acetate. The required fractions were combined and the solvent evaporated in vacuo. The residue was redissolved in methanol (~10 mL) and transferred to a tarred vial before being concentrated under a stream of nitrogen and dried in vacuo to give a brown crunchy foam. The material was redissolved in DMSO (~5 mL) before being directly purified by MDAP (6×1 mL injection; formic). The required fractions were concentrated under a stream of nitrogen then dissolved in methanol and combined. The solvent was evaporated in vacuo to give a light brown oily residue. The residue was dissolved in methanol (~10 mL) and transferred to a tarred vial. The solvent was evaporated under a stream of nitrogen and the residue dried in vacuo to give the product as a light brown crunchy foam. This was dissolved in DMSO (3 mL) before being directly purified by MDAP (1×3 mL injection; TFA). The required fractions were concentrated under a stream of nitrogen, redissolved in methanol (10 mL) and transferred to a tarred vial. The solvent was evaporated under a stream of nitrogen and dried in vacuo to give the desired product as a white solid, 6-((1H-pyrrolo[2,3-b]pyridin-4-yl)methyl)-$N^2$-methyl-$N^4$-((1S,2S)-2-methylcyclopropyl)pyridine-2,4-dicarboxamide (303.6 mg, 0.835 mmol, 45% yield).

LCMS (2 min Formic): Rt=0.61 min, $[MH]^+$=364.3.

$^1$H NMR (600 MHz, DMSO-d6) δ ppm 11.96 (br s, 1H) 8.85 (d, J=4.0 Hz, 1H) 8.73-8.67 (m, 1H) 8.24 (d, J=1.5 Hz, 1H) 8.23 (d, J=5.0 Hz, 1H) 7.84 (d, J=1.5 Hz, 1H) 7.53-7.49 (m, 1H) 7.14 (d, J=5.0 Hz, 1H) 6.71 (dd, J=3.0, 1.5 Hz, 1H) 4.55 (s, 2H) 0.46-0.50 (m, 1H) 0.73-0.77 (m, 1H) 0.90-0.97 (m, 1H) 1.03 (d, J=6.0 Hz, 3H) 2.51-2.55 (m, 1H) 2.86 (d, J=5.0 Hz, 3H)

Example 81: i-Methyl-6-((S*)-1-(1-methyl-1H-pyrrolo[2,3-c]pyridin-4-yl)ethyl)-$N^4$-((1S,2S)-2-methylcyclopropyl)pyridine-2,4-dicarboxamide

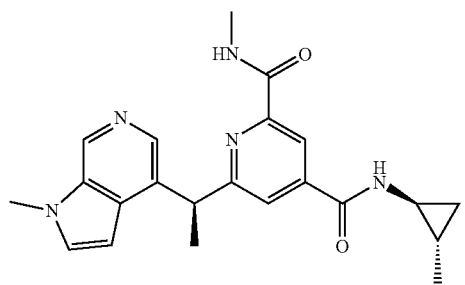 [SMILES: CNC(=O)c1cc(C(=O)N[C@H]2C[C@@H]2C)cc([C@@H](C)c2cncc3c2ccn3C)n1]

6-((S*)-1-(1H-Pyrrolo[2,3-c]pyridin-4-yl)ethyl)-$N^2$-methyl-$N^4$-((1S,2S)-2-methylcyclopropyl)pyridine-2,4-dicarboxamide (58 mg, 0.138 mmol, example 49, 90% wt.) was dissolved in THF (1 mL) and cooled to −78° C. in a cardice/acetone bath under $N_2$. LiHMDS (1M in THF, 0.69 mL, 0.690 mmol) was added dropwise and the reaction mixture left to stir for 45 min. Methyl iodide (0.03 mL, 0.240 mmol, 8M in THF) was added and the resultant mixture was stirred for 2 h. Further MeI (0.01 mL) was added and the reaction mixture was stirred for 30 min. MeOH (1 mL) was added and the solvent was then removed in vacuo. MeOH (0.9 mL) was added and the mixture was purified directly by MDAP (high pH). The combined organic phases were dried over a hydrophobic filter then the solvent was removed in vacuo to give a mixture of two products. This was purified by flash chromatography on a SNAP column (10 g) eluting with 80 to 100% (25% EtOH in EtOAc)/cyclohexane. The combined organic phases were concentrated in vacuo to give $N^4$-methyl-6-((S*)-1-(1-methyl-1H-pyrrolo[2,3-c]pyridin-4-yl)ethyl)-$N^4$-((1S,2S)-2-methylcyclopropyl)pyridine-2,4-dicarboxamide (2.1 mg, 4.83 μmol, 3% yield) as a colourless oil.

LCMS (2 min Formic): Rt=0.51 min, $[MH]^+$=392.4

Example 82: 6-((1-(2-Hydroxyethyl)-1H-indol-4-yl)methyl)-$N^2$-methyl-$N^4$-((1S,2S)-2-methylcyclopropyl)pyridine-2,4-dicarboxamide

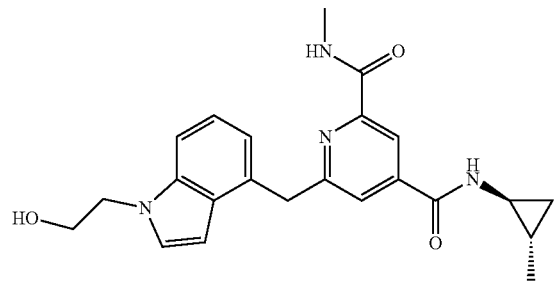 [SMILES: CNC(=O)c1cc(C(=O)N[C@H]2C[C@@H]2C)cc(Cc2cccc3c2ccn3CCO)n1]

To a solution of 6-((1H-indol-4-yl)methyl)-$N^2$-methyl-$N_4$-((1S,2S)-2-methylcyclopropyl)pyridine-2,4-dicarboxamide (Example 18, 67 mg, 0.185 mmol) in DMF (0.9 mL) was added sequentially potassium carbonate (38.3 mg, 0.277 mmol) and 1,3-dioxolan-2-one (65.1 mg, 0.739 mmol). The reaction was heated to 90° C. and stirred for 1 h. Heating was continued for ~21 h in total. The reaction was allowed to cool and the DMF suspension filtered and added directly to two MDAP vials and diluted with MeOH/DMSO to (2×0.9 mL). These were purified by MDAP (high pH). The appropriate fractions were collected and concentrated in vacuo to afford the product as a yellow solid, 6-((1-(2-hydroxyethyl)-1H-indol-4-yl)methyl)-$N^2$-methyl-$N^4$-((1S,2S)-2-methylcyclopropyl)pyridine-2,4-dicarboxamide (21 mg, 0.052 mmol, 28% yield)

LCMS (2 min Formic): Rt=0.89 min, $[MH]^+$=407.4

Example 83: 6-(Indolin-4-ylmethyl-$N^2$-methyl-$N^4$-((1S,2S)-2-methylcyclopropyl)pyridine-2,4-dicarboxamide

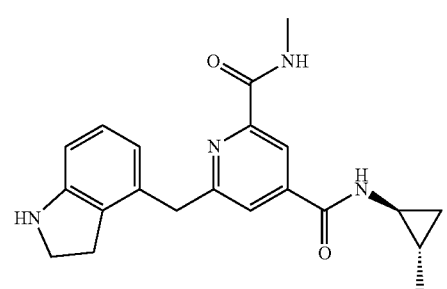

A solution of benzyl 4-((6-(methylcarbamoyl)-4-(((1S,2S)-2-methylcyclopropyl)carbamoyl)pyridin-2-yl)methyl)

indoline-1-carboxylate (149 mg, 0.299 mmol) in ethanol (10 mL) was hydrogenated using a 10% palladium on carbon cartridge on a Thales H-Cube apparatus using ethanol as the carrier solvent, using a single pass. The solvent was evaporated in vacuo to give a yellow oil. The residue was redissolved in DCM (~4 mL) plus one drop of methanol. The solution was applied to a 10 g SNAP silica cartridge. The sample was purified by flash column chromatography eluting with a gradient of 0-25% ethanol in ethyl acetate. The appropriate fractions were combined and the solvent evaporated in vacuo. The residue was redissolved in methanol and the solution applied to a 10 g SNAP Silica cartridge. The solvent was allowed to evaporate before the column was dried in vacuo. The sample was purified by flash column chromatography eluting with a gradient of 70-100% ethyl acetate in cyclohexane. The appropriate fractions were combined and the solvent evaporated in vacuo. The residue was dissolved in methanol (~10 mL) and evaporated under a stream of nitrogen and the residue dried in vacuo. The residue was dissolved in DMSO (2 mL) and MDAP (high pH). The desired fractions were combined and the solvent evaporated in vacuo. The residue was redissolved in methanol (~10 mL) before being concentrated under a stream of nitrogen and dried in vacuo to give 6-(indolin-4-ylmethyl)-$N^2$-methyl-$N^4$-((1S,2S)-2-methylcyclopropyl)pyridine-2,4-dicarboxamide (37.3 mg, 0.102 mmol, 34.2% yield) as a white solid.

LCMS (2 min High pH): Rt=0.90 min, [MH]$^+$=365.6.

$^1$H NMR (400 MHz, CDCl$_3$) δ ppm 8.15 (d, J=1.5 Hz, 1H) 7.99-8.09 (m, 1H) 7.76 (d, J=1.7 Hz, 1H) 6.99 (t, J=7.6 Hz, 1H) 6.56 (d, J=7.8 Hz, 3H) 4.14 (s, 2H) 3.80 (br. s., 1H) 3.56 (t, J=8.3 Hz, 2H) 3.06 (d, J=5.1 Hz, 3H) 2.94 (t, J=8.4 Hz, 2H) 2.60 (dq, J=7.1, 3.5 Hz, 1H) 1.16 (d, J=6.1 Hz, 3H) 1.00 (dquind, J=9.2, 6.1, 6.1, 6.1, 6.1, 3.4 Hz, 1H) 0.80 (ddd, J=9.2, 5.4, 3.9 Hz, 1H) 0.63-0.71 (m, 1H)

Example 84: 6-(1-(1H-Pyrrolo[2,3-b]pyridin-4-yl)ethyl)-$N^2$-methyl-$N^4$-((1S,2S)-2-methylcyclopropyl)pyridine-2,4-dicarboxamide, Mixture of Diastereomers

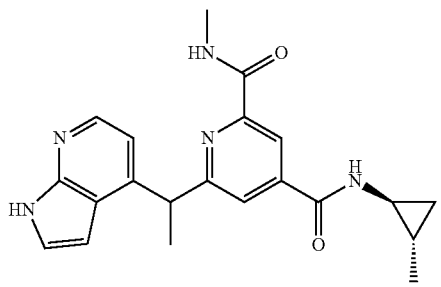

To a solution of 2-(1-(1H-pyrrolo[2,3-b]pyridin-4-yl)ethyl)-6-(methylcarbamoyl)isonicotinic acid (14 mg, 0.015 mmol, 35% wt.) in DMF (0.7 mL) was added DIPEA (0.01 mL, 0.057 mmol) followed by HATU (11 mg, 0.029 mmol) and (1S,2S)-2-methylcyclopropan-1-amine, hydrochloride (3 mg, 0.028 mmol). The resulting reaction mixture was stirred at rt for 1 h. The reaction was purified directly by MDAP (high pH). The desired fraction was concentrated in vacuo to give 6-(1-(1H-pyrrolo[2,3-b]pyridin-4-yl)ethyl)-$N^2$-methyl-$N^4$-((1S,2S)-2-methylcyclopropyl)pyridine-2,4-dicarboxamide (1.6 mg, 3.82 µmol, 25% yield) as a colourless oil LCMS (2 min Formic): Rt=0.65 min, [MH]$^+$=378.4

Example 85: $N^4$-((1R,5S,6r)-3,3-difluorobicyclo[3.1.0]hexan-6-yl)-6-(hydroxy(phenyl)methyl)-$N^2$-methylpyridine-2,4-dicarboxamide Isomer 1

Example 86: $N^4$-((1R,5S,6r)-3,3-difluorobicyclo[3.1.0]hexan-6-yl)-6-(hydroxy(phenyl)methyl)-$N^4$-methylpyridine-2,4-dicarboxamide Isomer 2

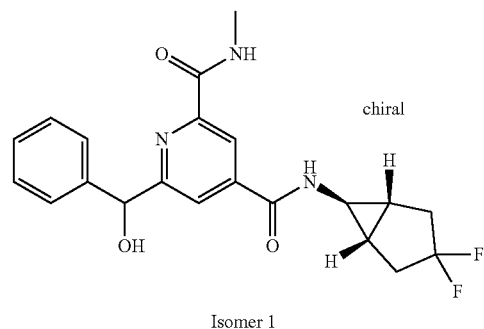

Isomer 1

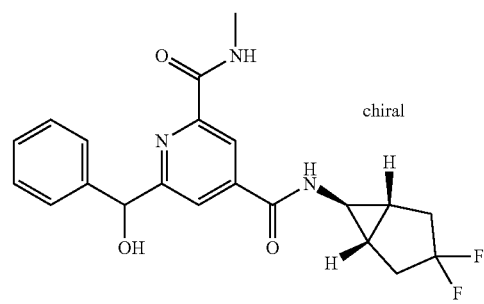

Isomer 2

Example 73 (32 mg) was purified by chiral HPLC. The racemate was dissolved in EtOH (1 mL). Injection: 1 mL of the solution was injected onto the column [10% EtOH (+0.2% isopropylamine)/Heptane (+0.2% isopropylamine), flow rate=30 mL/min, detection wavelength=215 nm, 4. Ref 550, 100, Column 30 mm×25 cm Chiralpak IC (5 µm), lot no. IC10028-01]. Total number of injections=1. Fractions from 24 to 29 mins were bulked and labelled peak 1. Fractions from 33 to 38 mins were bulked and labelled peak 2. Each set of the bulked pure fractions were concentrated in vacuo and then transferred to tared vials and dried in vacuo.

The fractions corresponding to peak 1 were collected to afford $N^4$-((1R,5S,6r)-3,3-difluorobicyclo[3.1.0]hexan-6-yl)-6-(hydroxy(phenyl)methyl)-$N^2$-methylpyridine-2,4-dicarboxamide Isomer 1 (11.9 mg).

LCMS (2 min high pH): Rt=0.91 minutes, m/z=402 for [MH]$^+$

The fractions corresponding to peak 2 were collected to afford $N^4$-((1R,5S,6r)-3,3-difluorobicyclo[3.1.0]hexan-6-yl)-6-(hydroxy(phenyl)methyl)-$N^2$-methylpyridine-2,4-dicarboxamide Isomer 2 (11.5 mg).

LCMS (2 min high pH): Rt=0.91 minutes, m/z=402 for [MH]$^+$

Example 87: 6-(2-Cyano-1-phenylethyl)-N²-methyl-N⁴-((1S,2S)-2-methylcyclopropyl)pyridine-2,4-dicarboxamide 1:1 Mixture of Diastereomers at the Undefined Stereocentre

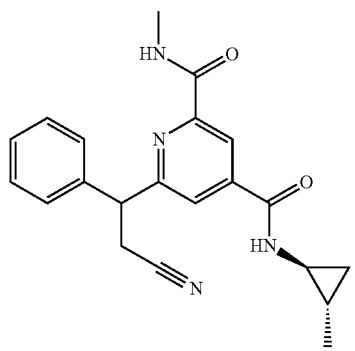 [SMILES: CNC(=O)c1cc(C(=O)N[C@H]2C[C@@H]2C)cc(C(CC#N)c2ccccc2)n1]

To a solution of 2-(6-(methylcarbamoyl)-4-(((1S,2S)-2-methylcyclopropyl)carbamoyl)pyridin-2-yl)-2-phenylethyl methanesulfonate (58 mg, 0.108 mmol, 80% wt.) in DMSO (1.5 mL) was added NaCN (13 mg, 0.265 mmol) and Et₃N (0.05 ml, 0.359 mmol). The reaction mixture was heated under nitrogen at 160° C. for 30 minutes. Water (5 mL) was added to the combined organic phases. The organic layer was separated and the aqueous layer was extracted with further portions of EtOAc (3×10 mL). The combined organic phases was dried (hydrophobic frit) then concentrated in vacuo. This was purified on a SNAP column 10 g, eluting with 0-80% EtOAc/cyclohexane. The desired fraction was concentrated in vacuo to give 6-(2-cyano-1-phenylethyl)-N²-methyl-N⁴-((1S,2S)-2-methylcyclopropyl)pyridine-2,4-dicarboxamide (27.4 mg, 0.068 mmol, 63.3% yield, ~90% purity).

LCMS (2 min Formic): Rt=0.93 min, [MH]⁺=363.4.

Example 88: 6-((1H-Pyrrolo[2,3-b]pyridin-4-yl)methyl)-N⁴-((1R,5S,6r)-3,3-difluorobicyclo[3.1.0]hexan-6-yl)-N²-methylpyridine-2,4-dicarboxamide

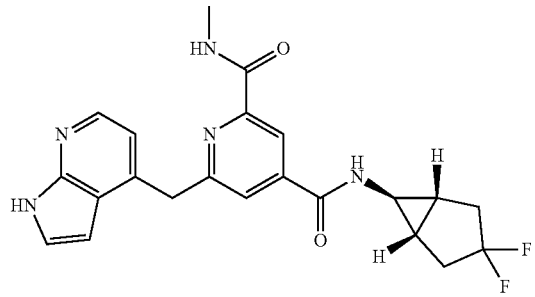

2-((1H-Pyrrolo[2,3-b]pyridin-4-yl)methyl)-6-(methylcarbamoyl)isonicotinic acid (100 mg, 0.097 mmol, 30% wt.), (1R,5S,6r)-3,3-difluorobicyclo[3.1.0]hexan-6-amine, hydrochloride (24.59 mg, 0.145 mmol), HATU (55.1 mg, 0.145 mmol) and Et₃N (0.027 ml, 0.193 mmol) were combined in a RBF and DCM (5 mL) was added, then the mixture stirred for 1 h at rt. The mixture was washed with water, dried and evaporated in vacuo and the residue purified by MDAP (formic) to give the desired product (9.5 mg, 0.022 mmol, 23% yield) as a pale yellow gum.

LCMS (2 min Formic): Rt=0.68 min, [MH]⁺=426.4

Example 89: 6-((1H-Indol-4-yl)methyl)-N²-cyclopropyl-N²-ethylpyridine-2,4-dicarboxamide

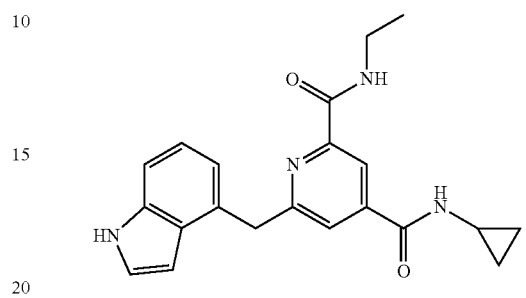

To a suspension of 2-((1H-indol-4-yl)methyl)-6-(ethylcarbamoyl)isonicotinic acid (49.3 mg, 0.152 mmol) and HATU (85.0 mg, 0.224 mmol) in DMF (1.0 mL) was added cyclopropylamine (0.016 mL, 0.229 mmol) and DIPEA (0.080 mL, 0.457 mmol). The resulting orange solution was stirred at room temperature for 1 hour, after which the volatiles were evaporated under a stream of nitrogen to give a sticky orange solid. This was redissolved in DMSO (2 mL) and directly purified by MDAP (high pH).

The required fractions were combined and evaporated in vacuo to give 6-((1H-indol-4-yl)methyl)-N²-cyclopropyl-N⁴-ethylpyridine-2,4-dicarboxamide (36.1 mg, 0.100 mmol, 65.3% yield) as a white solid.

LCMS (2 min High pH): Rt=0.94 min, [MH]⁺=363.3.

Example 90: (±)-N⁴-cyclopropyl-6-((3-fluorophenyl)(hydroxy)methyl)-N²-methylpyridine-2,4-dicarboxamide

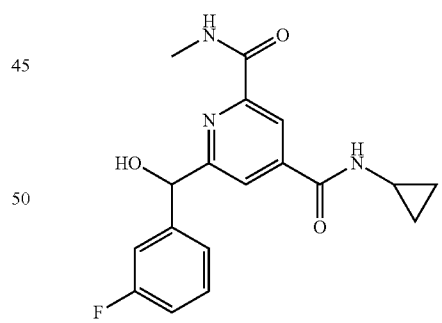

2-((3-Fluorophenyl)(hydroxy)methyl)-6-(methylcarbamoyl)isonicotinic acid (480 mg, 1.578 mmol) was suspended in DCM (10 ml) and triethylamine (0.440 ml, 3.16 mmol) and HATU (660 mg, 1.735 mmol) were added, followed by cyclopropanamine (180 mg, 3.16 mmol) and the resulting solution was stirred for 2 h at room temperature. The mixture was washed with water (10 ml) and 0.5M aq. HCl (10 ml), dried and evaporated in vacuo and the residue purified by chromatography on a 25 g silica column eluting with 0-25% ethanol in ethyl acetate. Product-containing fractions were evaporated in vacuo to give (+)-N²-cyclopropyl-6-((3-fluorophenyl)(hydroxy)methyl)-N²-methylpyridine-2,4-dicarboxamide (282 mg, 0.821 mmol, 52.1% yield) as a colourless gum.

LCMS (2 min Formic) Peak R_t=0.80 minutes, m/z=344 for [MH]⁺

Example 91: (+/−)-N⁴-Cyclopropyl-6-(hydroxy(o-tolyl)methyl)-N²-methylpyridine-2,4-dicarboxamide

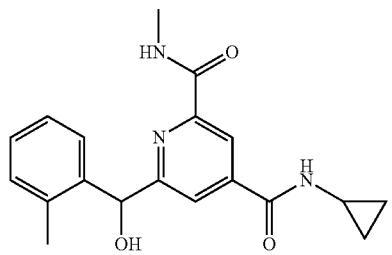

2-(Hydroxy(o-tolyl)methyl)-6-(methylcarbamoyl)isonicotinic acid (230 mg, 0.766 mmol) was suspended in DCM (20 mL), then Et₃N (0.320 mL, 2.298 mmol), HATU (349 mg, 0.919 mmol) and cyclopropanamine (87 mg, 1.532 mmol) were added and the mixture was stirred at rt for 24 h. The mixture was diluted with EtOAc (30 mL) and washed with water (2×50 mL) and brine, then dried and evaporated in vacuo to give a pale yellow gum. The crude product was dissolved in DCM and loaded onto a silica column (25 g), then eluted with 0-100% EtOAc/cyclohexane and the product-containing fractions were evaporated in vacuo to give N⁴-cyclopropyl-6-(hydroxy(o-tolyl)methyl)-N²-methylpyridine-2,4-dicarboxamide (105 mg, 0.309 mmol, 40% yield) as a colourless foam.

LCMS (2 min Formic): Rt=0.82 min, [MH]⁺=340.2

Example 92: (S*)—N⁴-Cyclopropyl-6-(hydroxy(2-methoxyphenyl)methyl)-N²-methylpyridine-2,4-dicarboxamide Example 93: (R*)—N⁴-Cyclopropyl-6-(hydroxy(2-methoxyphenyl)methyl)-N²-methylpyridine-2,4-dicarboxamide

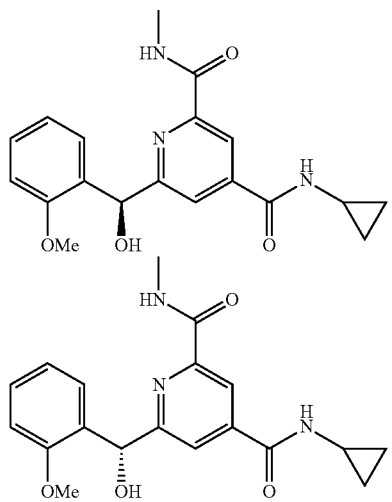

TFA (0.910 mL, 11.81 mmol) was added to a solution of tert-butyl 2-(hydroxy(2-methoxyphenyl)methyl)-6-(methylcarbamoyl)isonicotinate (0.44 g, 1.181 mmol) in DCM (5 mL) at rt and the mixture was stirred for 4 h, then evaporated in vacuo to give a yellow gum. This was dissolved in a mixture of DCM and methanol and re-evaporated to give a beige solid. The crude was carried through to the next step without purification. The solid was suspended in DCM (5 mL) and Et₃N (0.494 mL, 3.54 mmol), HATU (0.539 g, 1.418 mmol) and cyclopropanamine (0.135 g, 2.363 mmol) were added, then the mixture was stirred overnight at rt. The solution was washed with water (10 mL), dried and evaporated in vacuo and the residue purified by chromatography on a silica column (25 g) eluting with 0-100% EtOAc/cyclohexane. The product-containing fractions were evaporated in vacuo to give N⁴-cyclopropyl-6-(hydroxy(2-methoxyphenyl)methyl)-N²-methylpyridine-2,4-dicarboxamide (105 mg, 0.295 mmol, 25% yield) as a colourless gum. The racemate (100 mg) was purified by chiral HPLC. The diastereomeric mixture was dissolved in EtOH (1 mL). Injection: 1 mL of the solution was injected onto the column (30% EtOH/heptane, flow rate=30 mL/min, detection wavelength, 215 nm, 4. Ref. 550, 100, Column 30 mm×25 cm Chiralcel OD-H, Lot No. ODH1158-01 (5 μm)). Fractions from 5.75-7 min were bulked and labelled peak 1. Fractions from 7.75-10 min were bulked and labelled peak 2. The bulked fractions were transferred and concentrated in vacuo into weighed flasks.

The fractions corresponding to peak 1 were collected to afford example 92 (36 mg) LCMS (2 min Formic): Rt=0.78 min, [MH]⁺=356.2 The fractions corresponding to peak 2 were collected to afford example 93 (36 mg) LCMS (2 min Formic): Rt=0.78 min, [MH]⁺=356.2

Example 94: N₄-cyclopropyl-6-((3-fluorophenyl)(hydroxy)methyl)-N₂-methylpyridine-2,4-dicarboxamide Enantiomer 1

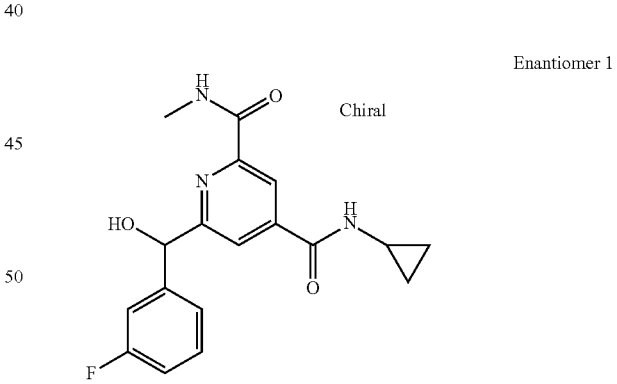

Example 90 (282 mg) was purified by chiral HPLC. The racemate was dissolved in EtOH (3 mL). Injection: 1 mL of the solution was injected onto the column [40% EtOH (+0.2% isopropylamine)/Heptane (+0.2% isopropylamine), flow rate=30 mL/min, detection wavelength=215 nm, 4. Ref 550, 100, Column 30 mm×25 cm Chiralpak AD-H (5 μm), lot no. ADH13231]. Total number of injections=3. Fractions from 5.75 to 7 mins were bulked and labelled peak 1. Fractions from 8.25 to 10.5 mins were bulked and labelled peak 2. Each set of the bulked pure fractions were concentrated in vacuo and then transferred to tarred vials and dried in vacuo.

The fractions corresponding to peak 1 were collected to afford N4-cyclopropyl-6-((3-fluorophenyl)(hydroxy)methyl)-N2-methylpyridine-2,4-dicarboxamide Enantiomer 1 (70 mg).

LCMS (2 min Formic) Peak R$_f$=0.80 minutes, m/z=344 for [MH]$^+$

Example 95: 6-((R*)-(3-Fluorophenyl)(hydroxy)methyl)-1-((1S,2S)-2-methylcyclopropyl)pyridine-2,4-dicarboxamide Example 96: 6-((S*)-(3-Fluorophenyl(hydroxy)methyl-1-((1S,2S)-2-methylcyclopropyl)pyridine-2,4-dicarboxamide

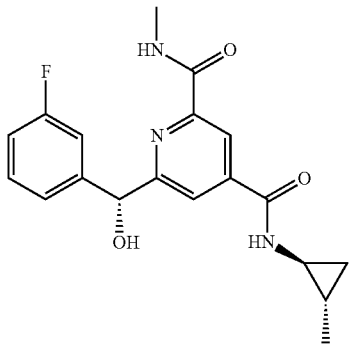

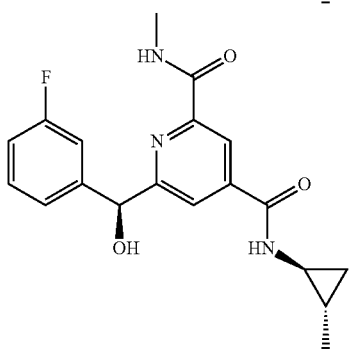

Example 76 (300 mg) was purified by chiral HPLC. The racemate was dissolved in EtOH (3 mL). Injection: 1 mL of the solution was injected onto the column (20% EtOH (+0.2% isopropylamine)/heptane (+0.2% isopropylamine), flow rate=30 mL/min, detection wavelength=215 nm, Column 30 mm×25 cm Chiralpak AD-H (5 μm)). Total number of injections=3. Fractions from 9-11 min were bulked and labelled peak 1. Fractions from 14.5-18 min were bulked and labelled peak 2. The bulked fractions were concentrated in vacuo and then transferred to weighed flasks.

The fractions corresponding to peak 1 were collected to afford example 95 (120 mg)

LCMS (2 min Formic): Rt=0.89 min, [MH]$^+$=358.3.

The fractions corresponding to peak 2 were collected to afford example 96 (118 mg)

LCMS (2 min Formic): Rt=0.89 min, [MH]$^+$=358.3.

Example 97: 6-(imidazo[1,2-a]pyridin-5-ylmethyl)-N2-methyl-N4-((1S,2S)-2-methylcyclopropyl)pyridine-2,4-dicarboxamide

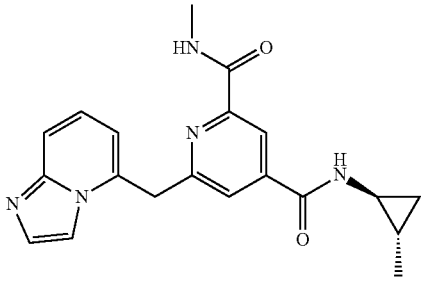 [SMILES: CNC(=O)c1cc(C(=O)N[C@H]2C[C@@H]2C)cc(Cc2cccc3nccn23)n1]

To a solution of the crude 2-(imidazo[1,2-a]pyridin-5-ylmethyl)-6-(methylcarbamoyl)isonicotinic acid (260 mg, 0.293 mmol) in N,N-dimethylformamide (1 mL) was added DIPEA (0.256 mL, 1.466 mmol) followed by HATU (167 mg, 0.440 mmol) and (1S,2S)-2-methylcyclopropan-1-amine hydrochloride (64 mg, 0.595 mmol). The resulting reaction mixture was stirred at room temperature open to the air for 1.5 hrs. Further portions of HATU (167 mg, 0.440 mmol), (1S,2S)-2-methylcyclopropan-1-amine hydrochloride (64 mg, 0.595 mmol) and DIPEA (0.256 mL, 1.466 mmol) were added and reaction mixture continued to stir at room temperature. Further portions of HATU (167 mg, 0.440 mmol), (1S,2S)-2-methylcyclopropan-1-amine hydrochloride (64 mg, 0.595 mmol) and DIPEA (0.256 mL, 1.466 mmol) were added and reaction mixture continued to stir at room temperature. The reaction mixture was concentrated and purified by MDAP (Ammonium carbonate buffered, method C in 2×1 mL injection of DMF). Fractions containing desired product were concentrated in vacuo to give 6-(imidazo[1,2-a]pyridin-5-ylmethyl)-N$_2$-methyl-N$_4$-((1S,2S)-2-methylcyclopropyl)pyridine-2,4-dicarboxamide (42 mg, 0.104 mmol, 35.5% yield) as a pale yellow solid.

LCMS (2 min High pH) Peak R$_f$=0.77 minutes, m/z=364 for [MH]

Example 98: N2-methyl-N4-((1S,2S)-2-methylcyclopropyl)-6-(1-(2-oxoindolin-4-yl)ethyl)pyridine-2,4-dicarboxamide Isomer 1

Example 99: N2-methyl-N4-((1S,2S)-2-methylcyclopropyl)-6-(1-(2-oxoindolin-4-yl)ethyl)pyridine-2,4-dicarboxamide Isomer 2

Isomer 1

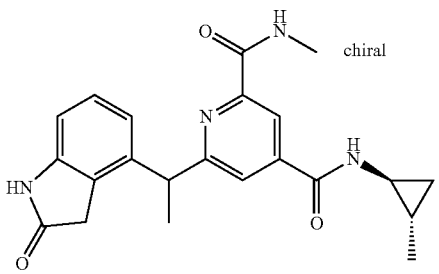

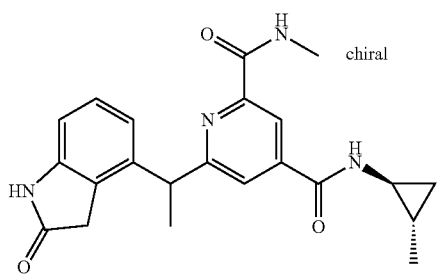

Isomer 2

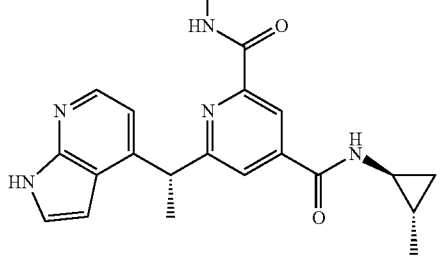

N2-methyl-N4-((1S,2S)-2-methylcyclopropyl)-6-(1-(2-oxoindolin-4-yl)ethyl)pyridine-2,4-dicarboxamide (39 mg) was purified by chiral HPLC. The racemate was dissolved in EtOH (2 mL). Injection: 2 mL of the solution was injected onto the column [20% EtOH (+0.2% isopropylamine)/Heptane (+0.2% isopropylamine), flow rate=30 mL/min, detection wavelength=215 nm, 4. Ref 550, 100, Column 30 mm×25 cm Chiralcel OD-H (5 µm), lot no. ODH11158-01]. Total number of injections=1. Fractions from 8.5 to 10 mins were bulked and labelled peak 1. Fractions from 11.5 to 15 mins were bulked and labelled peak 2. Each set of the bulked pure fractions were concentrated in vacuo and then transferred to tared vials and dried in vacuo.

The fractions corresponding to peak 1 were collected to afford N2-methyl-N4-((1S,2S)-2-methylcyclopropyl)-6-(1-(2-oxoindolin-4-yl)ethyl)pyridine-2,4-dicarboxamide Isomer 1 (16 mg).

LCMS (2 mins formic) Peak $R_t$=0.85 minutes, m/z=393 for [MH]$^+$

The fractions corresponding to peak 2 were collected to afford N2-methyl-N4-((1S,2S)-2-methylcyclopropyl)-6-(1-(2-oxoindolin-4-yl)ethyl)pyridine-2,4-dicarboxamide Isomer 2 (17 mg).

LCMS (2 mins formic) Peak $R_t$=0.85 minutes, m/z=393 for [MH]$^+$

Example 100: 6-((S*)-1-(1H-Pyrrolo[2,3-b]pyridin-4-yl)ethyl)-N$^2$-methyl-N$^4$-((1S,2S)-2-methylcyclopropyl)pyridine-2,4-dicarboxamide Example 101: 6-((*)-1-(1H-Pyrrolo[2,3-b]pyridin-4-yl)ethyl)-N$^2$-methyl-N$^4$-((1S,2S)-2-methylcyclopropyl)pyridine-2,4-dicarboxamide

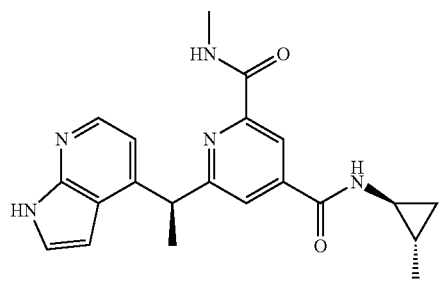

Example 84 (110 mg) was purified by chiral HPLC. The racemate was dissolved in EtOH (3 mL). Injection: 1 mL of the solution was injected onto the column (10% EtOH (+0.2% isopropylamine)/heptane (+0.2% isopropylamine), flow rate=30 mL/min, detection wavelength=215 nm, Column 30 mm×25 cm Chiralcel OJ-H (5 µm), Lot No. OJH10027-01). Total number of injections=4. Fractions from 13-15 min were bulked and labelled peak 1. Fractions from 15-17 min were bulked and labelled mix. Fractions from 17-20 min were bulked and labelled peak 2. The bulked mixed fractions were concentrated in vacuo and reprocessed using the above method. The bulked pure fractions were concentrated in vacuo and then transferred to weighed flasks.

The fractions corresponding to peak 1 were collected to afford example 100 (33 mg)

LCMS (2 min Formic): Rt=0.67 min, [MH]$^+$=378.3.

The fractions corresponding to peak 2 were collected to afford example 101 (35 mg)

LCMS (2 min Formic): Rt=0.67 min, [MH]$^+$=378.3.

Example 102: 6-((S*)-2-Cyano-1-phenylethyl)-N$^2$-methyl-N$^4$-((1S,2S)-2-methylcyclopropyl)pyridine-2,4-dicarboxamide Example 103: 6-((R*)-2-Cyano-1-phenylethyl)-N$^2$-methyl-N$^4$-((1S,2S)-2-methylcyclopropyl)pyridine-2,4-dicarboxamide

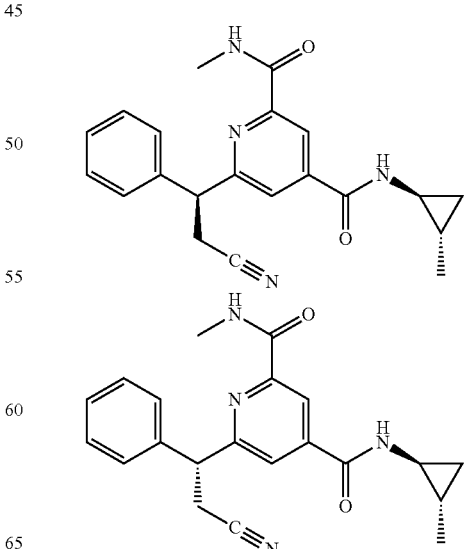

Example 87 (21 mg) was purified by chiral HPLC. The racemate was dissolved in EtOH (1 mL). Injection: 1 mL of the solution was injected onto the column (10% EtOH/heptane, flow rate=20 mL/min, detection wavelength=215 nm, Column 2 cm×25 cm Chiralpak AD (10 μm), Lot No. AD00CJ-LE004). Total number of injections=3. Fractions from 22-26 min were bulked and labelled peak 1. Fractions from 26-29 min were bulked and labelled mix. Fractions from 29-36 min were bulked and labelled peak 2. The bulked mixed fractions were concentrated in vacuo and reprocessed using the above method. The bulked pure fractions were concentrated in vacuo and then transferred to weighed flasks. Peak 2 was further purified by chiral HPLC. The racemate was dissolved in EtOH. Injection: 20 μL of the solution was injected onto the column (15% EtOH/heptane, flow rate=1 mL/min, detection wavelength=215 nm, Column 4.6 mm id×25 cm Chiralpak AD-H, Lot No. ADHCE-PC014). Total number of injections=15. Fractions for the major component were bulked and labelled peak 2.

The fractions corresponding to peak 1 were collected to afford example 100 (33 mg)

LCMS (2 min Formic): Rt=0.94 min, [MH]$^+$=363.2.

The fractions corresponding to peak 2 were collected to afford example 101 (35 mg)

LCMS (2 min Formic): Rt=0.94 min, [MH]$^+$=363.2.

Example 104: N2-methyl-6-((7-methyl-1H-pyrrolo[2,3-c]pyridin-4-yl)methyl)-N4-((1S,2S)-2-methyl-cyclopropyl)pyridine-2,4-dicarboxamide

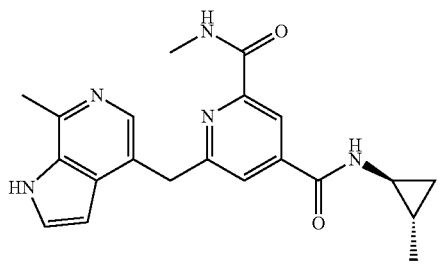 [SMILES: CNC(=O)c1cc(C(=O)N[C@H]2C[C@@H]2C)cc(Cc2cnc(C)c3[nH]ccc23)n1]

2-((7-methyl-1H-pyrrolo[2,3-c]pyridin-4-yl)methyl)-6-(methylcarbamoyl)isonicotinic acid, Lithium salt (36.5 mg, 0.083 mmol) was taken up in DMF (2 mL). DIPEA (0.043 mL, 0.248 mmol) then (1S,2S)-2-methylcyclopropan-1-amine hydrochloride (25 mg, 0.232 mmol) were added followed by HATU (47.1 mg, 0.124 mmol). The reaction was stirred at room temperature. An additional portion of HATU (47.1 mg, 0.124 mmol) and (1S,2S)-2-methylcyclopropan-1-amine hydrochloride (25 mg, 0.232 mmol) were added and stirring continued. The reaction was concentrated to give a brown oil. The crude product was purified by MDAP (high pH method). The appropriate fractions were concentrated in vacuo to give the desired product (6 mg, 0.015 mmol, 18.28% yield) as a cream solid.

LCMS (2 min High pH): Rt=0.79 min, [MH]$^+$=378.6.

Example 105: 6-((S*-Methoxy(1H-pyrrolo[2,3-b]pyridin-4-yl)methyl)-N$^2$-methyl-N$^4$-((1S,2S)-2-methylcyclopropyl)pyridine-2,4-dicarboxamide Example 106: 6-((R*-Methoxy(1H-pyrrolo[2,3-b]pyridin-4-yl)methyl)-N$^2$ methyl-N$^4$-((1S,2S)-2-methylcyclopropyl)pyridine-2,4-dicarboxamide

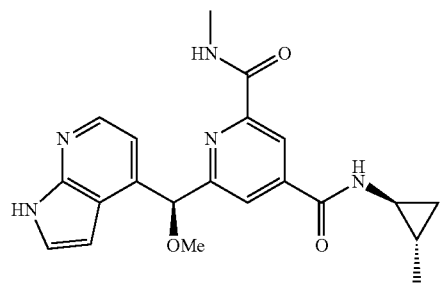

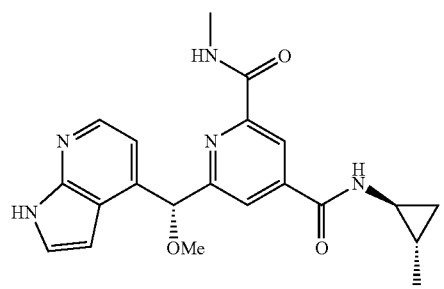

The racemate, (40 mg) was purified by chiral HPLC. The diastereomeric mixture was dissolved in EtOH (1 mL). Injection: 1 mL of the solution was injected onto the column (15% EtOH (+0.2% isopropylamine)/heptane, flow rate=30 mL/min, detection wavelength, 215 nm, 4. Ref. 550, 100, Column 30 mm×25 cm Chiralpak IA, Lot No. IA11157-01 (5 μm)). Fractions from 24-26 min were bulked and labelled peak 1. Fractions from 35-44 min were bulked and labelled peak 2. The bulked fractions were transferred and concentrated in vacuo into weighed flasks.

The fractions corresponding to peak 1 were collected to afford example 105 (16 mg)

LCMS (2 min High pH): Rt=0.81 min, [MH]$^+$=394.3

The fractions corresponding to peak 2 were collected to afford example 106 (15 mg)

LCMS (2 min High pH): Rt=0.81 min, [MH]$^+$=394.3

$^1$H NMR (400 MHz, DMSO-d6) δ ppm 11.66 (br. s., 1H) 8.94 (d, J=4.0 Hz, 1H) 8.66 (q, J=4.8 Hz, 1H) 8.29 (d, J=1.5 Hz, 1H) 8.22 (d, J=5.0 Hz, 1H) 8.07 (d, J=1.5 Hz, 1H) 7.40-7.47 (m, 1H) 7.25 (d, J=5.3 Hz, 1H) 6.69 (dd, J=3.4, 1.9 Hz, 1H) 5.85 (s, 1H) 3.42 (s, 3H) 2.87 (d, J=4.8 Hz, 3H) 2.56 (dq, J=7.5, 3.8 Hz, 1H) 1.05 (d, J=6.0 Hz, 3H) 0.91-1.01 (m, 1H) 0.79 (dt, J=8.6, 4.6 Hz, 1H) 0.50 (dt, J=7.5, 5.4 Hz, 1H)

Example 107: N⁴-((1R,3R,5S,6r)-3-hydroxybicyclo[3.1.0]hexan-6-yl)-N⁴-methyl-6-((S)-1-phenylethyl)pyridine-2,4-dicarboxamide Example 108: N⁴-((1R,3S,5S,6r)-3-hydroxybicyclo[3.1.0]hexan-6-yl)-N²-methyl-6-((S)-1-phenylethyl)pyridine-2,4-dicarboxamide

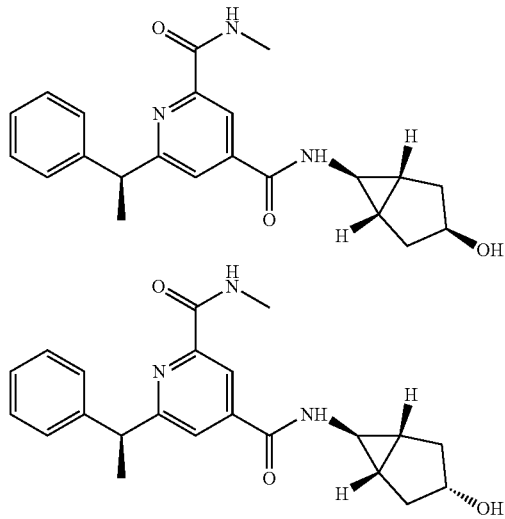

N⁴-((1R,5S,6r)-3-((tert-butyldimethylsilyl)oxy)bicyclo[3.1.0]hexan-6-yl)-N²-methyl-6-((S)-1-phenylethyl)pyridine-2,4-dicarboxamide (156.7 mg, 0.279 mmol) was taken up in DCM (4 mL) and 4M HCl in dioxane (0.698 mL, 2.79 mmol) was added. The reaction was stirred 1 h at room temperature. The reaction mixture was diluted with water (20 mL) and extracted with AcOEt (3×20 mL), the combined organics were filtered through a hydrophobic frit and concentrated in vacuo to a yellow gum. It was purified by MDAP (High pH method).

The fractions corresponding to peak 1 were collected to afford example 107 (49.5 mg, 0.130 mmol, 46.7% yield) as a yellow solid.

LCMS (2 min Formic): Rt=0.93 min, [MH]⁺=380.3

The fractions corresponding to peak 2 were collected to afford example 108 (24.6 mg, 0.065 mmol, 23.21% yield) as a yellow solid.

LCMS (2 min Formic): Rt=0.90 min, [MH]⁺=380.3

Examples 109-116

Examples 109-116 were prepared in an analogous manner to the previous examples

| Ex No. | Name | Structure | [MH]⁺ | Rt (min) |
|---|---|---|---|---|
| 109 | 6-(2-hydroxy-1-phenylpropyl)-N²-methyl-N⁴-((1S,2S)-2-methylcyclopropyl)pyridine-2,4-dicarboxamide | 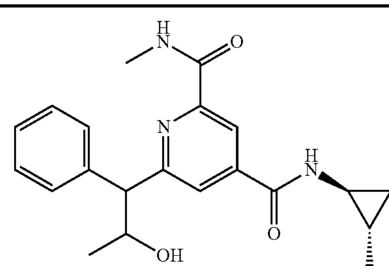 | 368.4 | 0.86 (formic) |
| 110 | 6-((1S*,2R*)-2-hydroxy-1-phenylpropyl)-N²-methyl-N⁴-((1S,2S)-2-methylcyclopropyl)pyridine-2,4-dicarboxamide | 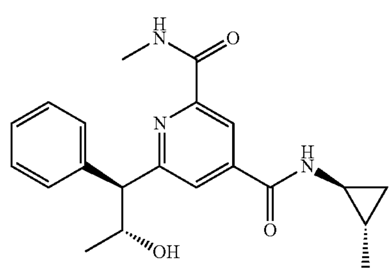 [SMILES: CNC(=O)c1cc(C(=O)N[C@H]2C[C@@H]2C)cc([C@H](c2ccccc2)[C@@H](C)O)n1] | 368.4 | 0.85 (formic) |
| 111 | 6-((1R*,2S*)-2-hydroxy-1-phenylpropyl)-N²-methyl-N⁴-((1S,2S)-2-methylcyclopropyl)pyridine-2,4-dicarboxamide | 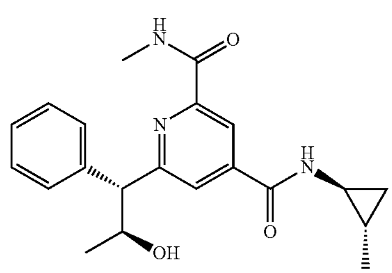 [SMILES: CNC(=O)c1cc(C(=O)N[C@H]2C[C@@H]2C)cc([C@@H](c2ccccc2)[C@H](C)O)n1] | 368.4 | 0.85 (formic) |

| Ex No. | Name | Structure | [MH]+ | Rt (min) |
|---|---|---|---|---|
| 112 | 6-((R)-hydroxy (o-tolyl)methyl)-N²-methyl-N⁴-((1S,2S)-2-methylcyclopropyl)pyridine-2,4-dicarboxamide | 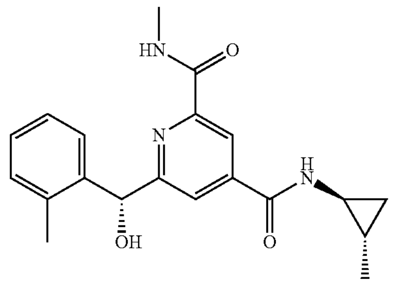 [SMILES: CNC(=O)c1cc(C(=O)N[C@H]2C[C@@H]2C)cc([C@H](O)c2ccccc2C)n1] | 354.3 | 0.90 (formic) |
| 113 | 6-(1-(1H-pyrrolo[2,3-c]pyridin-4-yl)propyl)-N²-methyl-N⁴-((1S,2S)-2-methylcyclopropyl)pyridine-2,4-dicarboxamide | 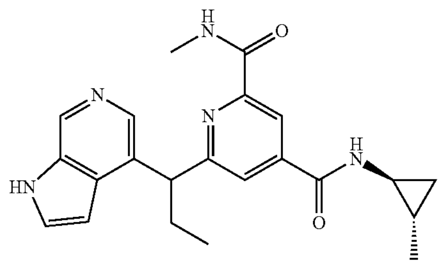 [SMILES: CCC(c1cc(C(=O)N[C@H]2C[C@@H]2C)cc(C(=O)NC)n1)c1cncc2[nH]ccc12] | 392.4 | 0.58 (formic) |
| 114 | (S*)-N⁴-cyclopropyl-6-((3-fluorophenyl)(hydroxy)methyl)-N²-methylpyridine-2,4-dicarboxamide | 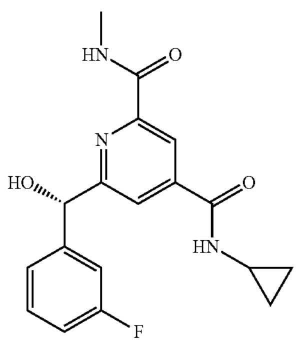 [SMILES: CNC(=O)c1cc(C(=O)NC2CC2)cc([C@@H](O)c2cccc(F)c2)n1] | 344.2 | 0.80 (formic) |
| 116 | (R*)-N⁴-cyclopropyl-6-(hydroxy(o-tolyl)methyl)-N²-methylpyridine-2,4-dicarboxamide | | 340.2 | 0.80 (formic) |
| 116 | (S*)-N⁴-cyclopropyl-6-(hydroxy(o-tolyl)methyl)-N²-methylpyridine-2,4-dicarboxamide | | 340.2 | 0.80 (formic) |

Example 117: 6-benzyl-N⁴-((1R,3r,5S,6r)-3-hydroxybicyclo[3.1.0]hexan-6-yl)-N²-methylpyridine-2,4-dicarboxamide Example 118: 6-benzyl-N⁴-((1R,3s 5S,6r)-3-hydroxybicyclo[3.1.0]hexan-6-yl)-N²-methylpyridine-2,4-dicarboxamide

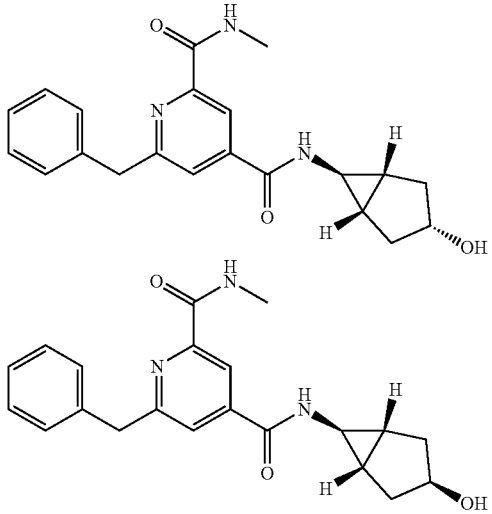

6-benzyl-N⁴-((1R,5S,6r)-3-((tert-butyldimethylsilyl)oxy)bicyclo[3.1.0]hexan-6-yl)-N²-methylpyridine-2,4-dicarboxamide (113.5 mg, 0.208 mmol) was taken up in DCM (3 mL) and 4M HCl in dioxane (0.260 mL, 1.038 mmol) was added. The reaction was stirred 1 h at room temperature. The reaction mixture was diluted with water and extracted 3 times with ethyl acetate, the combined organics were filtered through a hydrophobic frit and concentrated in vacuo to a yellow solid which was purified by MDAP (High pH method). The fractions corresponding to peak 1 were collected to afford example 117 (16.0 mg, 0.044 mmol, 21.09% yield) as a white solid.
LCMS (2 min Formic): Rt=0.83 min, [MH]⁺=366.2
The fractions corresponding to peak 2 were collected to afford example 118 (30.3 mg, 0.083 mmol, 39.9% yield) as a white solid.
LCMS (2 min Formic): Rt=0.87 min, [MH]⁺=366.2

Example 119: N⁴-((1R,3r,5S,6r)-3-hydroxybicyclo[3.1.0]hexan-6-yl)-6-(methoxy(phenyl)methyl)-N²-methylpyridine-2,4-dicarboxamide Example 120: N⁴-((1R,3s,5S,6r)-3-hydroxybicyclo[3.1.0]hexan-6-yl)-6-(methoxy(phenyl)methyl)-N²-methylpyridine-2,4-dicarboxamide

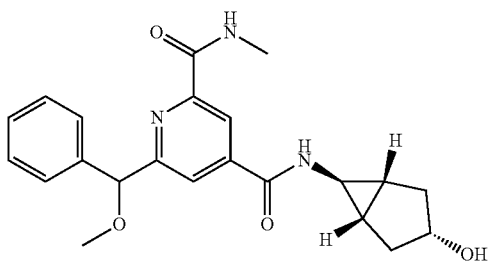

-continued

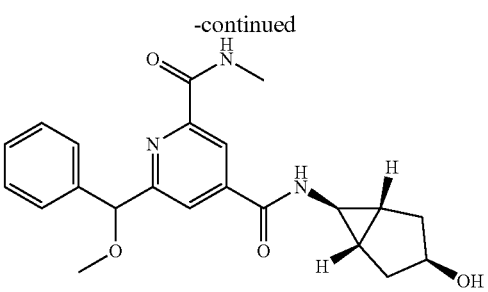

N₄-((1R,5S,6r)-3-((tert-butyldimethylsilyl)oxy)bicyclo[3.1.0]hexan-6-yl)-6-(methoxy(phenyl)methyl)-N₂-methylpyridine-2,4-dicarboxamide (168.3 mg, 0.147 mmol) was taken up in DCM (4 mL) and 4M HCl in dioxane (0.368 mL, 1.473 mmol) was added. The reaction was stirred 1.25 h at room temperature. The reaction mixture was diluted with water and extracted 3 times with AcOEt, the combined organics were filtered through a hydrophobic frit and concentrated in vacuo to a yellow gum. It was purified by MDAP (High pH method) to give the separated desired products N⁴-((1R,3r,5S,6r)-3-hydroxybicyclo[3.1.0]hexan-6-yl)-6-(methoxy(phenyl)methyl)-N²-methylpyridine-2,4-dicarboxamide (31.1 mg, 0.079 mmol, 53.4% yield) and N⁴-((1R,3s,5S,6r)-3-hydroxybicyclo[3.1.0]hexan-6-yl)-6-(methoxy(phenyl)methyl)-N²-methylpyridine-2,4-dicarboxamide (18.8 mg, 0.048 mmol, 32.3% yield) as white solids.
Example 119: LCMS (2 min Formic): Rt=0.86 mins, MH+=396.3
Example 120: LCMS (2 min Formic): Rt=0.81 mins, MH+=396.3

Example 121: N⁴-((1R,3S,5S,6r)-3-hydroxybicyclo[3.1.0]hexan-6-yl)-6-((R*)-methoxy(phenyl)methyl)-N²-methylpyridine-2,4-dicarboxamide Example 122: N⁴-((1R,3S,5S,6r)-3-hydroxybicyclo[3.1.0]hexan-6-yl)-6-((S*)-methoxy(phenyl)methyl)-N²-methylpyridine-2,4-dicarboxamide

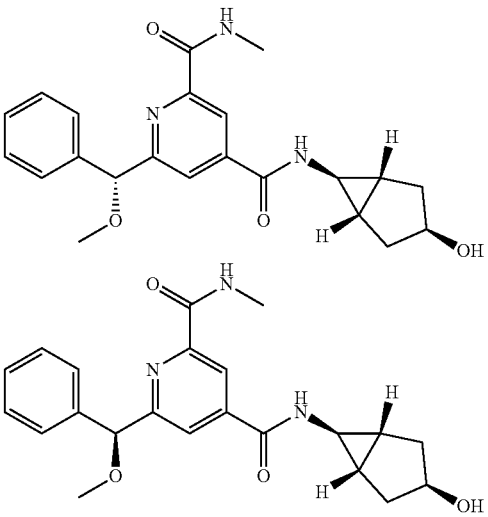

N⁴-((1R,3s,5S,6r)-3-hydroxybicyclo[3.1.0]hexan-6-yl)-6-(methoxy(phenyl)methyl)-#-methylpyridine-2,4-dicarboxamide (16 mg, 0.040 mmol) was separated by chiral chromatography using the following conditions:
Sample dissolved in 1 ml EtOH.
Injection; 1 ml of the solution was injected onto the column.
Solvents used: 20% EtOH(+0.2% isopropylamine)/Heptane (+0.2% isopropylamine), f=30 ml/min, wavelength, 215 nm, 4. Ref 550,100
Column 30 mm×25 cm Chiralpak AD-H (5 μm), Lot No ADH14252-01

The fractions corresponding to the first eluting enantiomer were combined and concentrated to dryness under reduced pressure to give the desired product, example 121, $N^4$-((1R,3S,5S,6r)-3-hydroxybicyclo[3.1.0]hexan-6-yl)-6-((R*)-methoxy(phenyl)methyl)-$N^2$-methylpyridine-2,4-dicarboxamide (3 mg, 7.59 μmol, 18.75% yield) as a white solid.

LCMS (2 min Formic): Rt=0.81 mins, MH+=396.3

The fractions corresponding to the second eluting enantiomer were combined and concentrated to dryness under reduced pressure to give the desired product, example 122, $N^4$-((1R,3R,5S,6r)-3-hydroxybicyclo[3.1.0]hexan-6-yl)-6-((S*)-methoxy(phenyl)methyl)-$N^2$-methylpyridine-2,4-dicarboxamide (5 mg, 0.013 mmol, 31.3% yield) as a white solid.

LCMS (2 min Formic): Rt=0.81 mins, MH+=396.3

Example 123: $N^4$-((1R,3R,5S,6r)-3-hydroxybicyclo[3.1.0]hexan-6-yl)-6-((R)-methoxy(phenyl)methyl)-$N^2$-methylpyridine-2,4-dicarboxamide Example 124: $N^4$-((1R,3S,5S,6r)-3-hydroxybicyclo[3.1.0]hexan-6-yl)-6-((S*-methoxy(phenyl)methyl)-$N^2$-methyridine-2,4-dicarboxamide

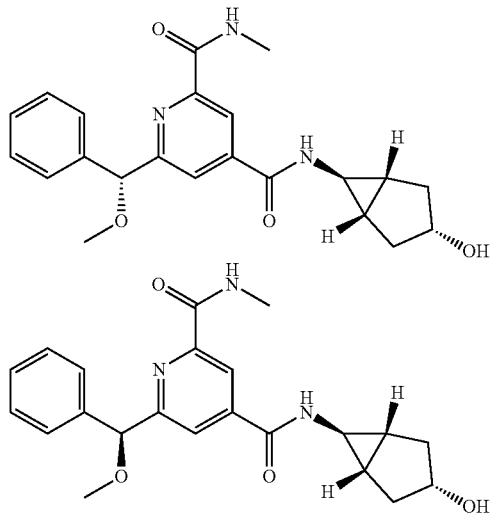

$N^4$-((1R,3r, 5S,6r)-3-hydroxybicyclo[3.1.0]hexan-6-yl)-6-(methoxy(phenyl)methyl)-$N^2$-methylpyridine-2,4-dicarboxamide (29 mg, 0.073 mmol) was submitted for chiral separation using the following conditions:
Sample dissolved in 1.5 ml EtOH
Injection; 1.5 ml of the solution was injected onto the column.
Solvents used: 20% EtOH(+0.2% isopropylamine)/Heptane (+0.2% isopropylamine),
f=30 ml/min, wavelength, 215 nm, 4. Ref 550,100
Column: 30 mm×25 cm Chiralcel OJ-H (5 μm), Lot No OJH10027-01

The fractions corresponding to the first eluting enantiomer were combined and concentrated to dryness under reduced pressure to give the desired product, example 123, $N^4$-((1R,3R,5S,6r)-3-hydroxybicyclo[3.1.0]hexan-6-yl)-6-((R*)-methoxy(phenyl)methyl)-$N^2$-methylpyridine-2,4-dicarboxamide (6 mg, 0.015 mmol, 20.69% yield) as a white solid.

LCMS (2 min Formic): Rt=0.85 mins, MH+=396.3

The fractions corresponding to the second eluting enantiomer were combined and concentrated to dryness under reduced pressure to give the desired product, example 124, $N^4$-((1R,3S,5S,6r)-3-hydroxybicyclo[3.1.0]hexan-6-yl)-6-((S*)-methoxy(phenyl)methyl)-$N^2$-methylpyridine-2,4-dicarboxamide (6 mg, 0.015 mmol, 20.69% yield) as a yellow solid.

LCMS (2 min Formic): Rt=0.85 mins, MH+=396.3

Biological Data

The compounds of formula (I) may be tested in one or more of the following assays:

Time Resolved Fluorescence Resonance Energy Transfer (TR-FRET) Assay

Bromodomain binding was assessed utilising a time resolved fluorescent resonance energy transfer (TR-FRET) competition assay. To enable this approach a known, high affinity, pan-BET interacting small molecule was labelled with Alexa Fluor® 647, which is a far-red-fluorescent dye (Reference Compound X). Reference Compound X acts as a reporter of bromodomain binding and is the acceptor fluorophore component of the TR-FRET pair. Europium chelate, conjugated to an anti-6*His antibody, was utilised as the donor fluorophore in the TR-FRET pair. The anti-6*His antibody binds selectively to a six Histidine purification epitope added to the amino-terminus of each of the BET tandem bromodomain protein constructs used in this study. A TR-FRET signal is generated when the donor and acceptor fluorophores are in close proximity, between 20-80 Å, which is enabled in this assay by binding of Reference Compound X to the bromodomain protein.

Reference Compound X: 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

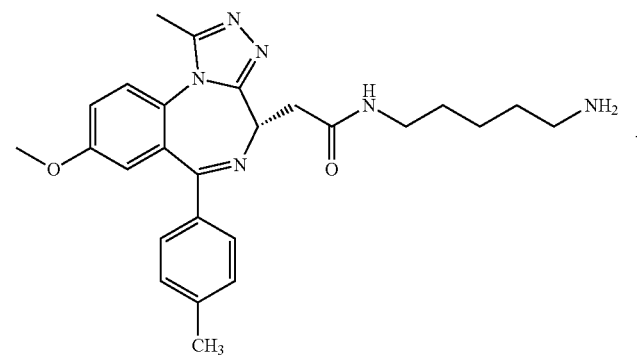

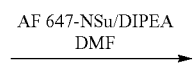

AF 647-NSu/DIPEA
DMF

-continued

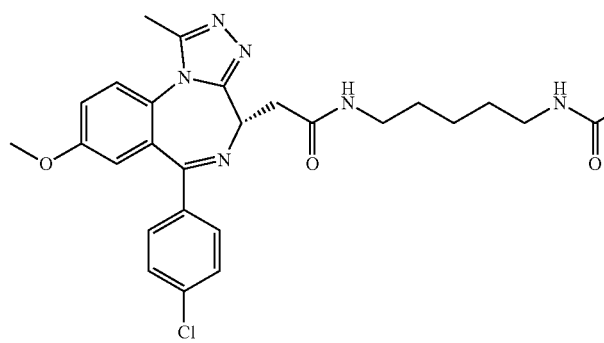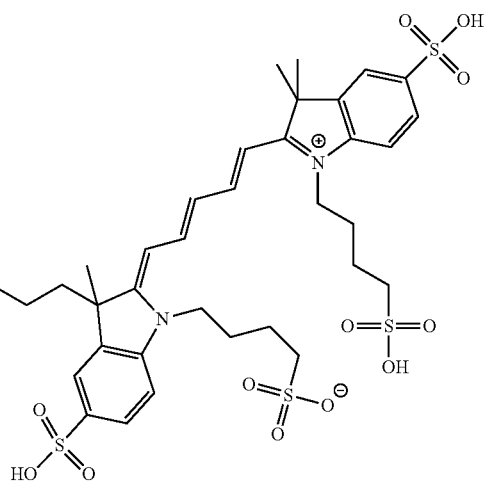

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 μmol) in DMF (40 μL) was added a solution of AlexaFluor647-ONSu (2.16 mg, 1.966 μmol) also in DMF (100 μL). The mixture was basified with DIPEA (1 μl, 5.73 μmol) and agitated overnight on a vortex mixer.

The reaction mixture was evaporated to dryness. The solid was dissolved in MeCN/water/AcOH (5/4/1, <1 mL) filtered and was applied to a Phenomenex Jupiter $C_{18}$ preparative column and eluted with the following gradient (A=0.1% trifluoroacetic acid in water, B=0.1% TFA/90% MeCN/10% water): Flow rate=10 mL/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M+H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle:

In order to generate a TR-FRET signal, donor fluorophore is excited by a laser at A337 nm, which subsequently leads to emission at A618 nm. If the acceptor fluorophore is in close proximity then energy transfer can occur, which leads to emission of Alexa Fluor® 647 at A665 nm. In the presence of competitor compound, Reference Compound X can be displaced from binding to the bromodomain. If displacement occurs, the acceptor fluorophore is no longer in proximity to the donor fluorophore, which prevents fluorescent energy transfer and, subsequently, a loss of Alexa Fluor® 647 emission at λ665 nm.

The competition of the compounds of formula (I) with Reference Compound X for binding to the BET family (BRD2, BRD3, BRD4 and BRDT) was assessed using protein truncates spanning both bromodomain 1 (BD1) and bromodomain 2 (BD2). In order to monitor differential binding to either BD1 or BD2, single residue mutations of key tyrosines to alanine were made in the acetyl lysine binding pockets. To validate this approach, a double residue mutant tandem domain protein was produced for each of the BET family members. Utilising a Fluorescence Polarisation approach, binding affinities for each of the single and double mutants for Reference Compound X were determined. The affinities of the double mutant tandem proteins for Reference Compound X were greatly reduced in comparison to the non mutated, wild type tandem BET proteins (>1000 fold reduction in Kd). The affinities of the single mutated bromdomain tandem proteins for Reference Compound X were equipotent with the corresponding non-mutated BET protein. These data demonstrated that single mutations of Tyrosine to Alanine reduce the Kd of the interaction between the mutated bromodomain and Reference Compound X by >1000 fold. In the TR-FRET competition assay, Reference Compound X is used at a concentration that is equivalent to the Kd for the non-mutated bromodomain, which ensures that no binding at the mutated bromodomain is detected.

Protein Production:

Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in *E. coli* cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 μL/mL protease inhibitor cocktail and extracted from the *E. coli* cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1+BD2 Mutant TR-FRET Competition Assays:

All assay components were dissolved in an assay buffer composing of 50 mM HEPES pH7.4, 50 mM NaCl, 5% Glycerol, 1 mM DTT and 1 mM CHAPS. Reference Compound X was diluted, in assay buffer containing 20 nM single mutant, tandem bromodomain protein, to a concentration equivalent to 2*Kd for this bromodomain. The solution containing bromodomain and Reference Compound X was added to dose response dilutions of test compound or DMSO vehicle (a maximum of 0.5% DMSO is used in this assay) in Greiner 384 well black low volume microtitre plates and subsequently incubated for 30 minutes at room temperature. An equal volume of 3 nM of anti-6*His Europium chelate was added to all wells, followed by a further 30 minute incubation at room temperature. TR-FRET was detected using a Perkin Elmer Multimode plate reader, by exciting the donor fluorophore at λ337 nm and subsequently, after a delay of 50 μsecs, measuring emission of the donor and acceptor fluorophores at λ615 nm and λ665 nm, respectively. In order to control these assays, 16 replicates each of uninhibited (DMSO vehicle) and inhibited (10*IC$_{50}$ concentrations of Example 11 of WO 2011/054846A1) TR-FRET assays were included on every microtitre plate.

cA four parameter curve fit of the following form was then applied:

$$y=a+((b-a)/(1+(10\hat{\ }x/10\hat{\ }c)\hat{\ }d)$$

Where 'a' is the minimum, 'b' is the Hill slope, 'c' is the pIC$_{50}$ and 'd' is the maximum.

All compounds (Examples) were each tested in the BRD4 BD1 and the BRD4 BD2 TR-FRET assays essentially as described above. Those of skill in the art will recognise that in vitro binding assays and cell-based assays for functional activity are subject to experimental variability. Accordingly, it is to be understood that the pIC$_{50}$ values given below are exemplary only. pIC$_{50}$ values are expressed as log$_{10}$ units.

All tested compounds were found to have a pIC$_{50}$≥5.0 in at least one assay described above.

Examples 54 and 116 were found to have a pIC$_{50}$≥5.0 and <6.0 in the BRD4 BD2 assay.

All other tested compounds were found to have a pIC$_{50}$≥6.0 in the BRD4 BD2 assay. In particular, Example 30 was found to have a pIC$_{50}$ of 8.0 (n=4) in the BRD4 BD2 assay; Example 46 was found to have a pIC$_{50}$ of 7.1 (n=3) in the BRD4 BD2 assay; Example 49 was found to have a pIC$_{50}$ of 7.9 (n=2) in the BRD4 BD2 assay; Example 52 was found to have a pIC$_{50}$ of 7.7 (n=1) in the BRD4 BD2 assay; Example 80 was found to have a pIC$_{50}$ of 7.4 (n=8) in the BRD4 BD2 assay; Example 83 was found to have a pIC$_{50}$ of 7.5 (n=5) in the BRD4 BD2 assay; Example 106 was found to have a pIC$_{50}$ of 7.6 (n=2) in the BRD4 BD2 assay; Example 117 was found to have a pIC$_{50}$ of 7.3 in the BRD4 BD2 assay; Example 118 was found to have a pIC$_{50}$ of 7.3 in the BRD4 BD2 assay; Example 119 was found to have a pIC$_{50}$ of 8.2 in the BRD4 BD2 assay; Example 120 was found to have a pIC$_{50}$ of 7.8 in the BRD4 BD2 assay; Example 121 was found to have a pIC$_{50}$ of 7.2 in the BRD4 BD2 assay; Example 122 was found to have a pIC$_{50}$ of 7.4 in the BRD4 BD2 assay; Example 123 was found to have a pIC$_{50}$ of 7.8 in the BRD4 BD2 assay; and Example 124 was found to have a pIC$_{50}$ of 7.3 in the BRD4 BD2 assay.

Calculation of Selectivity for BRD4 BD2 Over BRD4 BD1

Selectivity for BRD4 BD2 over BRD4 BD1 was calculated as follows:

Selectivity=BRD4BD2pIC$_{50}$−BRD4BD1pIC$_{50}$

All Examples were found to have selectivity for BRD4 BD2 over BRD4 BD1 of ≥1 log unit in at least one of the TR-FRET assays described above, and hence are at least 10 fold selective for BRD4 BD2 over BRD4 BD1.

Examples 1 to 108 and 117 to 124 were found to have selectivity for BRD4 BD2 over BRD4 BD1 of ≥2 log unit in at least one of the TR-FRET assays described above, and hence are at least 100 fold selective for BRD4 BD2 over BRD4 BD1.

Examples 12, 13, 18, 24, 28, 30, 48, 52, 62, 63, 67, 68, 69, 71, 73, 80, 82, 84, 87, 88, 92, 95, 99, 100, 103, 106, 107 119, 122 and 123 were found to have selectivity for BRD4 BD2 over BRD4 BD1 of ≥3 log unit in at least one of the TR-FRET assays described above, and hence are at least 1000 fold selective for BRD4 BD2 over BRD4 BD1.

Example 30 was found to have selectivity for BRD4 BD2 over BRD4 BD1 of 3.3 log units in at least one of the TR-FRET assays described above, and hence is at least 1000-fold selective for BRD4 BD2 over BRD4 BD1.

Example 46 was found to have a selectivity for BRD4 BD2 over BRD4 BD1 of 2.8 log units in at least one of the TR-FRET assays described above, and hence is at least 100-fold selective for BRD4 BD2 over BRD4 BD1.

Example 49 was found to have a selectivity for BRD4 BD2 over BRD4 BD1 of 2.8 log units in at least one of the TR-FRET assays described above, and hence is at least 100-fold selective for BRD4 BD2 over BRD4 BD1.

Example 52 was found to have a selectivity for BRD4 BD2 over BRD4 BD1 of 3.2 log units in at least one of the TR-FRET assays described above, and hence is at least 1000-fold selective for BRD4 BD2 over BRD4 BD1.

Example 80 was found to have a selectivity for BRD4 BD2 over BRD4 BD1 of 3.0 log units in at least one of the TR-FRET assays described above, and hence is at least 1000-fold selective for BRD4 BD2 over BRD4 BD1.

Example 83 was found to have a selectivity for BRD4 BD2 over BRD4 BD1 of 2.9 log units in at least one of the TR-FRET assays described above, and hence is at least 100-fold selective for BRD4 BD2 over BRD4 BD1.

Example 106 was found to have a selectivity for BRD4 BD2 over BRD4 BD1 of 3.0 log units in at least one of the TR-FRET assays described above, and hence is at least 1000-fold selective for BRD4 BD2 over BRD4 BD1.

Example 117 was found to have a selectivity for BRD4 BD2 over BRD4 BD1 of 2.9 log units in at least one of the TR-FRET assays described above, and hence is at least 100-fold selective for BRD4 BD2 over BRD4 BD1.

Example 118 was found to have a selectivity for BRD4 BD2 over BRD4 BD1 of 2.9 log units in at least one of the TR-FRET assays described above, and hence is at least 100-fold selective for BRD4 BD2 over BRD4 BD1.

Example 119 was found to have a selectivity for BRD4 BD2 over BRD4 BD1 of 3.1 log units in at least one of the TR-FRET assays described above, and hence is at least 1000-fold selective for BRD4 BD2 over BRD4 BD1.

Example 120 was found to have a selectivity for BRD4 BD2 over BRD4 BD1 of 2.8 log units in at least one of the TR-FRET assays described above, and hence is at least 100-fold selective for BRD4 BD2 over BRD4 BD1.

Example 121 was found to have a selectivity for BRD4 BD2 over BRD4 BD1 of 2.7 log units in at least one of the TR-FRET assays described above, and hence is at least 100-fold selective for BRD4 BD2 over BRD4 BD1.

Example 122 was found to have a selectivity for BRD4 BD2 over BRD4 BD1 of 3.1 log units in at least one of the TR-FRET assays described above, and hence is at least 1000-fold selective for BRD4 BD2 over BRD4 BD1.

Example 123 was found to have a selectivity for BRD4 BD2 over BRD4 BD1 of 3.0 log units in at least one of the TR-FRET assays described above, and hence is at least 1000-fold selective for BRD4 BD2 over BRD4 BD1.

Example 124 was found to have a selectivity for BRD4 BD2 over BRD4 BD1 of 2.8 log units in at least one of the TR-FRET assays described above, and hence is at least 100-fold selective for BRD4 BD2 over BRD4 BD1.

The invention claimed is:
1. A compound of formula (I)

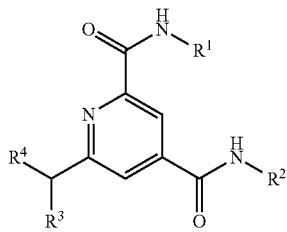

(I)

or a pharmaceutically acceptable salt thereof
wherein:
$R^1$ is —$C_{1-3}$alkyl or cyclopropyl;
$R^2$ is —$C_{0-3}$alkyl-$C_{3-7}$cycloalkyl, wherein said $C_{3-7}$cycloalkyl group is optionally substituted one, two, or three times by $R^5$;
$R^3$ is —H, —$C_{1-4}$alkyl, cyclopropyl, fluoro, chloro, —$CH_2F$, —$C_{0-3}$alkyl$OR^{10}$, or —$C_{0-3}$alkylCN;
$R^4$ is phenyl or heteroaryl, wherein said phenyl or heteroaryl is optionally substituted one, two, or three times by $R^6$;
each $R^5$ is independently selected from fluoro, —$C_{1-6}$alkyl-$R^{13}$, —$OCH_3$, —O—$C_{2-6}$alkyl-$R^{13}$, —CN, —OH, —$SO_2C_{1-3}$alkyl, and —$NR^{14}R^{15}$;
each $R^6$ is independently selected from oxo, halo, —$OCF_3$, —$OCHF_2$, —$C_{1-4}$alkyl, —$C_{0-3}$alkyl-$OR^8$, —$C_{0-3}$alkyl-$NR^{14}R^{15}$, —$C_{0-3}$alkyl-$CONR^{11}R^{12}$, —$C_{0-3}$ alkyl-heterocyclyl, —$C_{0-3}$alkyl-O—$C_{1-2}$alkyl-heterocyclyl, —CN, and —$SO_2R^7$, wherein said heterocyclyl is optionally substituted by one or two substituents independently selected from —$C_{1-3}$alkyl, —OH, and fluoro;
$R^7$ is —$C_{1-3}$alkyl or —$NR^{11}R^{12}$;
$R^8$ is —H, —$C_{1-3}$alkyl, —$C_{2-3}$alkyl-$NR^{11}R^{12}$, —$C_{2-3}$ alkyl-OH, or —$C_{2-3}$alkyl-O—$C_{1-3}$alkyl;
$R^9$ is —H, —$C_{1-3}$alkyl, —$C_{2-3}$alkyl-$NR^{11}R^{12}$, or —$C_{2-3}$alkyl-OH;
$R^{10}$ is —H or —$C_{1-3}$alkyl;
$R^{11}$ is independently selected from —H and —$C_{1-3}$alkyl;
$R^{12}$ is independently selected from —H and —$C_{1-3}$alkyl;
or $R^{11}$ and $R^{12}$ can join together with the nitrogen to which they are attached, form a heterocyclyl optionally containing a further heteroatom selected from nitrogen, oxygen, and sulphur, wherein said heterocyclyl is optionally substituted by one or two substituents independently selected from —$C_{1-3}$alkyl, —OH, and fluoro;
$R^{13}$ is —H, —$OR^9$, —$NR^{14}R^{15}$ or —CN;
$R^{14}$ is independently selected from —H, —C(O)OC(CH$_3$)$_3$, —C(O)$C_{1-3}$alkyl, —$C_{1-6}$alkyl, $C_{3-7}$cycloalkyl, heterocyclyl, —$C_{2-3}$alkyl-OH and —$C_{2-3}$alkyl-O—$C_{1-3}$ alkyl, wherein —$C_{1-6}$alkyl and $C_{3-7}$cycloalkyl may be optionally substituted by one, two or three fluoro;
$R^{15}$ is independently selected from —H, —C(O)OC(CH$_3$)$_3$, —C(O)$C_{1-3}$alkyl, —$C_{1-6}$alkyl, $C_{3-7}$cycloalkyl, heterocyclyl, —$C_{2-3}$alkyl-OH and —$C_{2-3}$alkyl-O—$C_{1-3}$ alkyl, wherein —$C_{1-6}$alkyl and $C_{3-7}$cycloalkyl may be optionally substituted by one, two or three fluoro;
or $R^{14}$ and $R^{15}$ can join together with the nitrogen to which they are attached, form a heterocyclyl optionally containing a further heteroatom selected from nitrogen, oxygen, and sulphur, wherein said heterocyclyl is optionally substituted by one or two substituents independently selected from —$C_{1-3}$alkyl, —OH and fluoro.

2. The compound or pharmaceutically acceptable salt thereof according to claim 1, wherein $R^1$ is methyl.

3. The compound or pharmaceutically acceptable salt thereof according to claim 1, wherein $R^2$ is cyclopropyl.

4. The compound or pharmaceutically acceptable salt thereof according to claim 3, wherein $R^2$ is unsubstituted.

5. The compound or pharmaceutically acceptable salt thereof according to claim 3, wherein $R^2$ is substituted once by $R^5$, wherein $R^5$ is methyl.

6. The compound or pharmaceutically acceptable salt thereof according to claim 1, wherein $R^3$ is —H, methyl, ethyl, fluoro, —$OCH_3$, —OH, —$CH_2F$, —$CH_2OH$, —CH(OH)CH$_3$, —$CH_2OMe$, or —$CH_2CN$.

7. The compound or pharmaceutically acceptable salt thereof according to claim 1, wherein $R^4$ is unsubstituted phenyl or phenyl substituted once by $R^6$.

8. The compound or pharmaceutically acceptable salt thereof according to claim 1, wherein $R^4$ is unsubstituted pyrrolopyridinyl.

9. The compound or pharmaceutically acceptable salt thereof according to claim 7, wherein $R^4$ is substituted by once by $R^6$, wherein $R^6$ is selected from oxo, fluoro, —$OCH_2CH_2OH$, —$OCH_2CH(CH_3)OH$, methyl, —$OCH_3$, —OH, and —$OCH_2CH_2$-3-(4,4 difluoropiperidinyl).

10. A compound which is selected from:
(+/−)-N$^4$-Cyclopropyl-N$^2$-methyl-6-(1-phenylethyl)pyridine-2,4-dicarboxamide;
6-Benzyl-N$^4$-cyclopropyl-N$^2$-methylpyridine-2,4-dicarboxamide;
6-Benzyl-N$^4$-cyclobutyl-N$^2$-methylpyridine-2,4-dicarboxamide;
(+/−)-N$^4$-Cyclobutyl-N$^2$-methyl-6-(1-phenylethyl)pyridine-2,4-dicarboxamide;
(S*)—N$^4$-Cyclopropyl-N$^2$-methyl-6-(1-phenylethyl)pyridine-2,4-dicarboxamide;
(R*)—N$^4$-Cyclopropyl-N$^2$-methyl-6-(1-phenylethyl)pyridine-2,4-dicarboxamide;
6-Benzyl-N$^2$-methyl-N$^4$-((1S,2S)-2-methylcyclopropyl)pyridine-2,4-dicarboxamide;
6-((1H-Indazol-7-yl)methyl)-N$^4$-cyclopropyl-N$^2$-methylpyridine-2,4-dicarboxamide;
6-(3-(2-Hydroxyethoxy)benzyl)-N$^2$-methyl-N$^4$-((1S,2S)-2-methylcyclopropyl)pyridine-2,4-dicarboxamide;
N$^4$-Cyclopropyl-6-(2-fluorobenzyl)-N$^2$-methylpyridine-2,4-dicarboxamide;
N$^4$-((1S,2S)-2-(Hydroxymethyl)cyclopropyl)-6-(3-methoxybenzyl)-N$^2$-methylpyridine-2,4-dicarboxamide;
N$^4$-Cyclopropyl-6-(3-methoxybenzyl)-N$^2$-methylpyridine-2,4-dicarboxamide;

6-(3-Methoxybenzyl)-N²-methyl-N⁴-((1S,2S)-2-methyl-cyclopropyl)pyridine-2,4-dicarboxamide;

(+/−)-6-Benzyl-N⁴-((trans)-2-hydroxycyclobutyl)-N²-methylpyridine-2,4-dicarboxamide;

6-Benzyl-N⁴-((1r,4r)-4-hydroxycyclohexyl)-N²-methyl-pyridine-2,4-dicarboxamide;

(S)—N⁴-Cyclopropyl-6-(3-(2-hydroxypropoxy)benzyl)-N²-methylpyridine-2,4-dicarboxamide;

N⁴-Cyclopropyl-6-(3-(2-hydroxyethoxy)benzyl)-N²-methylpyridine-2,4-dicarboxamide;

6-((1H-Indol-4-yl)methyl)-N²-methyl-N⁴-((1S,2S)-2-methylcyclopropyl)pyridine-2,4-dicarboxamide;

N⁴-Cyclopropyl-6-(4-methoxybenzyl)-N²-methylpyridine-2,4-dicarboxamide;

N⁴-Cyclopropyl-N²-methyl-6-(2-methylbenzyl)pyridine-2,4-dicarboxamide;

6-((1H-Indol-4-yl)methyl)-N⁴-cyclopropyl-N²-methyl-pyridine-2,4-dicarboxamide;

N⁴-Cyclopropyl-6-(3-fluorobenzyl)-N²-methylpyridine-2,4-dicarboxamide;

N⁴-Cyclopropyl-N²-methyl-6-(3-methylbenzyl)pyridine-2,4-dicarboxamide;

N²-Methyl-N⁴-((1S,2S)-2-methylcyclopropyl)-6-((2-oxoindolin-4-yl)methyl)pyridine-2,4-dicarboxamide;

N⁴-Cyclopropyl-6-(indolin-4-ylmethyl)-N²-methylpyridine-2,4-dicarboxamide;

N⁴-Cyclopropyl-6-(3-hydroxybenzyl)-N²-methylpyridine-2,4-dicarboxamide;

(R)—N⁴-Cyclopropyl-6-(3-(2-hydroxypropoxy)benzyl)-N²-methylpyridine-2,4-dicarboxamide;

6-(Hydroxy(phenyl)methyl)-N²-methyl-N⁴-((1S,2S)-2-methylcyclopropyl)pyridine-2,4-dicarboxamide;

6-((R)-Hydroxy(phenyl)methyl)-N²-methyl-N⁴-((1S,2S)-2-methylcyclopropyl)pyridine-2,4-dicarboxamide;

6-((S)-Hydroxy(phenyl)methyl)-N²-methyl-N⁴-((1S,2S)-2-methylcyclopropyl)pyridine-2,4-dicarboxamide;

6-(Methoxy(phenyl)methyl)-N²-methyl-N⁴-((1S,2S)-2-methylcyclopropyl)pyridine-2,4-dicarboxamide;

6-(Hydroxy(pyridin-2-yl)methyl)-N²-methyl-N⁴-((1S,2S)-2-methylcyclopropyl)pyridine-2,4-dicarboxamide;

6-((1H-Indazol-4-yl)methyl)-N²-methyl-N⁴-((1S,2S)-2-methylcyclopropyl)pyridine-2,4-dicarboxamide;

N²-Methyl-N⁴-((1S,2S)-2-methylcyclopropyl)-6-(pyridin-2-ylmethyl)pyridine-2,4-dicarboxamide;

6-((S)-Fluoro(phenyl)methyl)-N²-methyl-N⁴-((1S,2S)-2-methylcyclopropyl)pyridine-2,4-dicarboxamide;

N²-Methyl-6-((2-methyl-1H-benzo[d]imidazol-4-yl)methyl)-N⁴-((1S,2S)-2-methylcyclopropyl)pyridine-2,4-dicarboxamide;

6-(3-(2-(4,4-Difluoropiperidin-3-yl)ethoxy)benzyl)-N²-methyl-N⁴-((1S,2S)-2-methylcyclopropyl)pyridine-2,4-dicarboxamide;

6-Benzyl-N⁴-((1r,3r)-3-hydroxycyclobutyl)-N²-methyl-pyridine-2,4-dicarboxamide;

6-((1H-Indol-3-yl)methyl)-N²-methyl-N⁴-((1S,2S)-2-methylcyclopropyl)pyridine-2,4-dicarboxamide;

6-(Hydroxy(6-methylpyridin-2-yl)methyl)-N²-methyl-N⁴-((1S,2S)-2-methylcyclopropyl)pyridine-2,4-dicarboxamide;

6-Benzyl-N²-methyl-N⁴-((1r,3r)-3-(methylsulfonyl)cyclobutyl)pyridine-2,4-dicarboxamide;

6-Benzyl-N⁴-cyclopentyl-N²-methylpyridine-2,4-dicarboxamide;

6-Benzyl-N⁴-(cyclopropylmethyl)-N²-methylpyridine-2,4-dicarboxamide;

6-((1H-Indol-4-yl)methyl)-N⁴-((1r,3r)-3-hydroxycyclobutyl)-N²-methylpyridine-2,4-dicarboxamide;

6-(hydroxy(1H-pyrrolo[3,2-c]pyridin-4-yl)methyl)-N²-methyl-N⁴-((1S,2S)-2-methylcyclopropyl)pyridine-2,4-dicarboxamide;

6-((1H-Pyrrolo[2,3-c]pyridin-4-yl)methyl)-N²-methyl-N⁴-((1S,2S)-2-methylcyclopropyl)pyridine-2,4-dicarboxamide;

(+/−)-N⁴-Cyclopropyl-6-(hydroxy(phenyl)methyl)-N²-methylpyridine-2,4-dicarboxamide;

6-(1-(1H-Pyrrolo[2,3-c]pyridin-4-yl)ethyl)-N²-methyl-N⁴-((1S,2S)-2-methylcyclopropyl)pyridine-2,4-dicarboxamide;

6-((S*)-1-(1H-Pyrrolo[2,3-c]pyridin-4-yl)ethyl)-N²-methyl-N⁴-((1S,2S)-2-methylcyclopropyl)pyridine-2,4-dicarboxamide;

6-((R*)-1-(1H-Pyrrolo[2,3-c]pyridin-4-yl)ethyl)-N²-methyl-N⁴-((1S,2S)-2-methylcyclopropyl)pyridine-2,4-dicarboxamide;

(S*)—N⁴-Cyclopropyl-6-(hydroxy(phenyl)methyl)-N²-methylpyridine-2,4-dicarboxamide;

(R*)—N⁴-Cyclopropyl-6-(hydroxy(phenyl)methyl)-N²-methylpyridine-2,4-dicarboxamide;

N⁴-((1r,3S)-3-Hydroxycyclobutyl)-N²-methyl-6-((S*)-1-phenylethyl)pyridine-2,4-dicarboxamide;

N²-Methyl-N⁴-((1S,2S)-2-methylcyclopropyl)-6-((2-oxopyridin-1(2H)-yl)methyl)pyridine-2,4-dicarboxamide;

6-Benzyl-N⁴-((1S,2S)-2-(hydroxymethyl)cyclopropyl)-N²-methylpyridine-2,4-dicarboxamide;

6-Benzyl-N⁴-(trans-3-methoxycyclobutyl)-N²-methyl-pyridine-2,4-dicarboxamide;

6-Benzyl-N⁴-((1r,3r)-3-(2-hydroxyethoxy)cyclobutyl)-N²-methylpyridine-2,4-dicarboxamide;

6-(2-Hydroxy-1-phenylethyl)-N²-methyl-N⁴-((1S,2S)-2-methylcyclopropyl)pyridine-2,4-dicarboxamide, mixture of diastereomers;

6-(Chloro(phenyl)methyl)-N²-methyl-N⁴-((1S,2S)-2-methylcyclopropyl)pyridine-2,4-dicarboxamide;

N²-methyl-N⁴-((1S,2S)-2-methylcyclopropyl)-6-(1-(pyridin-2-yl)ethyl)pyridine-2,4-dicarboxamide;

6-(2-Hydroxy-1-phenylpropyl)-N²-methyl-N⁴-((1S,2S)-2-methylcyclopropyl)pyridine-2,4-dicarboxamide;

6-(1-(3-(2-Hydroxyethoxy)phenyl)ethyl)-N²-methyl-N⁴-((1S,2S)-2-methylcyclopropyl)pyridine-2,4-dicarboxamide, mixture of diastereomers;

6-(2-hydroxy-1-phenylethyl)-N²-methyl-N⁴-((1S,2S)-2-methylcyclopropyl)pyridine-2,4-dicarboxamide Isomer 1;

6-(2-hydroxy-1-phenylethyl)-N²-methyl-N⁴-((1S,2S)-2-methylcyclopropyl)pyridine-2,4-dicarboxamide Isomer 2;

(+/−)-N⁴-((1R,5S,6r)-3,3-difluorobicyclo[3.1.0]hexan-6-yl)-6-(hydroxy(o-tolyl)methyl)-N²-methylpyridine-2,4-dicarboxamide;

6-(Hydroxy(o-tolyl)methyl)-N²-methyl-N⁴-((1S,2S)-2-methylcyclopropyl)pyridine-2,4-dicarboxamide, mixture of diastereomers;

6-((1H-Indol-4-yl)methyl)-N⁴-((1R,5S,6r)-3,3-difluorobicyclo[3.1.0]hexan-6-yl)-N²-methylpyridine-2,4-dicarboxamide;

6-(Hydroxy(1H-indol-4-yl)methyl)-N²-methyl-N⁴-((1S,2S)-2-methylcyclopropyl)pyridine-2,4-dicarboxamide, mixture of diastereomers;

6-(hydroxy(o-tolyl)methyl)-N²-methyl-N⁴-((1S,2S)-2-methylcyclopropyl)pyridine-2,4-dicarboxamide, Isomer 1;

6-((2-fluorophenyl)(hydroxy)methyl)-$N^2$-methyl-$N^4$-((1S,2S)-2-methylcyclopropyl)pyridine-2,4-dicarboxamide;

6-((S*)-1-(3-(2-Hydroxyethoxy)phenyl)ethyl)-$N^2$-methyl-$N^4$-((1S,2S)-2-methylcyclopropyl)pyridine-2,4-dicarboxamide;

6-((R*)-1-(3-(2-Hydroxyethoxy)phenyl)ethyl)-$N^2$-methyl-$N^4$-((1S,2S)-2-methylcyclopropyl)pyridine-2,4-dicarboxamide;

(+/−)-$N^4$-((1R,5S,6r)-3,3-Difluorobicyclo[3.1.0]hexan-6-yl)-6-(hydroxy(phenyl)methyl)-$N^2$-methylpyridine-2,4-dicarboxamide;

6-((R*)-1-(3-Fluoro-1H-pyrrolo[2,3-c]pyridin-4-yl)ethyl)-$N^2$-methyl-$N^4$-((1S,2S)-2-methylcyclopropyl)pyridine-2,4-dicarboxamide;

$N^4$-Cyclopropyl-$N^2$-methyl-6-(3-((1-methyl-1H-pyrazol-3-yl)methoxy)benzyl)pyridine-2,4-dicarboxamide;

6-((3-fluorophenyl)(hydroxy)methyl)-$N^2$-methyl-$N^4$-((1S,2S)-2-methylcyclopropyl)pyridine-2,4-dicarboxamide;

6-((S*)-2-Cyano-1-phenylethyl)-$N^2$-methyl-$N^4$-((1S,2S)-2-methylcyclopropyl)pyridine-2,4-dicarboxamide;

6-(1-(1H-pyrrolo[2,3-c]pyridin-4-yl)propyl)-N2-methyl-N4-((1 S,2S)-2-methylcyclopropyl)pyridine-2,4-dicarboxamide, Isomer 1;

6-(1-(1H-pyrrolo[2,3-c]pyridin-4-yl)propyl)-N2-methyl-N4-((1 S,2S)-2-methylcyclopropyl)pyridine-2,4-dicarboxamide, Isomer 2;

6-((1H-Pyrrolo[2,3-b]pyridin-4-yl)methyl)-$N^2$-methyl-$N^4$-((1S,2S)-2-methylcyclopropyl)pyridine-2,4-dicarboxamide;

$N^2$-Methyl-6-((S*)-1-(1-methyl-1H-pyrrolo[2,3-c]pyridin-4-yl)ethyl)-$N^4$-((1S,2S)-2-methylcyclopropyl)pyridine-2,4-dicarboxamide;

6-((1-(2-Hydroxyethyl)-1H-indol-4-yl)methyl)-$N^2$-methyl-$N^4$-((1S,2S)-2-methylcyclopropyl)pyridine-2,4-dicarboxamide;

6-(Indolin-4-ylmethyl)-$N^2$-methyl-$N^4$-((1S,2S)-2-methylcyclopropyl)pyridine-2,4-dicarboxamide;

6-(1-(1H-Pyrrolo[2,3-b]pyridin-4-yl)ethyl)-$N^2$-methyl-$N^4$-((1S,2S)-2-methylcyclopropyl)pyridine-2,4-dicarboxamide, mixture of diastereomers;

$N^4$-((1R,5S,6r)-3,3-difluorobicyclo[3.1.0]hexan-6-yl)-6-(hydroxy(phenyl)methyl)-$N^2$-methylpyridine-2,4-dicarboxamide, Isomer 1;

$N^4$-((1R,5S,6r)-3,3-difluorobicyclo[3.1.0]hexan-6-yl)-6-(hydroxy(phenyl)methyl)-$N^2$-methylpyridine-2,4-dicarboxamide, Isomer 2;

6-(2-Cyano-1-phenylethyl)-$N^2$-methyl-$N^4$-((1S,2S)-2-methylcyclopropyl)pyridine-2,4-dicarboxamide;

6-((1H-Pyrrolo[2,3-b]pyridin-4-yl)methyl)-$N^4$-((1R,5S,6r)-3,3-difluorobicyclo[3.1.0]hexan-6-yl)-$N^2$-methylpyridine-2,4-dicarboxamide;

6-((1H-Indol-4-yl)methyl)-$N^4$-cyclopropyl-$N^2$-ethylpyridine-2,4-dicarboxamide;

(±)-$N^4$-cyclopropyl-6-((3-fluorophenyl)(hydroxy)methyl)-$N^2$-methylpyridine-2,4-dicarboxamide;

(+/−)-$N^4$-Cyclopropyl-6-(hydroxy(o-tolyl)methyl)-$N^2$-methylpyridine-2,4-dicarboxamide;

(S*)—$N^4$-Cyclopropyl-6-(hydroxy(2-methoxyphenyl)methyl)-$N^2$-methylpyridine-2,4-dicarboxamide;

(R*)—$N^4$-Cyclopropyl-6-(hydroxy(2-methoxyphenyl)methyl)-$N^2$-methylpyridine-2,4-dicarboxamide;

N4-cyclopropyl-6-((3-fluorophenyl)(hydroxy)methyl)-N2-methylpyridine-2,4-dicarboxamide, Enantiomer 1;

6-((R*)-(3-Fluorophenyl)(hydroxy)methyl)-$N^2$-methyl-$N^4$-((1S,2S)-2-methylcyclopropyl)pyridine-2,4-dicarboxamide;

6-((S*)-(3-Fluorophenyl)(hydroxy)methyl)-$N^2$-methyl-$N^4$-((1S,2S)-2-methylcyclopropyl)pyridine-2,4-dicarboxamide;

6-(imidazo[1,2-a]pyridin-5-ylmethyl)-N2-methyl-N4-((1S,2S)-2-methylcyclopropyl)pyridine-2,4-dicarboxamide;

$N^2$-methyl-$N^4$-((1S,2S)-2-methylcyclopropyl)-6-(1-(2-oxoindolin-4-yl)ethyl)pyridine-2,4-dicarboxamide Isomer 1;

$N^2$-methyl-$N^4$-((1S,2S)-2-methylcyclopropyl)-6-(1-(2-oxoindolin-4-yl)ethyl)pyridine-2,4-dicarboxamide Isomer 2;

6-((S*)-1-(1H-Pyrrolo[2,3-b]pyridin-4-yl)ethyl)-$N^2$-methyl-$N^4$-((1S,2S)-2-methylcyclopropyl)pyridine-2,4-dicarboxamide;

6-((R*)-1-(1H-Pyrrolo[2,3-b]pyridin-4-yl)ethyl)-$N^2$-methyl-$N^4$-((1S,2S)-2-methylcyclopropyl)pyridine-2,4-dicarboxamide;

6-((S*)-2-Cyano-1-phenylethyl)-$N^2$-methyl-$N^4$-((1S,2S)-2-methylcyclopropyl)pyridine-2,4-dicarboxamide;

6-((R*)-2-Cyano-1-phenylethyl)-$N^2$-methyl-$N^4$-((1S,2S)-2-methylcyclopropyl)pyridine-2,4-dicarboxamide;

$N^2$-methyl-6-((7-methyl-1H-pyrrolo[2,3-c]pyridin-4-yl)methyl)-N4-((1S,2S)-2-methylcyclopropyl)pyridine-2,4-dicarboxamide;

6-((S*)-Methoxy(1H-pyrrolo[2,3-b]pyridin-4-yl)methyl)-$N^2$-methyl-$N^4$-((1S,2S)-2-methylcyclopropyl)pyridine-2,4-dicarboxamide;

6-((R*)-Methoxy(1H-pyrrolo[2,3-b]pyridin-4-yl)methyl)-$N^2$-methyl-$N^4$-((1S,2S)-2-methylcyclopropyl)pyridine-2,4-dicarboxamide;

$N^4$-((1R,3R,5S,6r)-3-hydroxybicyclo[3.1.0]hexan-6-yl)-$N^2$-methyl-6-((S)-1-phenylethyl)pyridine-2,4-dicarboxamide;

$N^4$-((1R,3S,5 S,6r)-3-hydroxybicyclo[3.1.0]hexan-6-yl)-$N^2$-methyl-6-((S)-1-phenylethyl)pyridine-2,4-dicarboxamide;

6-(2-hydroxy-1-phenylpropyl)-$N^2$-methyl-$N^4$-((S,2S)-2-methylcyclopropyl)pyridine-2,4-dicarboxamide;

6-((1 S*,2R*)-2-hydroxy-1-phenylpropyl)-$N^2$-methyl-$N^4$-((1S,2S)-2-methylcyclopropyl)pyridine 2,4-dicarboxamide;

6-((1R*,2S*)-2-hydroxy-1-phenylpropyl)-$N^2$-methyl-$N^4$-((1S,2S)-2-methylcyclopropyl)pyridine-2,4-dicarboxamide;

6-((R)-hydroxy(o-tolyl)methyl)-$N^2$-methyl-$N^4$-((1S,2S)-2-methylcyclopropyl)pyridine-2,4-dicarboxamide;

6-(1-(1H-pyrrolo[2,3-c]pyridin-4-yl)propyl)-$N^2$-methyl-$N^4$-((1S,2S)-2-methylcyclopropyl)pyridine-2,4-dicarboxamide;

(S*)—$N^4$-cyclopropyl-6-((3-fluorophenyl)(hydroxy)methyl)-$N^2$-methylpyridine-2,4-dicarboxamide;

(R*)—$N^4$-cyclopropyl-6-(hydroxy(o-tolyl)methyl)-$N^2$-methylpyridine-2,4-dicarboxamide;

(S*)—$N^4$-cyclopropyl-6-(hydroxy(o-tolyl)methyl)-$N^2$-methylpyridine-2,4-dicarboxamide;

6-benzyl-$N^4$-((1R,3r,5S,6r)-hydroxybicyclo[3.1.0]hexan-6-yl)-$N^2$-methylpyridine-2,4-dicarboxamide;

6-benzyl-$N^4$-((1R,3s,5S,6r)-hydroxybicyclo[3.1.0]hexan-6-yl)-$N^2$-methylpyridine-2,4-dicarboxamide;

$N^4$-((1R,3r,5S,6r)-3-hydroxybicyclo[3.1.0]hexan-6-yl)-6-(methoxy(phenyl)methyl)-$N^2$-methylpyridine-2,4-dicarboxamide;

N⁴-((1R,3s,5S,6r)-3-hydroxybicyclo[3.1.0]hexan-6-yl)-6-(methoxy(phenyl)methyl)-N²-methylpyridine-2,4-dicarboxamide;

N⁴-((1R,3S,5S,6r)-3-hydroxybicyclo[3.1.0]hexan-6-yl)-6-((R*)-methoxy(phenyl)methyl)-N²-methylpyridine-2,4-dicarboxamide;

N⁴-((1R,3S,5S,6r)-3-hydroxybicyclo[3.1.0]hexan-6-yl)-6-((S*)-methoxy(phenyl)methyl)-N2-methylpyridine-2,4-dicarboxamide;

N⁴-((1R,3R,5S,6r)-3-hydroxybicyclo[3.1.0]hexan-6-yl)-6-((R*)-methoxy(phenyl)methyl)-N²-methylpyridine-2,4-dicarboxamide;

N⁴-((1R,3S,5S,6r)-3-hydroxybicyclo[3.1.0]hexan-6-yl)-6-((S*)-methoxy(phenyl)methyl)-N²-methylpyridine-2,4-dicarboxamide;

or a pharmaceutically acceptable salt thereof.

11. A pharmaceutical composition comprising a compound or a pharmaceutically acceptable salt thereof according to claim 1 and one or more pharmaceutically acceptable excipients.

12. A combination comprising a compound or a pharmaceutically acceptable salt thereof according to claim 1 together with one or more other therapeutically active agents.

\* \* \* \* \*